(12) United States Patent
Park et al.

(10) Patent No.: US 9,814,784 B2
(45) Date of Patent: Nov. 14, 2017

(54) ANTIBODY-LINKER-DRUG CONJUGATE, PREPARATION METHOD THEREFOR, AND ANTICANCER DRUG COMPOSITION CONTAINING SAME

(71) Applicant: Celltrion, Inc., Incheon (KR)

(72) Inventors: Young Jun Park, Incheon (KR); Jin-kyo Jeong, Incheon (KR); Young Mi Choi, Incheon (KR); Minseob Lee, Incheon (KR); Yeon Jung Kim, Incheon (KR); Kyoung Suk Kim, Incheon (KR); Joon hun Choi, Incheon (KR); Jin Seo Lee, Incheon (KR); Eun Joo Cho, Incheon (KR); Hyunnam Song, Incheon (KR); Sung Jun Park, Incheon (KR); Jong-hyoup Lee, Incheon (KR); Matthew Sangyup Lee, Incheon (KR); In-Suk Lee, Incheon (KR); Joon woo Kim, Incheon (KR); Seung Suh Hong, Incheon (KR)

(73) Assignee: CELLTRION, INC., Incheon (KR)

( * ) Notice: Subject to any disclaimer, the term of this patent is extended or adjusted under 35 U.S.C. 154(b) by 42 days.

(21) Appl. No.: 14/655,357

(22) PCT Filed: Jan. 2, 2014

(86) PCT No.: PCT/KR2014/000005
§ 371 (c)(1),
(2) Date: Jun. 25, 2015

(87) PCT Pub. No.: WO2014/107024
PCT Pub. Date: Jul. 10, 2014

(65) Prior Publication Data
US 2015/0366990 A1 Dec. 24, 2015

(30) Foreign Application Priority Data

| Jan. 3, 2013 | (KR) | 10-2013-0000771 |
|---|---|---|
| Feb. 19, 2013 | (KR) | 10-2013-0017585 |
| Feb. 19, 2013 | (KR) | 10-2013-0017587 |
| Feb. 19, 2013 | (KR) | 10-2013-0017588 |
| Feb. 19, 2013 | (KR) | 10-2013-0017591 |

(51) Int. Cl.
| A61K 47/48 | (2006.01) |
|---|---|
| C07D 403/12 | (2006.01) |
| C07D 207/416 | (2006.01) |
| C07K 16/30 | (2006.01) |
| A61K 38/08 | (2006.01) |

(52) U.S. Cl.
CPC ........ *A61K 47/48715* (2013.01); *A61K 38/08* (2013.01); *A61K 47/48415* (2013.01); *A61K 47/48438* (2013.01); *A61K 47/48484* (2013.01); *A61K 47/48569* (2013.01); *A61K 47/48584* (2013.01); *C07D 207/416* (2013.01); *C07D 403/12* (2013.01); *C07K 16/30* (2013.01)

(58) Field of Classification Search
CPC .................. A61K 47/48; A61K 47/48715
USPC ..................... 424/179.1; 530/391.9
See application file for complete search history.

(56) References Cited

U.S. PATENT DOCUMENTS

| 6,214,345 B1 | 4/2001 | Firestone et al. |
|---|---|---|
| 7,750,116 B1 | 7/2010 | Doronina et al. |
| 7,964,566 B2 | 6/2011 | Doronina et al. |
| 2007/0092940 A1* | 4/2007 | Eigenbrot ........ A61K 47/48538 435/69.1 |
| 2013/0066055 A1* | 3/2013 | Lerchen ........... A61K 47/48038 530/391.9 |

FOREIGN PATENT DOCUMENTS

WO WO 2013092983 * 6/2013 ............. A61K 47/48

OTHER PUBLICATIONS

Sharkey et al. "Use of Antibodies and Immunoconjugates for the Therapy of more Accessible Cancers", Advanced Drug Delivery Reviews, 60, pp. 1407-1420, 2008.
Chari "Targeted Cancer Therapy: Conferring Specificity to Cytotoxic Drugs" Accounts of Chemical Research, pp. 98-107, vol. 41, No. 1, Jan. 2008.
Hamblett et al. "Effects of Drug Loading on the Antitumor Activity of Monoclonal Antibody Drug Conjugate" Clinical Cancer Research, vol. 10, pp. 7063-7070, Oct. 2004.
Ducry et al. "Antibody—Drug Conjugates: Linking Cytotoxic Payloads to Monoclonal Antibodies", Bioconjugate Chem. pp. 5-13, 2010.
Alley et al. "Contribution of Linker Stability to the Activities of Anticancer Immunoconjugates" Bioconjugate Chem, pp. 759-765, 2008.

* cited by examiner

*Primary Examiner* — Yan Xiao
(74) *Attorney, Agent, or Firm* — Baker & Hostetler LLP

(57) ABSTRACT

The present invention relates to an antibody-linker-drug conjugate in which an antibody and a cytotoxic drug are conjugated through an enzyme cleavable peptide linker capable of directly binding to a lysine residue of an antibody, a preparation method therefor, and
an anticancer drug composition containing the same as an active ingredient.

24 Claims, 15 Drawing Sheets

ANTIBODY-LINKER-DRUG CONJUGATE, PREPARATION METHOD THEREFOR, AND ANTICANCER DRUG COMPOSITION CONTAINING SAME

CROSS-REFERENCE TO RELATED APPLICATIONS

This application is the National Stage of International Application No. PCT/KR2014/000005, filed Jan. 2, 2014, which claims the benefit of and priority to Korean Application No. 10-2013-0000771, filed Jan. 3, 2013; Korean Application No. 10-2013- 0017585, filed Feb. 19, 2013; Korean Application No. 10-2013-0017587, filed Feb. 19, 2013; Korean Application No. 10-2013-0017588, filed Feb. 19, 2013; and Korean Application No. 10-2013-0017591 filed Feb. 19, 2013, the entireties of which are incorporated herein by reference for any and all purposes.

TECHNICAL FIELD

The present invention relates to an antibody-linker-drug conjugate, a preparation method therefor, and an anticancer drug composition comprising the same as an active ingredient. More particularly, the present invention relates to an antibody-linker-drug conjugate in which an antibody is coupled with a cytotoxic drug via an enzyme-cleavable peptide linker that can directly bond to a lysine residue of the antibody, a preparation method therefor, and an anticancer drug composition comprising the same as an active ingredient.

BACKGROUND ART

Antibodies are immunological proteins that bind specifically to antigens. At present, many monoclonal antibodies have been developed as anti-cancer agents or are used in cancer therapy. However, almost all antibodies, although inhibitory of the growth of cancer cells and thus suppressive of the progression of cancer, have very limited application in the therapy of cancers [Sharkey et al., Adv. Drug Del. Rev., 2008, 1407-1420]. As an alternative to antibody therapeutic agents to overcome this limitation, an antibody-drug conjugate (ADC), in which an antibody is coupled with a drug, has arisen [Chari, Acc. Chem. Res., 41(2008), 98-107]. As used herein, the term "ADC" refers to a highly potent biopharmaceutical drug that comprises a cytotoxic drug or toxin conjugated with a monoclonal antibody (mAb) capable of allowing the cytotoxic drug or toxin to be selectively delivered into a target tumor cell (internalization). Given to patients, ADCs bind to target cells via the antibody moiety and are internalized into the cells, wherein the cytotoxic drug or toxin moiety is separated from the conjugate and exerts its therapeutic efficacy [Hamblett et al., Clin. Cancer Res., 10:7063-7070, Oct. 15, 2004].

For the preparation of ADCs, a suitable form of linker is usually used to couple an antibody with a cytotoxic drug. Representative among the linkers are hydrazones, disulfides, and peptides. Fundamentally, the effective performance of an ADC requires at least a certain functional level of all three components: mAb, linker, and cytotoxic drug [Chari, Acc. Chem. Res., 41(2008), 98-107].

U.S. Pat. No. 6,214,345 discloses an ADC in which a cytotoxic drug, such as doxorubicin, Taxol, etc., is coupled to an antibody via an enzyme-cleavable peptide linker that can be cleaved by the lysosomal protease cathepsin. Also, U.S. Pat. No. 7, 964,566 discloses an ADC in which a cytotoxic drug, such as MeVal-Val-Dil-Dap-norephedrine (MMAE) and MeVal-Val-Dil-Dap-Phe (MMAF), is attached to an antibody through an enzyme-cleavable peptide linker.

According to conventional preparation methods of ADCs using enzyme-cleavable peptide linkers, attachment between linkers and antibodies is achieved by reducing a disulfide bond in antibodies to a thiol group in the presence of a reducing agent such as dithiothreitol (DTT), and bonding the linkers to the thiol group of the antibodies. However, cleavage of an intracellular disulfide bond of an antibody by use of a reducing agent necessarily causes a structural modification of the antibody itself, which may result in a negative influence on the affinity of the antibody to its antigen. Also, such reduction may cause the antibody to undergo partial degradation, making it difficult to purify the final ADC. Further, when reduced from the intramolecular disulfide bond to a thiol group, the antibodies readily aggregate together, lowering the final production yield of ADC.

Instead of the reduction of intramolecular disulfide bonds of antibodies to thiol groups, thiolation may be achieved by reacting a reagent for sulfhydryl addition, such as 2-iminotholane (Traut's reagent), with a lysine residue of an antibody. In this case, the number of the thiolation reagent attached to an antibody shows a wide distribution ranging from zero to less than ten. Thus, the linker cannot cover all the produced thiol groups, resulting in co-existence of coupled and uncoupled thiol groups in the same antibody. Due to the thiol groups that remain uncoupled with the linker and are thus unnecessary, and residues from the thiolation reagent, the ADC prepared by this conventional method is therefore poor in performance, particularly, in pharmacokinetic properties in vivo.

DISCLOSURE

Technical Problem

Leading to the present invention, intensive and thorough research into the development of ADCs without a structural modification of the antibody resulted in the finding that ADCs employing an enzyme-cleavable peptide linker capable of directly bonding to a lysine residue of an antibody can overcome the problems encountered with conventional ADCs.

It is therefore an object of the present invention to provide an antibody-linker-drug conjugate in which an antibody is conjugated with a cytotoxic drug via an enzyme-cleavable peptide linker capable of directly bonding to a lysine residue of the antibody.

It is another object to provide a method for preparing an antibody-linker-drug conjugate at high yield.

It is a further object to provide an anticancer agent composition comprising the antibody-linker-drug conjugate as an active ingredient.

Technical Solution

In accordance with an aspect thereof, the present invention addresses an antibody-linker-drug conjugate represented by Chemical Formula I, I-1, I-2, I-3, or I-4, or a pharmaceutically acceptable salt thereof:

[Chemical Formula I]

wherein,
Ab stands for an antibody,
L stands for a linker,
D stands for a drug, and
n is an integer ranging from 1 to 5;

[Chemical Formula I-1]

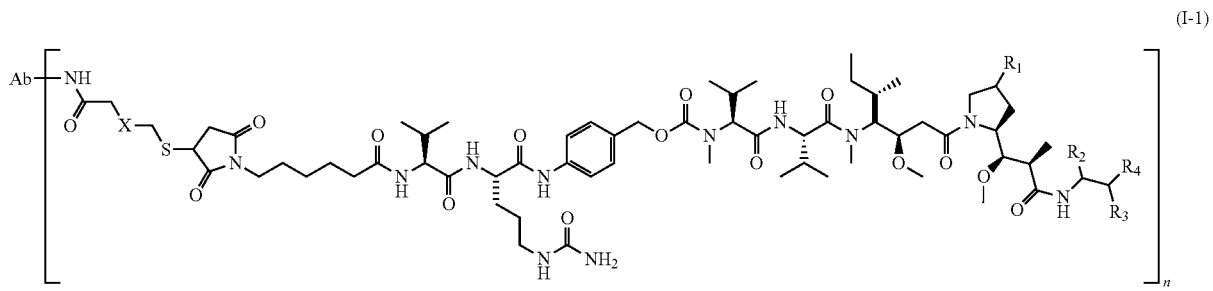

wherein,
Ab stands for an antibody,
X is $C_1$-$C_8$ alkyl or $C_3$-$C_6$ cycloalkyl,
$R_1$ is a hydrogen atom, hydroxy, $C_1$-$C_4$ alkoxy, or oxo (=O),
$R_2$ is a hydrogen atom or $C_1$-$C_4$ alkyl,
$R_3$ is a hydrogen atom, hydroxy, $C_1$-$C_4$ alkoxy, amino, oxo (=O), or hydroxyimino (=N—OH),
$R_4$ is aryl, and
n is an integer ranging from 1 to 5;

[Chemical Formula I-2]

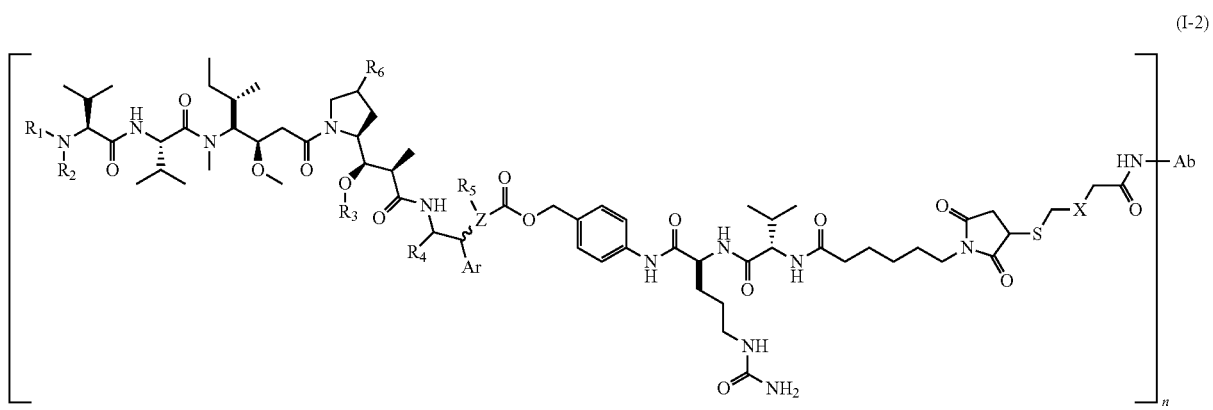

wherein,
Ab stands for an antibody,
X is $C_1$-$C_8$ alkyl or $C_3$-$C_6$ cycloalkyl,
$R_1$, $R_2$, $R_3$, and $R_4$ are each independently a hydrogen atom, or $C_1$-$C_4$ alkyl,
Ar stands for aryl group,
Z is a nitrogen atom, or an oxygen atom,
$R_5$ is a hydrogen atom or $C_1$-$C_4$ alkyl when Z is a nitrogen atom, or is absent when Z is an oxygen atom,
$R_6$ is a hydrogen atom, hydroxy, $C_1$-$C_4$ alkoxy, or oxo (=O), and
n is an integer ranging from 1 to 5;

[Chemical Formula I-3]

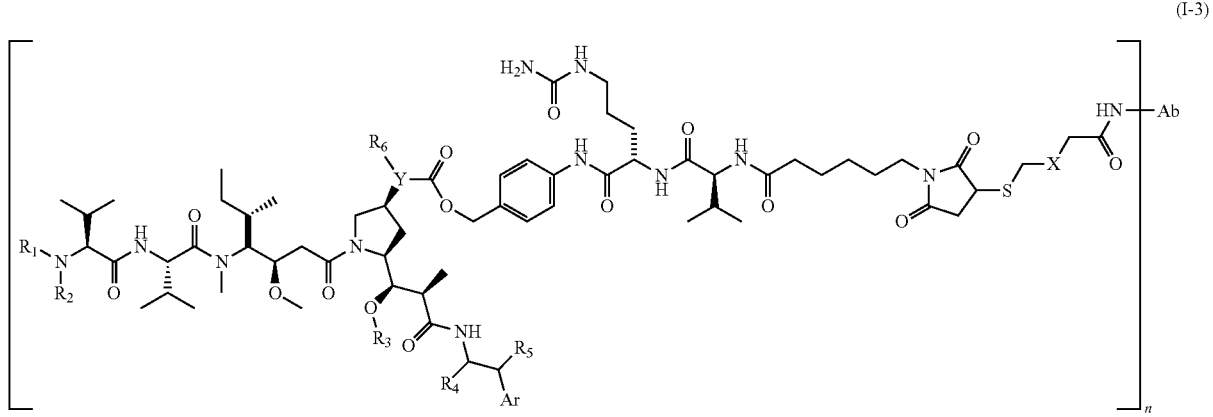

(I-3)

wherein,
Ab stands for an antibody,
X is $C_1$-$C_8$ alkyl, or $C_3$-$C_6$ cycloalkyl,
$R_1$, $R_2$, $R_3$, and $R_4$ are each independently a hydrogen atom, or $C_1$-$C_4$ alkyl,
$R_5$ is a hydrogen atom, hydroxy, $C_1$-$C_4$ alkoxy, amino, oxo (=O), or hydroxyimino (=N—OH),
Ar stands for aryl group,
Y is a nitrogen atom or an oxygen atom,
$R_6$ is a hydrogen atom or $C_1$-$C_4$ alkyl when Y is a nitrogen atom; or is absent when Y is an oxygen atom, and
n is an integer ranging from 1 to 5.

including, for example, but not limited to, methyl, ethyl, n-propyl, n-butyl, n-pentyl, and n-octyl.

As used herein, the term "$C_3$-$C_6$ cycloalkyl" refers to a cyclic hydrocarbon composed of 3 to 6 carbon atoms, including, for example, but not limited to, cyclopropyl, cyclobutyl, cyclopentyl, and cyclohexyl.

The term "$C_1$-$C_4$ alkoxy," as used herein, refers to a straight or branched alkoxy composed of 1 to 4 carbon atoms, including, for example, but not limited to, methoxy, ethoxy, and n-propanoxy.

The term "$C_1$-$C_4$ alkyl," as used herein, refers to a straight or branched hydrocarbon composed of 1 to 4 carbon atoms,

[Chemical Formula I-4]

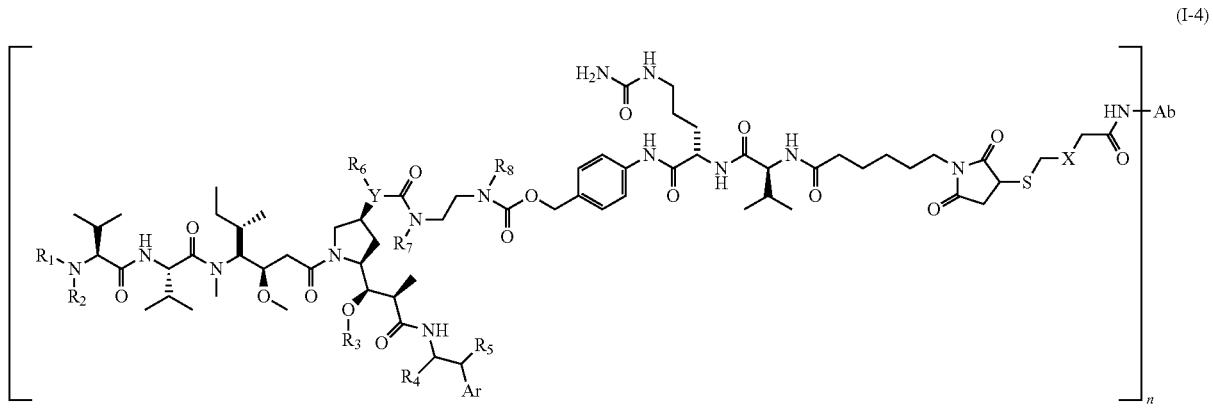

(I-4)

wherein,
Ab stands for an antibody,
X is $C_1$-$C_8$ alkyl or $C_3$-$C_6$ cycloalkyl,
$R_1$, $R_2$, $R_3$, $R_4$, $R_7$, and $R_8$ are each independently a hydrogen atom or $C_1$-$C_4$ alkyl,
$R_5$ is a hydrogen atom, hydroxy, $C_1$-$C_4$ alkoxy, amino, oxo (=O), or hydroxyimino (=N—OH),
Ar stands for aryl group,
Y is a nitrogen atom or an oxygen atom,
$R_6$ is a hydrogen atom or $C_1$-$C_4$ alkyl when Y is a nitrogen atom, or is absent when Y is an oxygen atom, and
n is an integer ranging from 1 to 5.

As used herein, the term "$C_1$-$C_8$ alkyl" refers to a straight or branched hydrocarbon composed of 1 to 8 carbon atoms, including, for example, but not limited to, methyl, ethyl, n-propyl, i-propyl, n-butyl, i-butyl, and t-butyl.

As used herein, the term "aryl" is intended to encompass all of an aromatic group, a heteroaromatic group, and a partially reduced derivative thereof. The term "aromatic group" refers 5 to 15-membered single or fused rings, preferably 6, 10 or 14-membered single or fused rings, and the term "heteroaromatic group" refers to aromatic group containing at least one hetero atom such as an oxygen atom, a sulfur atom, or a nitrogen atom. Examples of the aryl group include, but are not limited to, phenyl, naphthyl, pyridinyl, furanyl, thiophenyl, indolyl, quinolinyl, imidazolinyl, oxazolyl, thiazolyl, and tetrahydronaphthyl.

One or more hydrogen atoms on the $C_1$-$C_8$ alkyl group, the $C_3$-$C_6$ cycloalkyl group, the $C_1$-$C_4$ alkoxy group, the $C_1$-$C_4$ alkyl group, and the aryl group may be substituted by $C_1$-$C_4$ alkyl, $C_2$-$C_4$ alkenyl, $C_2$-$C_4$ alkynyl, $C_3$-$C_{10}$ cycloalkyl, $C_1$-$C_4$ haloalkyl, $C_1$-$C_4$ alkoxy, $C_1$-$C_4$ thioalkoxy, aryl, acyl, hydroxy, thio, a halogen atom, amino, alkoxycarbonyl, carboxy, carbamoyl, cyano, nitro, etc.

As used herein, the term "antibody" is intended to cover as broad a range of antibodies as possible, including an intact monoclonal or polyclonal antibody, a multi-specific antibody constructed from two or more different intact antibodies (e.g., a bispecific antibody), and an antibody fragment exhibiting an intended biological activity. An antibody is a protein, produced by the immune system, which can recognize and bind to a specific antigen. With regard to the structure, an antibody is a Y-shaped molecule that consists of four polypeptide chains (two heavy chains and two light chains), each having a variable region and a constant region. The variable region at each tip of the "Y" of an antibody binds to and interacts with a target antigen. The variable region contains a complementarity determining region (CDR) that recognizes and binds an epitope on its specific antigen while the constant region in the tail part of the "Y" is recognized by and interacts with the immune system. Generally, a target antigen has a plurality of antigenic determinants, called epitopes, which are recognized by CDRs on antibodies. Respective antibodies that specifically bind to different epitopes have different structures. Hence, one antigen may be recognized by one or more antibodies corresponding to its epitopes.

In one exemplary embodiment of the present invention, the antibody may be one that can immunospecifically bind to a cancer cell antigen. Antibodies immune-specific for cancer cell antigens may be commercially available, or may be prepared using a method known in the art, such as recombinant expression technology. Nucleotide sequences coding for antibodies immunospecific for cancer cell antigens may be obtained from the GenBank Database or documents, or may be prepared using conventional cloning and sequencing techniques. Examples of the antibodies available for cancer therapy include Herceptin (Trastuzumab marketed by Genentech), which is a humanized anti-HER2 antibody for treating metastatic breast cancers, Rituxan (Rituximab marketed by Genentech), which is a chimeric anti-CD20 for treating non-Hodgkin lymphomas, Erbitux (Cetuximab marketed by ImClone Systems), which is a chimetic anti-EGFR antibody for the treatment of epidermal growth factor positive cancers, such as head and neck cancer, and Vitaxin (MedImmune Inc.), which is a humanized anti-integrin $\alpha v \beta 3$ antibody for the treatment of sarcomas, but are not limited thereto.

In the antibody-linker-drug conjugate of the present invention, the linker-drug moiety is directly bonded to a lysine residue of the antibody moiety. Hence, the antibody-linker-drug conjugate of the present invention does not undergo an undesired antibody protein modification attributable to the reduction of intramolecular disulfide bonds and the residues of the thiolation reagent, but allows for least abnormal fragmentation or aggregation of the antibody moiety. The antibody-linker-drug conjugate of the present invention has a normal antibody structure at a rate of 90% or higher, preferably at a 92% or higher, more preferably at a rate of 97% or higher, and still more preferably at a rate of 98% or higher.

In a preferred embodiment of the present invention, the antibody-linker-drug conjugate may be represented by:
i) Chemical Formula I-1,
wherein,
Ab is an antibody immunospecifically binding to a cancer cell antigen,
X is $C_1$-$C_8$ alkyl or $C_3$-$C_6$ cycloalkyl,
$R_1$ is a hydrogen atom, hydroxy, or $C_1$-$C_4$ alkoxy,
$R_2$ is a hydrogen atom or $C_1$-$C_4$ alkyl,
$R_3$ is a hydrogen atom, oxo (=O) or hydroxyimino (=N—OH), and
$R_4$ is phenyl unsubstituted or substituted with at least one substituent selected from $C_1$-$C_4$ alkyl, $C_1$-$C_4$ alkoxy, and a halogen atom;
ii) Chemical Formula I-2,
wherein,
Ab is an antibody immunospecifically binding to a cancer cell antigen,
X is $C_1$-$C_8$ alkyl or $C_3$-$C_6$ cycloalkyl,
$R_1$, $R_2$, and $R_4$ are each independently a hydrogen atom or $C_1$-$C_4$ alkyl,
$R_3$ is $C_1$-$C_4$ alkyl,
Ar is phenyl unsubstituted or substituted with at least one substituent selected from the group consisting of $C_1$-$C_4$ alkyl, $C_1$-$C_4$ alkoxy, and a halogen atom,
Z is a nitrogen atom,
$R_5$ is a hydrogen atom or $C_1$-$C_4$ alkyl, and
$R_6$ is a hydrogen atom, hydroxy, or $C_1$-$C_4$ alkoxy;
iii) Chemical Formula I-3,
wherein,
Ab is an antibody immunospecifically binding to a cancer cell antigen,
X is $C_1$-$C_8$ alkyl or $C_3$-$C_6$ cycloalkyl,
$R_1$, $R_2$, and $R_4$ are each independently a hydrogen atom or $C_1$-$C_4$ alkyl,
$R_3$ is $C_1$-$C_4$ alkyl,
$R_5$ is a hydrogen atom, amino, oxo (=O), or hydroxyimino (=N—OH),
Ar is phenyl or naphthylunsubstituted or substituted with at least one substituent selected from the group consisting of $C_1$-$C_4$ alkyl, $C_1$-$C_4$ alkoxy, and a halogen atom,
Y is a nitrogen atom or an oxygen atom, and
$R_6$ is a hydrogen atom or $C_1$-$C_4$ alkyl when Y is a nitrogen atom, or is absent when Y is an oxygen atom; or
iv) Chemical Formula I-4
wherein,
Ab is an antibody immunospecifically binding to a cancer cell antigen,
X is $C_1$-$C_8$ alkyl or $C_3$-$C_6$ cycloalkyl,
$R_1$, $R_2$, $R_4$, $R_7$, and $R_8$ are each independently a hydrogen atom or $C_1$-$C_4$ alkyl,
$R_3$ is $C_1$-$C_4$ alkyl,
$R_5$ is a hydrogen atom, amino, oxo (=O), or hydroxyimino (=N—OH),
Ar is phenyl or naphthylunsubstituted or substituted with at least one substituent selected from the group consisting of $C_1$-$C_4$ alkyl, $C_1$-$C_4$ alkoxy, and a halogen atom,
Y is a nitrogen atom or an oxygen atom, and
$R_6$ is a hydrogen atom or $C_1$-$C_4$ alkyl when Y is a nitrogen atom, or is absent when Y is an oxygen atom.

In a more preferred exemplary embodiment of the present invention, the antibody-linker-drug conjugate is represented by:
i) Chemical Formula I-1,
wherein,
Ab is trastuzumab,
X is methyl, n-propyl, n-pentyl, n-octyl, or cyclopropyl,
$R_1$ is a hydrogen atom, hydroxy, or methoxy,
$R_2$ is a hydrogen atom, or methyl,

9

R₃ is a hydrogen atom, oxo (=O) or hydroxyimino (=N—OH), and

R₄ is phenyl unsubstituted or substituted with at least one substituent selected from the group consisting of methyl, methoxy, and a halogen atom;

ii) Chemical Formula I-2, wherein,

Ab is trastuzumab,

X is methyl, n-propyl, n-pentyl, n-octyl, or cyclopropyl,

R₁, R₂, and R₃ are each methyl,

R₄ is a hydrogen atom, or methyl,

Ar is phenyl unsubstituted or substituted with at least one substituent selected from the group consisting of methyl, methoxy, and a halogen atom, Z is a nitrogen atom, R₅ is a hydrogen atom, or methyl, and R₆ is a hydrogen atom, hydroxy, or methoxy;

iii) Chemical Formula I-3, wherein,

Ab is trastuzumab,

X is methyl, n-propyl, n-pentyl, n-octyl, or cyclopropyl,

R₁, R₂, and R₃ are each methyl,

R₄ is a hydrogen atom, or methyl,

R₅ is a hydrogen atom, oxo (=O), or hydroxyimino (=N—OH),

Ar is phenyl or naphthylunsubstituted or substituted with at least one substituent selected from the group consisting of methyl, methoxy, and a halogen atom,

10

Y is a nitrogen atom or an oxygen atom, and

R₆ is a hydrogen atom or methyl when Y is a nitrogen atom, or is absent when Y is an oxygen atom;

iv) Chemical Formula I-4 wherein,

Ab is trastuzumab,

X is methyl, n-propyl, n-pentyl, n-octyl, or cyclopropyl,

R₁, R₂, and R₃ are each methyl,

R₄, R₇, and R₈ are each independently a hydrogen atom or methyl,

R₅ is a hydrogen atom, oxo (=O), or hydroxyimino (=N—OH),

Ar is phenyl or naphthylunsubstituted or substituted with at least one substituent selected from the group consisting of methyl, methoxy, and a halogen atom, Y is a nitrogen atom or an oxygen atom, R₆ is a hydrogen atom or methyl when Y is a nitrogen atom, or is absent when Y is an oxygen atom.

As used herein, the term "pharmaceutically acceptable salt" is intended to encompass all nontoxic inorganic salts and organic salts. Examples include, but are not limited to, chlorates, sulfates, nitrates, phosphates, acetates, benzene sulfonates, and citrates.

Representative antibody-linker-drug conjugates of the present invention are as follows:

(I-5)

(I-6)

n = 3; (I-7)
n - 5; (I-8)
n = 8; (I-9)

-continued
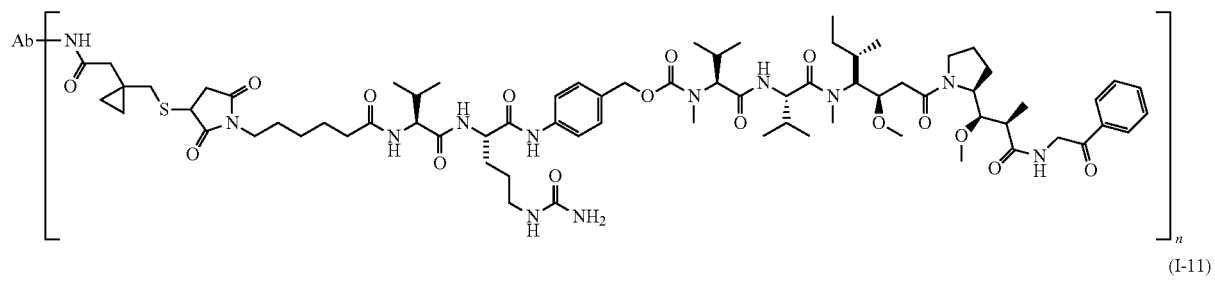
(I-10)
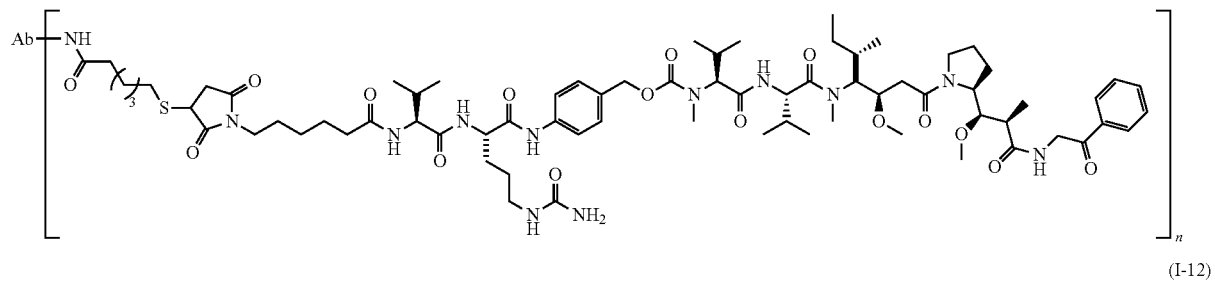
(I-11)
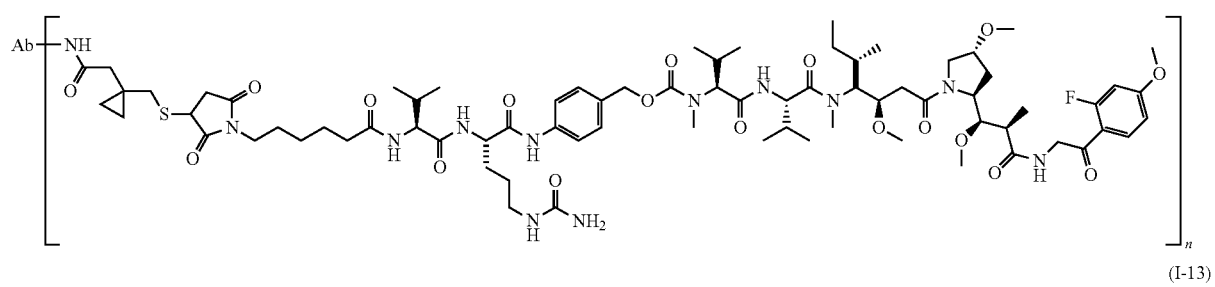
(I-12)
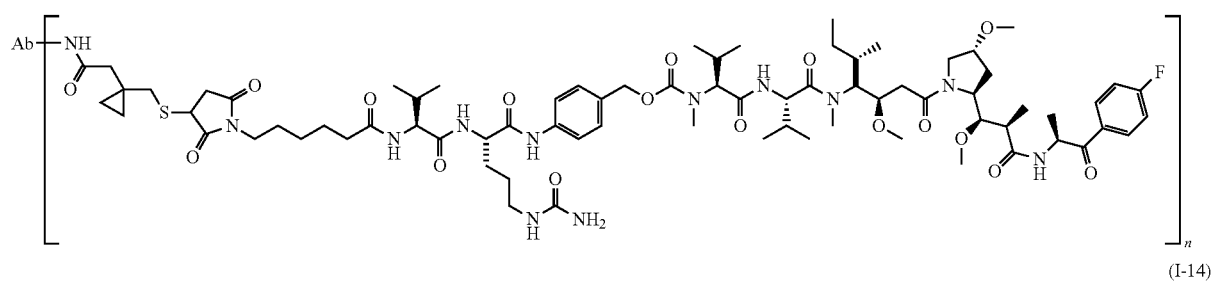
(I-13)
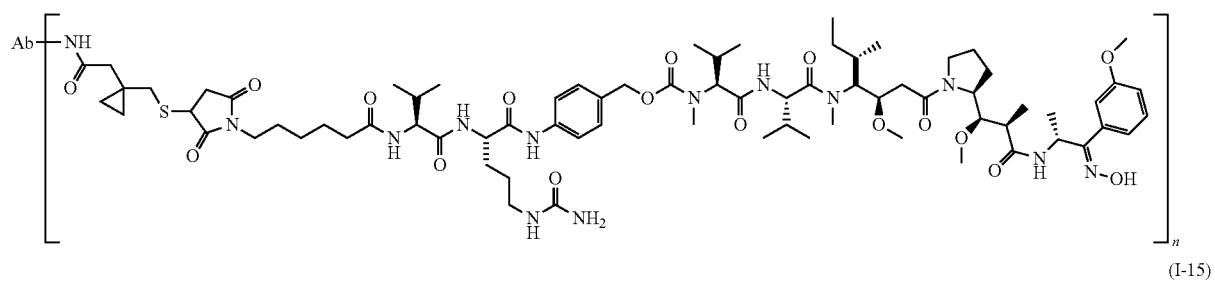
(I-14)
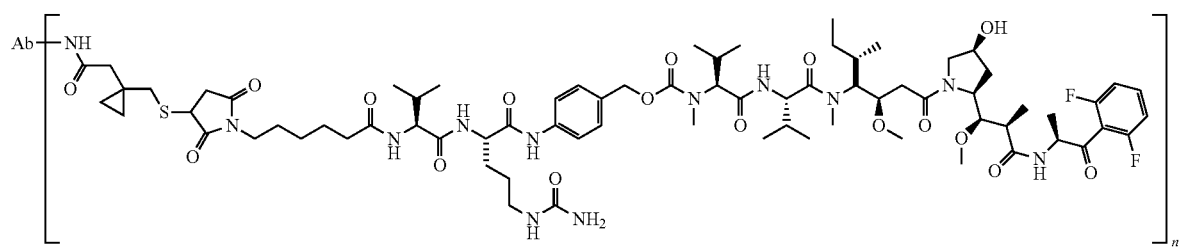
(I-15)

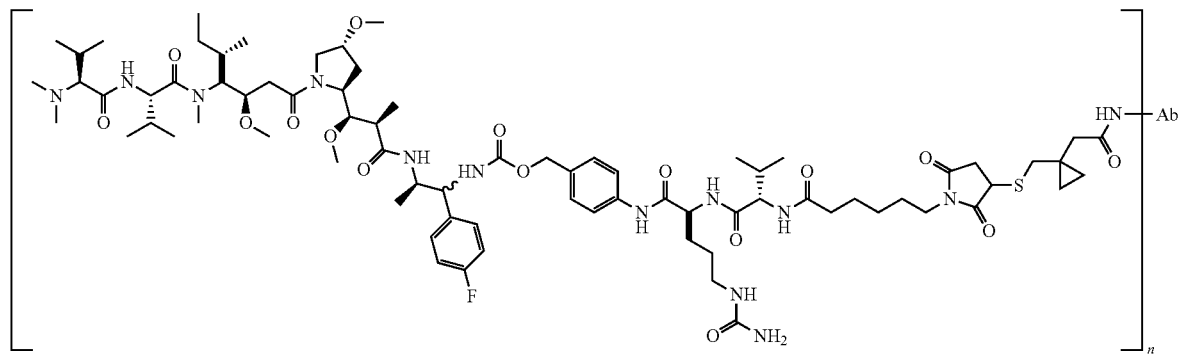
(I-16)
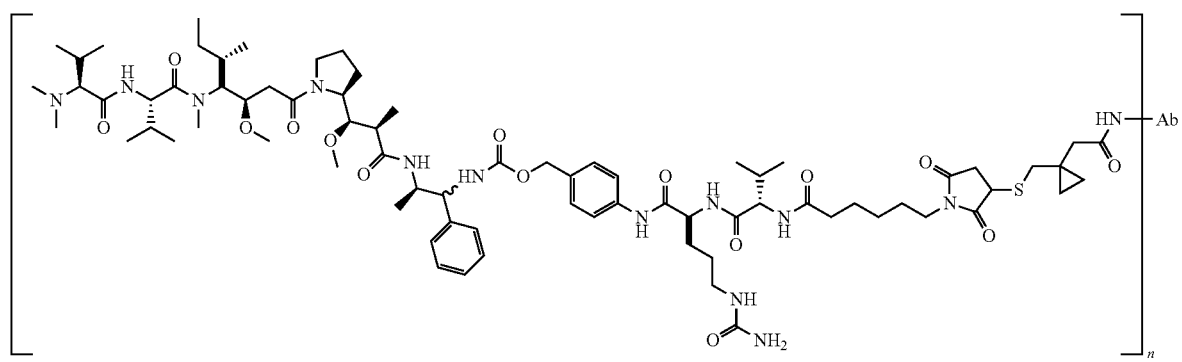
(I-17)
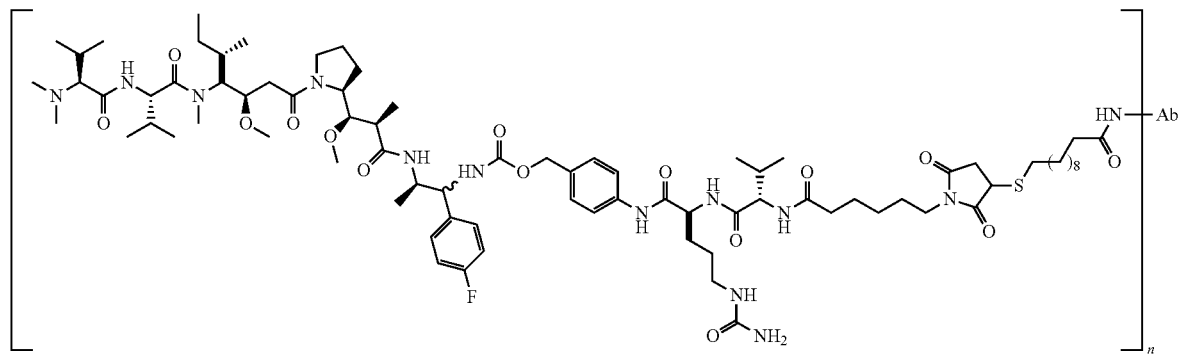
(I-18)
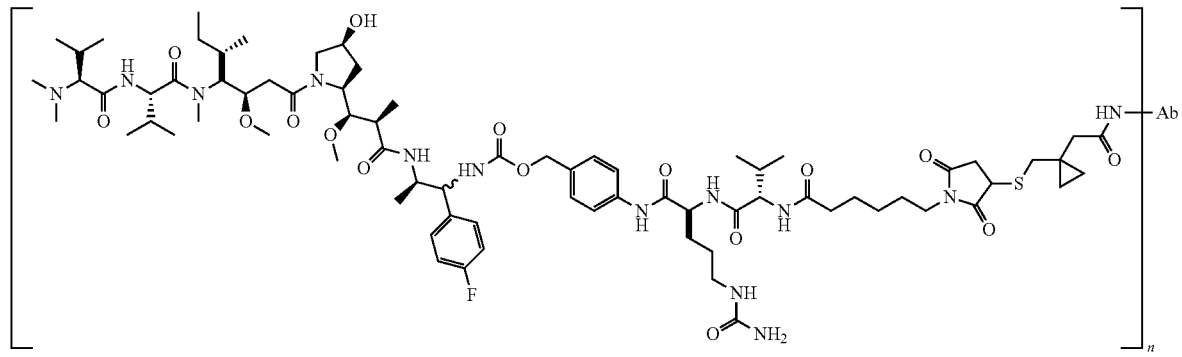
(I-19)

-continued
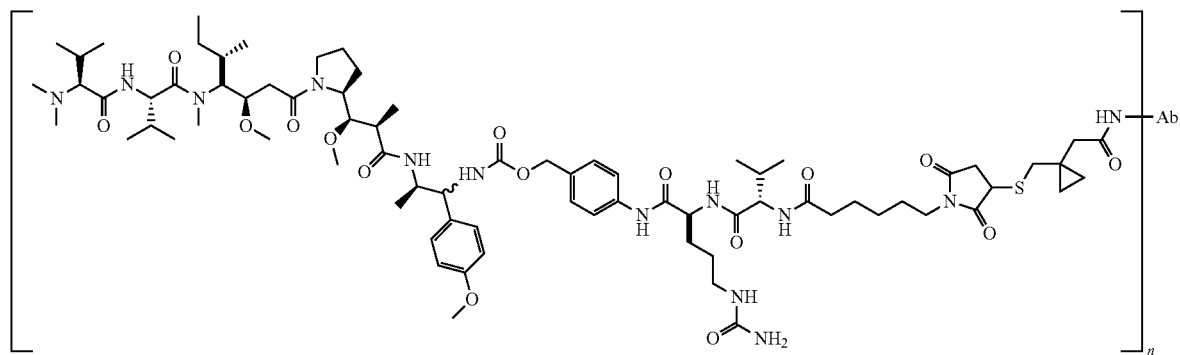
(I-20)
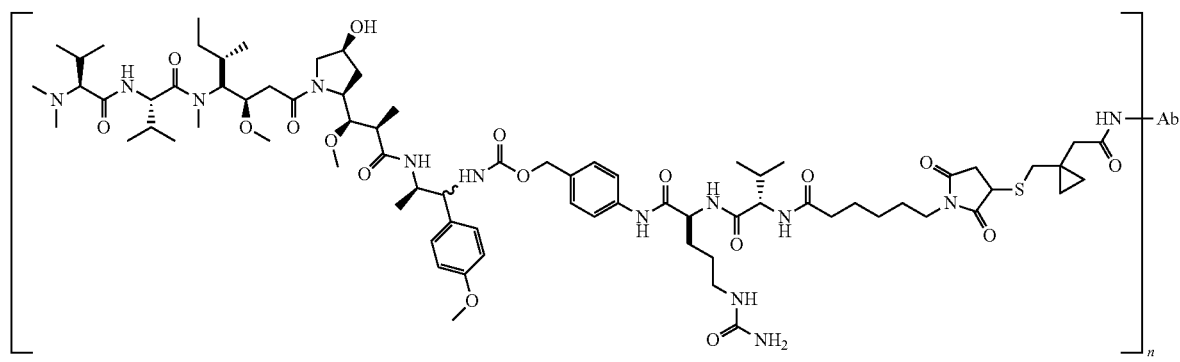
(I-21)
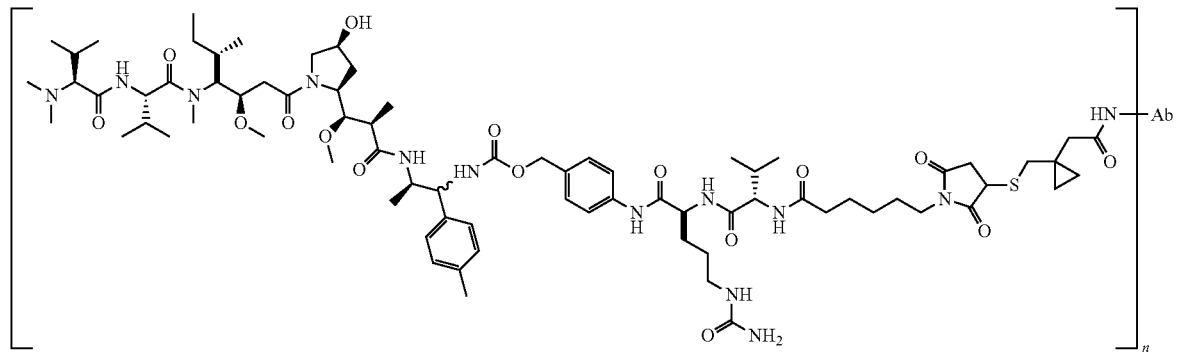
(I-22)
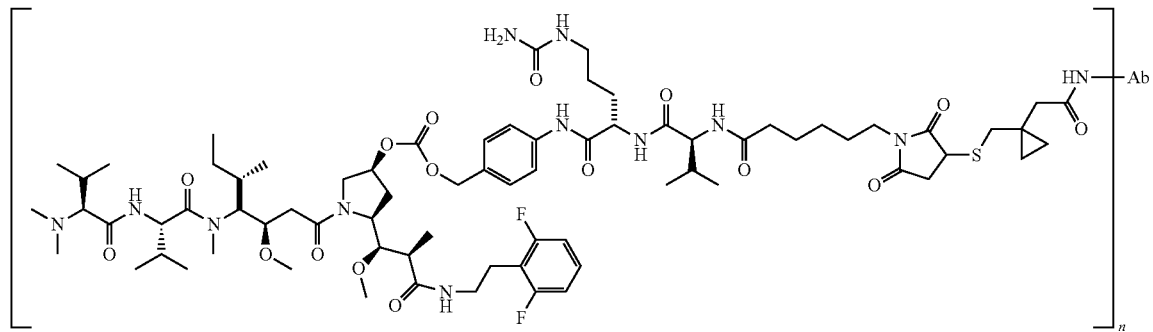
(I-23)

(I-24)
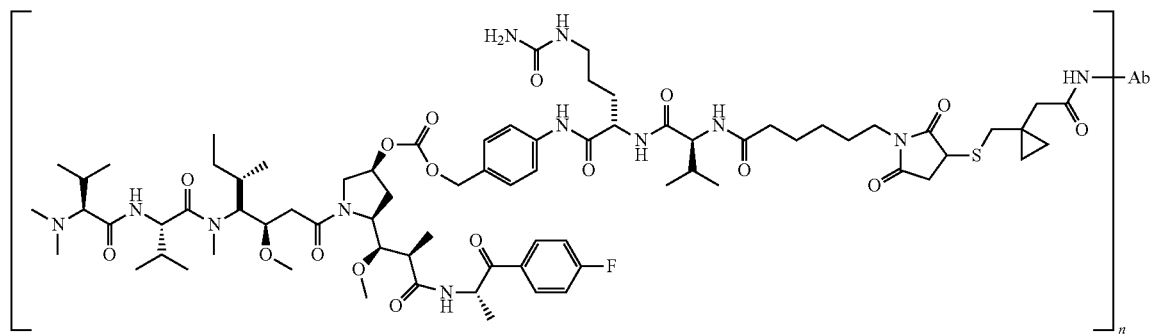
(I-25)
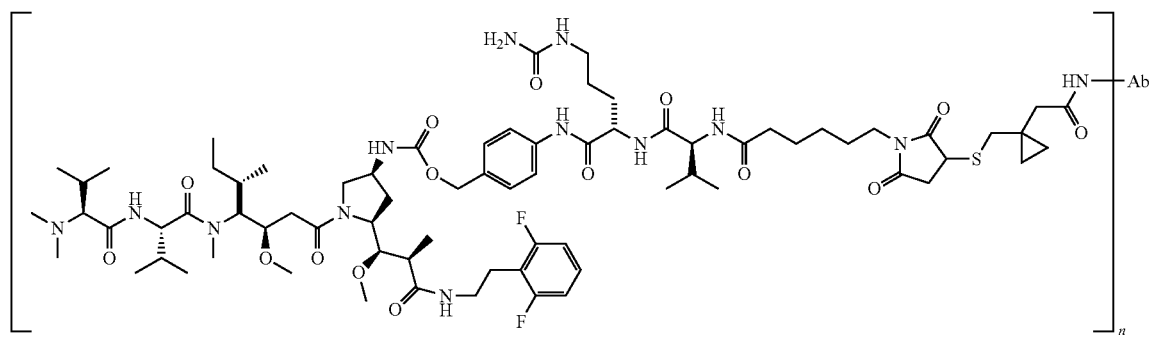
(I-26)
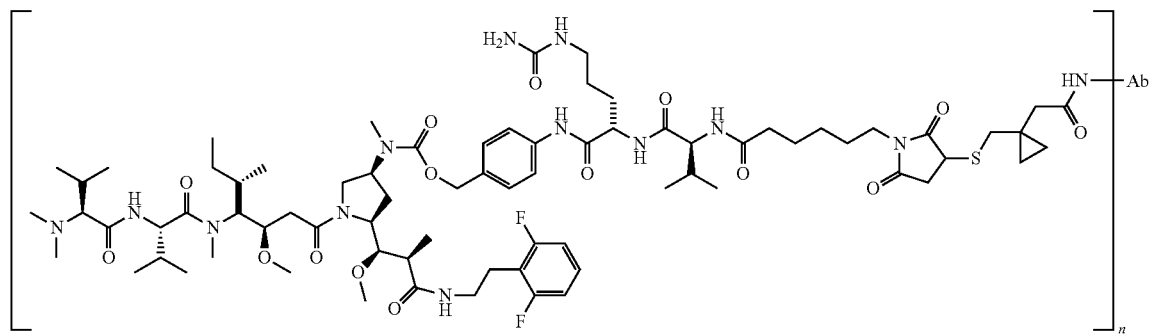
(I-27)
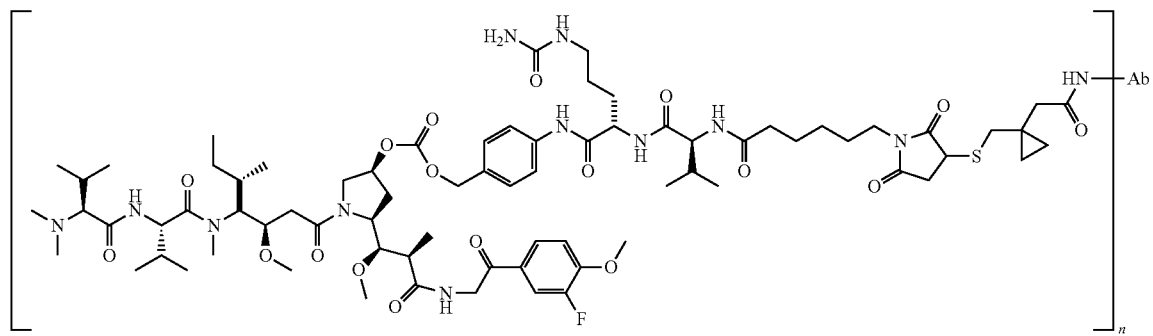

-continued
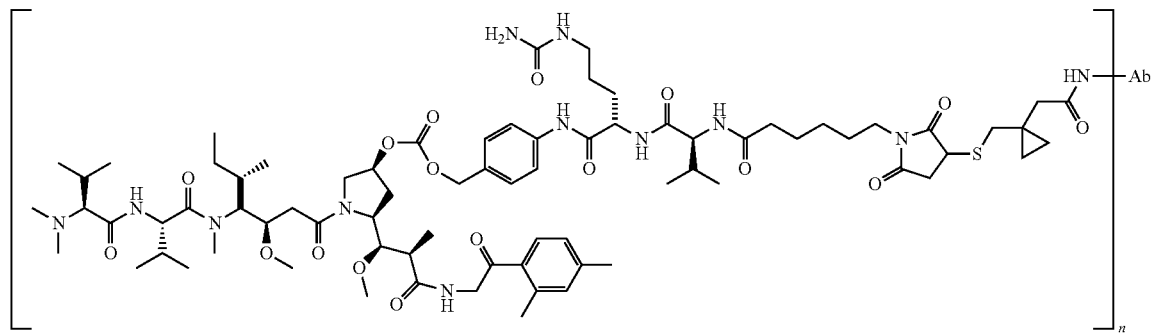
(I-28)
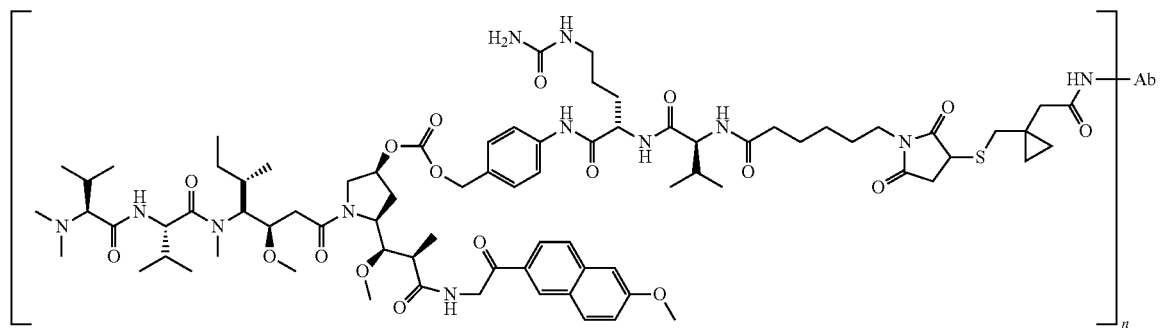
(I-29)
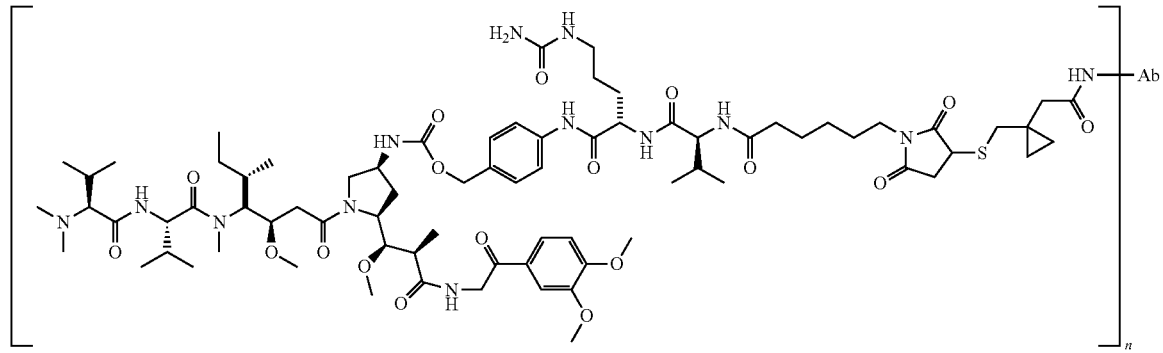
(I-30)
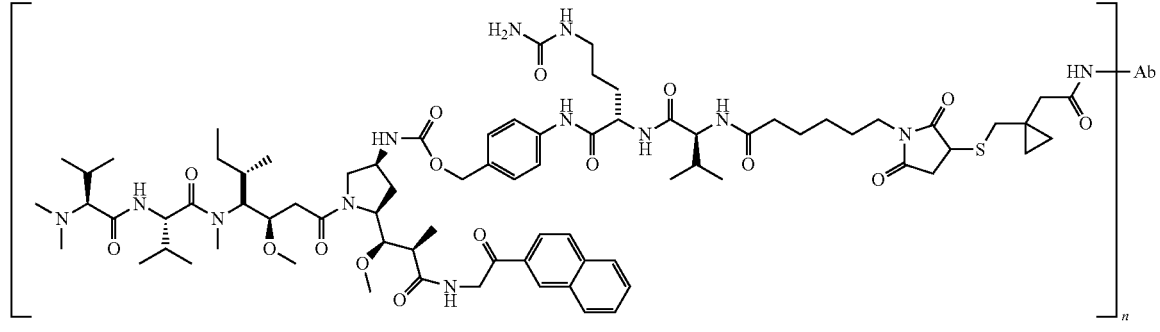
(I-31)

(I-32)
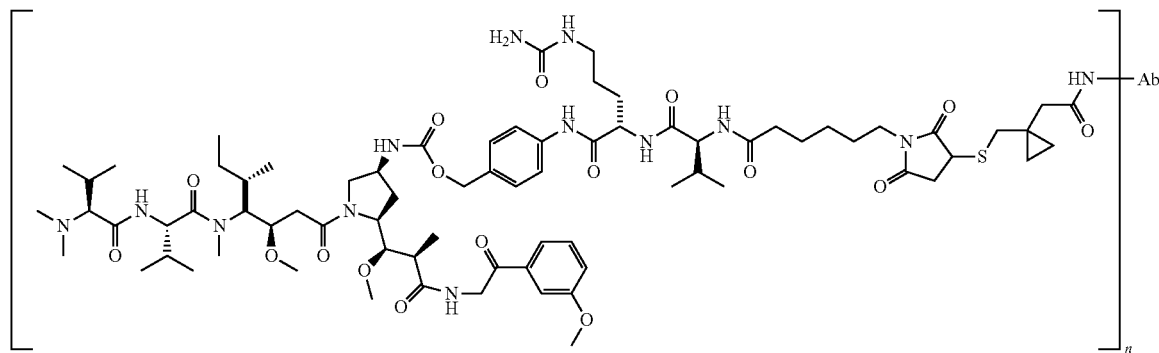
(I-33)
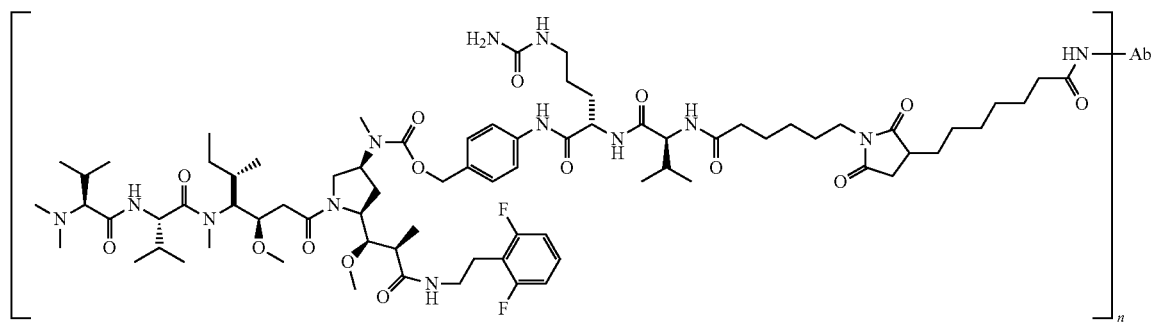
(I-34)
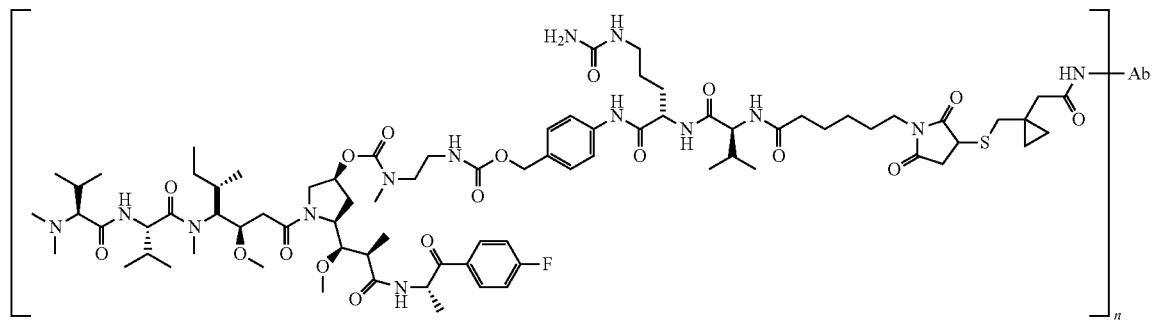
(I-35)
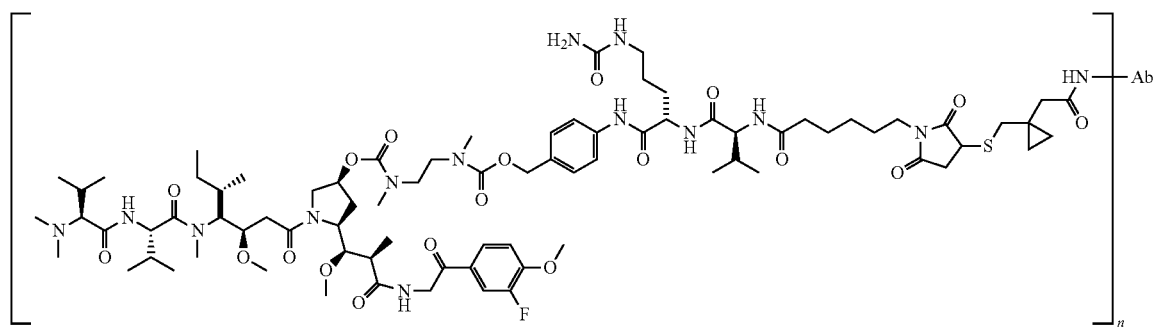

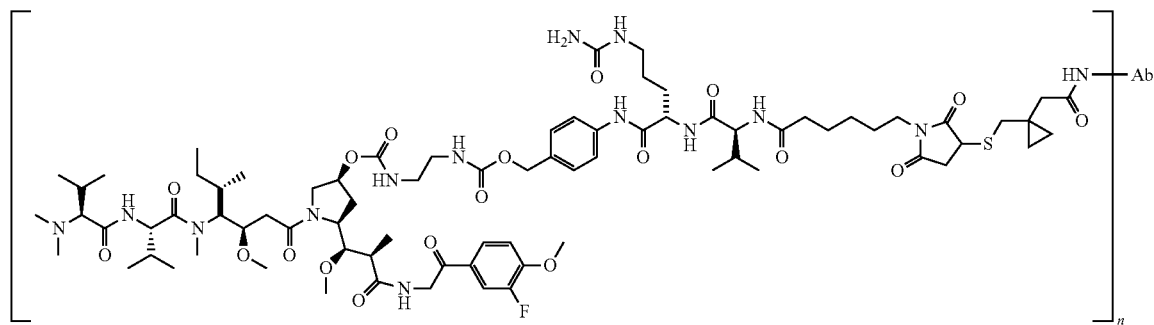
(I-36)
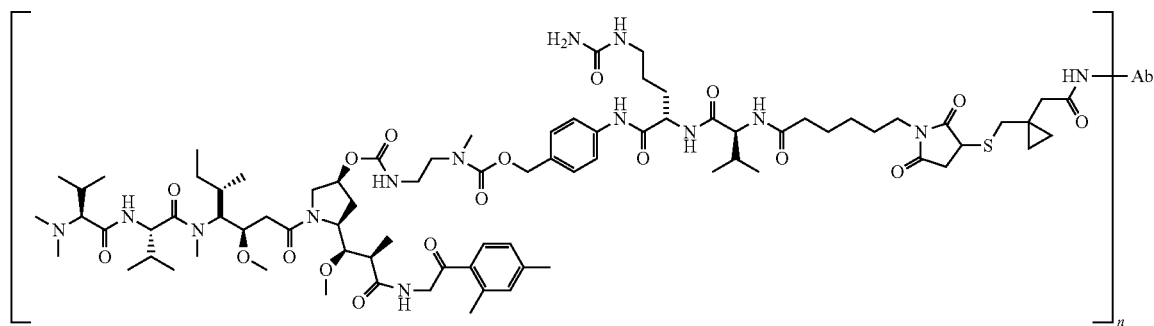
(I-37)
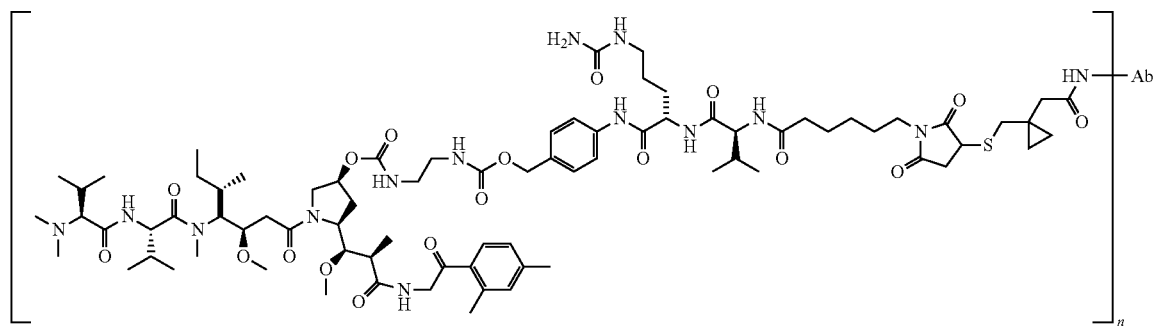
(I-38)
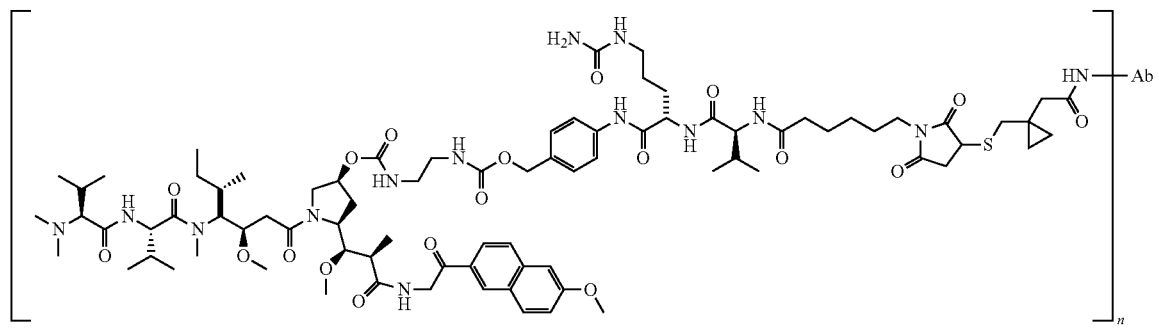
(I-39)

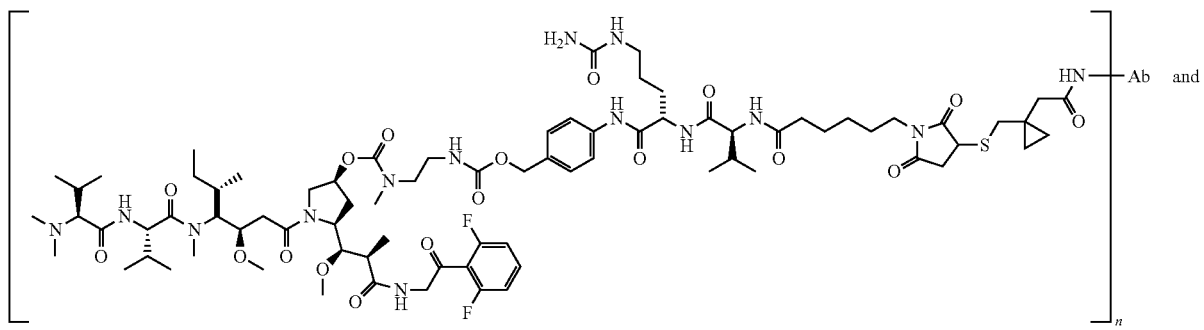

(I-40)

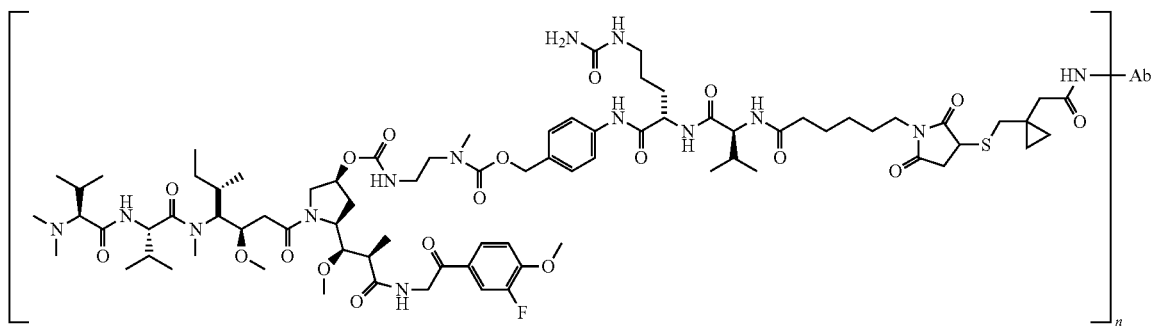

(I-41)

wherein, n is an integer ranging from 1 to 5.

In accordance with another aspect thereof, the present invention addresses a method for preparing an antibody-linker-drug conjugate represented by Chemical Formula I-1, I-2, I-3, or I-4, comprising the steps of:

(i) condensating a compound of the following Chemical Formula II-1 with a dolastatin 10 derivative of each of the following Chemical Formulas III-1, and III-3 to give compounds of the following Chemical Formulas IV-1, IV-2, and IV-3, respectively, or condensating a compound of the following Chemical Formula II-2 with a dolastatin 10 derivative of the following Chemical Formula III-4 to give a compound of the following Chemical Formula IV-4;

(ii) subjecting the compound of each of the following Chemical Formulas IV-1, IV-2, IV-3, and IV-4 to an addition reaction with a compound of the following Chemical Formula V to give compounds of the following Chemical Formulas VI-1, VI-2, VI-3, and VI-4, respectively;

(iii) condensating the compound of each of the following Chemical Formulas VI-1, VI-2, VI-3 and VI-4 with N-hydroxysuccinimide to give compounds of the following Chemical Formulas VII-1, VII-2, VII-3 and VII-4, respectively; and (iv) reacting the compound of the following Chemical Formula VII-1, VII-2, VII-3 or VII-4 with an antibody.

[Chemical Formula II-1]

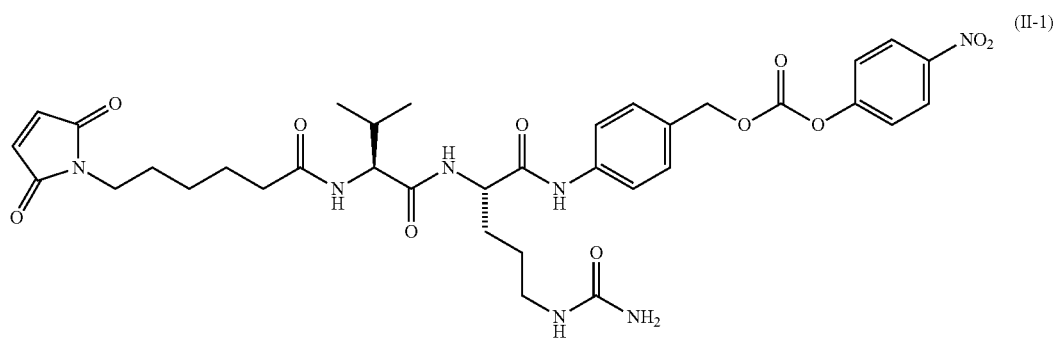

(II-1)

[Chemical Formula II-2]

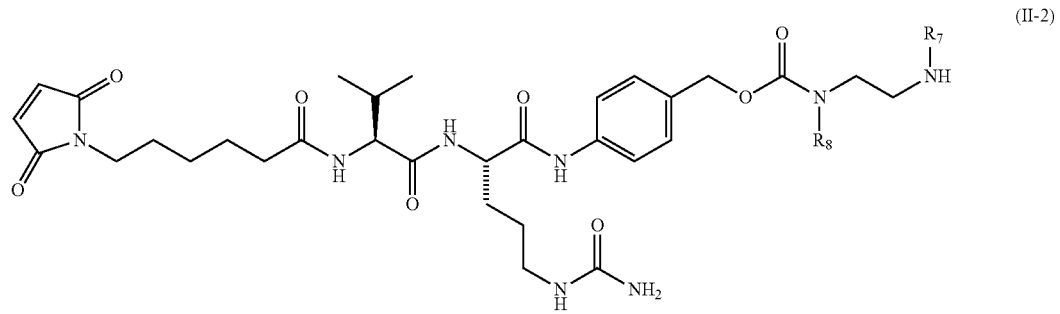

wherein $R_7$ and $R_8$ are each as defined in Chemical Formula I-4.

[Chemical Formula III-1]

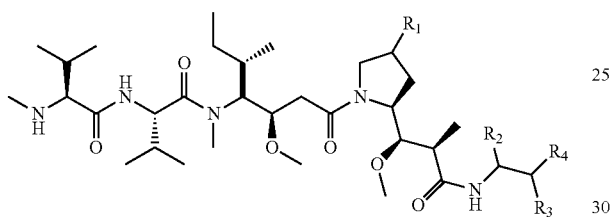

wherein $R_1$, $R_2$, $R_3$, and $R_4$ are each as defined in Chemical Formula I-1.

[Chemical Formula III-2]

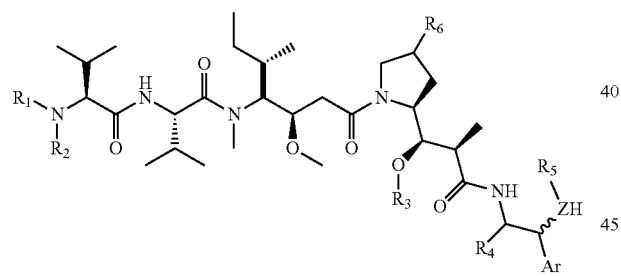

wherein $R_1$, $R_2$, $R_3$, $R_4$, $R_5$, $R_6$, Ar, and Z are each as defined in Chemical Formula I-2.

[Chemical Formula III-3]

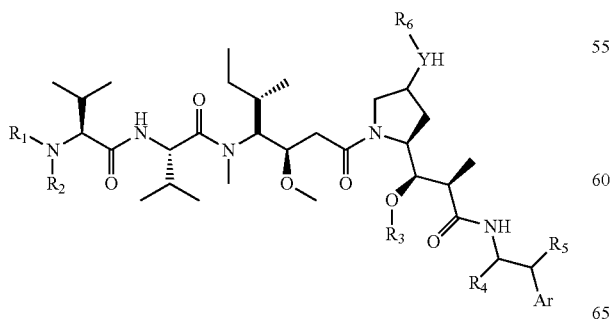

wherein $R_1$, $R_2$, $R_3$, $R_4$, $R_5$, $R_6$, Ar, and Y are each as defined in Chemical Formula I-3.

[Chemical Formula III-4]
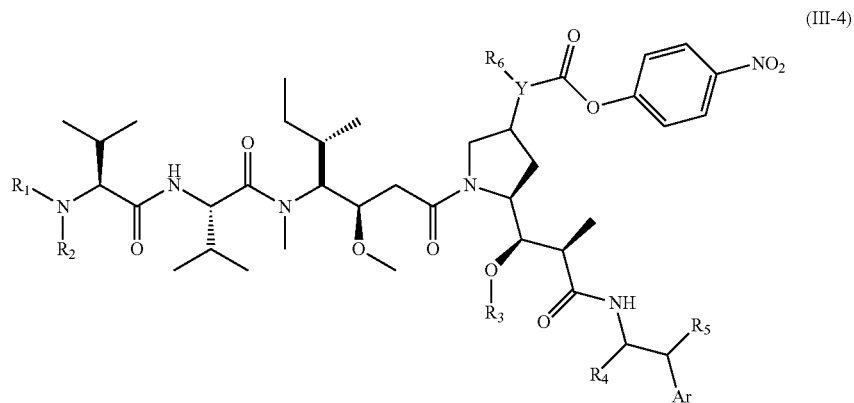
(III-4)
wherein $R_1$, $R_2$, $R_3$, $R_4$, $R_5$, $R_6$, Ar, and Y are each as defined in Chemical Formula I-4.
[Chemical Formula IV-1]
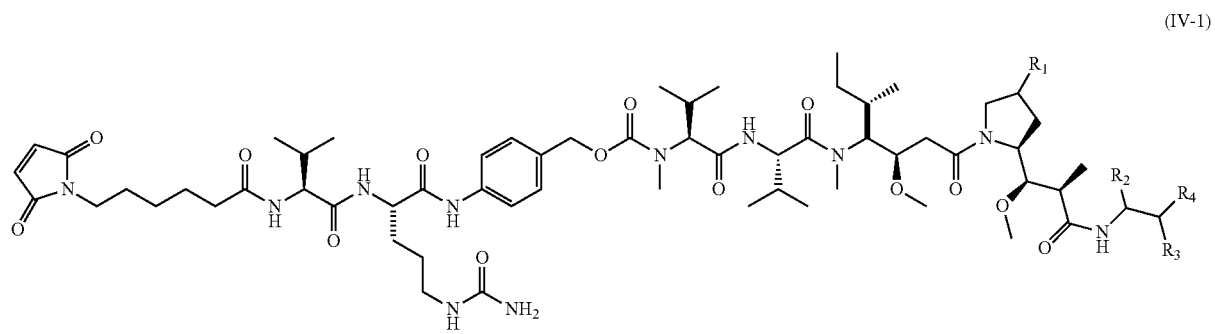
(IV-1)
wherein $R_1$, $R_2$, $R_3$, and $R_4$ are each as defined in Chemical Formula I-1.
[Chemical Formula IV-2]
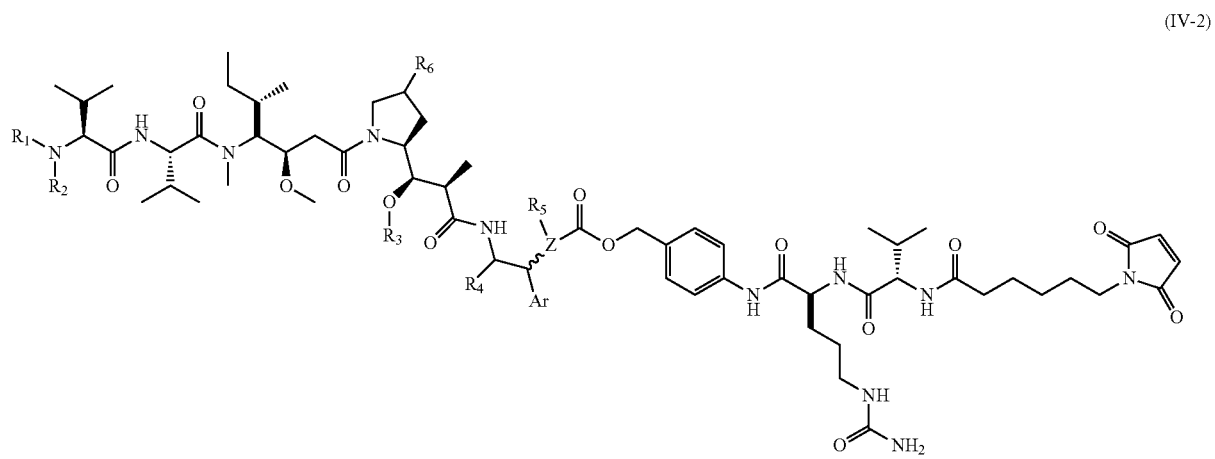
(IV-2)
wherein $R_1$, $R_2$, $R_3$, $R_4$, $R_5$, $R_6$, Ar, and Z are each as defined in Chemical Formula I-2.

[Chemical Formula IV-3]
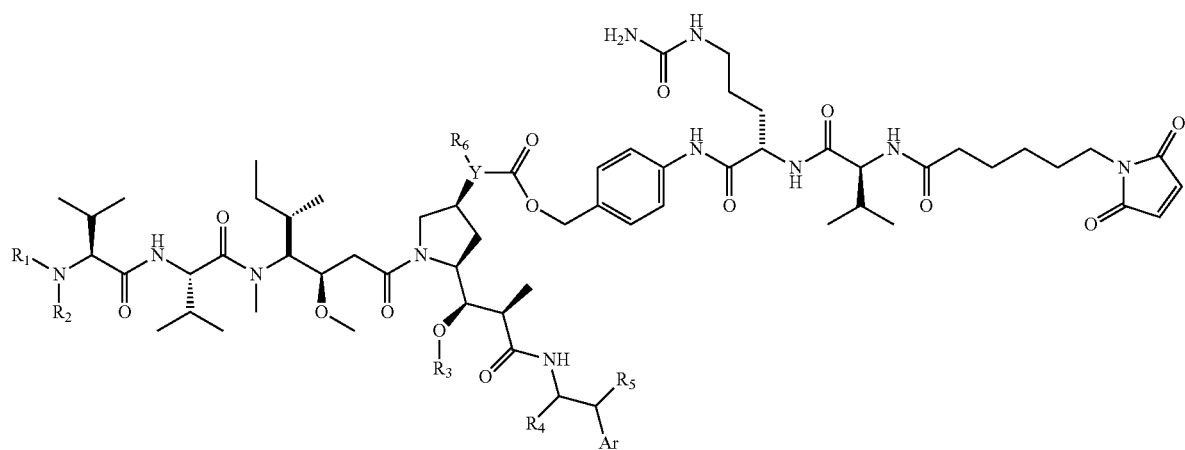
(IV-3)
wherein $R_1$, $R_2$, $R_3$, $R_4$, $R_5$, $R_6$, Ar, and Y are each as defined in Chemical Formula I-3.
[Chemical Formula IV-4]
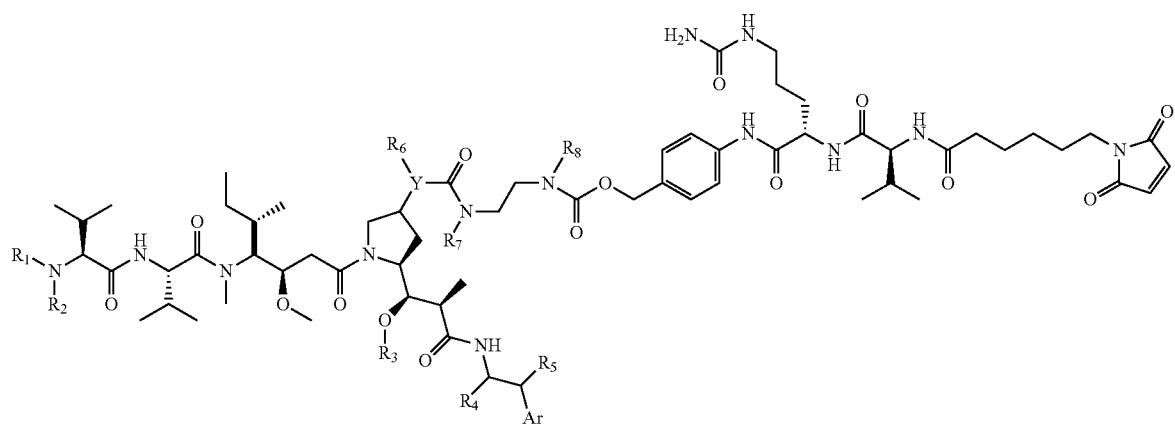
(IV-4)
wherein $R_1$, $R_2$, $R_3$, $R_4$, $R_5$, $R_6$, $R_7$, $R_8$, Ar, and Y are each as defined in Chemical Formula I-4.
[Chemical Formula V]
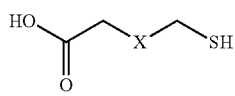
(V)
wherein X is as defined in Chemical Formula I-1, I-2, I-3, or I-4.

[Chemical Formula VI-1]
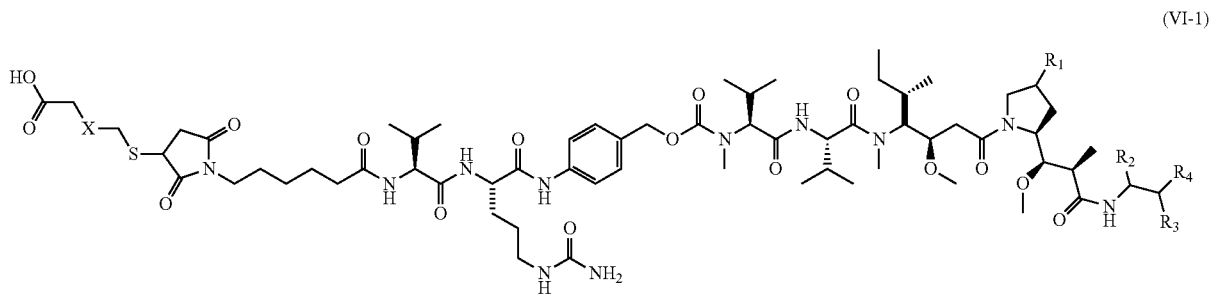
(VI-1)
wherein $R_1$, $R_2$, $R_3$, $R_4$ and X are each as defined in Chemical Formula I-1.
[Chemical Formula VI-2]
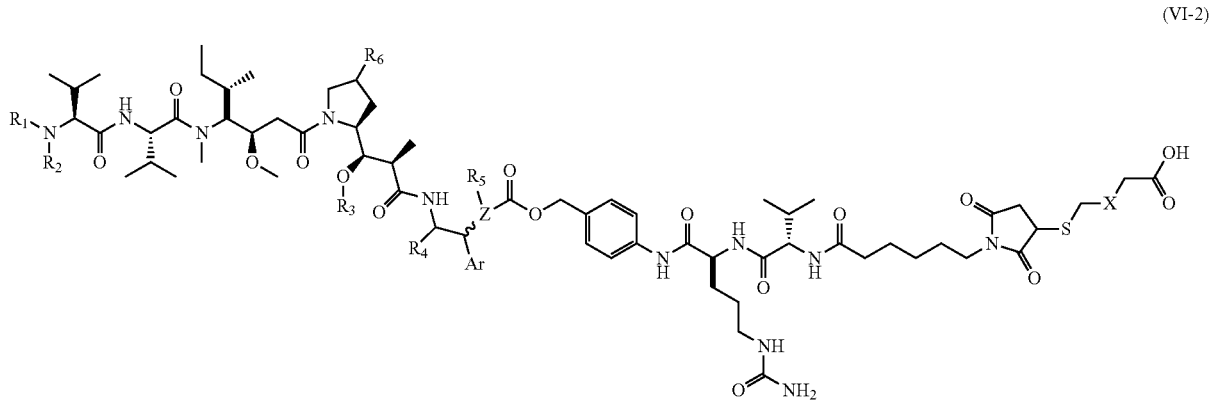
(VI-2)
wherein $R_1$, $R_2$, $R_3$, $R_4$, $R_5$, $R_6$, Ar, X, and Z are each as defined in Chemical Formula I-2.
[Chemical Formula VI-3]
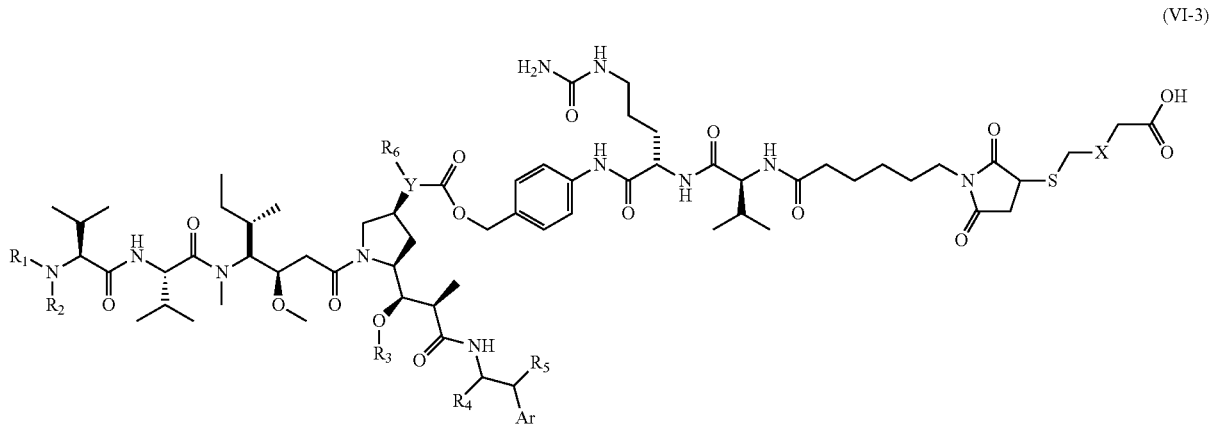
(VI-3)
wherein $R_1$, $R_2$, $R_3$, $R_4$, $R_5$, $R_6$, Ar, X, and Y are each as defined in Chemical Formula I-3.

[Chemical Formula VI-4]
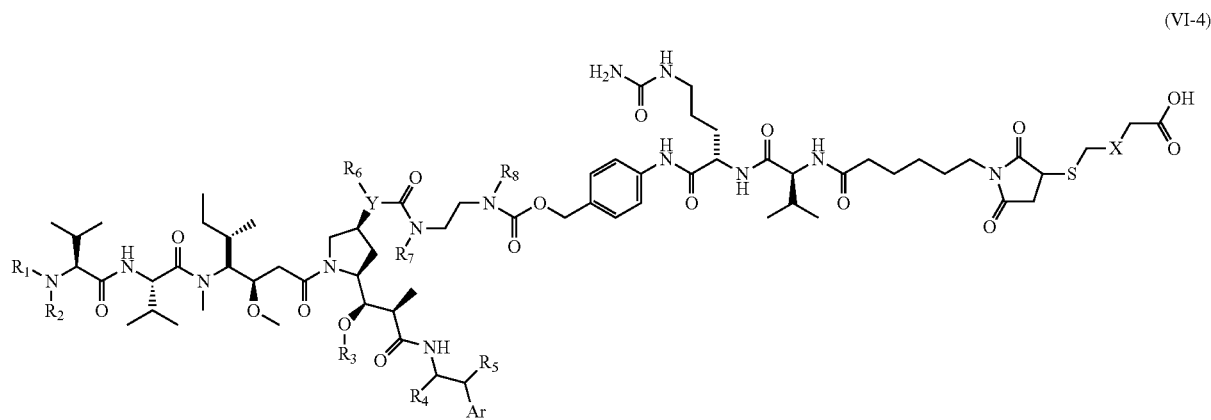
(VI-4)
wherein $R_1$, $R_2$, $R_3$, $R_4$, $R_5$, $R_6$, $R_7$, $R_8$, Ar, X, and Y are each as defined in Chemical Formula I-4.
[Chemical Formula VII-1]
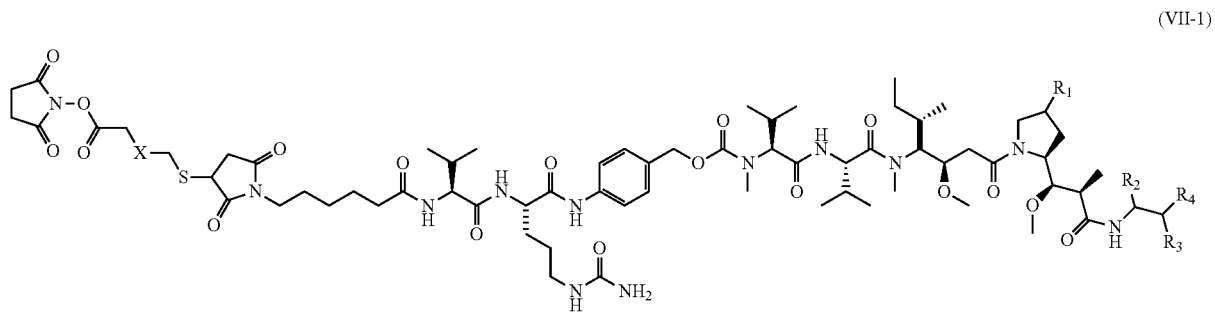
(VII-1)
wherein $R_1$, $R_2$, $R_3$, $R_4$, and X are each as defined in Chemical Formula I-1.
[Chemical Formula VII-2]
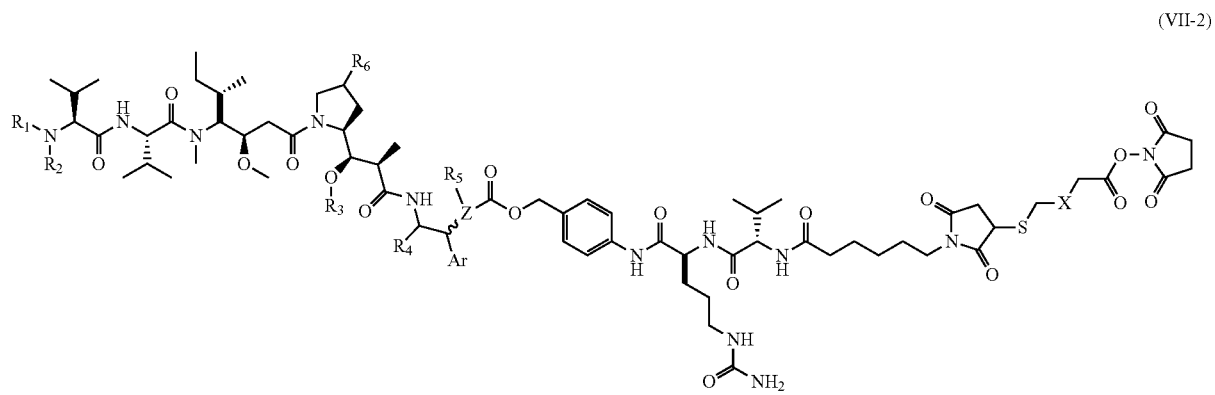
(VII-2)
wherein $R_1$, $R_2$, $R_3$, $R_4$, $R_5$, $R_6$, Ar, X, and Z are each as defined in Chemical Formula I-2.

[Chemical Formula VII-3]

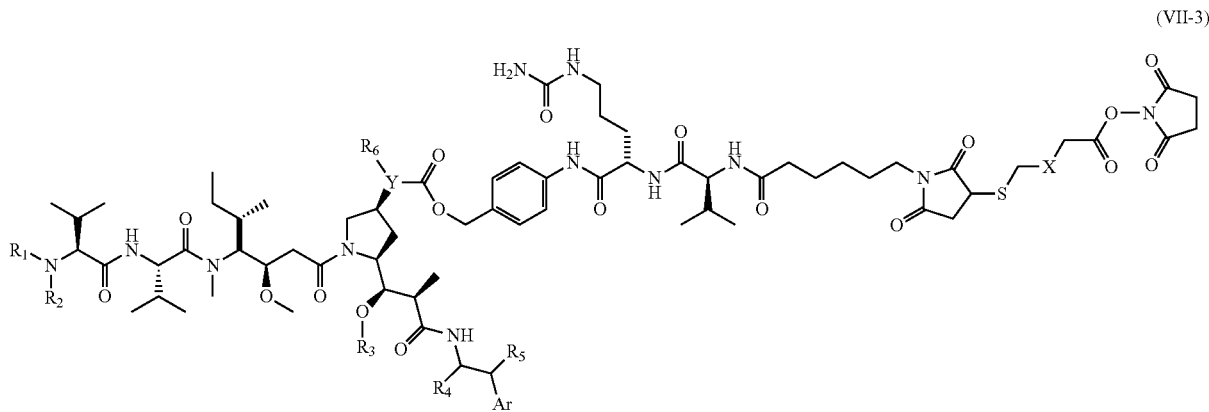

(VII-3)

wherein $R_1$, $R_2$, $R_3$, $R_4$, $R_5$, $R_6$, Ar, X, and Y are each as defined in Chemical Formula I-3.

[Chemical Formula VII-4]

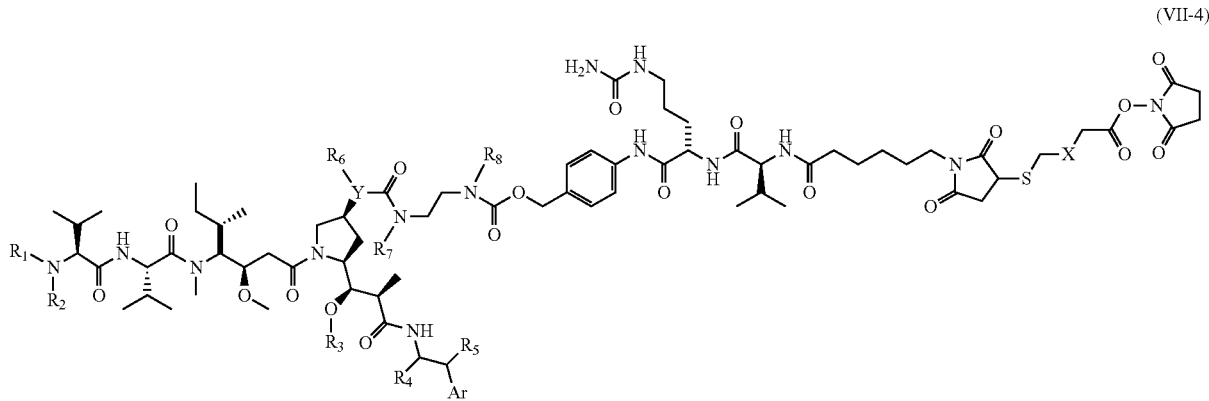

(VII-4)

wherein $R_1$, $R_2$, $R_3$, $R_4$, $R_5$, $R_6$, $R_7$, $R_8$, Ar, X, and Y are each as defined in Chemical Formula I-4.

Below, methods for preparing antibody-linker-drug conjugates of Chemical Formulas I-1 to I-4 will be explained in detail with reference to Reaction Schemes I-1 to I-4. The methods elucidated in Reaction Schemes I-1 to I-4 are merely representative illustrations, and may be modified for unit operation order, reaction reagents, and reaction conditions as the occasion demands.

[Reaction Scheme I-1]
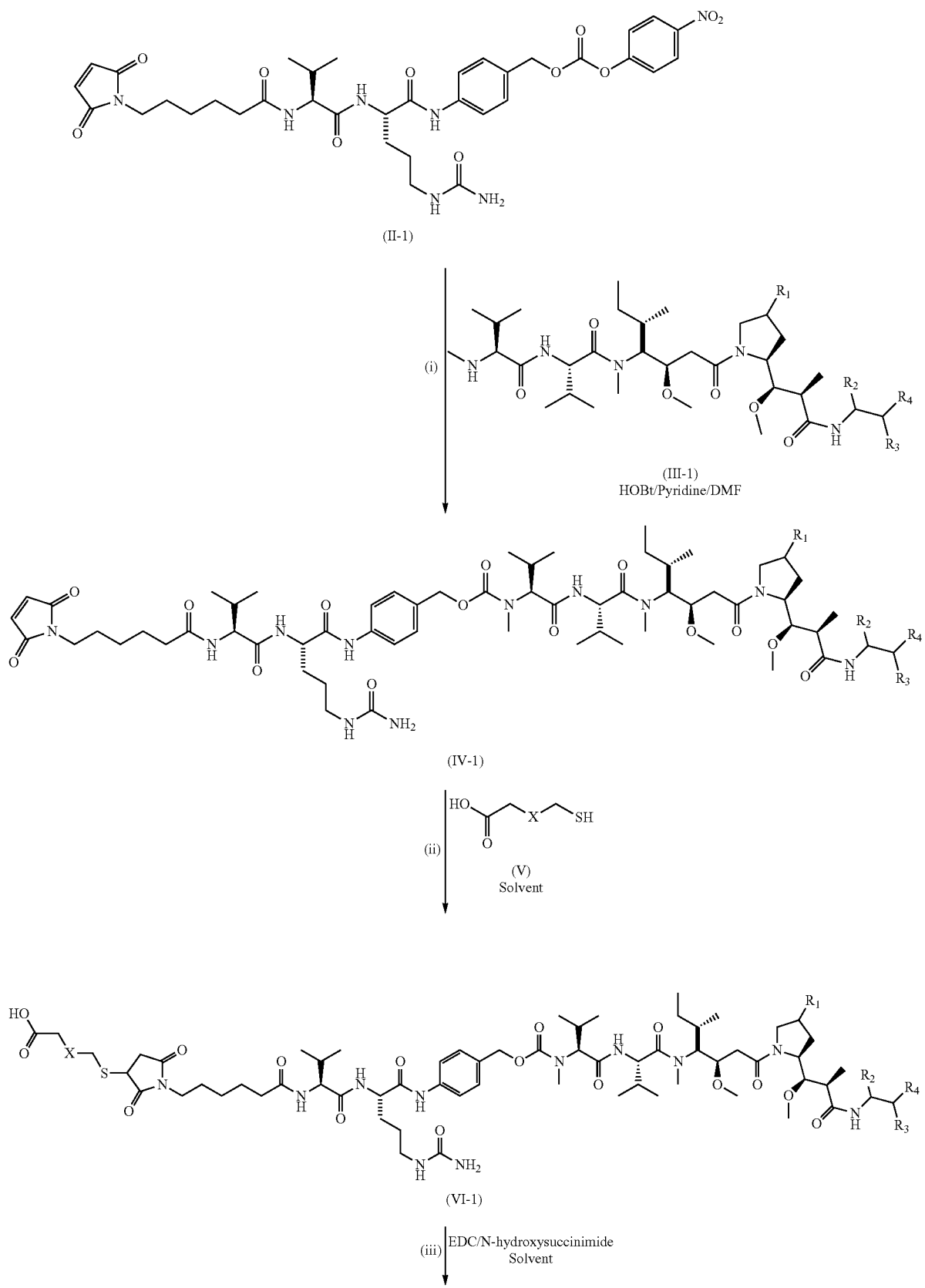

-continued
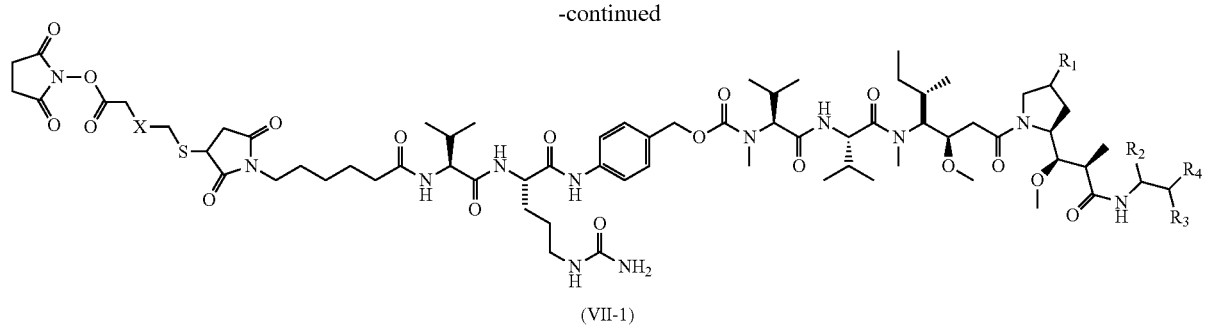
(VII-1)
(iv) Herceptin
Phosphate buffer
Solvent
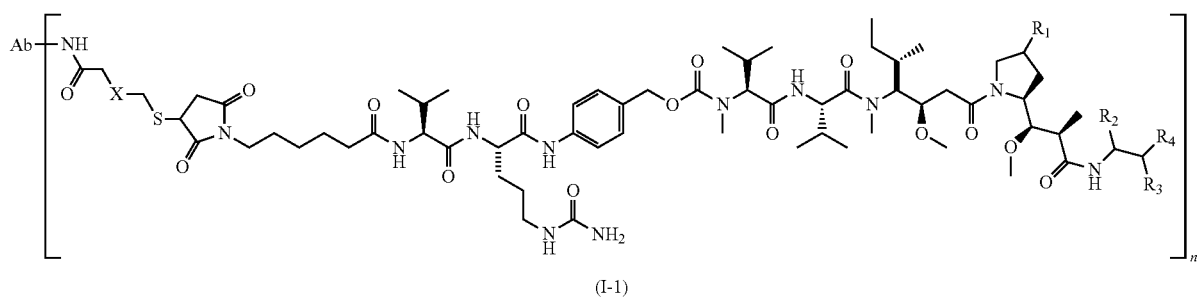
(I-1)
[Reaction Scheme I-2]
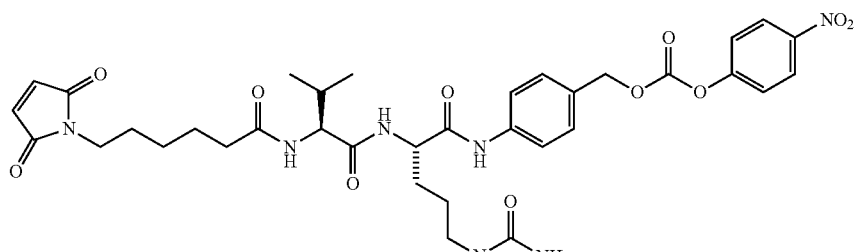
(II-1)
(i)
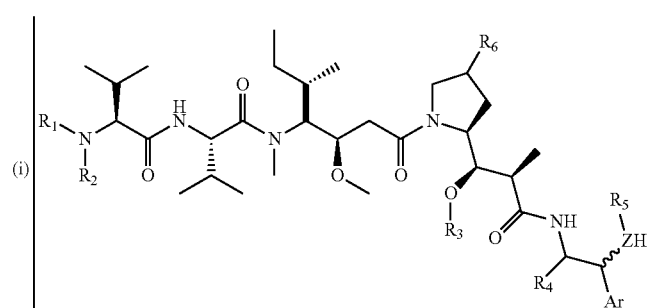
(III-2)
HOBt/Pyridine/DMF

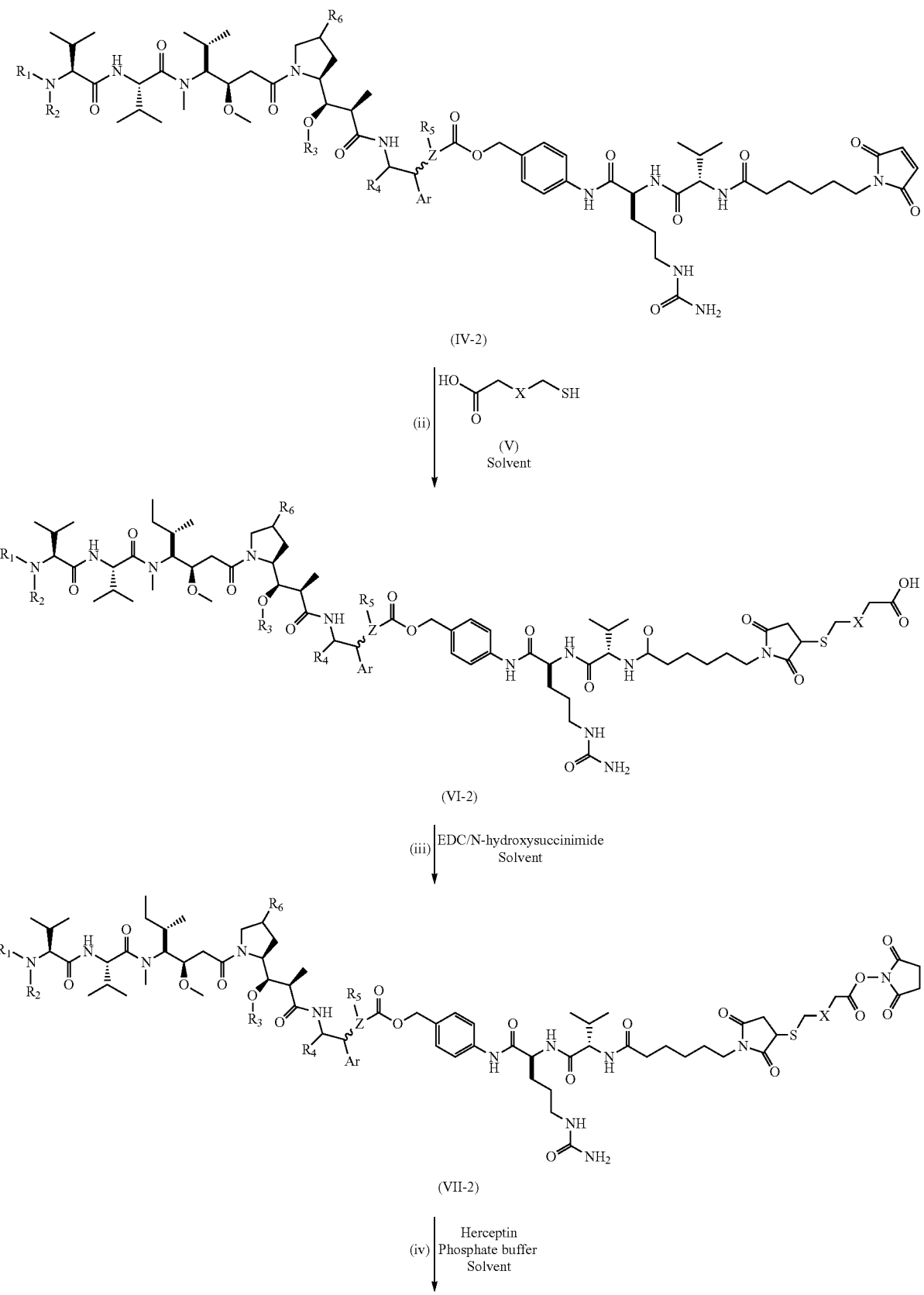

-continued
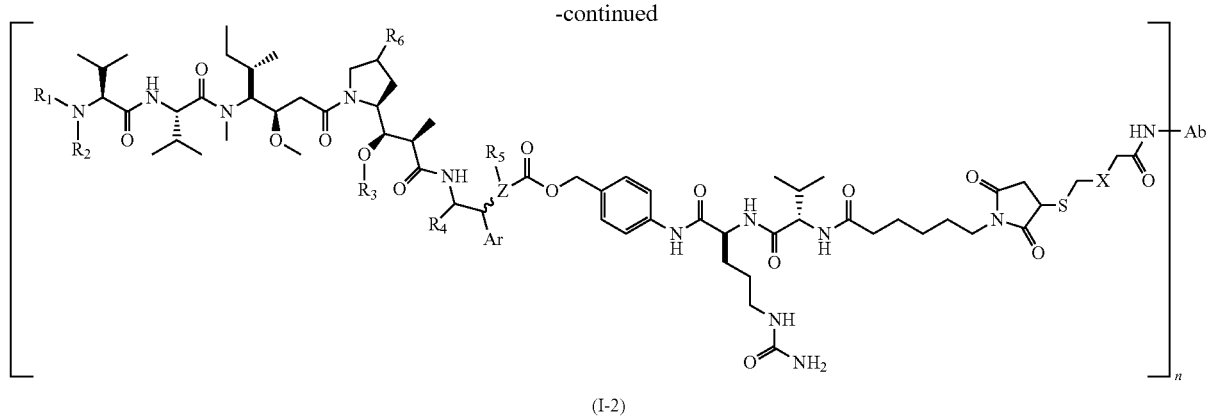
(I-2)
[Reaction Scheme I-3]
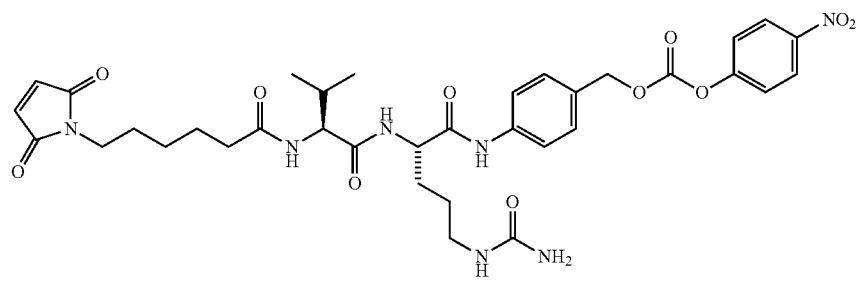
(II-1)
(i)
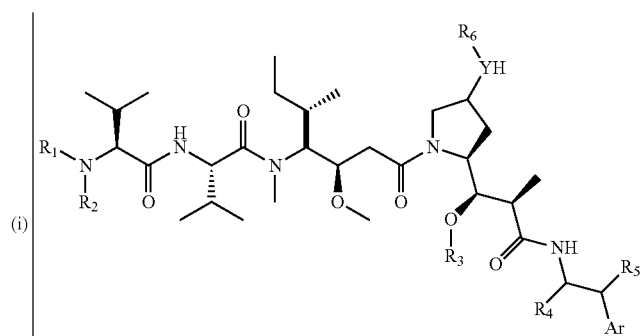
(III-3)
HOBt/Pyridine/DMF

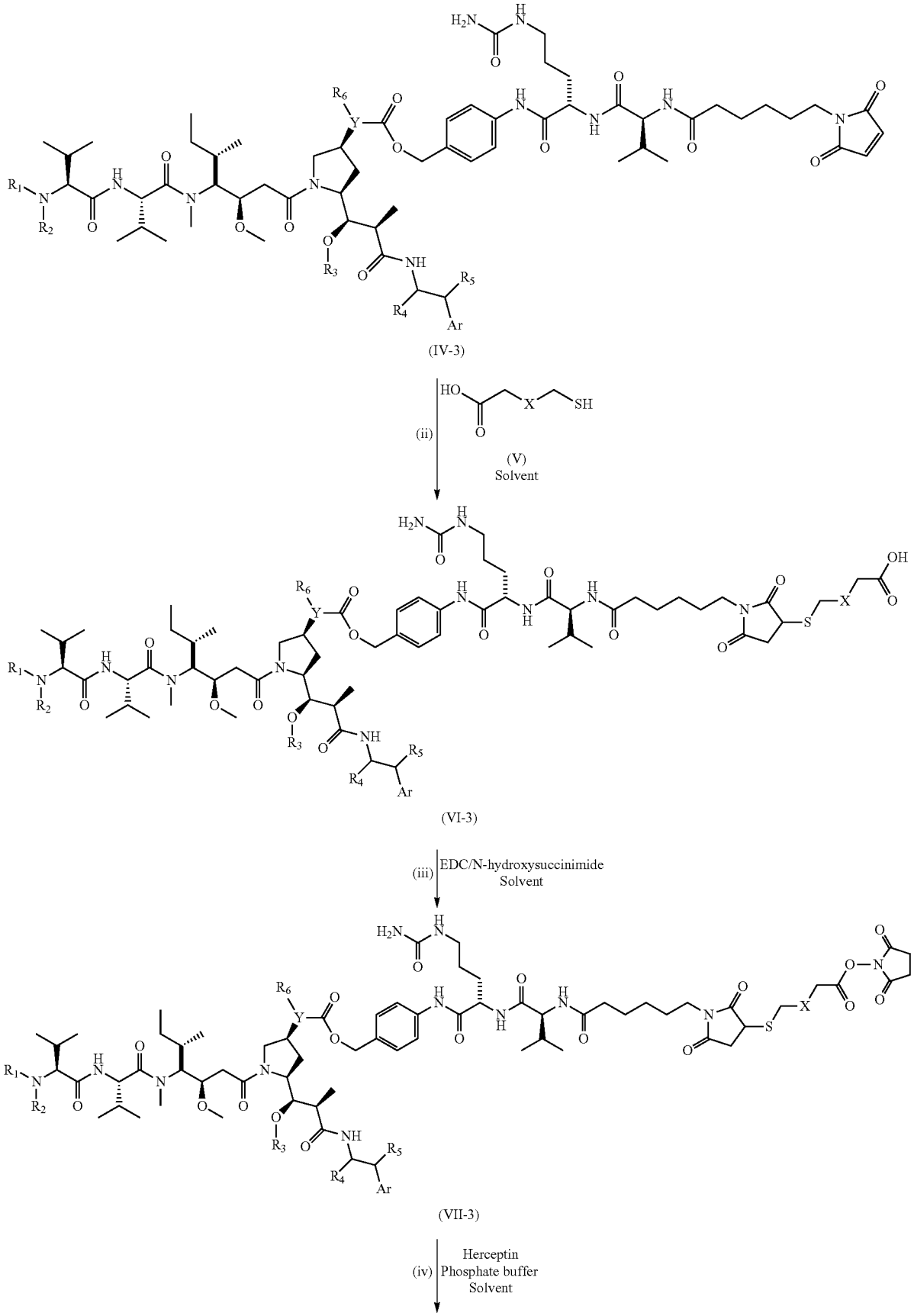

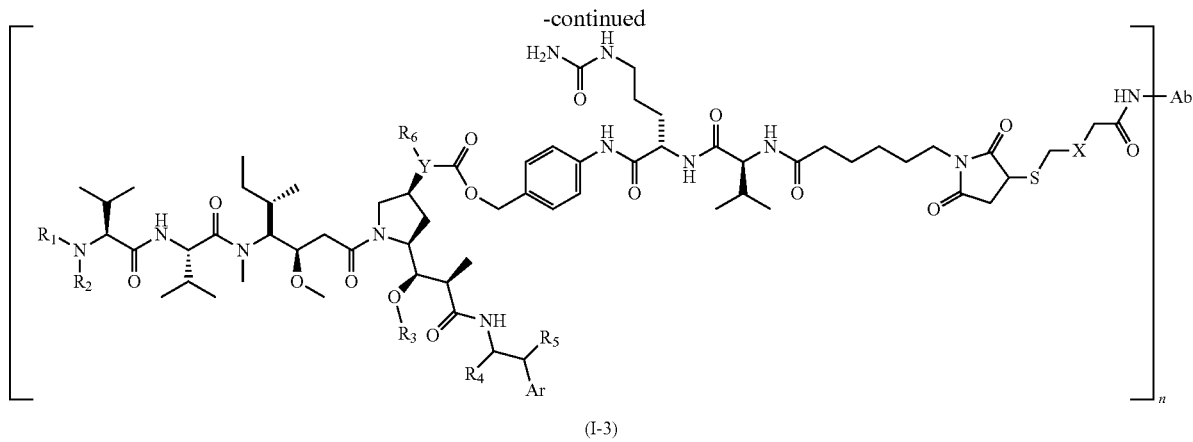
(I-3)
[Reaction Scheme I-4]
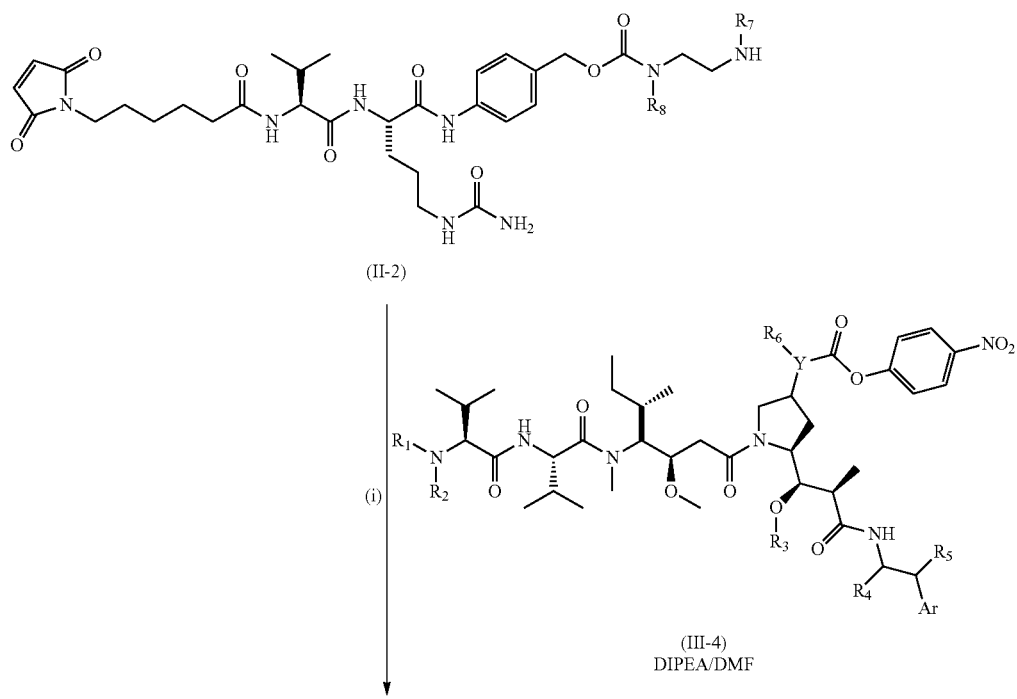
(II-2)
(III-4)
DIPEA/DMF

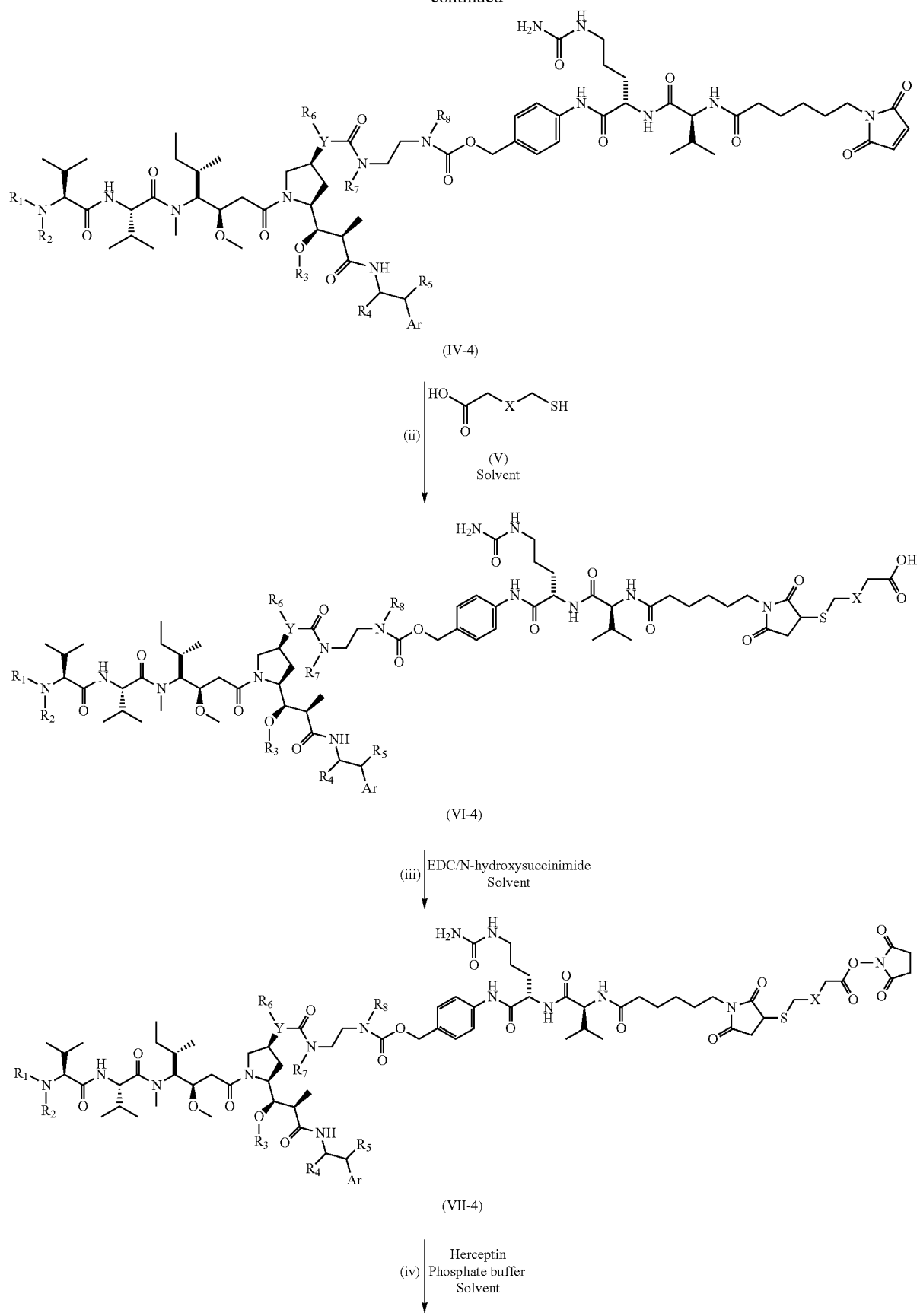

-continued

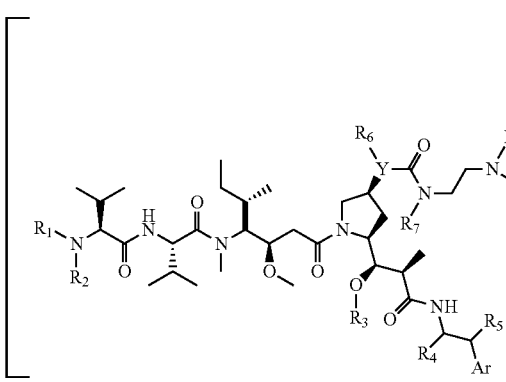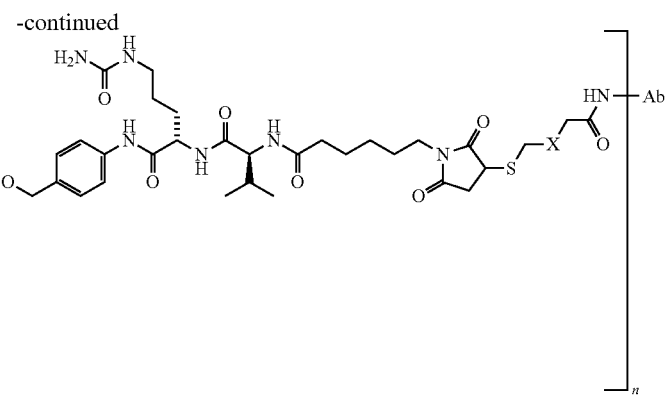

(I-4)

In step (i), the compound of Chemical Formula II-1 is condensed with a dolastatin 10 derivative of each of Chemical Formulas III-1, III-2, and III-3 to give compounds of Chemical Formulas IV-1, IV-2, and IV-3, respectively, or the compound of Chemical Formula II-2 is condensed with a dolastatin 10 derivative of Chemical Formula III-4 to give a compound of Chemical Formula IV-4.

The condensation reaction may be carried out in the presence of a condensing agent. Examples of the condensing agent available in this reaction include hydroxybenzotriazole (HOBt), hydroxyazabenzotriazole (HOAt), and hydroxysuccinimide (HOSu), but are not limited thereto.

If necessary for the condensation reaction, the condensing agent may be used together with an organic base, such as pyridine, or diisopropylethylamine.

For a reaction solvent, selection may be made of dimethylformamide (DMF), dimethylacetamide (DMA), dimethylsulfoxide (DMSO), or N-methyl-2-pyrrolidone (NMP). The temperature for the condensation reaction is preferably set to range from 20 to 25° C.

In step (ii), the compound of Chemical Formula IV-1, IV-2, IV-3, or IV-4 is subjected to an addition reaction with the compound of Chemical Formula V to give an amount of Chemical Formula VI-1, VI-2, VI-3, or VI-4.

For this addition reaction, dimethylsulfoxide (DMSO), acetonitrile (MeCN), or dimethylformamide (DMF) may be used as a solvent while the reaction temperature is set to be between 20 and 25° C.

In step (iii), the compound of Chemical Formula VI-1, VI-2, VI-3, or VI-4 is condensed with N-hydroxysuccinimide to activate the carboxylic acid of the compound of Chemical Formula VI-1, VI-2, VI-3, or VI-4.

This condensation reaction may be carried out in the presence of a condensing agent. Non-limiting, illustrative examples of the condensing agent include dicyclohexylcarbodiimide (DCC) and (3-dimethylaminopropyl)carbodiimide (EDC).

As a solvent for this condensation reaction, dimethylformamide (DMF), dimethylacetamide (DMA), or dichloromethane (DCM) may be used, while the reaction temperature is preferably set to be between 20 and 25° C.

In step (iv), the compound of Chemical Formula VII-1, VII-2, VII-3, or VII-4 is reacted with an antibody to afford the final product antibody-linker-drug conjugate of Chemical Formula I-1, I-2, I-3, or I-4.

For this reaction, a phosphate buffer with a pH of 6.0 to 8.0 may be used as a solvent. Since the solubilities of the linker-cytotoxic drugs represented by Chemical Formula VII-1, VII-2, VII-3, and VII-4 in the phosphate buffer vary depending on the kind of the cytotoxic drugs, an organic solvent such as dimethylformamide (DMF), dimethylsulfoxide (DMSO), dimethylacetamide (DMA), and/or acetonitrile (MeCN), 1,4-dioxane may be used in mixture with the phosphate buffer as needed. In this regard, the organic solvent preferably amounts to 50% or less of the mixed solvent.

Based on the antibody, the compound of Chemical Formula VII-1, VII-2, VII-3, or VII-4 is preferably used in an amount of 3 to 25 equivalents. In this context, the resulting antibody-linker-drug conjugate has a DAR (drug-antibody ratio), that is, the number of drugs linked to one antibody molecule, of about 1 to 5.

The compound of Chemical Formula II-1 or II-2 is an enzyme cleavable peptide linker known in the art, and can be easily prepared using the method described in U.S. Pat. No. 6,214,345.

In addition, the dolastatin 10 derivative of Chemical Formula III-1, III-3, or III-4 is a cytotoxic drug, and can be synthesized using the method described in co-pending Korean Patent Application No. 10-2012-0104710, filed on Sep. 20, 2012 by the present assignee, or in U.S. Pat. No. 5,599,902, which are both hereby incorporated by reference in their entireties into this application.

For instance, the dolastatin 10 derivatives of Chemical Formula III-1, III-2, III-3, and III-4 can be synthesized as illustrated in the following Reaction Schemes II-1 to II-4, respectively.

[Reaction Scheme II-1]
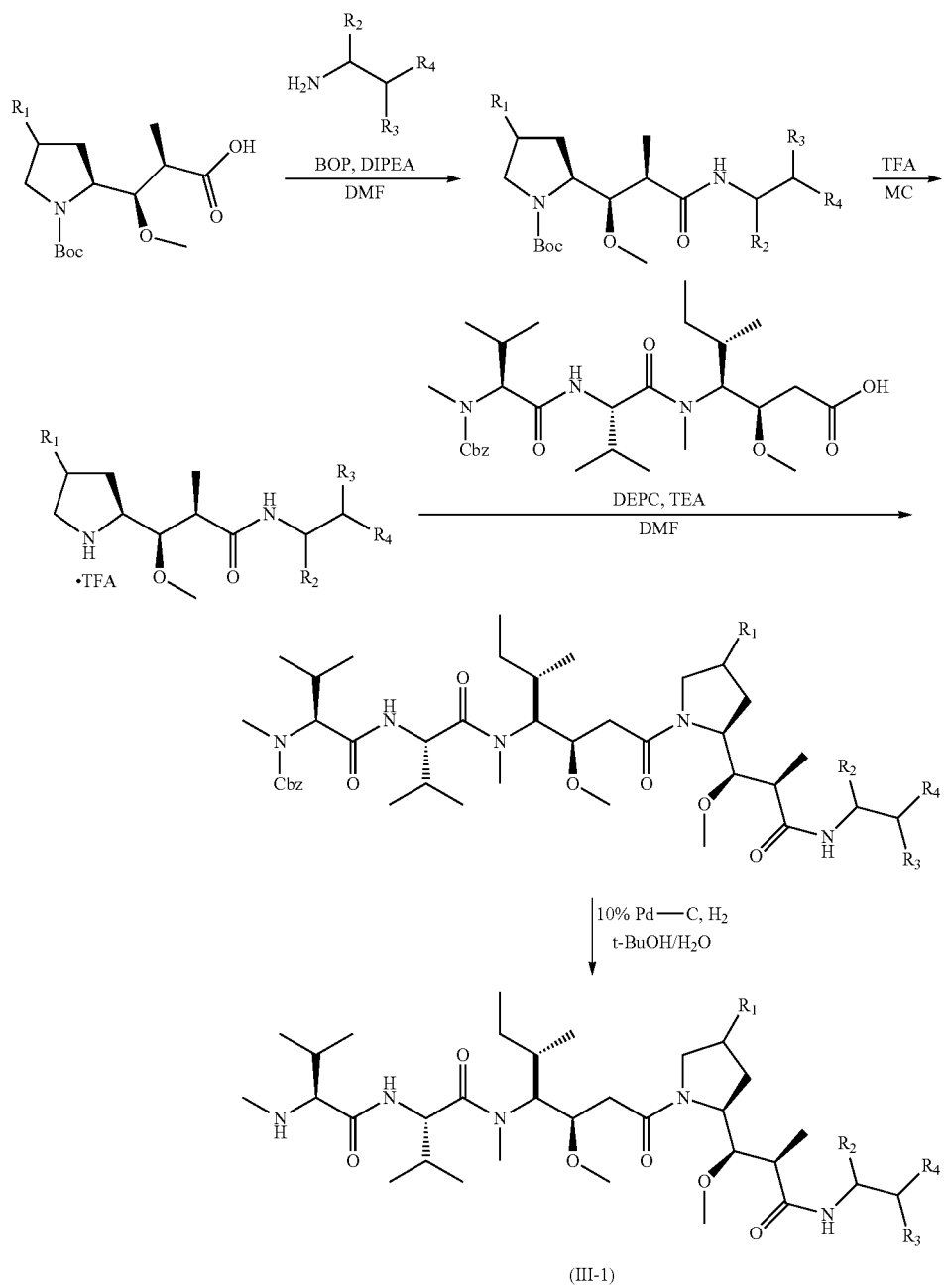
[Reaction Scheme II-2]
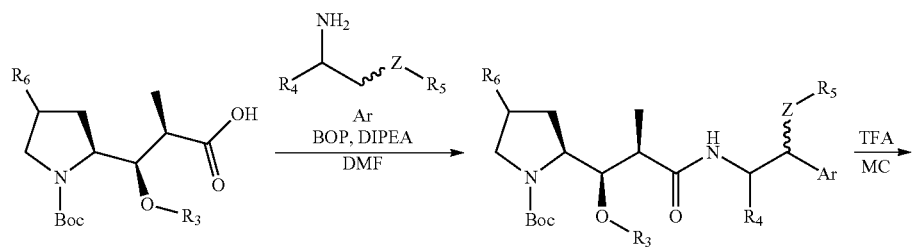

-continued
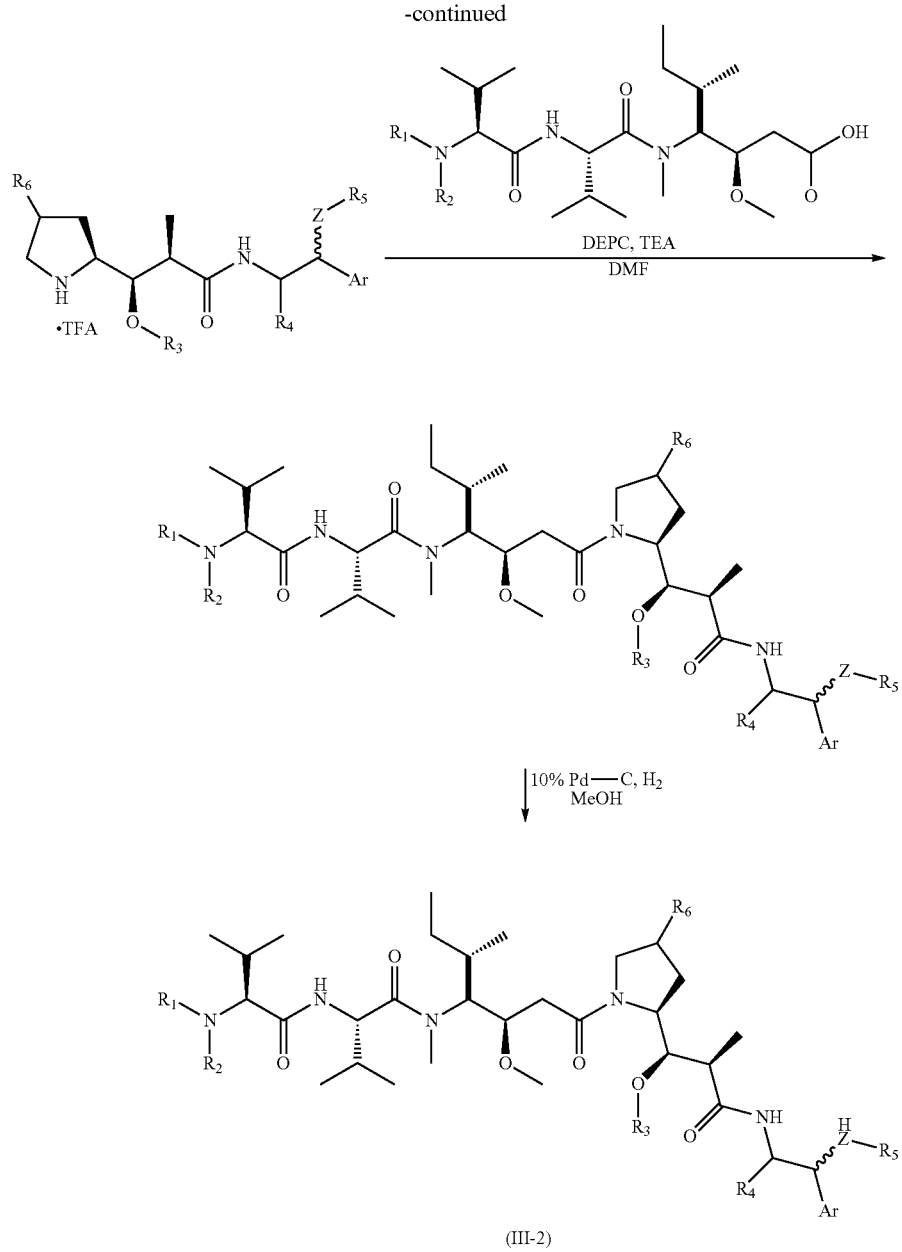
(III-2)
[Reaction Scheme II-3]
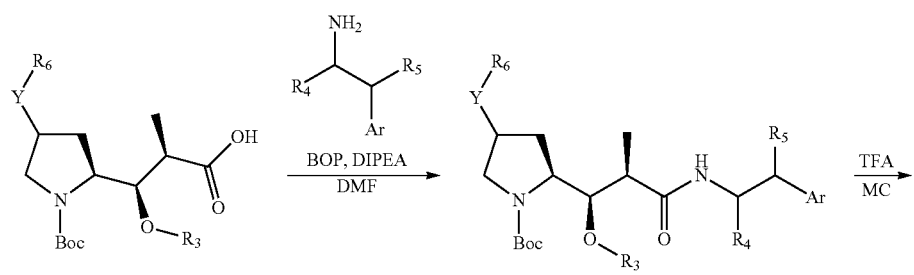

-continued
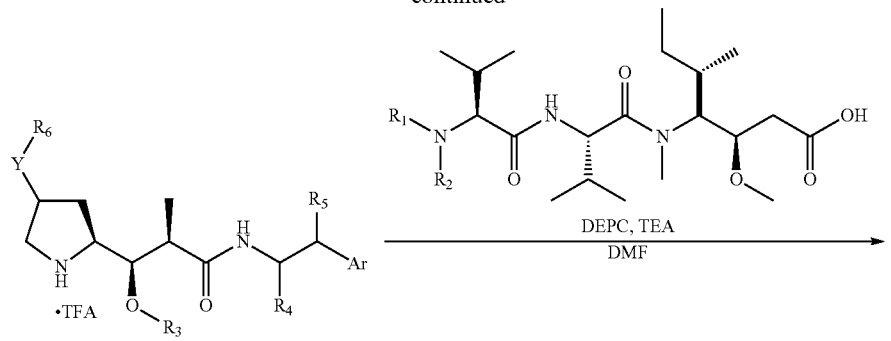
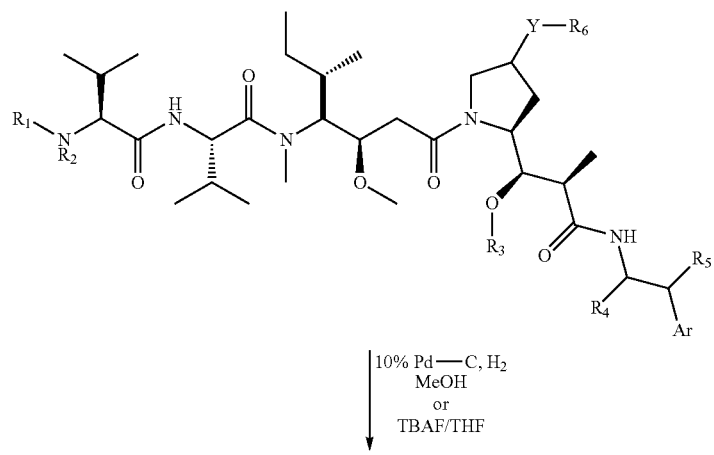
(III-3)
[Reaction Scheme II-4]
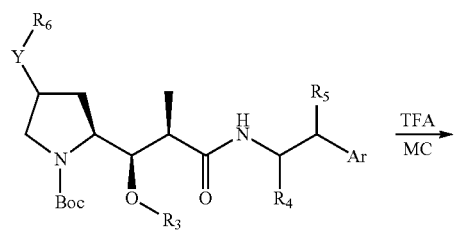

-continued

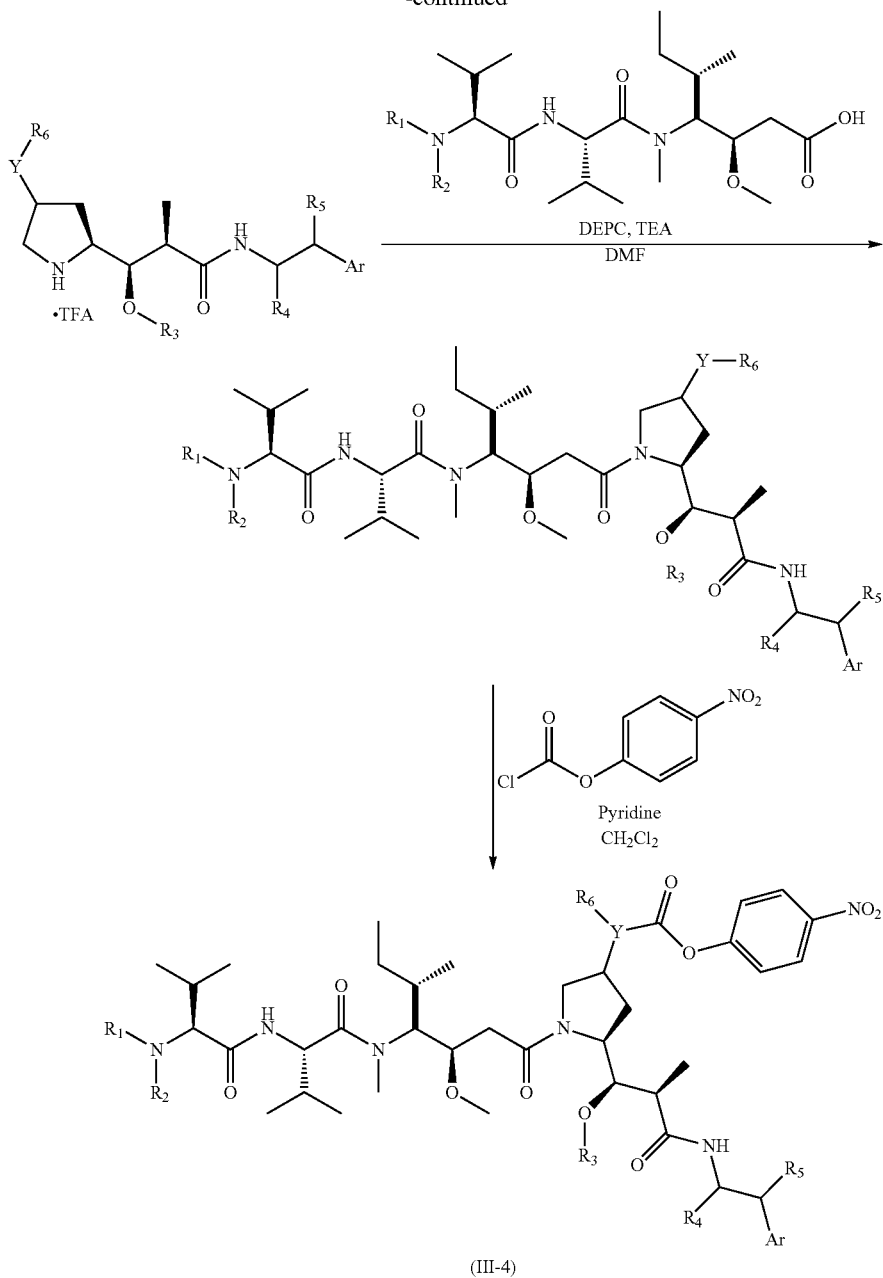

(III-4)

The antibody-linker-drug conjugate of the present invention exhibits excellent antitumor activity (Test Examples 4 and 6).

Contemplated in accordance with a further aspect of the present invention is therefore an anticancer composition, comprising the antibody-linker-drug conjugate of one of Chemical Formulas I-1 to I-4, or a pharmaceutically acceptable salt thereof together with a pharmaceutically acceptable carrier, particularly for the treatment of breast cancer.

The anticancer composition according to the present invention can be administered orally (for example, ingestion or inhalation) or parenterally (for example, injection, deposit, transplant, suppository). For injection, administration may be performed intravenously, subcutaneously, intramuscularly, or intraperitoneally. According to the administration route, the anticancer composition of the present invention may be formulated into a tablet, a capsule, a granule, a fine subtilae, a powder, a sublingual tablet, a suppository, a paste, an injection, an emulsion, a suspension, a syrup, a spray, etc. When the anticancer composition of the present invention is prepared in various formulations, pharmaceutically acceptable carriers typical of each formulation may be used. Examples of such pharmaceutically acceptable carriers include excipients, binders, disintegrating agents, lubricants, preservatives, antioxidants, isotonic agents, buffers, coating agents, sweeteners, solubilizers, bases, dispersants, humectants, suspending agents, stabilizers, colorants, etc.

In the anticancer composition of the present invention, the content of the compound of the present invention or a pharmaceutically acceptable salt thereof, although varying depending on the formulation, ranges from approximately 0.01 to 95% by weight.

The effective dosage of the anticancer composition of the present invention depends on various factors, including the kind, weight, gender, and severity of disease of the mammal subjects, including humans. Typically, the compound according to the present invention may be administered at a daily dose ranging from 0.01 to 50 mg per kg of weight for an oral route and from 0.01 to 10 mg per kg of weight for a parenteral route. The compound may be administered in a single dose, or may be divided into multiple doses per day according to the instructions of a physician or pharmacist.

Advantageous Effects

As described above, the antibody-linker-drug conjugate of the present invention, in which the linker-drug moiety is bonded directly to a lysine residue of the antibody moiety, does not undergo unnecessary modifications, and allows for the effective and selective delivery of the cytotoxic drug while guaranteeing in vivo stability. Even a single dose of the antibody-linker-drug conjugate of the present invention is effective for the therapy of cancer, especially breast cancer. Further, the antibody-linker-drug conjugate can be prepared at high yield using the method of the present invention.

MODE FOR INVENTION

Figure 1:
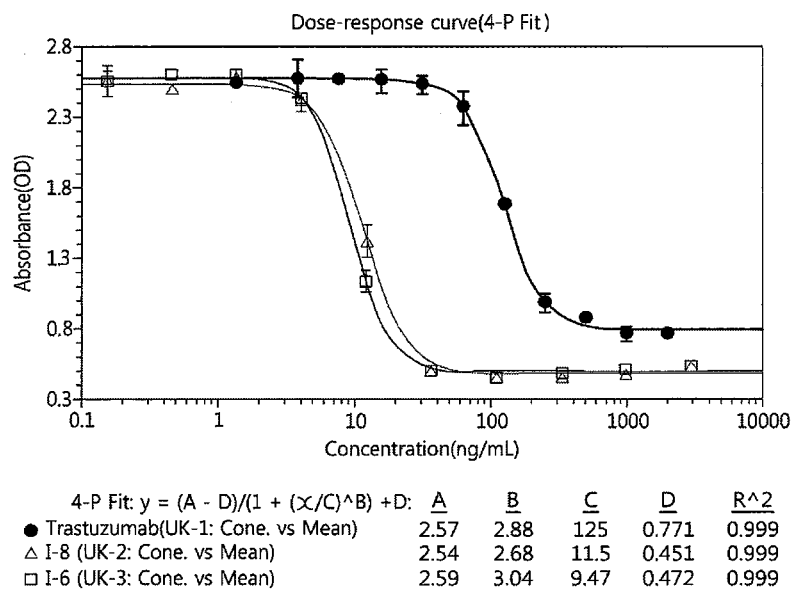
FIG. 1 is a dose-response curve showing in vitro antiproliferative activity of antibody-linker-drug conjugates (I-6) and (I-8) according to the present invention against BT-474 cells.

A better understanding of the present invention may be obtained through the following examples, which are set forth to illustrate, but are not to be construed as limiting the present invention.

PREPARATION EXAMPLE 1

Preparation of Compounds of Chemical Formula II-1 and II-2

PREPARATION EXAMPLE 1-1

Preparation of Compound (II-1)

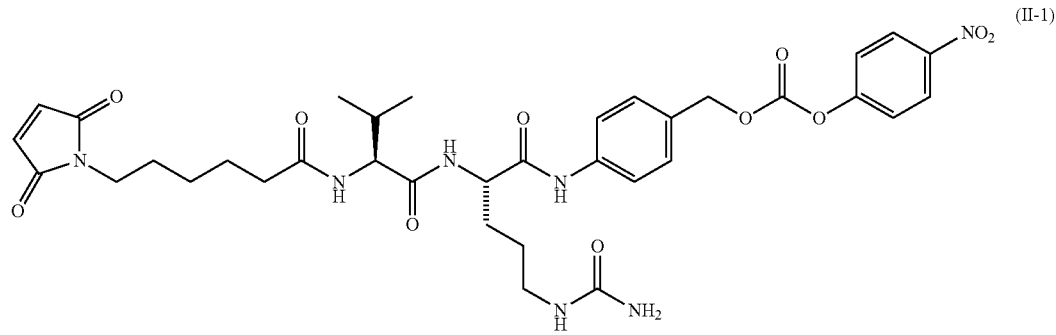 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

Under an argon stream, 6-(2,5-dioxo-2,5-dihydro-1H-pyrrol-1-yl)-N-((S)-1-(((S)-1-(4-(hydroxymethyl)phenyl)amino)-1-oxo-5-ureidopentan-2-yl)amino)-3-methyl-1-oxobutan-2-yl)hexanamide (5.0 g, 8.7 mmol, Dubowchik et al., Bioconjugate Chem., 2002, 13 (4), pp 855-869) was dissolved in 60 mL of anhydrous dimethylformamide, added with N, N-diisopropylethylamine (3.0 mL, 17.4 mmol), and cooled to 0° C. To the mixture was added at once bis(4-nitrophenyl) carbonate (7.94 g, 26.1 mmol), followed by stirring at room temperature for 15 hrs. After completion of the reaction, the reaction mixture was concentrated in a vacuum, and the concentrate was purified by silica gel column chromatography to obtain the title compound (3.65 g, 57%) as a pale yellow solid.

$^1$H NMR (400 MHz, DMSO-$d_6$) δ 0.83 (d, J=6.8 Hz, 3H), 0.86 (d, J=6.8 Hz, 3 H), 1.09 (t, J=7.2 Hz, 1 H), 1.19 (m, 2 H), 1.34-1.76 (m, 7 H), 1.96 (m, 1 H), 2.15 (m, 2 H), 2.99 (m, 2 H), 3.37 (m, 2 H), 4.19 (t, J=7.8 Hz, 1 H), 4.39 (m, 1 H), 5.24 (s, 2 H), 5.41 (s, 2 H), 5.97 (brt, J=5.6 Hz, 1 H), 7.00 (s, 2H), 7.41 (d, J=8.4 Hz, 2 H), 7.57 (d, J=7.2 Hz, 2H), 7.65 (d, J=8.4 Hz, 2 H), 7.80 (d, J=8.4 Hz, 1 H), 8.09 (d, J=7.2 Hz, 1 H), 8.31 (d, J=7.2 Hz, 2H), 10.05 (brs, 1 H)

Under an argon stream, 6-(2,5-dioxo-2,5-dihydro-1H-pyrrol-1-yl)-N-((S)-1-(((S)-1-((4-(hydroxymethyl)phenyl)amino)-1-oxo-5-ureidopentan-2-yl)amino)-3-methyl-1-oxobutan-2-yl)hexanamide (5.0 g, 8.7 mmol, Dubowchik et al., Bioconjugate Chem., 2002, 13 (4), pp 855-869) was dissolved in 60 mL of anhydrous dimethylformamide, added with N, N-diisopropylethylamine (3.0 mL, 17.4 mmol), and then cooled to 0° C. To the mixture was added at once bis(4-nitrophenyl) carbonate (7.94 g, 26.1 mmol), followed by stirring at room temperature for 15 hrs. After completion of the reaction, the reaction mixture was concentrated in a high vacuum, and the concentrate was purified by silica gel column chromatography to obtain 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (3.65 g, 57%) as a pale yellow solid.

$^1$H NMR (400 MHz, DMSO-$d_6$) δ 0.83 (d, J=6.8 Hz, 3 H), 0.86 (d, J=6.8 Hz, 3 H), 1.09 (t, J=7.2 Hz, 1 H), 1.19 (m, 2 H), 1.34-1.76 (m, 7 H), 1.96 (m, 1 H), 2.15 (m, 2 H), 2.99 (m, 2 H), 3.37 (m, 2 H), 4.19 (t, J=7.8 Hz, 1 H), 4.39 (m, 1 H), 5.24 (s, 2 H), 5.41 (s, 2 H), 5.97 (brt, J=5.6 Hz, 1 H), 7.00 (s, 2H), 7.41 (d, J=8.4 Hz, 2 H), 7.57 (d, J=7.2 Hz, 2 H), 7.65 (d, J=8.4 Hz, 2 H), 7.80 (d, J=8.4 Hz, 1 H), 8.09 (d, J=7.2 Hz, 1 H), 8.31 (d, J=7.2 Hz, 2 H), 10.05 (brs, 1 H)

Under an argon stream, 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbon-

PREPARATION EXAMPLE 1-2

Preparation of Compound (II-3)

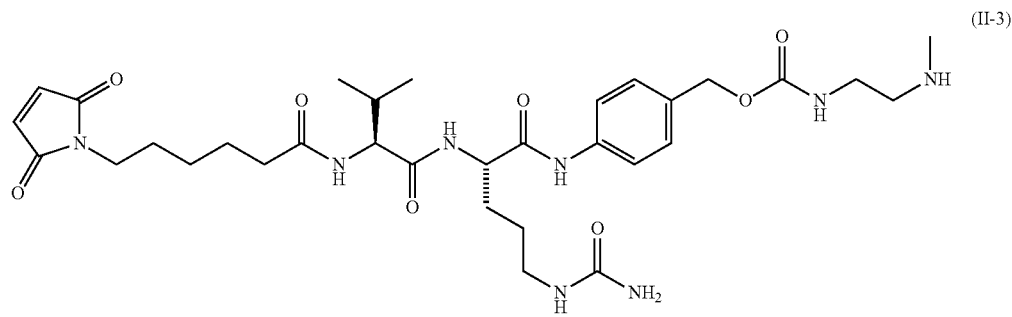 [SMILES: CNCCNC(=O)OCc1ccc(NC(=O)[C@H](CCCNC(N)=O)NC(=O)[C@@H](NC(=O)CCCCCN2C(=O)C=CC2=O)C(C)C)cc1]

ate (3.65 g, 4.95 mmol) was dissolved in 90 mL of anhydrous dimethylformamide, and stirred, together with t-butyl(2-aminoethyl)(methyl)carbamate (0.86 g, 4.95 mmol), at 20-25° C. for 2 hrs. After completion of the reaction, the reaction mixture was completely concentrated in a high vacuum, and the concentrate was purified by silica gel column chromatography to obtain an amino-protected derivative of compound (II-3) (3.8 g, 99%).

LC-MS m/z: 773.5 [M+H]$^+$

To a solution of the amino-protected derivative of compound (II-3) (146 mg, 0.186 mmol) in 5 mL of dichloromethane was dropwise added 2 mL of trifluoroacetic acid, followed by stirring at 20-25° C. for 2 hrs. After completion of the reaction, the reaction solvent was removed by vacuum concentration, and then trifluoroacetic acid was completely removed by adding 5 mL of toluene twice to obtain a concentrated TFA salt of the title compound.

PREPARATION EXAMPLE 1-3

Preparation of Compound (II-4)

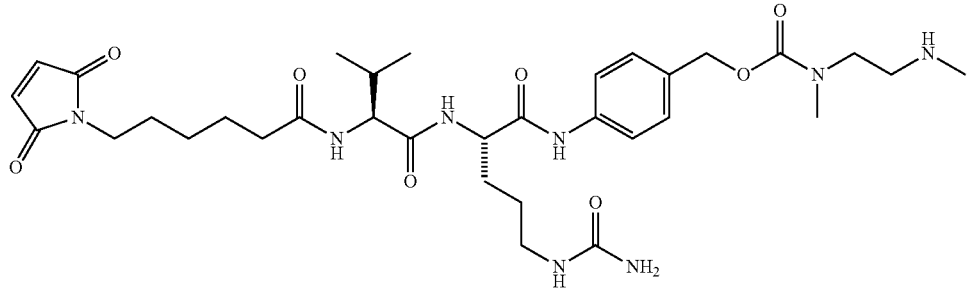

(II-4)

Under an argon stream, 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (6.8 g, 9.22 mmol) was dissolved in 150 mL of anhydrous dimethylformamide, and stirred, together with t-butyl methyl(2-(methylamino)ethyl)carbamate (1.82 g, 9.68 mmol) at 20-25° C. for 19 hrs. After completion of the reaction, the reaction mixture was completely concentrated in a high vacuum, and the concentrate was purified by silica gel column chromatography to obtain an amino-protected derivative of compound (II-4) (5.14 g, 71%).

$^1$H NMR (400 MHz, DMSO-d$_6$) δ 0.78-0.8 (d, 3 H), 0.8-0.83 (d, 3 H), 1.09-1.99 (m, 10 H), 1.33 (s, 9 H), 1.92 (m, 1 H), 2.07-2.19 (m, 2H), 2.66-2.73 (d, 3H), 2.8-2.81 (m, 3H), 2.9-3.0 (m, 2H), 3.37 (m, 2 H), 4.15 (t, 1 H), 4.34 (m, 1 H), 4.94 (s, 2 H), 5.38 (s, 2 H), 5.94 (brt, 1 H), 6.96 (s, 2H), 7.23 (d, 2 H), 7.55 (d, 2 H), 7.77 (d, 1 H), 8.04 (d, 1 H), 9.95 (brs, 1 H)

LC-MS m/z: 787.5 [1\4+H]$^+$

With the exception of using the amino-protected derivative of compound (II-4), the same procedure as in Preparation Example 1-2 was repeated to obtain a concentrated TFA salt of the title compound.

PREPARATION EXAMPLE 1-4

Preparation of Compound (II-5)

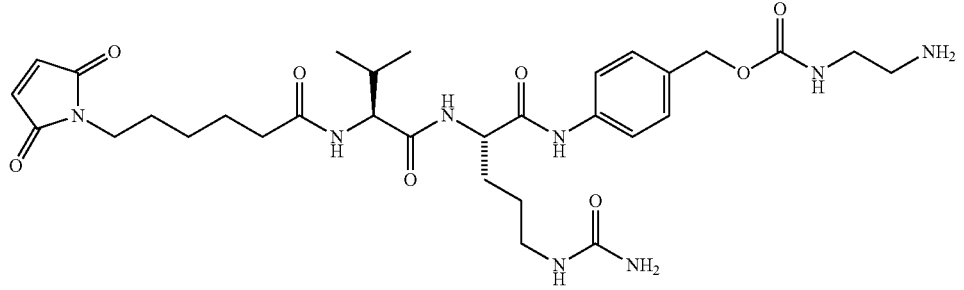

(II-5)

Under an argon stream, 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (6.8 g, 9.22 mmol) was dissolved in 80 mL of anhydrous dimethylformamide, and stirred, together with t-butyl(2-aminoethyl)carbamate (1.63 g, 10.14 mmol), at 20-25° C. for 15 hrs. After completion of the reaction, the reaction mixture was completely concentrated in a high vacuum, and the concentrate was purified by silica gel column chromatography to obtain an amino-protected derivative of compound (II-5) (4.13 g, 59%).

$^1$H NMR (400 MHz, DMSO-d$_6$) δ 0.78-0.8 (d, 3 H), 0.8-0.83 (d, 3 H), 1.09-1.99 (m, 10 H), 1.33 (s, 9 H), 1.92 (m, 1 H), 2.07-2.19 (m, 2H), 2.9-3.0 (m, 2H), 3.37 (m, 2 H), 4.15 (t, 1 H), 4.34 (m, 1 H), 4.94 (s, 2 H), 5.38 (s, 2 H), 5.94 (brt, 1 H), 6.76 (m, 1 H), 6.96 (s, 2H), 7.15 (m, 1H), 7.23 (d, 2 H), 7.55 (d, 2 H), 7.77 (d, 1 H), 8.04 (d, 1 H), 9.95 (brs, 1 H)

LC-MS m/z: 759.5 [M+H]$^+$

With the exception of using the amino-protected derivative of compound (II-5), the same procedure as in Preparation Example 1-2 was repeated to obtain a concentrated TFA salt of the title compound.

PREPARATION EXAMPLE 1-5

Preparation of Compound (II-6)

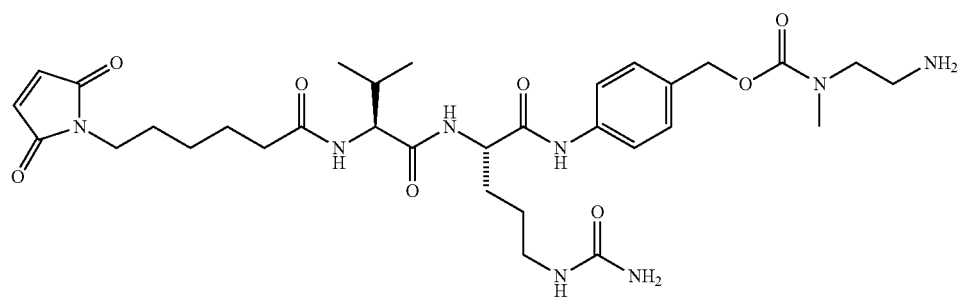

(II-6)

Under an argon stream, 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.74 g, 1 mmol) was dissolved in 30 mL of anhydrous dimethylformamide, and stirred, together with t-butyl (2-(methylamino)ethyl)carbamate (0.25 g, 1.4 mmol), at 20-25° C. for 15 hrs. After completion of the reaction, the reaction mixture was concentrated to the completion in a high vacuum, and the concentrate was purified by silica gel column chromatography to obtain an amino-protected derivative of compound (II-6) (0.36 g, 48%).

$^1$H NMR (400 MHz, DMSO-d$_6$) δ 0.79 (d, 3 H), 0.82 (d, 3 H), 1.13-1.7 (m, 10 H), 1.32-1.39 (d, 9 H), 1.89-1.93 (m, 1 H), 2.07-2.17 (m, 2 H), 2.79-2.82 (d, 2 H), 2.89-3.02 (m, 5H), 3.14 (d, 1 H), 3.2 (m, 1H), 4.15 (t, 1 H), 4.34 (m, 1 H), 4.9-4.94 (d, 2 H), 5.37 (s, 2 H), 5.941 (brt, 1 H), 6.81-6.85 (m, 1 H), 7.24 (d, 2H), 7.54 (d, 2 H), 7.76 (d, 1 H), 8.04 (d, 1 H), 9.95 (brs, 1 H)

LC-MS m/z: 773.5 [M+H]$^+$

With the exception of using the amino-protected derivative of compound (II-6), the same procedure as in Preparation Example 1-2 was repeated to obtain a concentrated TFA salt of the title compound.

PREPARATION EXAMPLE 2

Preparation of Compounds of Chemical Formulas III-1, III-2, III-3 and III-4

PREPARATION EXAMPLE 2-1

Preparation of Compound (III-5)

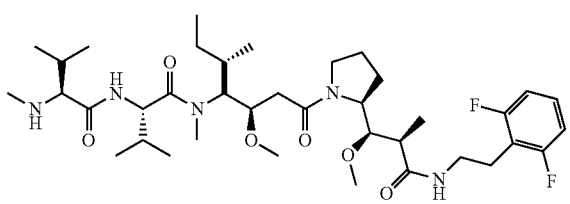

(III-5)

Under an argon stream, (2R,3R)-3-((S)-1-(t-butoxycarbonyl)pyrrolidin-2-yl)-3-methoxy-2-methylpropanic acid (0.63 g, 2.2 mmol) was dissolved in 10 mL of anhydrous dimethylformamide, and added with 2-(2,6-difluorophenyl)ethanamine (0.38 g, 2.4 mmol). The temperature was cooled to 0° C. before benzotriazol-1-yl-oxy-tris(dimethylamino) phosphoniumhexafluorophosphate (0.97 g, 2.2 mmol), and diisopropylethylamine (1.0 mL, 6.6 mmol) were sequentially added to the reaction mixture. Stirring was continued at room temperature for 15 hrs. After completion of the reaction, the resulting reaction mixture was concentrated in a high vacuum, and the concentrate was purified by silica gel column chromatography to afford (R)-t-butyl 2-((1R,2R)-3-((2,6-difluorophenethyl)amino)-1-methoxy-2-methyl-3-oxopropyl)pyrrolidine-1-carboxylate (0.60 g, 64%).

To a solution of this compound (0.6 g, 1.4 mmol) in 10 mL of dichloromethane was added 1 mL of trifluoroacetic acid, followed by stirring at room temperature for 3 hrs. After completion of the reaction, the reaction solvent was removed by vacuum concentration, and the residual trifluoroacetic acid was completely removed by adding 10 mL of dichloromethane twice to obtain a trifluoroacetic acid salt of (2R,3R)-N-(2,6-difluorophenethyl)-3-methoxy-2-methyl-3-((R)-pyrrolidin-2-yl)propanamide.

This concentrate (TFA salt) was dissolved, together with (5S,8S,11S,12R)-11-((S)-sec-butyl)-5,8-diisopropyl-12-methoxy-4,10-dimethyl-3,6,9-trioxo-1-methyl-2-oxa-4,7,10-triazatetradecan-14-oic acid (0.77 g, 1.4 mmol), in 10 mL of dimethylformamide, and sequentially added with diethyl cyanophosphate (DEPC) (0.23 mL, 1.54 mmol) and triethylamine (1.17 mL, 8.4 mmol) at 0° C. before being stirred at room temperature for 15 hrs. After completion of the reaction, the solvent was removed, and the residue was dissolved in 50 mL of ethylacetate and washed with 30 mL of distilled water. The organic layer was dried over anhydrous sodium sulfate, and concentrated in a vacuum. The concentrate was purified by silica gel column chromatography to afford an N-terminal amino-protected derivative of compound (III-5) (0.96 g, 80%).

$^1$H NMR (400 MHz, CDCl$_3$) δ 0.75-1.06 (m, 17 H), 1.18-1.38 (m, 5H), 1.71-2.15 (m, 7 H), 2.21-2.52 (m, 4 H), 2.87-2.91 (m, 4 H), 2.99 (s, 3 H), 3.10 (s, 3 H), 3.38 (s, 3 H), 3.43-3.51 (m, 3 H), 3.82 (m, 1 H), 4.09-4.15 (m, 4 H), 4.69 (m, 1H), 5.12-5.23 (m, 2 H), 6.50-6.60 (m, 2 H), 6.82-6.87 (m, 2 H), 7.13-7.17 (m, 1 H), 7.30-7.34 (m, 5 H)

The N-terminal amino-protected derivative of compound (III-5) (0.96 g, 1.1 mmol) was dissolved in a mixture of 18 mL of t-butyl alcohol and 2 mL of water, and stirred for 3 hrs in the presence of 10% palladium carbon (0.1 g) in a hydrogen atmosphere. After completion of the reaction, the reaction mixture was filtered through a Celite filter, and washed several times with methanol. Then, the solvent was removed in a vacuum to afford the title compound (0.79 g, 99%).

$^1$H NMR (400 MHz, CDCl$_3$) δ 0.78-0.98 (m, 16 H), 1.06 (m, 1 H), 1.16-1.27 (m, 4 H), 1.38 (m, 1 H), 1.65-1.76 (m, 6 H), 1.89-2.02 (m, 4 H), 2.31-2.38 (m, 5 H), 2.71-2.75 (m, 1 H), 2.88-2.89 (m, 2 H), 3.00 (s, 3 H), 3.29 (s, 3 H), 3.41-3.48 (m, 3 H), 3.79-3.82 (m, 1 H), 4.08-4.15 (m, 2 H), 4.72-4.86 (m, 2 H), 6.56 (m, 1 H), 6.79-6.85 (m, 2 H), 7.10-7.15 (m, 1 H), 7.16-7.22 (m, 1 H), 7.55 (d, 1 H)

PREPARATION EXAMPLE 2-2

Preparation of Compound (III-6)

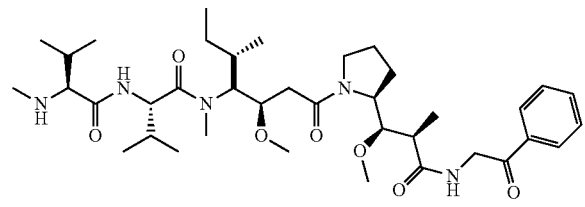

(III-6)

With the exception that 2-aminoacetophenone, instead of 2-(2,6-difluorophenyl)ethanamine, was used, the same procedure as in Preparation Example 2-1 was repeated to obtain the N-terminal amino-protected derivative of compound (III-6): 2.36 g (81%).

$^1$H NMR (400 MHz, CDCl$_3$) δ 0.71-1.04 (m, 17 H), 1.31-1.32 (m, 4H), 1.77-1.81 (m, 2 H), 1.92-2.04 (m, 4 H), 2.17-2.61 (m, 4 H), 2.89-2.95 (m, 3 H), 2.99 (s, 3 H), 3.30 (s, 3 H), 3.46 (m, 3 H), 3.43-3.52 (m, 1 H), 3.99-4.01 (m, 1 H), 4.09-4.15 (m, 1 H), 4.24 (m, 1 H), 4.69-4.76 (m, 6 H), 5.09-5.23 (m, 2 H), 6.46-6.49 (m, 1 H), 7.12 (m, 1 H), 7.26-7.34 (m, 5H), 7.50 (t, J=7.6 Hz, 2 H), 7.62 (t, J=7.2 Hz, 1 H), 7.97 (d, J=7.6 Hz, 2 H)

With the exception of using the amino-protected derivative of compound (III-6), the same procedure as in Preparation Example 2-1 was repeated to obtain the title compound: 1.89 g (96%).

$^1$H NMR (400 MHz, CDCl$_3$) δ 0.81-0.85 (m, 3 H), 0.92-1.14 (m, 13H), 1.25-1.43 (m, 5 H), 1.46-1.89 (m, 6 H), 1.92-2.22 (m, 5 H), 2.33 (s, 3 H), 2.45-2.54 (m, 2 H), 2.74 (d, J=4.8 Hz, 1 H), 3.02 (s, 3 H), 3.32 (s, 3 H), 3.43 (d, J=9.2 Hz, 3 H), 3.52-3.84 (m, 2 H), 3.92-4.06 (m, 2 H), 4.75-4.80 (m, 2 H), 4.94-5.23 (m, 1H), 6.76-6.94 (m, 1 H), 7.34-7.43 (m, 4H), 7.60 (m, 1 H)

PREPARATION EXAMPLE 2-3

Preparation of Compound (III-7)

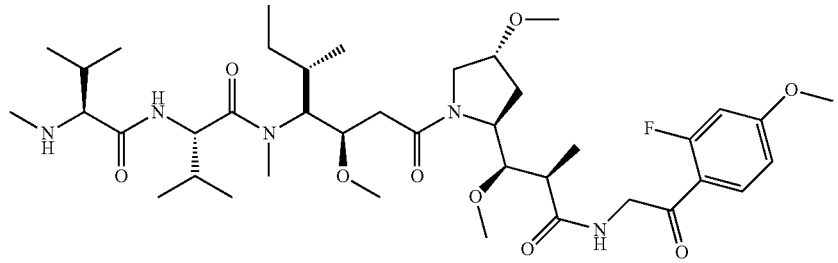

(III-7)

With the exception that (2R,3R)-3-((2S,4R)-1-(t-butoxycarbonyl)-4-methoxypyrrolidin-2-yl)-3-methoxy-2-methylpropanic acid and 2-amino-1-(2-fluoro-4-methoxyphenyl)ethanone were used respectively instead of (2R,3R)-3-((S)-1-(t-butoxycarbonyl)pyrrolidin-2-yl)-3-methoxy-2-methylpropanic acid and 2-(2,6-difluorophenyl)ethanamine, the same procedure as in Preparation Example 2-1 was repeated to afford the title compound. 0.18 g (89%).

$^1$H NMR (400 MHz, CDCl$_3$) δ 0.80-0.84 (m, 3 H), 0.88-1.03 (m, 17H), 1.32 (d, J=7.2 Hz, 3 H), 1.35-1.39 (m, 2 H), 1.98-2.10 (m, 4 H), 2.35 (s, 3 H), 2.36-2.51 (m, 3 H), 2.74 (m, 1 H), 3.02 (m, 3 H), 3.29 (s, 3 H), 3.34 (s, 3 H), 3.45 (s, 3H), 3.46-3.56 (m, 1 H), 3.87 (s, 3 H), 3.99 (dd, J=7.6 Hz, 2.8 Hz, 1 H), 4.10-4.15 (m, 1 H), 4.25-4.28 (m, 1 H), 4.58-4.64 (m, 2 H), 4.73-4.78 (m, 1 H), 6.67 (m, 1 H), 6.78 (qd, J=10.4 Hz, 2.8 Hz, 1 H), 7.95 (m, 1 H)

PREPARATION EXAMPLE 2-4

Preparation of Compound (III-8)

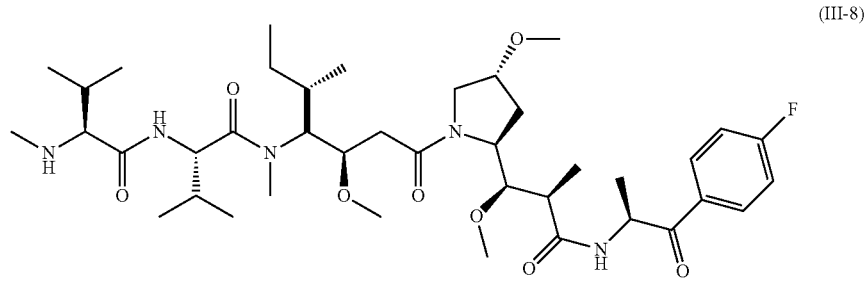 [SMILES: CC[C@H](C)[C@@H]([C@@H](CC(=O)N1C[C@H](OC)C[C@H]1[C@H](OC)[C@@H](C)C(=O)N[C@@H](C)C(=O)c1ccc(F)cc1)OC)N(C)C(=O)[C@@H](NC(=O)[C@@H](NC)C(C)C)C(C)C]

(III-8)

With the exception that (2R,3R)-3-((2S,4R)-1-(t-butoxycarbonyl)-4-methoxypyrrolidin-2-yl)-3-methoxy-2-methylpropanic acid and (S)-2-amino-1-(4-fluorophenyl)propan-1-one were used respectively instead of (2R,3R)-3-((S)-1-(t-butoxycarbonyl)pyrrolidin-2-yl)-3-methoxy-2-methylpropanic acid and 2-(2,6-difluorophenyeethanamine, the same procedure as in Preparation Example 2-1 was repeated to afford the title compound. 0.45 g (100%).

$^1$H NMR (400 MHz, CDCl$_3$) δ 0.71-1.03 (m, 20 H), 1.22 (d, 3 H), 1.33-1.37 (m, 4 H), 1.40-1.44 (m, 3 H), 1.60-1.81 (m, 4 H), 1.98 (m, 2 H), 2.26 (m, 2 H), 2.90 (s, 3 H), 3.21 (s, 3 H), 3.32 (s, 3 H), 3.43 (s, 3 H), 4.06-4.15 (m, 2 H), 4.22-4.27 (m, 2 H), 4.64-4.69 (m, 2 H), 5.09-5.13 (m, 2 H), 5.23-5.30 (m, 2 H), 5.50 (m, 1 H), 7.18 (t, 2 H), 8.01-8.05 (m, 2 H)

PREPARATION EXAMPLE 2-5

Preparation of Compound (III-9)

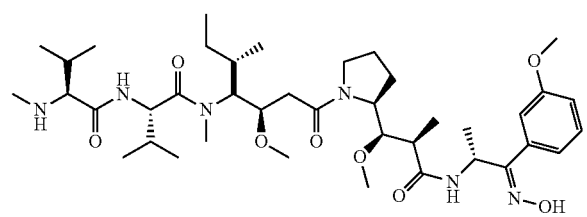

(III-9)

With the exception that (R,E)-2-amino-1-(3-methoxyphenyl)propan-1-one oxime was used instead of 2-(2,6-difluorophenyl)ethanamine, the same procedure as in Preparation Example 2-1 was repeated to afford the title compound. 0.17 g (94%).

$^1$H NMR (400 MHz, CDCl$_3$) δ 0.79-0.98 (m, 20 H), 1.01 (m, 4 H), 1.19-1.27 (m, 4 H), 1.79-1.83 (m, 2 H), 2.21-2.43 (m, 4H), 2.77 (m, 2 H), 3.00 (m, 2 H), 3.29 (s, 6 H), 3.42 (s, 3 H), 3.99-4.14 (m, 3 H), 4.15-4.37 (m, 3 H), 4.70 (m, 1 H), 5.21-5.23 (m, 2 H), 5.36 (m, 1 H), 7.03 (m, 1 H), 7.15 (m, 2 H), 7.49 (m, 1 H)

PREPARATION EXAMPLE 2-6

Preparation of Compound (III-10)

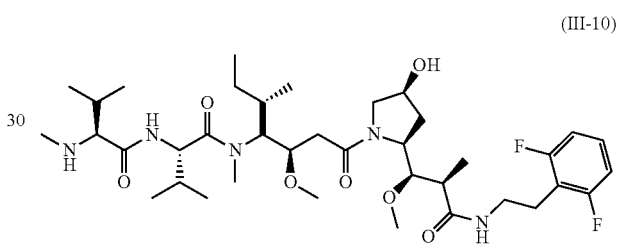

(III-10)

With the exception that (2R,3R)-3-((2S,4S)-1-(t-butoxycarbonyl)-4-((t-butyldimethylsilyl)oxy)pyrrolidin-2-yl)-3-methoxy-2-methylpropanic acid was used instead of (2R, 3R)-3-((S)-1-(t-butoxycarbonyl)pyrrolidin-2-yl)-3-methoxy-2-methylpropanic acid, the same procedure as in Preparation Example 2-1 was repeated to obtain a raw N-terminal amino- and hydroxy-protected derivative of compound (III-10). 1.0 g (100%).

To a solution of this compound (1.0 g, 1.02 mmol) in 10 mL of dimethylformamide was added 1.0 M tetrabutylammonium fluoride (3.1 mL, 3.1 mmol), followed by stirring for 5 hrs. After completion of the reaction, the solvent was removed, and the residue was dissolved in 50 mL of ethylacetate, and washed with a saturated sodium hydrogen carbonate solution and brine. The organic layer was dried over anhydrous sodium sulfate and concentrated in a vacuum. The concentrate was purified by silica gel column chromatography to afford an N-terminal amino-protected derivative of compound (III-10) (0.75 g, 84%).

ES-MS m/z: 874 [M+H]$^+$

With the exception of using the N-terminal amino-protected derivative of compound (III-10), the same procedure as in Preparation Example 2-1 was repeated to afford the title compound. 0.64 g (100%).

ES-MS m/z: 740 [M+H]$^+$

PREPARATION EXAMPLE 2-7

Preparation of Compound (III-11)

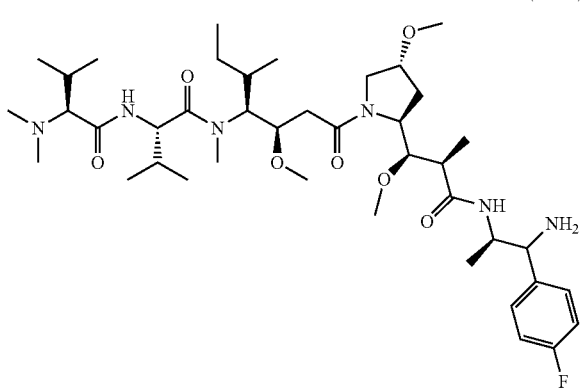
(III-11)

Under an argon stream, (2R,3R)-3-((2S,4R)-1-(t-butoxycarbonyl)-4-methoxypyrrolidin-2-yl)-3-methoxy-2-methylpropanic acid (0.70 g, 2.2 mmol) was dissolved in 10 mL of anhydrous dimethylformamide, and added with (2R)-1-azido-1-(4-fluorophenyl)propan-2-amine HCl (0.47 g, 2.4 mmol). The temperature was cooled to 0° C. before benzotriazol-1-yl-oxy-tris(dimethylamino)phosphoniumhexafluorophosphate (0.97 g, 2.2 mmol) and diisopropylethylamine (1.0 mL, 6.6 mmol) were sequentially added to the reaction mixture. Stirring was continued at room temperature for 15 hrs. After completion of the reaction, the resulting reaction mixture was concentrated in a high vacuum, and the concentrate was purified by silica gel column chromatography to afford (2S,4R)-t-butyl 2-((1R,2R)-3-(((2R)-1-azido-1-(4-fluorophenyl)propan-2-yl)amino)-1-methoxy-2-methyl-3-oxopropyl)-4-methoxypyrrolidine-1-carboxylate (0.61 g, 56%).

LC-MS m/z: 494.2 [M$^+$]$^+$, 516.3 [M+Na]$^+$

To a solution of this compound (0.61 g, 1.23 mmol) in 10 mL of dichloromethane was added 7 mL of trifluoroacetic acid, followed by stirring at 20-25° C. for 3 hrs. When the reaction was completed, the reaction solvent was removed by vacuum concentration, and the residual trifluoroacetic acid was completely removed by adding 5 mL of toluene twice, before a further reaction.

This concentrate (TFA salt) was dissolved, together with (3R,4S,5S)-4-((S)-2-((S)-2-(dimethylamino)-3-methylbutanamido)-N, 3-dimethylbutanamido)-3-methoxy-5-methyl heptanoic acid (0.53 g, 1.23 mmol), in 5 mL of dimethylformamide, and sequentially added with diethyl cyanophosphate (DEPC) (0.20 mL, 1.35 mmol) and triethylamine (1.56 mL, 11.09 mmol) at 0° C. before being stirred at room temperature for 16 hrs. When the reaction was completed, the solvent was removed, and the residue was dissolved in 20 mL of ethylacetate and extracted with 1 M potassium hydrogen sulfite, water, a saturated sodium hydrogen carbonate solution, and brine. The organic layer was dried over anhydrous sodium sulfate, and concentrated in a vacuum. The concentrate was purified by silica gel column chromatography to afford an N-terminal amino-protected derivative of compound (III-11) (0.25 g, 25%).

LC-MS m/z: 779.6[M+H]$^+$

The N-terminal amino-protected derivative of compound (III-11) (0.25 g, 0.31 mmol) was dissolved in a mixture of 10 mL of methyl alcohol, and stirred for 16 hrs in the presence of 10% palladium carbon (0.1 g) in a hydrogen atmosphere. After completion of the reaction, the reaction mixture was filtered through a Celite filter, and washed several times with methanol. Then, the solvent was removed in a vacuum to afford the title compound as a white solid (97 mg, 41%).

LC-MS m/z: 753[M$^+$]$^+$, 775[M+Na]$^+$ $^1$H NMR (400 MHz, CDCl$_3$) δ 0.72 (t, 3 H), 0.77-1.02 (m, 17 H), 1.01 (d, 3 H), 1.15 (d, 3 H), 1.32 (m, 1 H), 1.78 (brd, 2H), 1.85-2.12 (m, 4 H), 2.18 (S, 6 H), 2.32-2.50 (m, 4H), 3.30 (s, 3H), 3.38 (s, 6H), 3.48 (m, 1H), 4.00-4.15 (m, 4H), 4.32 (m, 2H), 4.85 (m, 2H), 6.60 (s, 1H), 6.88 (s, 1H), 6.99-7.06 (m, 2H), 7.22-7.32 (m, 2H)

PREPARATION EXAMPLE 2-8

Preparation of Compound (III-12)

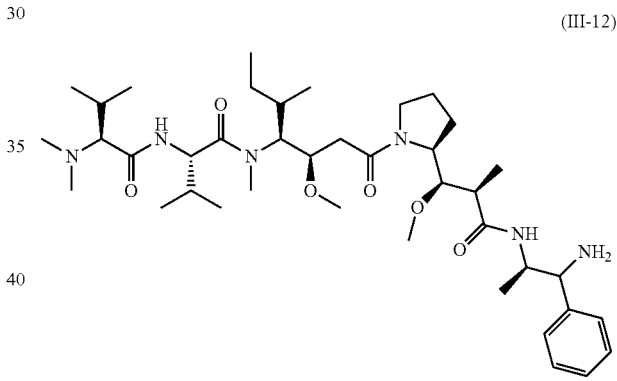
(III-12)

With the exception that (2R,3R)-3-((2S)-1-(t-butoxycarbonyl)pyrrolidin-2-yl)-3-methoxy-2-methylpropanic acid (92 mg, 0.32 mmol) and (2R)-1-azido-1-phenylpropan-2-amine HCl (68 mg, 0.32 mmol) were respectively used instead of (2R,3R)-3-((2S,4R)-1-(t-butoxycarbonyl)-4-methoxypyrrolidin-2-yl)-3-methoxy-2-methylpropanic acid and (2R)-1-azido-1-(4-fluorophenyl)propan-2-amine HCl, the same procedure as in Preparation Example 2-7 was repeated to afford the title compound (44 mg, 50%).

MALDI-TOF MS m/z: 731.6 [M+H]$^+$, 753.5 [M+Na]$^+$ $^1$H NMR (400 MHz, CDCl$_3$) δ 0.81 (t, 3 H), 0.88-1.07 (m, 17 H), 1.18 (d, 3 H), 1.21 (d, 3 H), 1.47 (m, 1 H), 1.74 (brd, 2H), 1.87-2.17 (m, 3 H), 2.24 (S, 6 H), 2.25-2.47 (m, 4H), 3.04 (s, 3H), 3.28-3.34 (m, 1H), 3.31 (s, 3H), 3.38 (s, 3H), 3.45 (m, 1H), 3.79 (d, 1H), 3.82 (m, 1H), 4.05-4.12 (m, 4H), 4.24 (m, 2H), 4.75 (m, 2H), 6.73 (s, 1H), 6.95 (d, 1H), 7.24-7.35 (m, 5H)

PREPARATION EXAMPLE 2-9

Preparation of Compound (III-13)

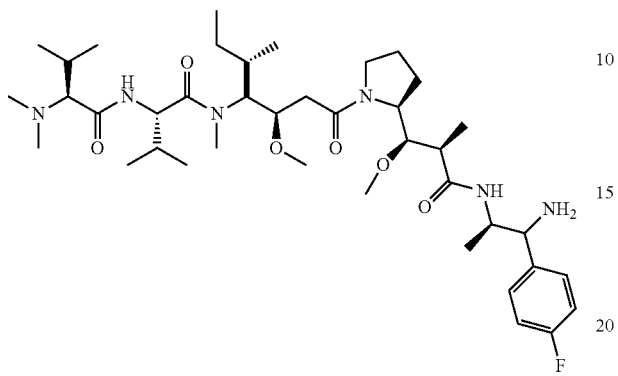
(III-13)

With the exception that (2R,3R)-3-((2S)-1-(t-butoxycarbonyl)pyrrolidin-2-yl)-3-methoxy-2-methylpropanic acid (0.80 g, 2.8 mmol), instead of (2R,3R)-3-((2S,4R)-1-(t-butoxycarbonyl)-4-methoxypyrrolidin-2-yl)-3-methoxy-2-methylpropanic acid, and (2R)-1-azido-1-(4-fluorophenyl)propan-2-amine HCl (0.64 g, 2.8 mmol) were used, the same procedure as in Preparation Example 2-7 was repeated to afford the title compound (0.5 g, 79%).

LC-MS m/z: 749.47 [M+H]$^+$, 771.44 [M+Na]$^+$ $^1$H NMR (400 MHz, CDCl$_3$) δ 0.82 (t, 3 H), 0.91-1.1 (m, 17 H), 1.16 (d, 3 H), 1.20 (d, 3 H), 1.35 (m, 1 H), 1.78 (brd, 2H), 1.87-2.10 (m, 4H), 2.24 (S, 6 H), 2.28-2.48 (m, 4H), 3.03 (s, 3H), 3.28-3.34 (m, 1H), 3.31 (s, 3H), 3.38 (s, 3H), 3.48 (m, 1H), 3.82 (d, 1H), 4.03-4.10 (m, 4H), 4.22 (m, 2H), 4.77 (m, 2H), 6.56 (d, 1H), 6.86 (s, 1H), 6.99-7.07 (m, 2H), 7.23-7.35 (m, 2H)

PREPARATION EXAMPLE 2-10

Preparation of Compound (III-14)

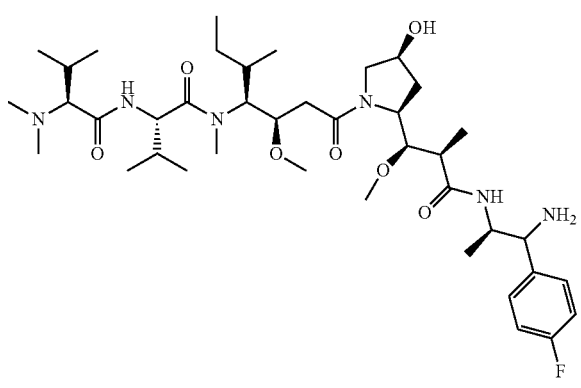
(III-14)

With the exception that (2R,3R)-3-((2S,4R)-1-(t-butoxycarbonyl)-4-hydroxypyrrolidin-2-yl)-3-methoxy-2-methylpropanic acid (340 mg, 1.12 mmol), instead of (2R,3R)-3-((2S,4R)-1-(t-butoxycarbonyl)-4-methoxypyrrolidin-2-yl)-3-methoxy-2-methylpropanic acid, and (2R)-1-azido-1-(4-fluorophenyl)propan-2-amine HCl (258 mg, 1.12 mmol) were used, the same procedure as in Preparation Example 2-7 was repeated to afford the title compound (350 mg, 71%).

LC-MS m/z: 765.46 [M$^+$]$^+$ $^1$H NMR (400 MHz, CDCl$_3$) δ 0.80 (t, 3 H), 0.90-1.09 (m, 17 H), 1.11 (d, 3 H), 1.25 (d, 3 H), 1.32 (m, 1 H), 1.78 (brd, 2H), 2.04-2.09 (m, 3 H), 2.23 (S, 6 H), 2.35-2.50 (m, 4H), 3.03 (s, 3H), 3.32 (s, 3H), 3.38 (m, 1H), 3.47 (s, 3H), 3.54-3.56 (m, 2H), 3.90 (m, 1H), 4.0-4.32 (m, 6H), 4.75 (m, 2H), 6.53 (s, 1H), 6.76 (d, 1H), 6.99-7.04 (m, 2H), 7.32-7.35 (m, 2H)

PREPARATION EXAMPLE 2-11

Preparation of Compound (III-15)

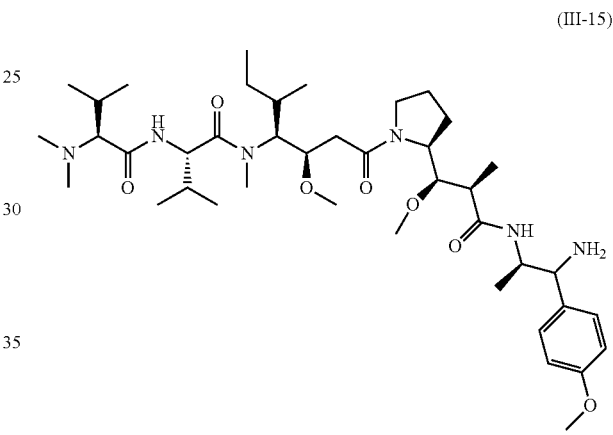
(III-15)

With the exception that (2R,3R)-3-((2S)-1-(t-butoxycarbonyl)pyrrolidin-2-yl)-3-methoxy-2-methylpropanic acid (0.17 g, 0.58 mmol) and (2R)-1-phthalimido-1-(4-methoxyphenyl)propan-2-amine HCl (0.2 g, 0.58 mmol) were used respectively instead of (2R,3R)-3-((2S,4R)-1-(t-butoxycarbonyl)-4-methoxypyrrolidin-2-yl)-3-methoxy-2-methylpropanic acid and (2R)-1-azido-1-(4-fluorophenyl)propan-2-amine HCl, the same procedure as in Preparation Example 2-7 was repeated to afford an amino-protected derivative of compound (III-15) (0.34 g, 94%).

LC-MS m/z: 891.62[M]$^+$

To a solution of the amino-protected derivative of compound (III-15) (0.34 g, 0.38 mmol) in 10 mL of ethanol was added 1 mL of hydrazine hydrate, followed by stirring at room temperature for 16 hrs. After completion of the reaction, the solvent was removed in a vacuum. The residue was purified by silica gel column chromatography to afford the title compound as a white solid (0.11 g, 38%).

LC-MS m/z: 761.56[M$^+$]$^+$, 783.60[M+Na]$^+$ $^1$H NMR (400 MHz, CDCl$_3$) δ 0.80 (m, 3H), 0.88-1.07 (m, 18H), 1.19 (d, 3 H), 1.15 (m, 1H), 1.22 (m, 1 H), 1.25 (d, 3H), 1.70-1.90 (m, 4H), 2.07 (S, 6 H), 2.26 (s, 3H), 2.28-2.48 (m, 4H), 3.06 (s, 3H), 3.32 (s, 3H), 3.38 (m, 1H), 3.43 (s, 3H), 3.50 (m, 1H), 3.76 (m, 1H), 3.80 (s, 3H), 3.78 (d, 1H), 3.90-4.25 (m, 4H), 4.54 (m, 2H), 6.89 (d, 2H), 7.35 (d, 2H)

PREPARATION EXAMPLE 2-12

Preparation of Compound (III-16)

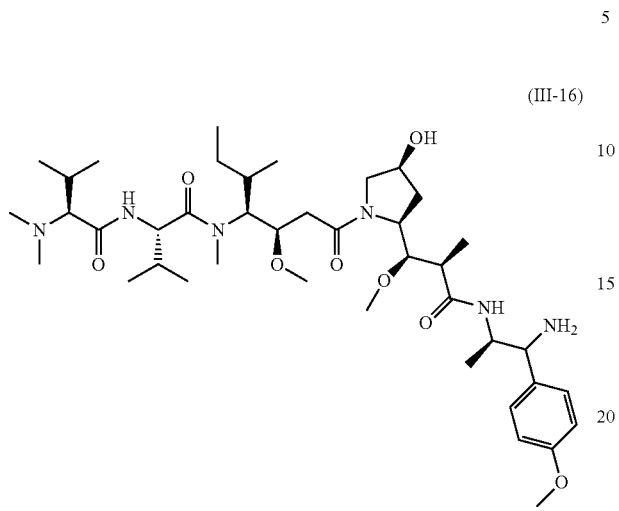

With the exception that (2R,3R)-3-((2S,4R)-1-(t-butoxycarbonyl)-4-hydroxypyrrolidin-2-yl)-3-methoxy-2-methylpropanic acid (0.36 g, 1.17 mmol) and (2R)-1-phthalimido-1-(4-methoxyphenyl)propan-2-amine HCl (0.41 g, 1.17 mmol) were used respectively instead of (2R,3R)-3-((2S,4R)-1-(t-butoxycarbonyl)-4-methoxypyrrolidin-2-yl)-3-methoxy-2-methylpropanic acid and (2R)-1-azido-1-(4-fluorophenyl)propan-2-amine HCl, the same procedure as in Preparation Example 2-7 was repeated to afford an amino-protected derivative of compound (III-16) (0.59 g, 74%).

LC-MS m/z: 907.54[M]$^+$

With the exception of using the amino-protected derivative of compound (III-16) (0.59 g, 0.65 mmol), the same procedure as in Preparation Example 2-11 was repeated to afford the title compound as a white solid (0.19 g, 38%).

LC-MS m/z: 777.42[M$^+$]$^+$, 799.39[M+Na]$^+$ $^1$H NMR (400 MHz, CDCl$_3$) δ 0.79-0.859 (m, 3H), 0.86-1.06 (m, 17H), 1.13 (d, 3H), 1.24-1.40 (m, 6H), 1.62-1.84 (m, 2H), 1.97-2.41 (m, 3H), 2.20-2.32 (m, 7H), 2.36-2.54 (m, 4H), 3.06 (s, 3H), 3.31 (s, 3H), 3.46 (t, 1H), 3.50 (s, 3H), 3.56 (brs, 1H), 3.62 (m, 1H), 3.67 (m, 1H), 3.72-3.77 (m, 1H), 3.80 (s, 3H), 3.97-4.28 (m, 4H), 4.30 (m, 1H), 4.68 (m, 1H), 4.72-4.83 (m, 1H), 6.89 (d, 2H), 7.33 (d, 2H)

PREPARATION EXAMPLE 2-13

Preparation of Compound (III-17)

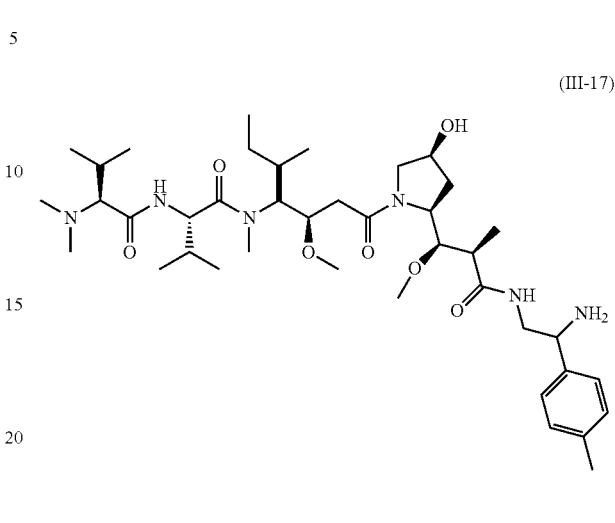

With the exception that (2R,3R)-3-((2S,4R)-1-(t-butoxycarbonyl)-4-hydroxypyrrolidin-2-yl)-3-methoxy-2-methylpropanic acid (1.43 g, 4.7 mmol) and 2-phthalimido-2-(p-tolyl)ethylamine HCl (1.65 g, 5.2 mmol) were used respectively instead of (2R,3R)-3-((2S,4R)-1-(t-butoxycarbonyl)-4-methoxypyrrolidin-2-yl)-3-methoxy-2-methylpropanic acid and (2R)-1-azido-1-(4-fluorophenyl)propan-2-amine HCl, the same procedure as in Preparation Example 2-7 was repeated to afford an amino-protected derivative of compound (III-17) (2.35 g, 78%).

LC-MS m/z: 878[M+1]$^+$

With the exception of using the amino-protected derivative of compound (III-7) (2.08 g, 2.37 mmol), the same procedure as in Preparation Example 2-11 was repeated to afford the title compound as a white solid (1.7 g, 94%).

LC-MS m/z: 748[M+1]$^+$ $^1$H NMR (400 MHz, CDCl$_3$) δ 0.79-0.84 (m, 3H), 0.91-1.03 (m, 19H), 1.24-1.29 (m, 4H), 1.29-1.40 (m, 1H), 1.90-2.14 (m, 4H), 2.25 (s, 6H), 2.32 (s, 3H), 2.38-2.48 (m, 3H), 3.03 (s, 3H), 3.14 (brd, 1H), 3.24-3.30 (m, 1H), 3.32 (s, 3H), 3.38-3.43 (m, 1H), 3.48 (s, 3H), 3.54-3.62 (m, 3H), 4.04-4.18 (m, 3H), 4.24-4.34 (m, 2H), 4.77-4.90 (m, 2H), 6.37 (m, 1H), 7.14-7.28 (m, 4H)

PREPARATION EXAMPLE 2-14

Preparation of Compound (III-18)

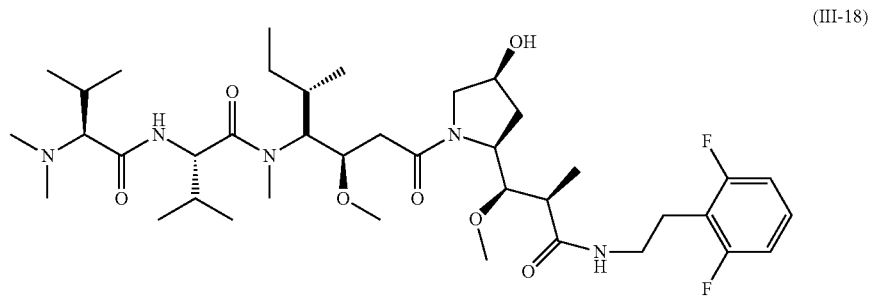 [SMILES: CC[C@H](C)[C@@H]([C@@H](CC(=O)N1C[C@@H](O)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

Under an argon stream, (2R,3R)-3-((2S,4S)-1-(t-butoxycarbonyl)-4-((t-butyldimethylsilyl)oxy)pyrrolidin-2-yl)-3-methoxy-2-methylpropanic acid (0.92 g, 2.2 mmol) was dissolved in 10 mL of anhydrous dimethylformamide, and added with 2-(2,6-difluorophenyl)ethanamine (0.38 g, 2.4 mmol). The temperature was cooled to 0° C. before benzotriazol-1-yl-oxy-tris(dimethylamino)phosphoniumhexafluorophosphate (0.97 g, 2.2 mmol) and diisopropylethylamine (1.0 mL, 6.6 mmol) were sequentially added to the reaction mixture. Stirring was continued at room temperature for 15 hrs. After completion of the reaction, the resulting reaction mixture was concentrated in a high vacuum, and the concentrate was purified by silica gel column chromatography to afford (2S,4S)-t-butyl 4-((t-butyldimethylsilyl)oxy)-2-((1R,2R)-3-((2,6-difluorophenethyl)amino)-1-methoxy-2-methyl-3-oxopropyl)pyrrolidine-1-carboxylate (0.87 g, 70.9%).

To a solution of this compound (0.87 g, 1.56 mmol) in 10 mL of dichloromethane was added 7 mL of trifluoroacetic acid, followed by stirring at 20-25° C. for 3 hrs. When the reaction was completed, the reaction solvent was removed by vacuum concentration, and the residual trifluoroacetic acid was completely removed by adding 5 mL of toluene twice, before a further reaction.

This concentrate (TFA salt) was dissolved, together with (3R,4S,5S)-4-((S)-2-((S)-2-(dimethylamino)-3-methylbutanamido)-N, 3-dimethylbutanamido)-3-methoxy-5-methylheptanoic acid (0.67 g, 1.56 mmol), in 5 mL of dimethylformamide, and sequentially added with diethyl cyanophosphate (DEPC) (0.26 mL, 1.56 mmol) and triethylamine (1.09 mL, 7.82 mmol) at room temperature before being stirred at room temperature for 16 hrs. After completion of the reaction, the solvent was removed, and the residue was dissolved in 20 mL of ethylacetate and extracted with 1 M potassium hydrogen sulfite, water, a saturated sodium hydrogen carbonate solution, and brine. The organic layer was dried over anhydrous sodium sulfate and concentrated in a vacuum. The concentrate was purified by silica gel column chromatography (ethylacetate: hexane=2: 1→ethylacetate) to afford a hydroxy-protected derivative of compound (III-18) (1.14 g, 84%).

$^1$H NMR (400 MHz, CDCl$_3$) δ 0.04 (s, 6 H), 0.81-1.06 (m, 19 H), 1.19 (m, 3 H), 1.46 (m, 2 H), 1.65 (m, 2 H), 1.97-2.17 (m, 3 H), 2.44-2.46 (m, 3 H), 2.71-2.80 (m, 3 H), 2.81-2.89 (m, 1 H), 2.91-2.94 (m, 2 H), 2.71-2.80 (m, 3 H), 3.04 (s, 3H), 3.26-3.33 (m, 2 H), 3.37 (s, 3 H), 3.74 (m, 2 H), 4.28-4.31 (m, 2H), 4.75-4.82 (m, 2 H), 6.18 (m, 1 H), 6.84-6.89 (m, 2 H), 7.15-7.19 (m, 1 H), 7.58 (d, 1 H)

A solution of the hydroxy-protected derivative of compound (III-18) (1.14 g, 1.31 mmol) in 95 mL of tetrahydrofuran was stirred, together with 1.0 M tetrabutylammonium fluoride (4.9 mL, 4.09 mmol), for 5 hrs, followed by terminating the reaction with a saturated aqueous ammonium chloride solution. Extraction with 450 mL of ethylacetate and 300 mL of water was conducted before vacuum concentration. The concentrate was purified by silica gel column chromatography (dichloromethane:methanol=9:1) to afford the title compound (0.45 g, 45%).

$^1$H NMR (400 MHz, CDCl$_3$) δ 0.79-1.05 (m, 19 H), 1.26 (m, 3 H), 1.45 (m, 2 H), 1.66 (m, 2 H), 1.97-2.17 (m, 3 H), 2.44-2.46 (m, 3 H), 2.71-2.80 (m, 3 H), 2.81-2.89 (m, 1 H), 2.91-2.94 (m, 2 H), 2.71-2.80 (m, 3 H), 3.04 (s, 3 H), 3.26-3.33 (m, 2 H), 3.37 (s, 3 H), 3.74 (m, 2 H), 4.28-4.31 (m, 2 H), 4.75-4.82 (m, 2 H), 6.18 (m, 1 H), 6.84-6.89 (m, 2 H), 7.15-7.19 (m, 1 H), 7.58 (d, 1 H)

LC-MS m/z: 754 [M$^+$]$^+$

PREPARATION EXAMPLE 2-15

Preparation of Compound (III-19)

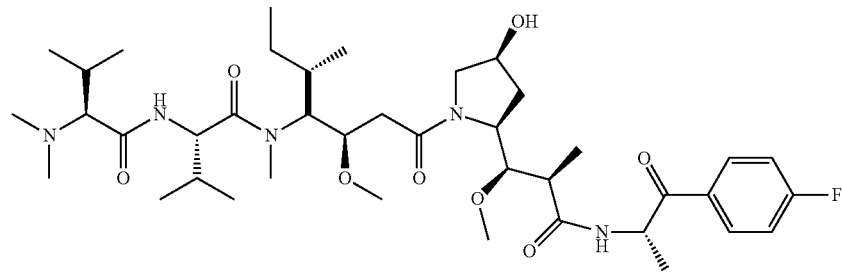

(III-19)

With the exception that (2S,4S)-t-butyl 4-((t-butyldimethylsilyl)oxy)-2-((1R,2R)-3-(((S)-1-(4-fluorophenyl)-1-oxopropan-2-yl)amino)-1-methoxy-2-methyl-3-oxopropyl)pyrrolidine-1-carboxylate (0.44 g, 0.78 mmol), obtained by using (S)-2-amino-1-(4-fluorophenyl)propan-1-one instead of 2-(2,6-difluorophenyl)ethanamine, was used, the same procedure as in Preparation Example 2-14 was repeated to afford the title compound. 0.34 g (58%).

LC-MS m/z: 764 [M$^+$]$^+$

PREPARATION EXAMPLE 2-16

Preparation of Compound (III-20)

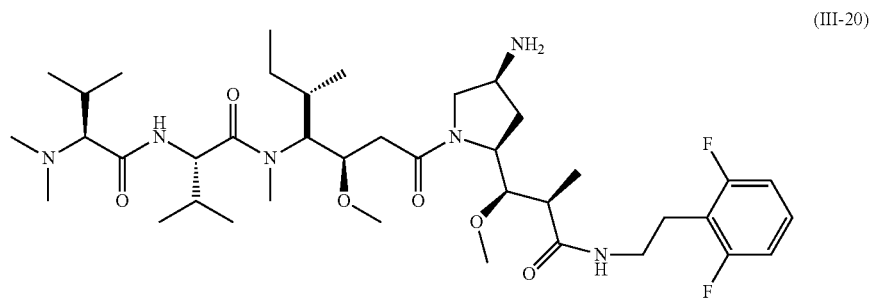 [SMILES: CC[C@H](C)[C@@H]([C@@H](CC(=O)N1C[C@@H](N)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(III-20)

With the exception that (2S,4S)-t-butyl 4-azido-2-((1R,2R)-3-((2,6-difluorophenethyl)amino)-1-methoxy-2-methyl-3-oxopropyl)pyrrolidine-1-carboxylate (0.33 g, 0.71 mmol) was used instead of (2S,4S)-t-butyl 4-((t-butyldimethylsilyl)oxy)-2-((1R,2R)-3-((2,6-difluorophenethyl)amino)-1-methoxy-2-methyl-3-oxopropyl)pyrrolidine-1-carboxylate, the same procedure as in Preparation Example 2-14 was repeated to afford an amino-protected derivative of compound (III-20) (0.42 g, 76%).

$^1$H NMR (400 MHz, CDCl$_3$) δ 0.79-1.07 (m, 15 H), 1.20 (d, 2 H), 1.99-2.11 (m, 4 H), 2.18-2.28 (m, 5 H), 2.33-2.45 (m, 4 H), 2.90-3.27 (m, 6 H), 3.32-3.42 (m, 6 H), 3.47-3.54 (m, 2 H), 3.75-3.78 (m, 1 H), 3.85-3.98 (m, 2H), 4.19-4.21 (m, 1 H), 4.39-4.44 (m, 1 H), 4.46-4.80 (m, 1 H), 4.87-4.90 (m, 1 H), 6.17 (m, 1H), 6.84-6.95 (m, 2 H), 7.14-7.26 (m, 1 H)

The N-terminal amino-protected derivative of compound (III-20) (0.24 g, 0.31 mmol) was dissolved in 10 mL of methyl alcohol, and stirred for 14 hrs in the presence of 10% palladium carbon (15 mg) in a hydrogen atmosphere. After completion of the reaction, the reaction mixture was filtered through a Celite filter, and washed several times with methanol. Then, the solvent was removed in a vacuum to afford the title compound (0.23 g, 99%).

$^1$H NMR (400 MHz, CDCl$_3$) δ 0.79-1.03 (m, 14 H), 1.21-1.22 (m, 5H), 2.06-2.45 (m, 6 H), 2.89-3.02 (m, 4 H), 3.30-3.44 (m, 5 H), 3.47-3.52 (m, 2 H), 3.67-3.69 (m, 1 H), 3.71-4.39 (m, 3 H), 4.78-4.80 (m, 1 H), 6.17 (m, 1 H), 6.84-6.95 (m, 2 H), 7.14-7.26 (m, 1 H)

LC-MS m/z: 753 [M$^+$]$^+$, 775 [M+Na]$^+$

PREPARATION EXAMPLE 2-17

Preparation of Compound (III-21)

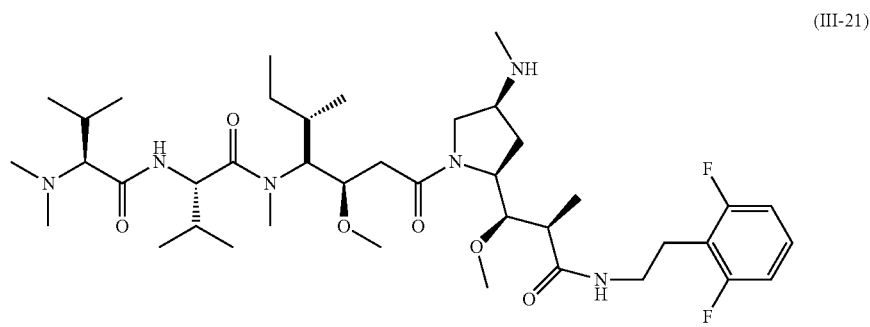 [SMILES: CC[C@H](C)[C@@H]([C@@H](CC(=O)N1C[C@@H](NC)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(III-21)

With the exception that (2S,4S)-t-butyl 4-(benzyl(methyl)amino)-2-((1R,2R)-3-((2,6-difluorophenethyl)amino)-1-methoxy-2-methyl-3-oxopropyl)pyrrolidine-1-carboxylate (0.13 g, 0.24 mmol) was used instead of (2S,4S)-t-butyl 4-((t-butyldimethylsilyl)oxy)-2-((1R,2R)-3-((2,6-difluorophenethyl)amino)-1-methoxy-2-methyl-3-oxopropyl)pyrrolidine-1-carboxylate, the same procedure as in Preparation Example 2-14 was repeated to afford an amino-protected derivative of compound (III-21) (0.13 g, 64%).

LC-MS m/z: 857.5 [M+]+

The N-terminal amino-protected derivative of compound (III-21) (0.13 g, 0.15 mmol) was dissolved in 10 mL of methyl alcohol, and stirred for 12 hrs in the presence of 10% palladium hydroxide (66 mg) under a hydrogen pressure (55 psi). After completion of the reaction, the reaction mixture was filtered through a Celite filter, and washed several times with methanol. Then, the solvent was removed in a vacuum to afford the title compound (115 mg, 100%).

LC-MS m/z 767.6[M+]+, 789.4[M+Na]+

PREPARATION EXAMPLE 2-18

Preparation of Compound (III-22)

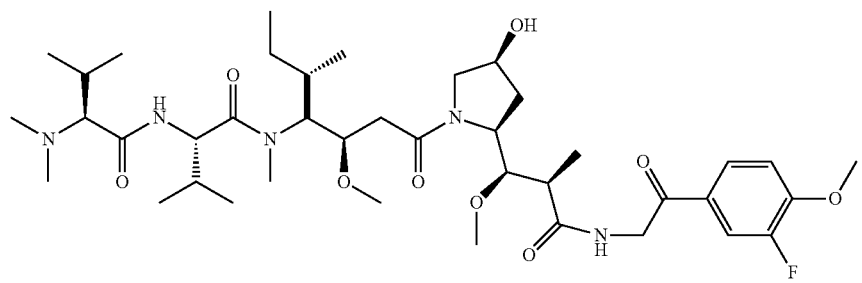
(III-22)

To a solution of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate (1.28 g, 2.73 mmol) in 30 mL of dichloromethane was dropwise added 10 mL of trifluoroacetic acid, followed by stirring at 20-25° C. for 3 hrs. When the reaction was completed, the reaction solvent was removed by vacuum concentration, and trifluoroacetic acid was completely removed by adding 5 ml of toluene twice, before a further reaction.

To a solution of (3R,4S,5S)-t-butyl 4-((S)-2-((S)-2-(dimethylamino)-3-methylbutanamido)-N, 3-dimethylbutanamido)-3-methoxy-5-methylheptanoate (1.33 g, 2.73 mmol) in 30 mL of dichloromethane was dropwise added 10 mL of trifluoroacetic acid, followed by stirring at 20-25° C. for 3 hrs. When the reaction was completed, the reaction was removed by vacuum concentration, and the trifluoroacetic acid was completely removed by adding 5 ml of toluene twice, before a further reaction.

Both the concentrates (TFA salts) were dissolved in 60 mL of dichloromethane, and sequentially added with diethyl cyanophosphate (DEPC) (0.52 mL, 3.28 mmol) and triethylamine (3.8 mL, 27.32 mmol) at 0° C. before being stirred at room temperature for 16 hrs. After completion of the reaction, the solvent was removed, and the residue was dissolved in 50 mL of ethylacetate and extracted with 1 M potassium hydrogen sulfite, water, a saturated sodium hydrogen carbonate solution, and brine. The organic layer was dried over anhydrous sodium sulfate, and concentrated in a vacuum. The concentrate was purified by silica gel column chromatography (ethylacetate: hexane=2:1→ethylacetate) to afford the title compound. (1.3 g, 60%).

$^1$H NMR (400 MHz, CDCl$_3$) δ 0.78-0.88 (m, 3 H), 0.91-1.07 (m, 17 H), 1.31-1.37 (m, 5 H), 1.99-2.11 (m, 3 H), 2.28 (s, 6 H), 2.43-2.62 (m, 6 H), 3.06 (s, 3H), 3.11-3.16 (m, 2 H), 3.34 (s, 3 H), 3.56 (s, 3H), 3.57-3.65 (m, 2 H), 3.97 (s, 3H), 4.08-4.09 (brs, 1H), 4.18-4.2 (d, 1H), 4.3 (brs, 1H), 4.39-4.42 (d, 2 H), 4.7-4.72 (t, 2H), 4.76-4.8 (m, 2H), 4.85-4.91 (brs, 1H), 7.03-7.1 (m, 1H), 7.69-7.78 (m, 2H)

LC-MS m/z: 780.8 [M+H]+, 802.8 [M+Na]+

PREPARATION EXAMPLE 2-19

Preparation of Compound (III-23)

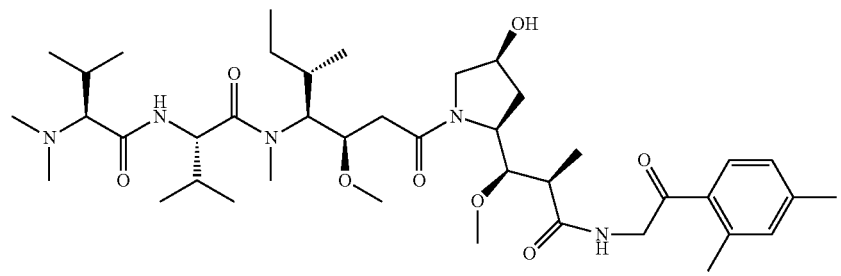
(III-23)

With the exception that (2S,4S)-t-butyl 2-((1R,2R)-3-((2-(2,4-dimethylphenyl)-2-oxoethyl)amino)-1-methoxy-2-methyl-3-oxopropyl)-4-hydroxypyrrolidine-1-carboxylate was used instead of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-18 was repeated to afford the title compound (3.2 g, 89%).

$^1$H NMR (400 MHz, CDCl$_3$) δ 0.79-0.85 (m, 3 H), 0.91-1.13 (m, 14 H), 1.15-1.19 (m, 3H), 1.35-1.38 (m, 5 H), 2.00-2.10 (m, 3 H), 2.18-2.24 (m, 3H), 2.37 (s, 3 H), 2.39-2.48 (m, 1H), 2.53 (s, 3H), 2.55-2.62 (m, 1H), 2.87 (s, 6H), 2.89 (s, 1H), 3.02 (s, 3H), 3.07-3.17 (m, 2H), 3.32 (s, 3H), 3.52 (s, 3H), 3.51-3.61 (m, 2H), 4.11-4.12 (brs, 1H), 4.16-4.18 (d, 1H), 4.30 (m, 1H), 4.37-4.4 (d, 1H), 4.64-4.66 (t, 2H), 4.69-4.74 (m, 2H), 6.90 (t, 1H), 7.09-7.11 (m, 2H), 7.66-7.68 (d, 2H)

LC-MS m/z: 760.6 [M+H]$^+$, 782.6 [M+Na]$^+$

PREPARATION EXAMPLE 2-20

Preparation of Compound (III-24)

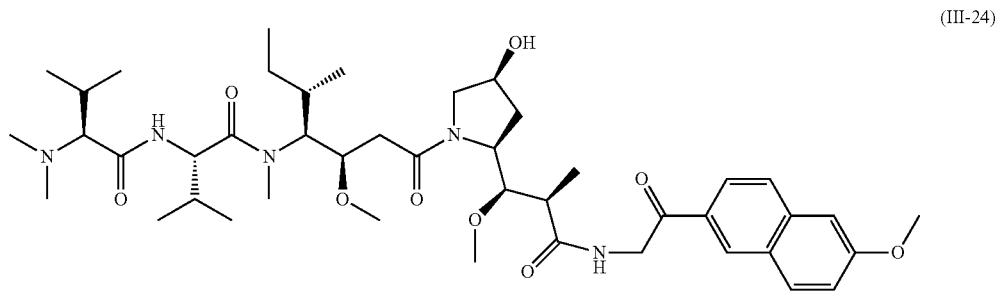

(III-24)

With the exception that (2S,4S)-t-butyl 4-hydroxy-2-(1R,2R)-1-methoxy-3-(2-(6-methoxynaphthalen-2-yl)-2-oxoethyl)amino)-2-methyl-3-oxopropyl)pyrrolidine-1-carboxylate was used instead of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-18 was repeated to afford the title compound (0.17 g, 67.5%).

$^1$H NMR (400 MHz, CDCl$_3$) δ 0.75-0.82 (m, 3H), 0.85-1.07 (m, 17H), 1.26-1.40 (m, 5H), 1.98-2.10 (m, 6H), 2.39-2.48 (m, 3H), 2.58-2.64 (m, 1H), 3.01 (s, 3H), 3.34 (s, 3H), 3.52-3.73 (m, 2H), 3.57 (s, 3H), 4.12 (brs, 1H), 4.19-4.21 (d, 1H), 4.25-4.31 (brs, 1H), 4.41-4.44 (d, 1H), 4.75-4.83 (m, 2H), 4.87-4.94 (m, 3H), 6.91-6.94 (t, 2H), 7.17 (s, 1H), 7.22-7.24 (d, 1H), 7.78-7.92 (m, 2H), 7.96-7.98 (d, 1H), 8.42 (s, 1H)

LC-MS m/z: 812.7 [M+H]$^+$, 834.7 [M+Na]$^+$

PREPARATION EXAMPLE 2-21

Preparation of Compound (III-25)

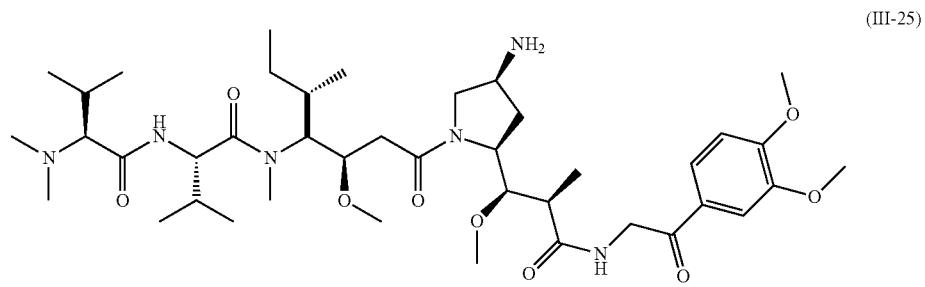

(III-25)

With the exception that (2S,4S)-t-butyl-4-azido-2((1R,2R)-3-((2-(3,4-dimethoxyphenyl)-2-oxoethyl)amino)-1-methoxy-2-methyl-3-oxopropyl)pyrrolidine-1-carboxylate (0.39 g, 0.77 mmol) was used instead of (2S,4S)-t-butyl 2-((1R,2R)-3-(2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-18 was repeated to afford an amino-protected derivative of compound (III-25) (0.56 g, 89%).

LC-MS m/z: 817.5 [M+H]$^+$, 839.5 [M+Na]$^+$

With the exception of using the amino-protected derivative of compound (III-25), the same procedure as in Preparation Example 2-16 was repeated to afford the title compound (0.38 g, 69%).

$^1$H NMR (400 MHz, CDCl$_3$) δ 0.79-0.82 (t, 3 H), 0.88-1.02 (m, 17 H), 1.23-1.28 (m, 1 H), 1.31-1.34 (m, 3 H), 1.96-2.12 (m, 2 H), 2.25-2.28 (m, 6 H), 2.36-2.52 (m, 2 H), 2.56-2.65 (m, 1 H), 2.98-3.03 (m, 3 H), 3.25-3.33 (m, 5 H), 3.47-3.49 (m, 1 H), 3.51-3.57 (m, 3 H), 3.72-3.73 (m, 1 H), 3.83-3.96 (d, 6 H), 4.09-4.16 (m, 2 H), 4.18-4.24 (m, 2 H), 4.25-4.36 (m, 1 H), 4.68-4.69 (m, 1 H), 4.74-4.88 m, 2 H), 4.82-4.88 (m, 1 H), 6.91-6.93 (d, 1 H), 7.50 (s, 1 H), 7.60-7.63 (d, 1 H)

PREPARATION EXAMPLE 2-22

Preparation of Compound (III-26)

(III-26)

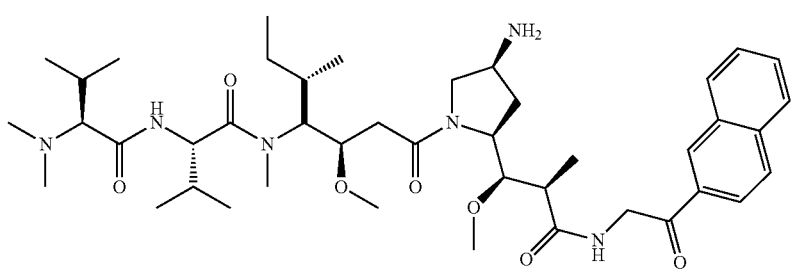

With the exception that (2S,4S)-t-butyl-4-azido-2-((1R,2R)-1-methoxy-2-methyl-3-((2-(naphthalen-2-yl)-2-oxoethyl)amino-3-oxopropyl)pyrrolidine-1-carboxylate (0.40 g, 0.81 mmol) was used instead of (2S,4S)-t-butyl 2-((1R,2R)-3-(2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-18 was repeated to afford an amino-protected derivative of compound (III-26) (0.60 g, 92%).

LC-MS m/z: 807.5 [M+H]$^+$, 829.5 [M+Na]$^+$

With the exception of using the amino-protected derivative of compound (III-26), the same procedure as in Preparation Example 2-16 was repeated to afford the title compound (0.28 g, 48%).

$^1$H NMR (400 MHz, CDCl$_3$) δ 0.78-0.82 (t, 3 H), 0.87-1.01 (m, 17 H), 1.22-1.28 (m, 1 H), 1.33-1.34 (m, 3 H), 1.80-2.12 (m, 2 H), 2.24-2.28 (m, 6 H), 2.38-2.50 (m, 2 H), 2.58-2.68 (m, 1 H), 2.95-3.05 (m, 3 H), 3.06-3.13 (m, 1 H), 3.20-3.23 (m, 1 H), 3.28-3.40 (m, 3 H), 3.43-3.45 (m, 1 H), 3.48-3.59 (m, 3 H), 3.60-3.67 (m, 1 H), 3.72-3.75 (m, 1 H), 4.04-4.17 (m, 2 H), 2.20-2.30 (m, 1 H), 4.32-4.36 (m, 1 H), 4.73-4.81 (m, 2 H), 4.85-4.86 (m, 1 H), 4.96-5.02 (m, 1 H), 7.57-7.65 (m, 2 H), 7.88-8.01 (m, 4 H), 8.51 (s, 1 H)

PREPARATION EXAMPLE 2-23

Preparation of Compound (III-27)

(III-27)

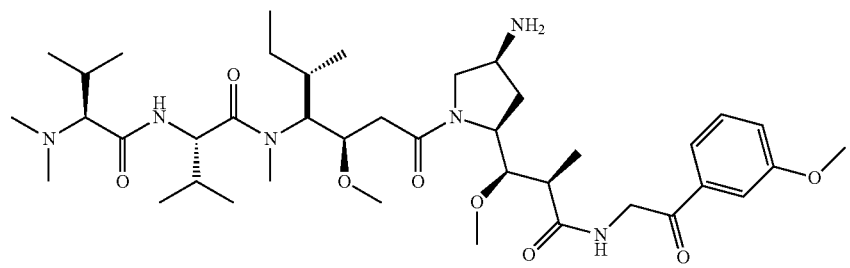

With the exception that (2S,4S)-t-butyl-4-azido-2-((1R,2R)-1-methoxy-3-((2-(3-methoxyphenyl)-2-oxoethyl)amino)-2-methyl-3-oxopropyl)pyrrolidine-1-carboxylate (0.30 g, 0.63 mmol) was used instead of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-18 was repeated to afford an amino-protected derivative of compound (III-27) (0.50 g, 100%).

LC-MS m/z: 787.4 [M+H]$^+$, 809.5 [M+Na]$^+$

With the exception of using the amino-protected compound of compound (III-27), the same procedure as in Preparation Example 2-16 was repeated to afford the title compound (0.23 g, 48%).

$^1$H NMR (400 MHz, CDCl$_3$) δ 0.78-0.82 (t, 3 H), 0.88-1.02 (m, 17 H), 1.25-1.29 (m, 3 H), 2.07-2.09 (m, 2 H), 2.18-2.31 (m, 6 H), 2.33-2.40 (m, 2 H), 2.52-2.64 (m, 1 H), 2.92-3.08 (m, 3 H), 3.20-3.25 (m, 1 H), 3.28-3.33 (m, 3 H), 3.38-3.40 (m, 1 H), 3.48-3.76 (m, 1 H), 3.78-3.88 (m, 3 H), 4.06-4.16 (m, 2 H), 4.19-4.28 (m, 1 H), 4.29-4.39 (m, 1 H), 4.70-4.71 (m, 1 H), 4.74-4.81 (m, 2 H), 4.88-4.95 (m, 1 H), 6.96-6.99 (d, 1 H), 7.38-7.42 (t, 1 H), 7.47 (s, 1 H), 7.53-7.55 (d, 1 H)

PREPARATION EXAMPLE 2-24

Preparation of Compound (III-28)

purified by silica gel column chromatography (ethylacetate:hexane=2:1→ethylacetate) to afford a hydroxy-protected compound (1.14 g, 84%).

$^1$H NMR (400 MHz, CDCl$_3$) δ 0.04 (s, 6 H), 0.81-1.06 (m, 19 H), 1.19 (m, 3 H), 1.46 (m, 2 H), 1.65 (m, 2 H), 1.97-2.17 (m, 3 H), 2.44-2.46 (m, 3 H), 2.71-2.80 (m, 3 H), 2.81-2.89 (m, 1 H), 2.91-2.94 (m, 2 H), 2.71-2.80 (m, 3 H) 3.04 (s, 3 H), 3.26-3.33 (m, 2 H), 3.37 (s, 3 H), 3.74 (m, 2 H), 4.28-4.31 (m, 2 H), 4.75-4.82 (m, 2 H), 6.18 (m, 1 H), 6.84-6.89 (m, 2 H), 7.15-7.19 (m, 1 H), 7.58 (d, 1 H)

A solution of the hydroxy-protected derivative of compound (1.14 g, 1.31 mmol) in 95 mL of tetrahydrofuran was stirred, together with 1.0 M tetrabutylammonium fluoride (4.9 mL, 4.09 mmol), for 5 hrs, followed by terminating the reaction with a saturated aqueous ammonium chloride solution. Extraction with 450 mL of ethylacetate and 300 mL of water was conducted before vacuum concentration. The concentrate was purified by silica gel column chromatography (dichloromethane:methanol=9:1) to afford (S)-2-((S)-2-(dimethylamino)-3-methylbutanamido)-N-((3R,4S,5S)-1-((2S,4S)-2-((1R,2R)-3-(((S)-1-(4-fluorophenyl)-1-oxopropan-2-yl)amino)-1-methoxy-2-methyl-3-oxopropyl)-4-hydroxypyrrolidin-1-yl)-3-methoxy-5-methyl-1-oxoheptan-4-yl)-N, 3-dimethylbutanamide (0.45 g, 45%).

$^1$H NMR (400 MHz, CDCl$_3$) δ 0.79-1.05 (m, 19 H), 1.26 (m, 3 H), 1.45 (m, 2 H), 1.66 (m, 2 H), 1.97-2.17 (m, 3 H), 2.44-2.46 (m, 3H), 2.71-2.80 (m, 3 H), 2.81-2.89 (m, 1 H),

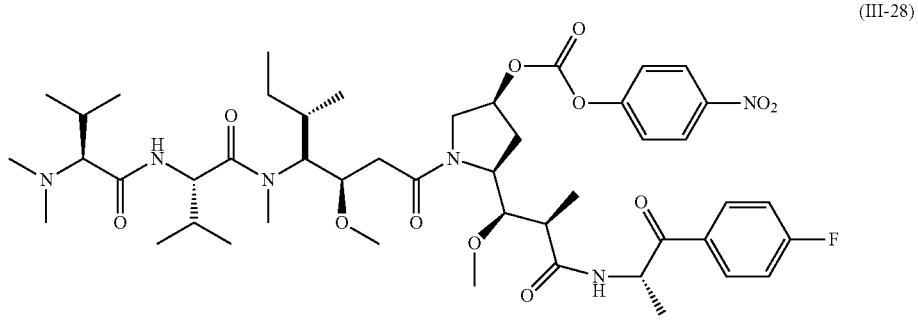 [SMILES: CC[C@H](C)[C@@H]([C@@H](CC(=O)N1C[C@@H](OC(=O)Oc2ccc([N+](=O)[O-])cc2)C[C@H]1[C@H](OC)[C@@H](C)C(=O)N[C@@H](C)C(=O)c1ccc(F)cc1)OC)N(C)C(=O)[C@@H](NC(=O)[C@H](C(C)C)N(C)C)C(C)C]

(III-28)

To a solution of (2S,4S)-t-butyl 4-((t-butyldimethylsilyl)oxy)-2-((1R,2R)-3-(((S)-1-(4-fluorophenyl)-1-oxopropan-2-yl)amino)-1-methoxy-2-methyl-3-oxopropyl)pyrrolidine-1-carboxylate (0.87 g, 1.56 mmol) in 10 mL of dichloromethane was dropwise added 7 mL of trifluoroacetic acid, followed by stirring at 20-25° C. for 3 hrs. When the reaction was completed, the reaction solvent was removed by vacuum concentration, and trifluoroacetic acid was completely removed by adding 5 ml of toluene twice before subsequent reactions.

This concentrate (TFA salt) was dissolved, together with (3R,4S,5S)-4-((S)-2-((S)-2-(dimethylamino)-3-methylbutanamido)-N, 3-dimethylbutanamido)-3-methoxy-5-methylheptanoic acid (0.67 g, 1.56 mmol), in 5 mL of dimethylformamide, and added with diethyl cyanophosphate (DEPC) (0.26 mL, 1.56 mmol) and triethylamine (1.09 mL, 7.82 mmol) at 0° C. before being stirred at room temperature for 16 hrs. After completion of the reaction, the solvent was removed, and the residue was dissolved in 20 mL of ethylacetate and extracted with 1 M potassium hydrogen sulfite, water, a saturated sodium hydrogen carbonate solution, and brine. The organic layer was dried over anhydrous sodium sulfate, and concentrated in a vacuum. The concentrate was 2.91-2.94 (m, 2 H), 2.71-2.80 (m, 3 H), 3.04 (s, 3 H), 3.26-3.33 (m, 2 H), 3.37 (s, 3 H), 3.74 (m, 2 H), 4.28-4.31 (m, 2 H), 4.75-4.82 (m, 2 H), 6.18 (m, 1 H), 6.84-6.89 (m, 2 H), 7.15-7.19 (m, 1 H), 7.58 (d, 1 H)

LC-MS m/z: 754 [M+H]$^+$

A solution of this compound (0.45 g, 0.59 mmol) in 20 mL of dichloromethane was cooled to −50 to −60° C. and added with pyridine (0.29 ml, 3.54 mmol). To the reaction mixture, drops of a solution of p-nitrophenyl chloroformate (0.71 g, 3.54 mmol) in 10 mL of dichloromethane were slowly added over 20 min, followed by stirring at −50 to −60° C. for 3 hrs. When the reaction was completed, 20 mL of dichloromethane was further added to the reaction mixture, which was then extracted with a 0.5 M potassium hydrogen sulfite solution. The organic layer was dried over anhydrous sodium sulfate, and concentrated in a vacuum. The concentrate was purified by silica gel column chromatography to afford the title compound (0.4 g, 74%).

LC-MS m/z: 929.6 [M+H]$^+$

PREPARATION EXAMPLE 2-25

Preparation of Compound (III-29)

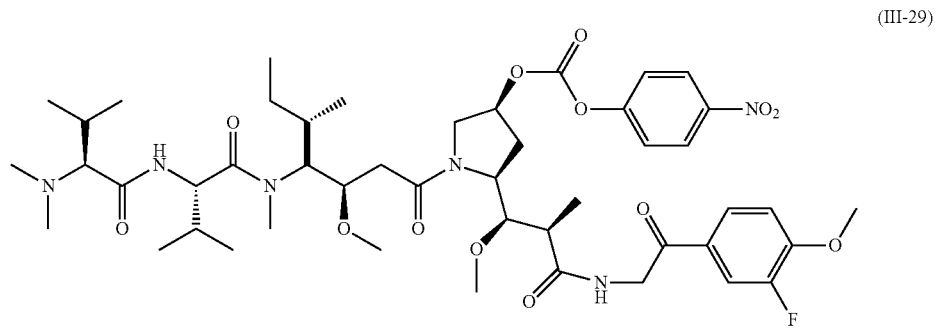

(III-29)

To a solution of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate (1.28 g, 2.73 mmol) in 30 mL of dichloromethane was dropwise added 10 mL of trifluoroacetic acid, followed by stirring at 20-25° C. for 3 hrs. When the reaction was completed, the reaction solvent was removed by vacuum concentration, and trifluoroacetic acid was completely removed by adding 10 ml of toluene twice, before a further reaction.

To a solution of (3R,4S,5S)-t-butyl 4-((S)-2-((S)-2-(dimethylamino)-3-methylbutanamido)-N, 3-dimethylbutanamido)-3-methoxy-5-methylheptanoate (1.33 g, 2.73 mmol) in 30 mL of dichloromethane was dropwise added 10 mL of trifluoroacetic acid, followed by stirring at 20-25° C. for 3 hrs. When the reaction was completed, the solvent was removed by vacuum concentration, and the trifluoroacetic acid was completely removed by adding 10 mL of toluene twice, before the subsequent reaction.

Both the concentrates (TFA salts) were dissolved in 60 mL of dichloromethane, and sequentially added with diethyl cyanophosphate (DEPC) (0.52 mL, 3.28 mmol) and triethylamine (3.8 mL, 27.32 mmol) at 0° C. before being stirred at room temperature for 16 hrs. After completion of the reaction, the solvent was removed, and the residue was dissolved in 50 mL of ethylacetate and extracted with 1 M potassium hydrogen sulfite, water, a saturated sodium hydrogen carbonate solution, and brine. The organic layer was dried over anhydrous sodium sulfate, and concentrated in a vacuum. The concentrate was purified by silica gel column chromatography (ethylacetate: hexane=2:1→ethylacetate) to afford (S)-2-((S)-2-(dimethylamino)-3-methylbutanamido)-N-((3R,4S,5S)-1-((2S,4S)-2-((1R,2R)-3-((2-(3-fluoro-4-methoxyphenyl)-2-oxoethyl)amino)-1-methoxy-2-methyl-3-oxopropyl)-4-hydroxypyrrolidin-1-yl)-3-methoxy-5-methyl-1-oxoheptan-4-yl)-N, 3-dimethylbutanamide (1.3 g, 60%).

$^1$H NMR (400 MHz, CDCl$_3$) δ 0.78-0.88 (m, 3 H), 0.91-1.07 (m, 17 H), 1.31-1.37 (m, 5 H), 1.99-2.11 (m, 3 H), 2.28 (s, 6 H), 2.43-2.62 (m, 6 H), 3.06 (s, 3H), 3.11-3.16 (m, 2 H), 3.34 (s, 3 H), 3.56 (s, 3H), 3.57-3.65 (m, 2 H), 3.97 (s, 3H), 4.08-4.09 (brs, 1H), 4.18-4.2 (d, 1H), 4.3 (brs, 1H), 4.39-4.42 (d, 2 H), 4.7-4.72 (t, 2 H), 4.76-4.8 (m, 2H), 4.85-4.91 (brs, 1H), 7.03-7.1 (m, 1H), 7.69-7.78 (m, 2H)

LC-MS m/z: 780.8 [M+H]$^+$, 802.8 [M+Na]$^+$

A solution of this compound (1.27 g, 1.63 mmol) in 20 mL of dichloromethane was cooled to −50 to −60° C. and added with pyridine (1.3 ml, 16.28 mmol). To the reaction mixture, drops of a solution of p-nitrophenyl chloroformate (16.28 g, 3.3 mmol) in 10 mL of dichloromethane were slowly added over 20 min, followed by stirring at −50 to −60° C. for 3 hrs. When the reaction was completed, 20 mL of dichloromethane was further added to the reaction mixture, which was then extracted with a 0.5 M potassium hydrogen sulfite solution. The organic layer was dried over anhydrous sodium sulfate, and concentrated in a vacuum. The concentrate was purified by silica gel column chromatography to afford the title compound (0.8 g, 54%).

LC-MS m/z: 945.7 [M+H]$^+$, 967.7 [M+Na]$^+$

PREPARATION EXAMPLE 2-26

Preparation of Compound (III-30)

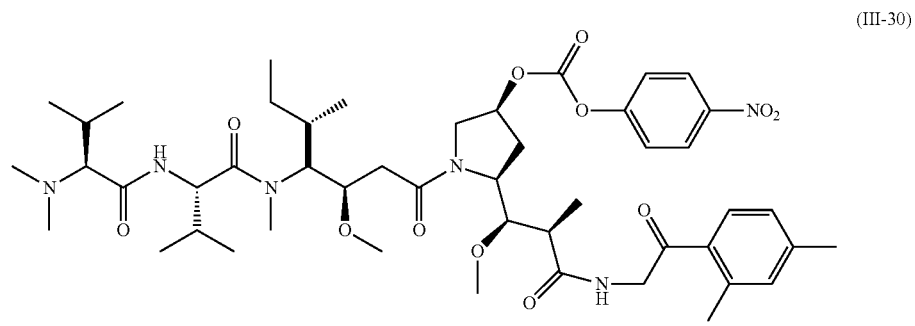

(III-30)

With the exception that (2S,4S)-t-butyl 2-((1R,2R)-3-((2-(2,4-dimethylphenyl)-2-oxoethyl)amino)-1-methoxy-2-methyl-3-oxopropyl)-4-hydroxypyrrolidine-1-carboxylate was used instead of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-25 was repeated to afford (S)-2-((S)-2-(dimethylamino)-3-methylbutanamido)-N-((3R,4S,5S)-1-((2S,4S)-2-((1R,2R)-3-((2-(2,4-dimethylphenyl)-2-oxoethyl)amino)-1-methoxy-2-methyl-3-oxopropyl)-4-hydroxypyrrolidin-1-yl)-3-methoxy-5-methyl-1-oxoheptan-4-yl)-N,3-dimethylbutanamide (3.2 g, 89%).

$^1$H NMR (400 MHz, CDCl$_3$) δ 0.79-0.85 (m, 3 H), 0.91-1.13 (m, 14 H), 1.15-1.19 (m, 3H), 1.35-1.38 (m, 5 H), 2.00-2.10 (m, 3 H), 2.18-2.24 (m, 3H), 2.37 (s, 3 H), 2.39-2.48 (m, 1H), 2.53 (s, 3H), 2.55-2.62 (m, 1H), 2.87 (s, 6H), 2.89 (s, 1H), 3.02 (s, 3H), 3.07-3.17 (m, 2H), 3.32 (s, 3H), 3.52 (s, 3H), 3.51-3.61 (m, 2H), 4.11-4.12 (brs, 1H), 4.16-4.18 (d, 1H), 4.30 (m, 1H), 4.37-4.4 (d, 1H), 4.64-4.66 (t, 2H), 4.69-4.74 (m, 2H), 6.90 (t, 1H), 7.09-7.11 (m, 2H), 7.66-7.68 (d, 2H)

LC-MS m/z: 760.6 [M+H]$^+$, 782.6 [M+Na]$^+$

With the exception of using this compound, the same procedure as in Preparation Example 2-25 was repeated to afford the title compound (1.6 g, 43%).

LC-MS m/z: 925.6 [M+H]$^+$, 947.6 [M+Na]$^+$

PREPARATION EXAMPLE 2-27

Preparation of Compound (III-31)

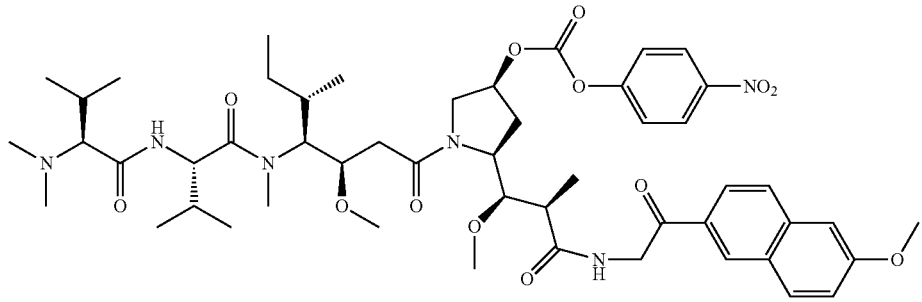

(III-31)

With the exception that (2S,4S)-t-butyl 4-hydroxy-2-((1R,2R)-1-methoxy-3-((2-(6-methoxynaphthalen-2-yl)-2-oxoethyl)amino)-2-methyl-3-oxopropyl)pyrrolidine-1-carboxylate was used instead of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-25 was repeated to afford (S)-2-((S)-2-(dimethylamino)-3-methylbutanamido)-N-((3R,4S,5S)-1-((2S,4S)-4-hydroxy-2-((1R,2R)-1-methoxy-3-((2-(6-methoxynaphthalen-2-yl)-2-oxoethyl)amino)-2-methyl-3-oxopropyl)pyrrolidin-1-yl)-3-methoxy-5-methyl-1-oxoheptan-4-yl)-N,3-dimethylbutanamide (0.17 g, 67.5%).

$^1$H NMR (400 MHz, CDCl$_3$) δ0.75-0.82 (m, 3H), 0.85-1.07 (m, 17H), 1.26-1.40 (m, 5H), 1.98-2.10 (m, 6H), 2.39-2.48 (m, 3H), 2.58-2.64 (m, 1H), 3.01 (s, 3H), 3.34 (s, 3H), 3.52-3.73 (m, 2H), 3.57 (s, 3H), 4.12 (brs, 1H), 4.19-4.21 (d, 1H), 4.25-4.31 (brs, 1H), 4.41-4.44 (d, 1H), 4.75-4.83 (m, 2H), 4.87-4.94 (m, 3H), 6.91-6.94 (t, 2H), 7.17 (s, 1H), 7.22-7.24 (d, 1H), 7.78-7.92 (m, 2H), 7.96-7.98 (d, 1H), 8.42 (s, 1H)

LC-MS m/z: 812.7 [M+H]$^+$, 834.7 [M+Na]$^+$

With the exception of using this compound, the same procedure as in Preparation Example 2-25 was repeated to afford the title compound (0.15 g, 87%).

LC-MS m/z: 977.9 [M+H]$^+$, 999.9 [M+Na]$^+$

PREPARATION EXAMPLE 2-28

Preparation of Compound (III-32)

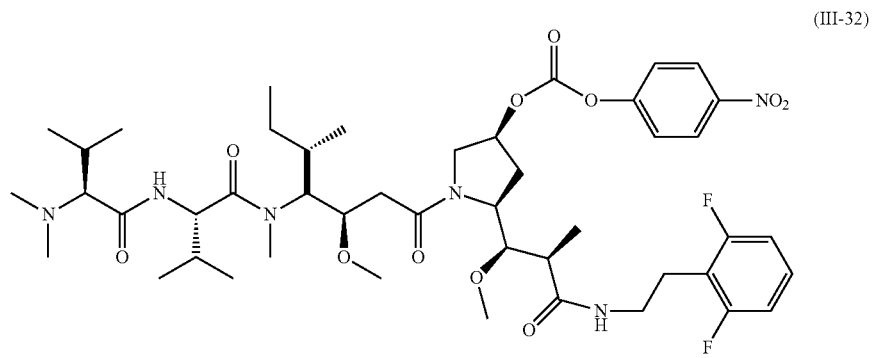 [SMILES: CC[C@H](C)[C@@H]([C@@H](CC(=O)N1C[C@@H](OC(=O)Oc2ccc([N+](=O)[O-])cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(III-32)

With the exception that (2S,4S)-t-butyl 4-((t-butyldimethylsilyl)oxy)-2-((1R,2R)-3-((2,6-difluorophenethyl)amino)-1-methoxy-2-methyl-3-oxopropyl)pyrrolidine-1-carboxylate (0.87 g, 70.9%) was used instead of (2S,4S)-t-butyl 2-((1R,2R)-3-((2-(3-fluoro-4-methoxyphenyl)-2-oxoethyl)amino)-1-methoxy-2-methyl-3-oxopropyl)-4-hydroxypyrrolidine-1-carboxylate, the same procedure as in Preparation Example 2-24 was repeated to afford (2S)-N-((3R,4S)-1-((2S,4S)-2-((1R, 2R)-3-((2,6-difluorophenethyl)amino)-1-methoxy-2-methyl-3-oxopropyl)-4-hydroxypyrrolidin-1-yl)-3-methoxy-5-methyl-1-oxoheptan-4-yl)-2-((S)-2-(dimethylamino)-3-methylbutanamido)-N,3-dimethylbutanamide (0.45 g, 45%).

$^1$H NMR (400 MHz, CDCl$_3$) δ 0.79-1.05 (m, 19 H), 1.26 (m, 3 H), 1.45 (m, 2 H), 1.66 (m, 2 H), 1.97-2.17 (m, 3 H), 2.44-2.46 (m, 3 H), 2.71-2.80 (m, 3 H), 2.81-2.89 (m, 1 H), 2.91-2.94 (m, 2 H), 2.71-2.80 (m, 3 H), 3.04 (s, 3 H), 3.26-3.33 (m, 2 H), 3.37 (s, 3 H), 3.74 (m, 2 H), 4.28-4.31 (m, 2 H), 4.75-4.82 (m, 2 H), 6.18 (m, 1 H), 6.84-6.89 (m, 2 H), 7.15-7.19 (m, 1 H), 7.58 (d, 1 H)

LC-MS m/z: 754 [M$^+$]$^+$

With the exception of using this compound, the same procedure as in Preparation Example 2-24 was repeated to afford the title compound (0.46 g, 83%).

LC-MS m/z: 920.1 [M+H]$^+$

PREPARATION EXAMPLE 3

Preparation of Compounds of Chemical Formula IV-1, IV-2, IV-3, and IV-4

PREPARATION EXAMPLE 3-1

Preparation of Compound (IV-5)

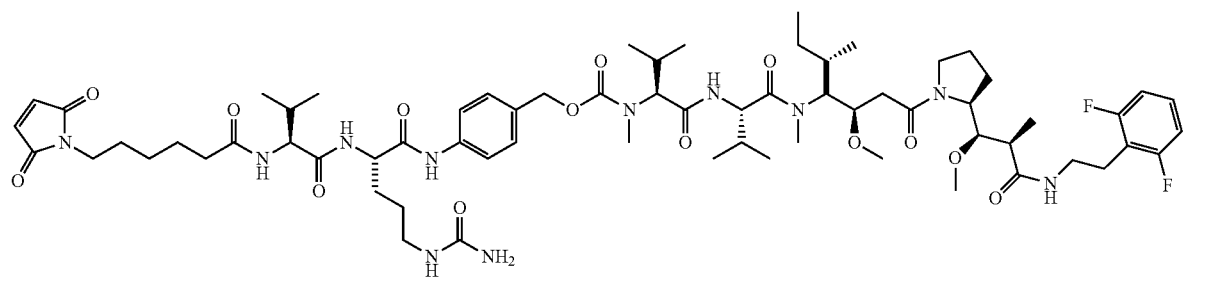

(IV-5)

Under an argon stream, compound (II-1) (0.37 g, 0.50 mmol), prepared in Preparation Example 1-1, was added to a solution of compound (III-5) (0.36 g, 0.50 mmol), prepared in Preparation Example 2-1, in 14 mL of anhydrous dimethylformamide. The reaction mixture was cooled to 0° C., and was sequentially added with HOBt (81 mg, 0.60 mmol) and 3.5 mL of anhydrous pyridine before being stirred at room temperature for 15 hrs. After completion of the reaction, vacuum concentration was carried out, and the residue was purified by silica gel column chromatography to afford the title compound as an ivory solid (0.49 g, 74%).

MALDI-TOF MS m/z: 1345.6 [M+Na]$^+$, 1361.6 [M+K]$^+$

PREPARATION EXAMPLE 3-2

Preparation of Compound (IV-6)

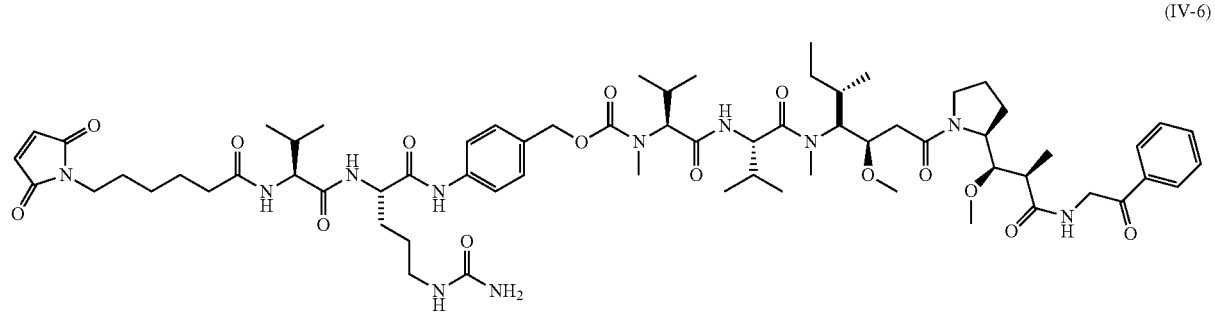 [SMILES: CC[C@H](C)[C@@H]([C@@H](CC(=O)N1CCC[C@H]1[C@H](OC)[C@@H](C)C(=O)NCC(=O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(IV-6)

With the exception that compound (III-6) (0.35 g, 0.50 mmol), prepared in Preparation Example 2-2, was used instead of compound (III-5), prepared in Preparation Example 2-1, the same procedure as in Preparation Example 3-1 was repeated to afford the title compound (0.42 g, 72%).

MALDI-TOF MS m/z: 1322.8 [M+Na]$^+$, 1339.0 [M+K]$^+$

PREPARATION EXAMPLE 3-3

Preparation of Compound (IV-7)

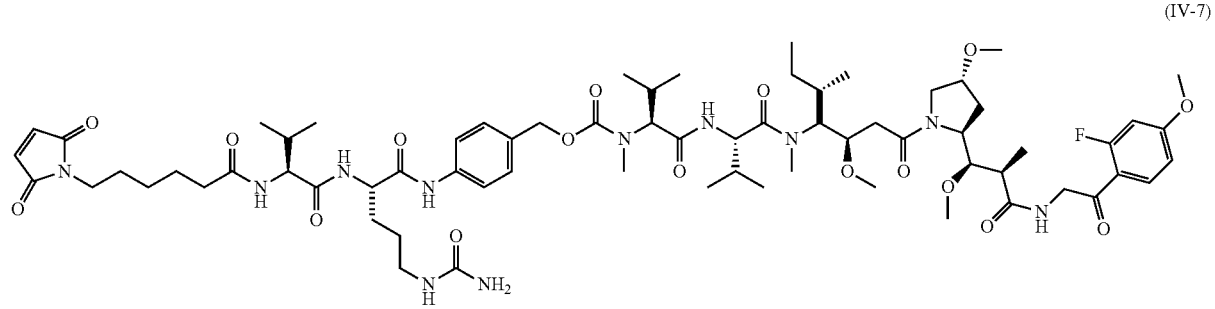 [SMILES: CC[C@H](C)[C@@H]([C@@H](CC(=O)N1C[C@H](OC)C[C@H]1[C@H](OC)[C@@H](C)C(=O)NCC(=O)c1ccc(OC)cc1F)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(IV-7)

With the exception that compound (III-7) (79 mg, 0.10 mmol), prepared in Preparation Example 2-3, was used instead of compound (III-5), prepared in Preparation Example 2-1, the same procedure as in Preparation Example 3-1 was repeated to afford the title compound (97 mg, 78%).

MALDI-TOF MS m/z: 1400.3 [M+Na]$^+$

PREPARATION EXAMPLE 3-4

Preparation of Compound (IV-8)

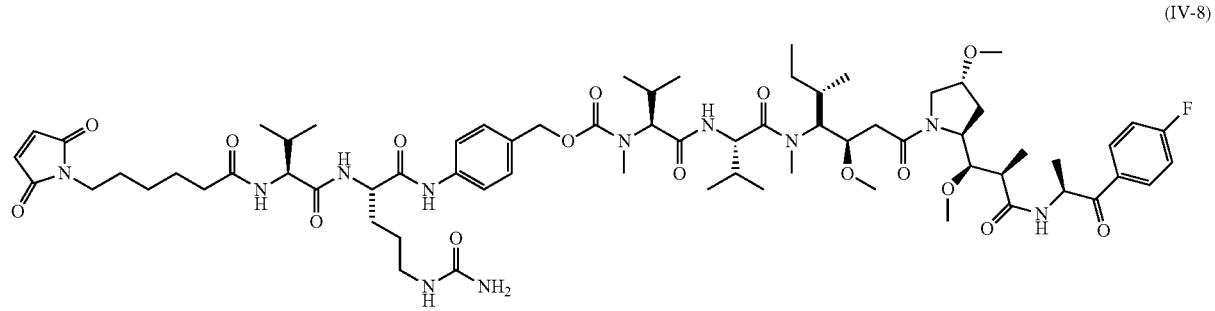 [SMILES: CC[C@H](C)[C@@H]([C@@H](CC(=O)N1C[C@H](OC)C[C@H]1[C@H](OC)[C@@H](C)C(=O)N[C@@H](C)C(=O)c1ccc(F)cc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(IV-8)

With the exception that compound (III-8) (104 mg, 0.14 mmol), obtained in Preparation Example 2-4, was used instead of compound (III-5), obtained in Preparation Example 2-1, the same procedure as in Preparation Example 3-1 was repeated to afford the title compound (86 mg, 48%).

MALDI-TOF MS m/z: 1386.9 [M+Na]$^+$, 1402.9 [M+K]$^+$

PREPARATION EXAMPLE 3-5

Preparation of Compound (IV-9)

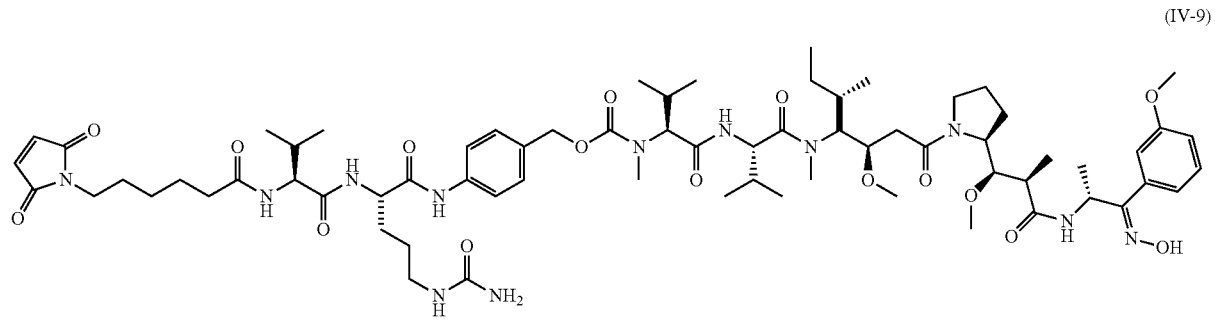 [SMILES: CC[C@H](C)[C@@H]([C@@H](CC(=O)N1CCC[C@H]1[C@H](OC)[C@@H](C)C(=O)N[C@H](C)/C(=N/O)c1cccc(OC)c1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(IV-9)

With the exception that compound (III-9) (65 mg, 0.085 mmol), obtained in Preparation Example 2-5, was used instead of compound (III-5), obtained in Preparation Example 2-1, the same procedure as in Preparation Example 3-1 was repeated to afford the title compound (43 mg, 41%).

MALDI-TOF MS m/z: 1381.6 [M+Na]$^+$

PREPARATION EXAMPLE 3-6

Preparation of Compound (IV-10)

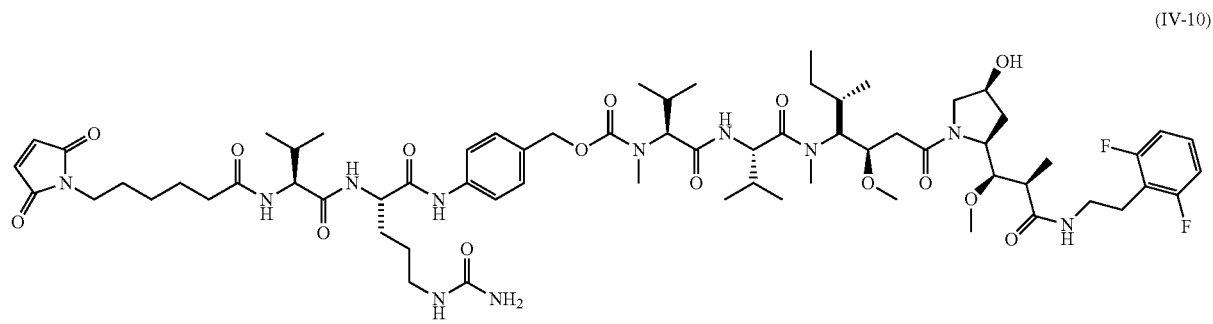 [SMILES: CC[C@H](C)[C@@H]([C@@H](CC(=O)N1C[C@@H](O)C[C@H]1[C@H](OC)[C@@H](C)C(=O)NCCc1c(F)cccc1F)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(IV-10)

With the exception that compound (III-10) (82 mg, 0.11 mmol), obtained in Preparation Example 2-6, was used instead of compound (III-5), obtained in Preparation Example 2-1, the same procedure as in Preparation Example 3-1 was repeated to afford the title compound (89 mg, 66%).

MALDI-TOF MS m/z: 1360.0 [M+Na]$^+$, 1377.2 [M+K]$^+$

PREPARATION EXAMPLE 3-7

Preparation of Compound (IV-11)

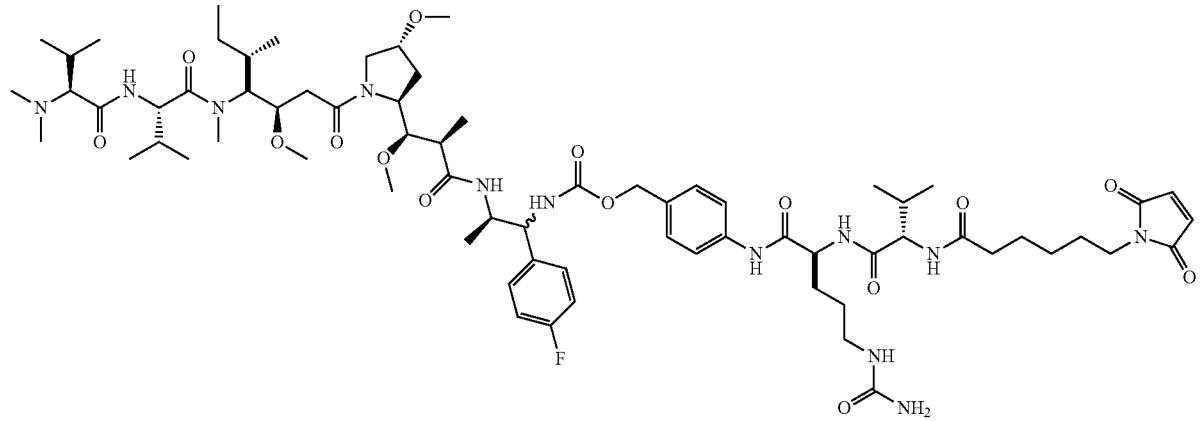

(IV-11)

Under an argon stream, compound (III-11)(89 mg, 0.116 mmol), obtained in Preparation Example 2-7, was dissolved in 8 mL of anhydrous dimethyl formamide, and added with compound (II-1)(78 mg, 0.106 mmol), obtained in Preparation Example 1-1. The reaction mixture was cooled to 0° C., and was sequentially added with HOBt (17 mg, 0.128 mmol) and 2.0 mL of anhydrous pyridine before being stirred at room temperature for 17 hrs. After completion of the reaction, vacuum concentration was carried out, and the residue was purified by silica gel column chromatography to afford the title compound (106 mg, 73%).

LC-MS m/z: 1377.8 [M$^+$]$^+$, 1400.8 [M+Na]$^+$

PREPARATION EXAMPLE 3-8

Preparation of Compound (IV-12)

With the exception that compound (III-12)(17 mg, 0.023 mmol), obtained in Preparation Example 2-8, was used instead of compound (III-11), obtained in Preparation Example 2-7, the same procedure as in Preparation Example 3-7 was repeated to afford the title compound (26 mg, 93%).

MALDI-TOF MS m/z: 1351.3 [M+Na]$^+$, 1367.7 [M+K]$^+$ $^1$H NMR (400 MHz, CD$_3$OD) δ 0.81-0.91 (m, 6H), 0.91-1.03 (m, 21H), 1.63 (d, 2H), 1.22 (d, 1H), 1.28 (m, 2H), 1.32 (m, 1H), 1.50-1.63 (m, 6H), 1.68 (m, 2H), 1.82-1.90 (m, 2H), 1.95 (s, 3H), 1.98 (m, 4H), 2.23-2.28 (m, 3H), 2.34 (brd, 1H), 2.40 (s, 6H), 2.58-2.70 (m, 1H), 2.80-2.85 (m, 1H), 2.91-2.98 (m, 1H), 3.12 (s, 3H), 3.15-3.27 (m, 2H), 3.26-3.33 (m, 8H, OCH$_3$), 3.34 (d, 2H), 3.42-3.48 (m, 5H, OCH$_3$), 3.52 (m, 1H), 3.7-3.96 (m, 2H), 3.96-4.08 (m, 2H), 4.15 (d, 1H), 4.18 (m, 1H), 4.44-4.54 (m, 2H), 4.66 (d, 1H), 4.54-5.10 (m, 5H), 6.76 (m, 1H), 7.02-7.12 (m, 2H), 7.23-7.28 (m, 2H), 7.30-7.38 (m, 2H), 7.51-7.58 (m, 2H)

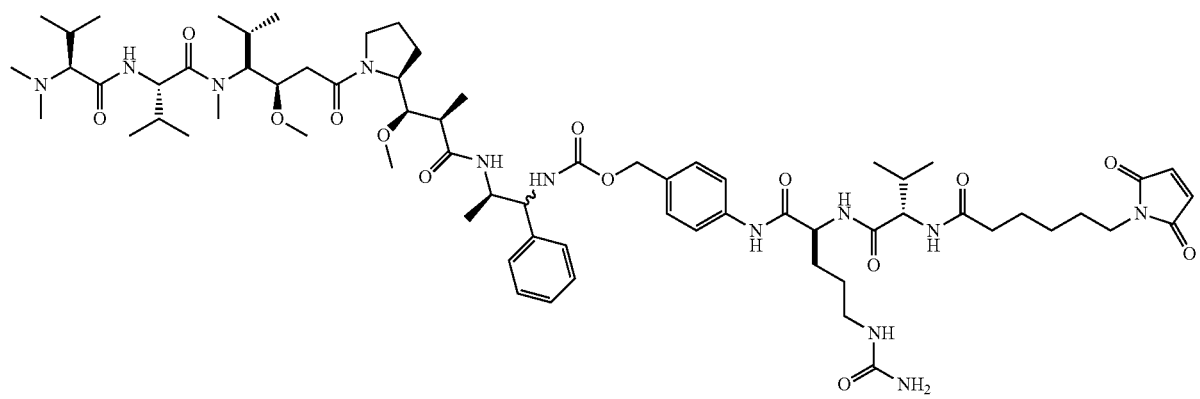

(IV-12)

PREPARATION EXAMPLE 3-9

Preparation of Compound (IV-13)

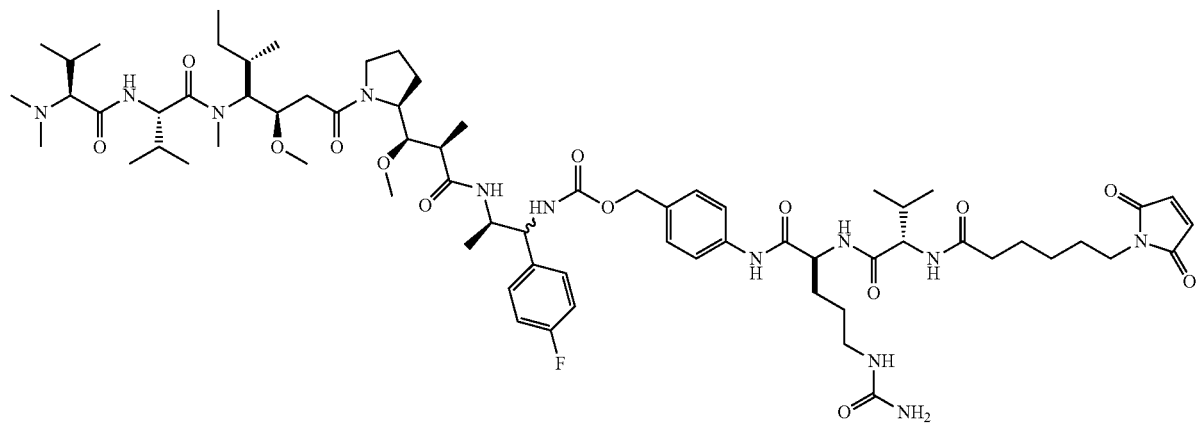

(IV-13)

With the exception that compound (III-13) (478 mg, 0.638 mmol), obtained in Preparation Example 2-9, was used instead of compound (III-11), obtained in Preparation Example 2-7, the same procedure as in Preparation Example 3-7 was repeated to afford the title compound (347 mg, 40%).

LC-MS m/z: 1347 [M$^+$]$^+$ $^1$H NMR (400 MHz, CD$_3$OD) δ 0.76-0.90 (m, 6H), 0.90-1.12 (m, 18H), 1.16 (m, 4H), 1.19 (m, 3H), 1.28 (m, 3H), 1.28 (m, 3H), 1.40 (m, 2H), 1.50-1.66 (m, 9H), 1.66-1.80 (m, 2H), 1.93 (s, 3H), 2.0-2.14 (m, 4H), 2.26 (m, 3H), 2.38 (d, 6H), 2.44 (m, 1H), 2.50-2.65 (m, 1H), 2.77 (m, 2H), 3.10-3.24 (m, 6H), 3.25-3.36 (m, 7H, OCH$_3$), 3.45 (t, 3H), 3.58 (m, 1H), 3.66 (m, 1H), 3.82 (m, 1H), 4.06 (m, 1H), 4.14 (m, 2H), 4.26 (m, 1H), 4.36 (m, 1H), 4.48 (m, 2H), 4.63 (m, 1H), 4.69 (m, 3H), 6.78 (s, 2H), 6.97 (m, 1H), 7.08 (m, 1H), 7.25 (m, 2H), 7.34 (m, 2H), 7.54 (m, 2H)

PREPARATION EXAMPLE 3-10

Preparation of Compound (IV-14)

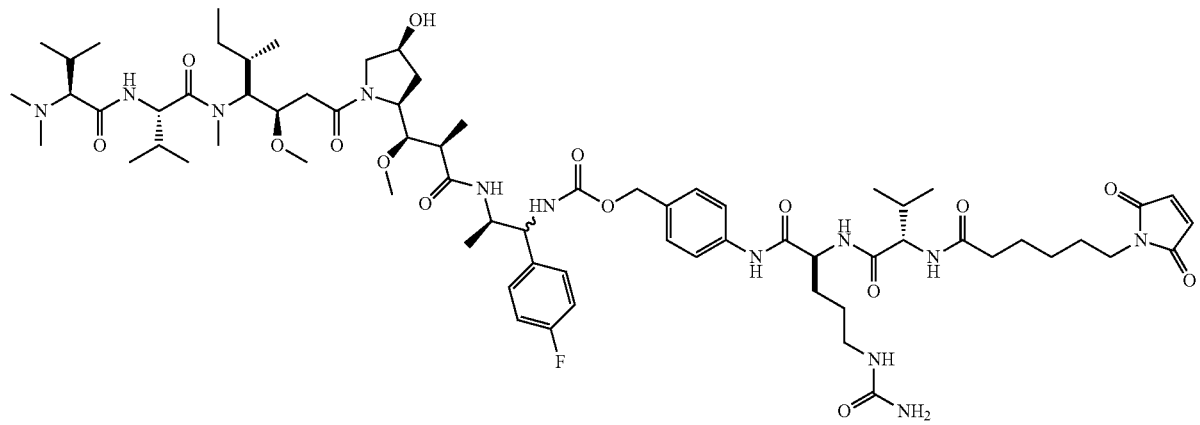

(IV-14)

With the exception that compound (III-14)(0.39 g, 0.51 mmol), obtained in Preparation Example 2-10, was used instead of compound (III-11), obtained in Preparation Example 2-7, the same procedure as in Preparation Example 3-7 was repeated to afford the title compound (453 mg, 65%).

LC-MS m/z: 1364[M+1]$^+$ $^1$H NMR (400 MHz, CD$_3$OD) δ 0.81-0.91 (m, 6H), 0.91-1.03 (m, 21H), 1.13 (d, 2H), 1.22 (d, 1H), 1.28 (m, 2H), 1.32 (m, 1H), 1.50-1.63 (m, 6H), 1.68 (m, 2H), 1.82-1.90 (m, 2H), 1.95 (s, 3H), 1.98 (m, 4H), 2.23-2.28 (m, 3H), 2.34 (brd, 1H), 2.40 (s, 6H), 2.58-2.70 (m, 1H), 2.80-2.85 (m, 1H), 2.91-2.98 (m, 1H), 3.12 (s, 3H), 3.15-3.27 (m, 2H), 3.27-3.33 (m, 8H, OCH$_3$), 3.34 (d, 2H), 3.42-3.48 (m, 5H, OCH$_3$), 3.52 (m, 1H), 3.7-3.96 (m, 2H), 3.96-4.08 (m, 2H), 4.15 (d, 1H), 4.18 (m, 1H), 4.44-4.54 (m, 2H), 4.66 (d, 1H), 4.74-5.10 (m, 5H), 6.76 (m, 1H), 7.02-7.12 (m, 2H), 7.23-7.28 (m, 2H), 7.30-7.38 (m, 2H), 7.51-7.58 (m, 2H)

PREPARATION EXAMPLE 3-11

Preparation of Compound (IV-15)

(IV-15)

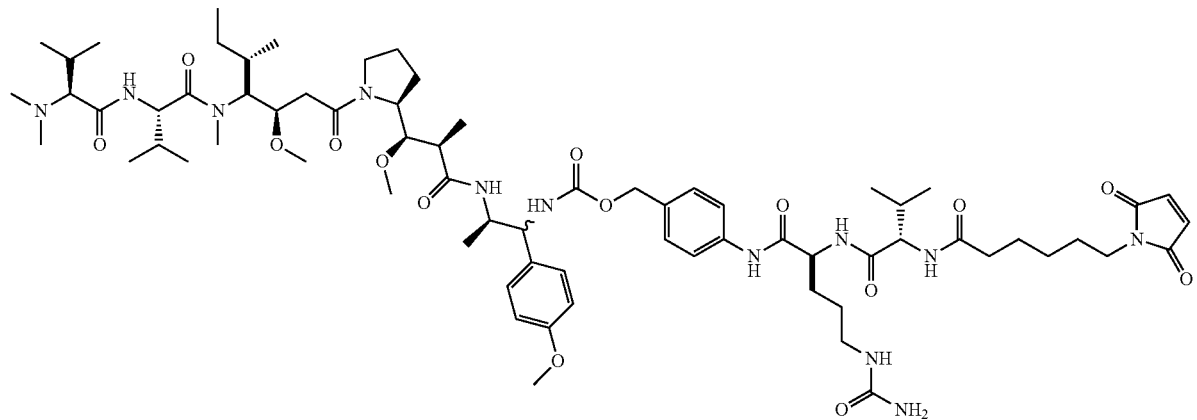

With the exception that compound (III-15)(110 mg, 0.144 mmol), obtained in Preparation Example 2-11, was used instead of compound (III-11), obtained in Preparation Example 2-7, the same procedure as in Preparation Example 3-7 was repeated to afford the title compound (82 mg, 42%).

LC-MS m/z: 1360 [M+1]$^+$ $^1$H NMR (400 MHz, CD$_3$OD) δ0.81-0.91 (m, 6H), 0.92-1.05 (m, 19H), 1.3-1.2 (m, 3H), 1.22 (d, 1H), 1.28 (m, 2H), 1.32 (m, 1H), 1.50-1.63 (m, 6H), 1.68 (m, 2H), 1.82-1.90 (m, 2H), 1.95 (s, 3H), 1.98 (m, 3H), 2.23-2.28 (m, 3H), 2.37 (d, 6H), 2.61 (m, 1H), 2.78 (m, 1H), 3.12 (s, 3H), 3.16-3.24 (m, 2H), 3.26-3.32 (m, 15H, OCH$_3$), 3.32-3.28 (m, 5H, OCH$_3$), 3.42-3.50 (m, 1H), 3.74 (d, 3H), 3.86 (m, 1H), 3.96-4.08 (m, 2H), 4.14 (d, 1H), 4.18-4.10 (m, 1H), 4.42-4.52 (m, 2H), 4.64-5.10 (m, 5H), 6.76 (d, 2H), 6.87 (m, 2H), 7.24 (m, 4H), 7.55 (m, 2H)

PREPARATION EXAMPLE 3-12

Preparation of Compound (IV-16)

(IV-16)

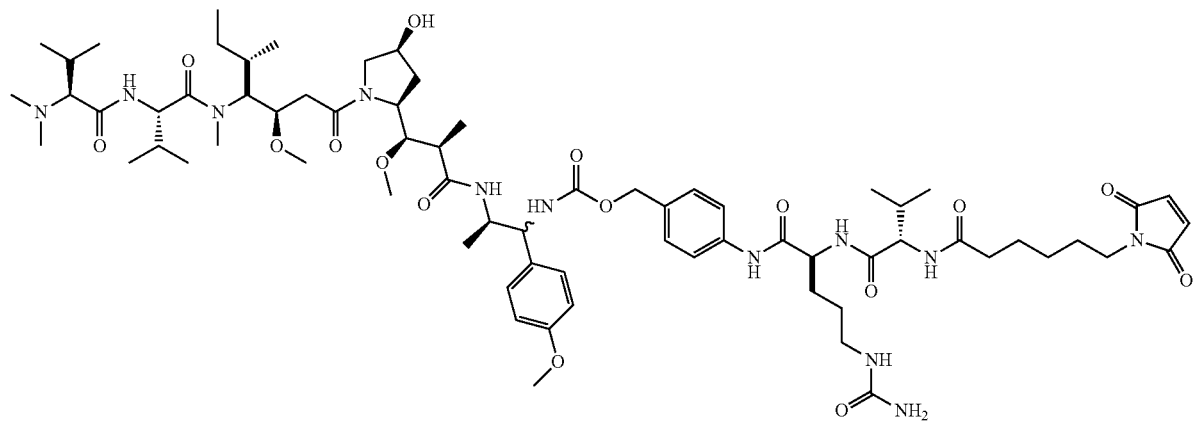

With the exception that compound (III-16)(179 mg, 0.23 mmol), obtained in Preparation Example 2-12, was used instead of compound (III-11), obtained in Preparation Example 2-7, the same procedure as in Preparation Example 3-7 was repeated to afford the title compound (268 mg, 85%).

LC-MS m/z: 1375 [M+1]

$^1$H NMR (400 MHz, DMSO-d$_6$) δ 0.71-0.80 (m, 5H), 0.80-0.98 (m, 18H), 0.98-1.10 (m, 4H), 1.18 (m, 2H), 1.50 (m, 6H), 1.55-1.75 (m, 4H), 1.81-2.00 (m, 8H), 2.05-2.30 (m, 5H), 2.26 (d, 6H), 2.40-2.61 (m, 1H), 2.65-2.80 (m, 2H), 2.90-3.08 (m, 6H), 3.15 (d, 3H), 3.30 (d, 3H), 3.42 (s, 2H), 3.67 (s, 3H), 3.70 (s, 3H), 3.15-3.43 (m, 3H), 3.85-4.05 (m, 4H), 4.18 (brt, 2H), 4.38 (m, 2H), 4.52 (t, 1H), 4.56-4.80 (m, 3H), 4.88 (d, 1H), 5.01 (m, 2H), 5.10 (d, 1H), 6.00 (m, 1H), 6.84-8.20 (m, 10H), 10.0 (d, 1H)

PREPARATION EXAMPLE 3-13

Preparation of Compound (IV-17)

(IV-17)

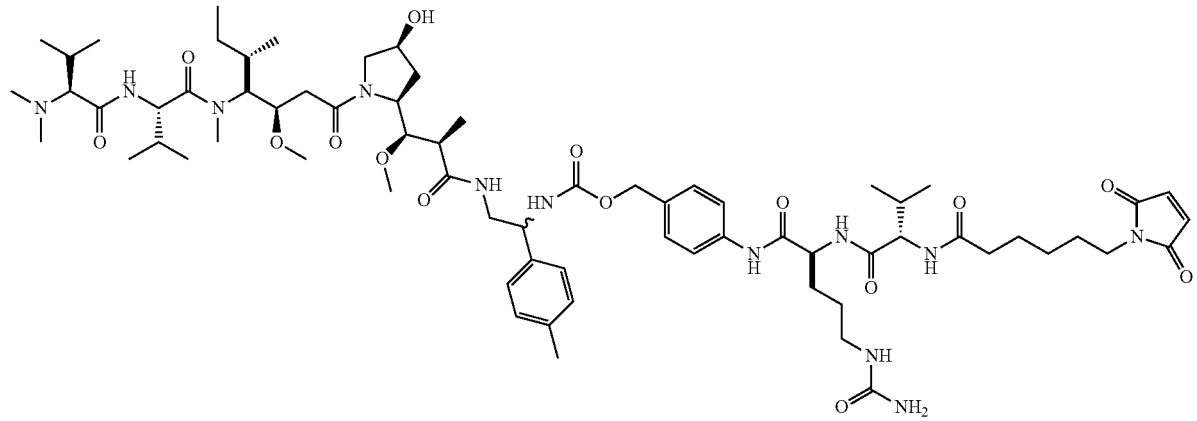

With the exception that compound (III-17)(327 mg, 0.431 mmol), obtained in Preparation Example 2-13, was used instead of compound (III-11), obtained in Preparation Example 2-7, the same procedure as in Preparation Example 3-7 was repeated to afford the title compound (440 mg, 75%).

LC-MS m/z: 1346 [M+1]$^+$ $^1$H NMR (400 MHz, CD$_3$OD) δ 0.81-1.02 (m, 23H), 1.13-1.20 (m, 3H), 1.25-1.32 (m, 2H), 1.40 (m, 1H), 1.50-1.63 (m, 6H), 1.72-1.78 (m, 2H), 1.82-1.98 (m, 3H), 1.96 (s, 3H), 2.00-2.09 (m, 4H), 2.15-2.30 (m, 5H), 2.34-2.42 (d, 6H), 2.40-2.60 (m, 3H), 2.75 (m, 1H), 2.98 (m, 1H), 3.05 (m, 3H), 3.16-3.24 (m, 2H), 3.26-3.35 (m, 8H, OCH$_3$), 3.38-3.48 (m, 6H, OCH$_3$), 3.52-3.60 (m, 1H), 3.65-3.80 (m, 1H), 3.90-4.16 (m, 5H), 4.48 (m, 1H), 4.63-5.10 (m, 8H), 6.76 (s, 2H), 7.09-7.28 (m, 6H), 7.53 (m, 2H)

PREPARATION EXAMPLE 3-14

Preparation of Compound (IV-18)

(IV-18)

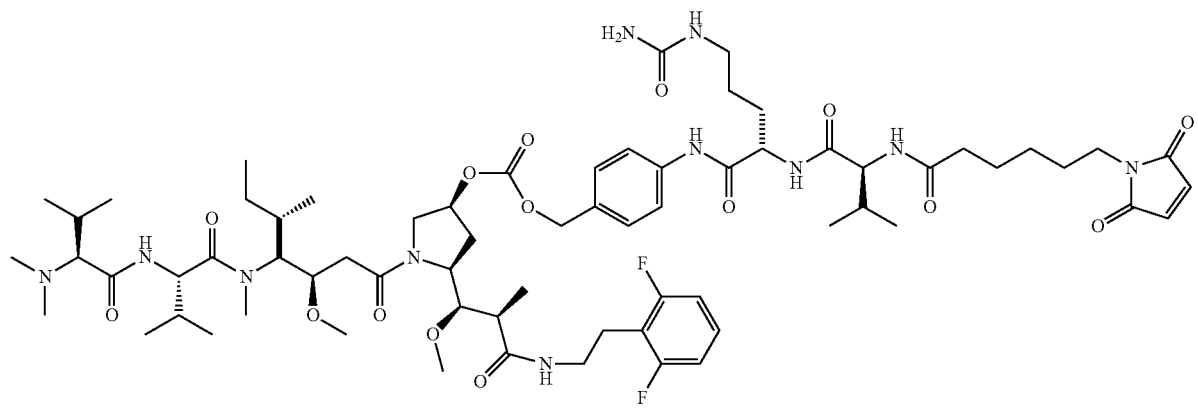

Under an argon stream, compound (III-18) (0.36 g, 0.48 mmol), obtained in Preparation Example 2-14, was dissolved in 10 mL of anhydrous dimethyl formamide, and added with compound (II-1)(0.32 g, 0.43 mmol), obtained in Preparation Example 1-1. The reaction mixture was cooled to 0° C., and was sequentially added with HOBt (70 mg, 0.52 mmol) and 2.5 mL of anhydrous pyridine before being stirred at room temperature for 15 hrs. After completion of the reaction, vacuum concentration was carried out, and the residue was purified by silica gel column chromatography to afford the title compound as an ivory solid (0.29 g, 51%).

LC-MS m/z: 1353 [M$^+$]$^+$, 1375 [M+Na]$^+$

PREPARATION EXAMPLE 3-15

Preparation of Compound (IV-19)

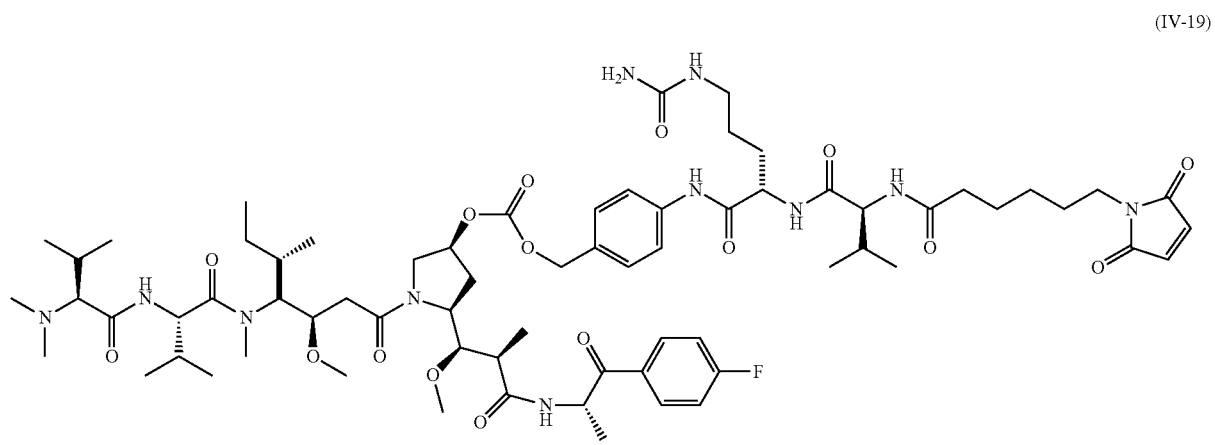 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)C=CC3=O)C(C)C)cc2)C[C@H]1[C@H](OC)[C@@H](C)C(=O)N[C@@H](C)C(=O)c1ccc(F)cc1)OC)N(C)C(=O)[C@@H](NC(=O)[C@H](C(C)C)N(C)C)C(C)C]

(IV-19)

With the exception that compound (III-19) (0.34 g, 0.45 mmol), obtained in Preparation Example 2-15, was used instead of compound (III-18), obtained in Preparation Example 2-14, the same procedure as in Preparation Example 3-14 was repeated to afford the title compound (0.28 g, 45%).

LC-MS m/z: 1362.8 [M$^+$]$^+$, 1384.8 [M+Na]$^+$

PREPARATION EXAMPLE 3-16

Preparation of Compound (IV-20)

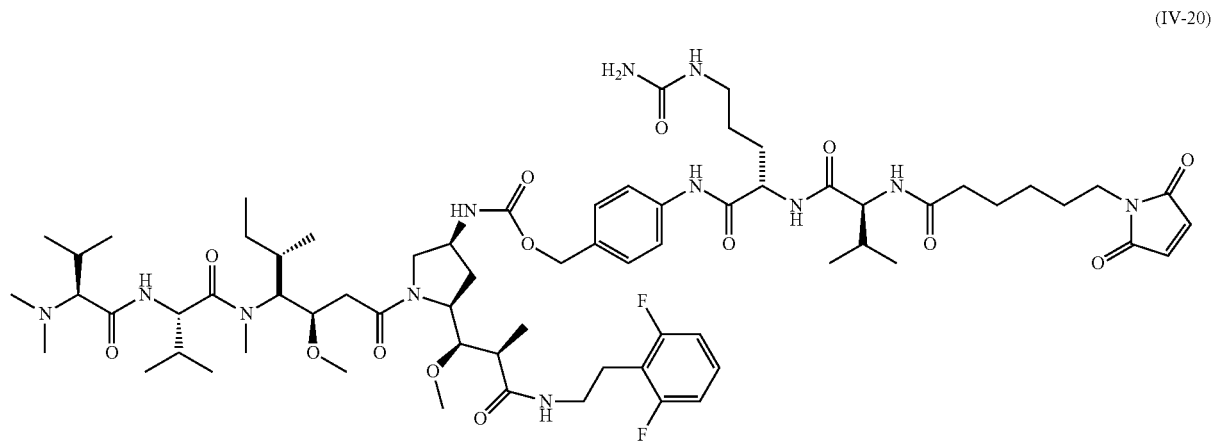 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)C=CC3=O)C(C)C)cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(IV-20)

With the exception that compound (III-20) (91 mg, 0.12 mmol), obtained in Preparation Example 3-14, was used instead of compound (III-18), obtained in Preparation Example 2-16, the same procedure as in Preparation Example 3-14 was repeated to afford the title compound (122 mg, 82%).

LC-MS m/z: 1352 [M+]+

PREPARATION EXAMPLE 3-17

Preparation of Compound (IV-21)

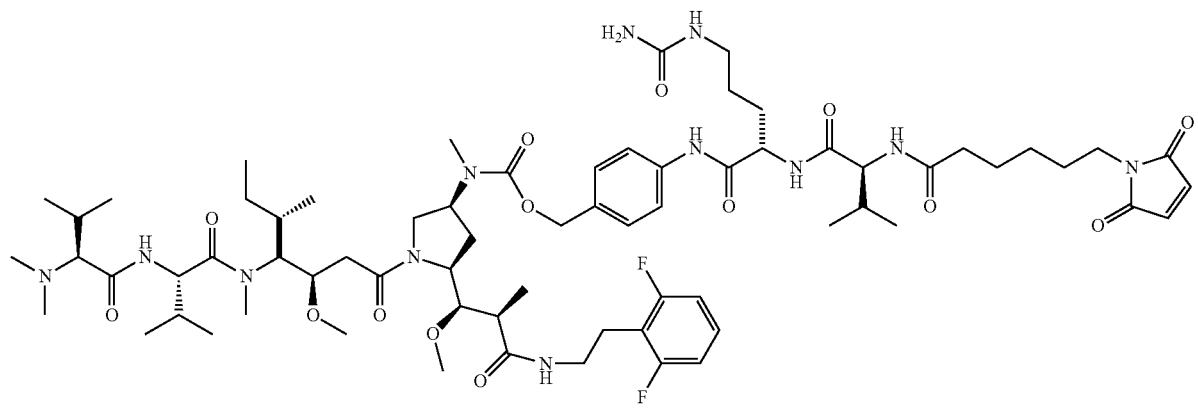

(IV-21)

With the exception that compound (III-21)(110 mg, 0.14 mmol), obtained in Preparation Example 2-17, was used instead of compound (III-18), obtained in Preparation Example 2-14, the same procedure as in Preparation Example 3-14 was repeated to afford the title compound (153 mg, 86%).

$^1$H NMR (400 MHz, DMSO-d$_6$) δ 0.70-0.77 (m, 5 H), 0.81-0.97 (m, 17 H), 1.02-1.07 (m, 3 H), 1.16-1.29 (m, 8 H), 1.34-1.40 (m, 1 H), 1.48-1.51 (m, 6 H), 1.54-1.63 (m, 1 H), 1.63-1.79 (m, 2 H), 1.91-1.97 (m, 5 H), 2.03-2.30 (m, 7 H), 2.35-2.44 (m, 1 H), 2.59-2.61 (m, 1 H), 2.61-2.69 (m, 1 H), 2.70-2.84 (m, 4 H), 3.07-3.12 (m, 1 H), 3.12-3.24 (m, 3 H), 3.26-3.40 (m, 3 H), 3.40-3.48 (m, 1 H), 3.62-4.03 (m, 4 H), 4.03-4.25 (m, 3 H), 4.25-4.68 (m, 4 H), 4.88-5.09 (s, 2 H), 5.35-5.47 (s, 2 H), 5.85-6.03 (t, 1 H), 6.85-7.10 (s, 2 H), 7.14-7.40 (m, 2 H), 7.56-7.66 (m, 1 H), 7.74-7.83 (d, 1 H), 7.90-8.22 (m, 3 H), 10.00 (brs, 1 H)

LC-MS m/z: 1366 [M+]+

PREPARATION EXAMPLE 3-18

Preparation of Compound (IV-22)

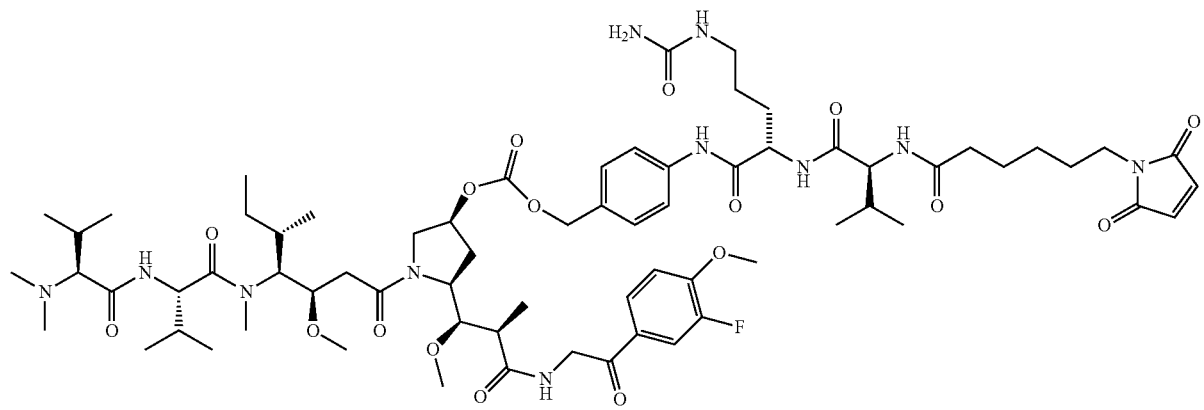

(IV-22)

A solution of compound (III-22) (1.27 g, 1.63 mmol), obtained in Preparation Example 2-18, in 20 mL of dichloromethane was cooled to −50 to −60° C., and added with pyridine (1.3 mL, 16.28 mmol). To the reaction mixture, drops of a solution of p-nitrophenyl chloroformate (16.28 g, 3.3 mmol) in 10 mL of dichloromethane were slowly added over 20 min, followed by stirring at −50 to −60° C. for 3 hrs. When the reaction was completed, 20 mL of dichloromethane was further added to the reaction mixture, which was then extracted with a 0.5 M potassium hydrogen sulfite solution. The organic layer was dried over anhydrous sodium sulfate, and concentrated in a vacuum. The concentrate was purified by silica gel column chromatography to afford (3S,5S)-1-((3R,4S,5S)-4-((S)-2-((S)-2-(dimethylamino)-3-methylbutanamido)-N, 3-dimethylbutanamido)-3-methoxy-5-methylheptanoyl)-5-(1R,2R)-3-((2-(3-fluoro-4-methoxyphenyl)-2-oxoethyl)amino)-1-methoxy-2-methyl-3-oxopropyl)pyrrolidin-3-yl (4-nitrophenyl) carbonate (0.8 g, 54%).

LC-MS m/z: 945.7 [M+H]$^+$, 967.7 [M+Na]$^+$

Under an argon stream, this compound (0.3 g, 0.32 mmol) was dissolved, together with t-butyl ((S)-1-(((S)-1-((4-(hydroxymethyl)phenyl)amino)-1-oxo-5-ureidopentan-2-yl)amino)-3-methyl-1-oxobutan-2-yl)carbamate (0.3 g, 0.64 mmol), in 10 mL of anhydrous dimethyl formamide, and added with 4-methylaminopyridine (0.039 g, 0.32 mmol). The reaction mixture was stirred at 20-25° C. for 19 hrs. After completion of the reaction, the reaction mixture was concentrated to the completion in a high vacuum, and the concentrate was purified by silica gel column chromatography to obtain an amino-protected derivative (0.1 g, 25%).

LC-MS m/z: 1285.5 [M+H]$^+$

To a solution of this amino-protected compound (0.18 g, 0.14 mmol) in 8 mL of dichloromethane was added 2 mL of trifluoroacetic acid, followed by stirring at 20-25° C. for 3 hrs. When the reaction was completed, trifluoroacetic acid was completely removed by adding 5 ml of toluene twice, before a further reaction.

This concentrate (TFA salt) was dissolved, together with 2,5-dioxopyrrolidin-1-yl 6-(2,5-dioxo-2,5-dihydro-1-pyrrol-1-yl)hexanoate, in 10 mL of dimethylformamide, and added with triethylamine (0.1 mL, 0.7 mmol) at room temperature before being stirred at room temperature for 18 hrs. After completion of the reaction, the reaction mixture was concentrated to the completion in a high vacuum, and the concentrate was purified by silica gel column chromatography to obtain the title compound (0.14 g, 71%).

$^1$H NMR (400 MHz, DMSO-d$_6$) δ 0.70-0.78 (m, 6H), 0.81-0.92 (m, 13H), 1.16-1.24 (23H), 1.46-1.51 (m, 4H), 1.84-1.97 (m, 3H), 3.06-3.17 (m, 12H), 3.30-3.38 (m, 15H), 3.84-3.93 (m, 3H), 4.08-4.85 (m, 8H), 4.86-5.04 (m, 1H), 5.10 (s, 2H), 5.40 (s, 2H), 6.03 (t, 1H), 7.00 (s, 1H), 7.15-7.35 (m, 2H), 7.53-7.55 (d, 1H), 7.77-7.98 (m, 2H), 8.10-8.12 (d, 1H), 8.19-8.48 (m, 1H), 9.44-9.49 (brs, 1H), 10.03 (s, 1H)

LC-MS m/z: 1378.7 [M+H]$^+$

PREPARATION EXAMPLE 3-19

Preparation of Compound (IV-23)

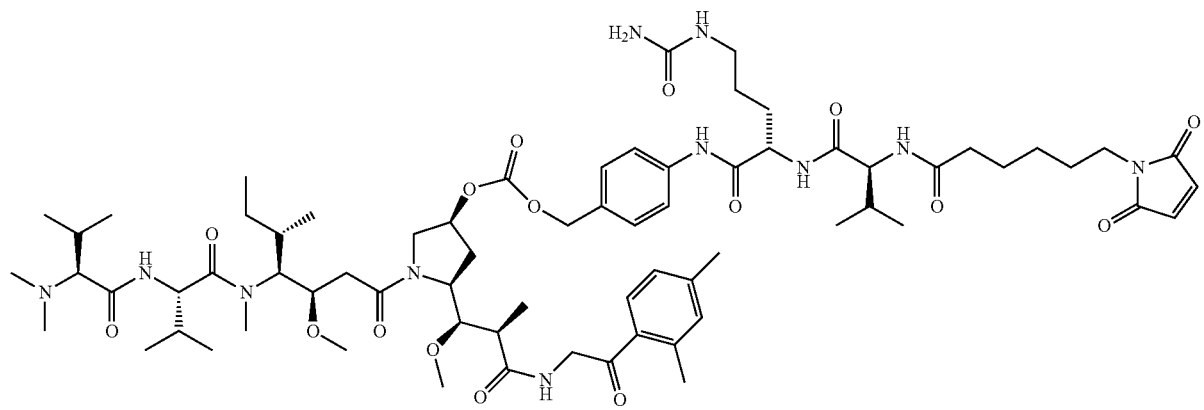

(IV-23)

With the exception that compound (III-23) (0.8 g, 0.865 mmol), obtained in Preparation Example 2-19, was used instead of compound (III-22), obtained in Preparation Example 2-18, the same procedure as in Preparation Example 3-18 was repeated to afford the title compound (0.22 g, 69%).

$^1$H NMR (400 MHz, DMSO-d$_6$) δ 0.73-0.75 (m, 4H), 0.81-0.92 (m, 11H), 1.16-1.19 (23H), 1.46-1.50 (m, 4H), 1.54-1.73 (m, 2H), 1.90-1.97 (m, 2H), 2.08-2.25 (m, 4H), 2.28-2.38 (m, 4H), 2.94-2.99 (m, 4H), 3.07-3.17 (m, 11H), 3.33-3.38 (m, 12H), 3.95-4.05 (m, 1H), 4.12-4.27 (m, 3H), 4.51-4.67 (m, 1H), 4.87-4.95 (m, 1H), 5.11 (s, 2H), 5.43 (s, 2H), 6.00 (t, 1H), 7.00 (s, 1H), 7.07-7.15 (m, 1H), 7.22-7.24 (d, 1H), 7.32-7.35 (m, H), 7.53-7.56 (d, 1H), 7.61-7.62 (d, 1H), 7.81-7.84 (d, 1H), 8.07-8.13 (m, 1H), 8.28-8.50 (m, 1H), 9.26 (brs, 1H), 9.91 (s, 1H), 10.06 (s, 1H)

LC-MS m/z: 1380.4 [M+H]$^+$

PREPARATION EXAMPLE 3-20

Preparation of Compound (IV-24)

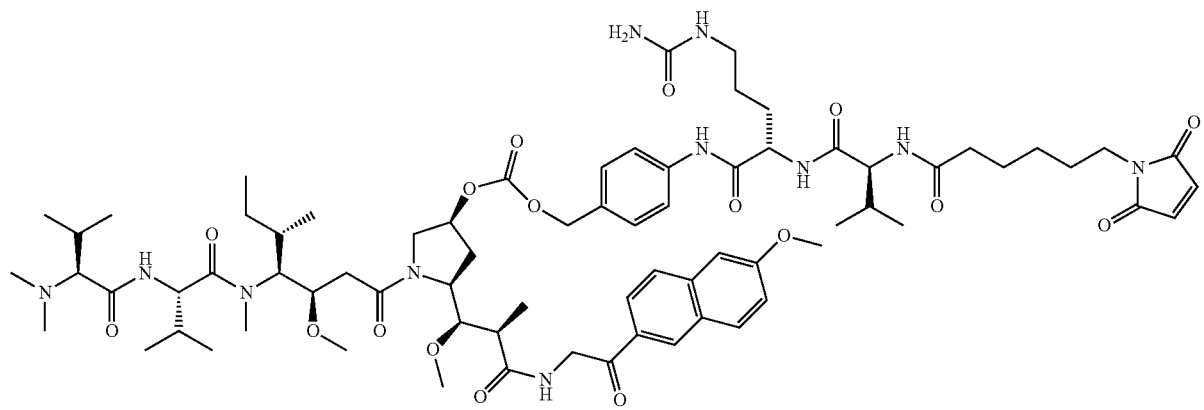

(IV-24)

With the exception that compound (III-24) (0.44 g, 0.45 mmol), obtained in Preparation Example 2-20, was used instead of compound (III-22), obtained in Preparation Example 2-18, the same procedure as in Preparation Example 3-18 was repeated to afford the title compound (0.16 g, 64%).

$^1$H NMR (400 MHz, DMSO-d$_6$) δ 0.48-0.50 (d, 1H), 0.58-0.59 (d, 1H), 0.68-0.77 (m, 4H), 0.81-0.92 (m, 14H), 1.16-1.23 (20H), 1.46-1.51 (m, 4H), 1.81-1.88 (m, 3H), 3.06-3.13 (m, 12H), 3.35-3.38 (m, 15H), 3.84-3.92 (m, 4H), 4.08-5.00 (m, 8H), 5.13 (s, 2H), 5.44 (s, 2H), 6.01-6.03 (t, 1H), 7.00 (s, 1H), 7.22-7.28 (m, 1H), 7.33-7.36 (m, 2H), 7.39-7.42 (d, 1H), 7.60-7.65 (d, 2H), 7.82-7.84 (d, 1H), 7.89-7.93 (m, 2H), 8.00-8.03 (d, 1H), 8.11-8.13 (d, 1H), 8.27-8.53 (m, 1H), 8.64 (s, 1H), 9.38 (brs, 1H), 10.06 (s, 1H)

LC-MS m/z: 1410.5 [M+H]$^+$

PREPARATION EXAMPLE 3-21

Preparation of Compound (IV-25)

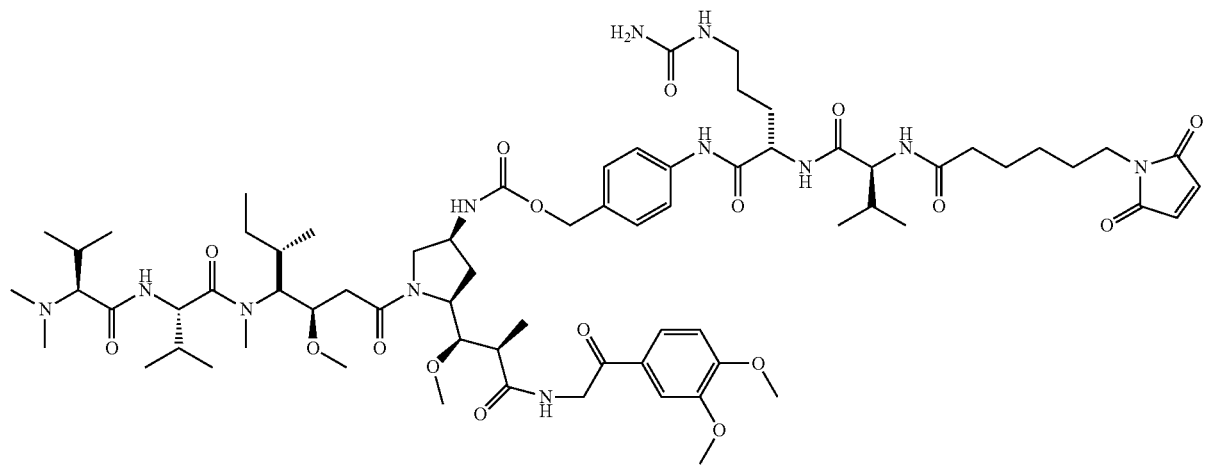

(IV-25)

With the exception that compound (III-25) (0.37 g, 0.47 mmol), obtained in Preparation Example 2-21, was used instead of compound (III-22), obtained in Preparation Example 2-18, the same procedure as in Preparation Example 3-14 was repeated to afford the title compound (0.47 g, 72%).

$^1$H NMR (400 MHz, DMSO-$d_6$) δ 0.57-0.78 (m, 8 H), 0.78-0.98 (m, 15H), 1.04-1.28 (m, 6 H), 1.28-1.39 (m, 1 H), 1.39-1.54 (m, 5 H), 1.54-1.63 (m, 1 H), 1.63-1.84 (m, 3 H), 1.84-2.03 (m, 3 H), 2.03-2.25 (m, 7H), 2.25-2.40 (m, 2 H), 2.53-2.69 (m, 3 H), 2.69-2.83 (m, 1 H), 2.85-3.06 (m, 5 H), 3.09-3.21 (m, 3 H), 3.26-3.42 (m, 3 H), 3.44-3.52 (m, 1 H), 3.74-3.88 (m, 6 H), 3.88-4.05 (m, 3 H), 4.07-4.16 (m, 1 H), 4.16-4.23 (m, 1 H), 4.23-4.34 (m, 1 H), 4.34-4.48 (m, 2 H), 4.48-4.57 (m, 1 H), 4.58-4.73 (m, 2 H), 4.97 (s, 2 H), 5.42 (s, 2 H), 5.93-6.04 (t, 1 H), 6.98-7.04 (s, 1 H), 7.04-7.12 (d, 1 H), 7.25-7.36 (m, 1 H), 7.42-7.48 (s, 1 H), 7.48-7.57 (m, 1 H), 7.57-7.64 (d, 1 H), 7.64-7.72 (m, 1 H), 7.77-7.86 (m, 1 H), 8.01-8.16 (m, 1 H), 10.01 (brs, 1 H), 10.56 (brs, 1 H)

LC-MS m/z: 1389.6 [M$^+$]$^+$, 1412.6 [M+Na]$^+$

PREPARATION EXAMPLE 3-22

Preparation of Compound (IV-26)

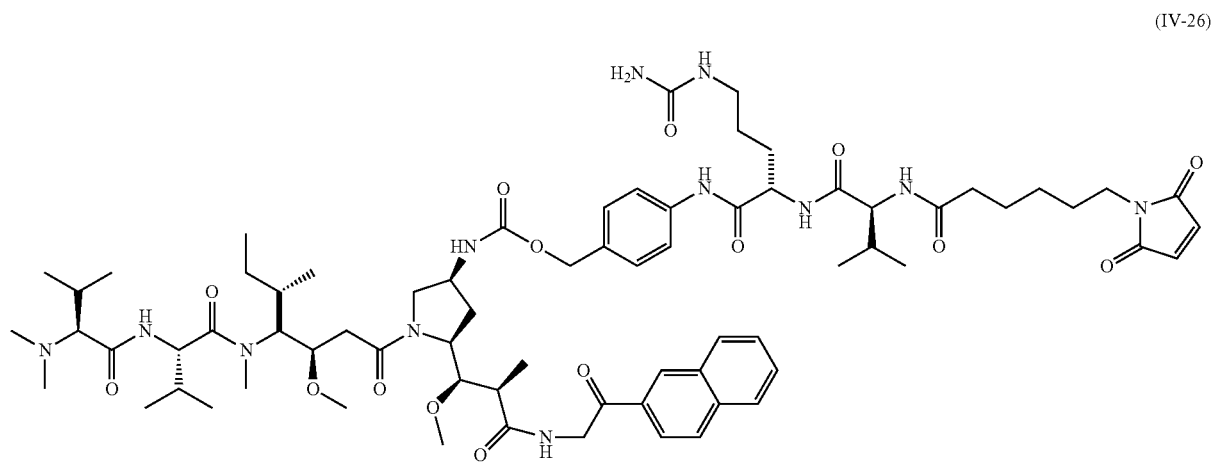 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)C=CC3=O)C(C)C)cc2)C[C@H]1[C@H](OC)[C@@H](C)C(=O)NCC(=O)c1ccc2ccccc2c1)OC)N(C)C(=O)[C@@H](NC(=O)[C@H](C(C)C)N(C)C)C(C)C]

(IV-26)

With the exception that compound (III-26)(0.28 g, 0.36 mmol), obtained in Preparation Example 2-22, was used instead of compound (III-22), obtained in Preparation Example 2-18, the same procedure as in Preparation Example 3-14 was repeated to afford the title compound (0.24 g, 48%).

$^1$H NMR (400 MHz, DMSO-$d_6$) δ 0.66-0.78 (m, 5 H), 0.78-1.06 (m, 19 H), 1.07-1.29 (m, 6 H), 1.29-1.38 (m, 1 H), 1.38-1.53 (m, 5 H), 1.53-1.63 (m, 1 H), 1.63-1.85 (m, 2 H), 1.85-2.02 (m, 3 H), 2.02-2.14 (m, 3 H), 2.14-2.27 (m, 6 H), 2.27-2.41 (m, 2 H), 2.56-2.60 (m, 3 H), 2.61-2.83 (m, 1 H), 2.86-3.08 (m, 5 H), 3.08-3.20 (m, 3 H), 3.20-3.27 (m, 1 H), 3.27-3.40 (m, 3 H), 3.45-3.63 (m, 1 H), 3.64-3.88 (m, 1 H), 3.88-4.06 (m, 2 H), 4.06-4.26 (m, 2 H), 4.28-4.46 (m, 1 H), 4.46-4.74 (m, 2 H), 4.74-4.91 (m, 1 H), 4.97 (s, 2 H), 5.43 (s, 2 H), 5.88-6.10 (t, 1 H), 7.01 (s, 1 H), 7.12-7.38 (m, 2 H), 7.38-7.72 (m, 4 H), 7.72-7.92 (m, 2 H), 7.92-8.22 (m, 3 H), 8.25-8.63 (m, 2 H), 8.73 (s, 1 H), 10.06 (brs, 1 H), 10.59 (brs, 1H)

LC-MS m/z: 1379.6 [M$^+$]$^+$, 1402.5 [M+Na]$^+$

PREPARATION EXAMPLE 3-23

Preparation of Compound (IV-27)

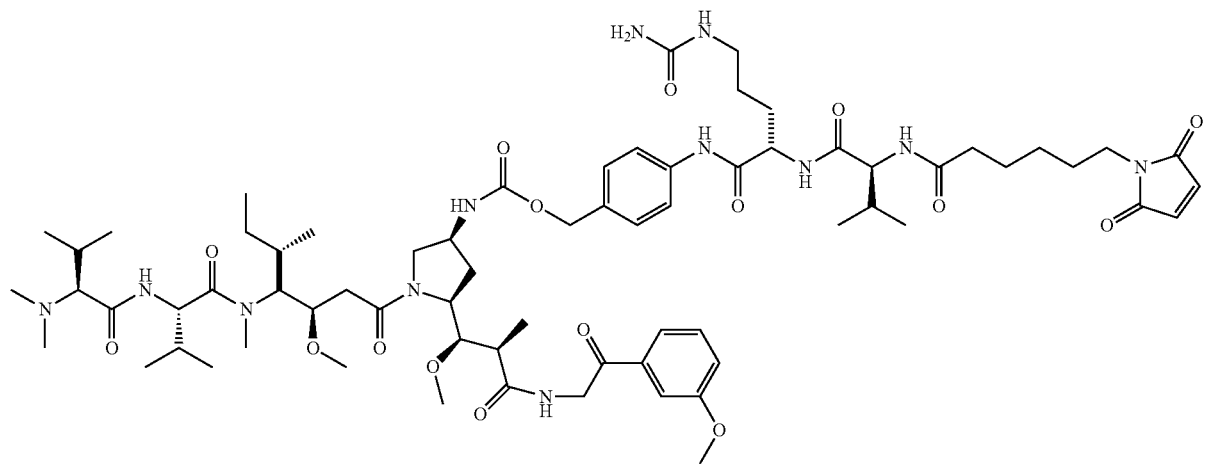

(IV-27)

With the exception that compound (HI-27) (0.24 g, 0.32 mmol), obtained in Preparation Example 2-18, was used instead of compound (III-22), obtained in Preparation Example 2-18, the same procedure as in Preparation Example 3-14 was repeated to afford the title compound (0.28 g, 64%).

$^1$H NMR (400 MHz, DMSO-$d_6$) δ 0.59-0.78 (m, 6 H), 0.78-0.97 (m, 15 H), 0.97-1.06 (m, 2 H), 1.06-1.28 (m, 6 H), 1.28-1.39 (m, 1 H), 1.39-1.54 (m, 5 H), 1.54-1.64 (m, 1 H), 1.64-1.84 (m, 3 H), 1.84-2.02 (m, 3 H), 2.05-2.29 (m, 8 H), 2.30-2.42 (m, 2 H), 2.55-2.60 (m, 3 H), 2.60-2.83 (m, 1 H), 2.86-3.06 (m, 5 H), 3.06-3.21 (m, 6 H), 3.21-3.32 (m, 3 H), 3.36-3.44 (m, 1H), 3.44-3.52 (m, 1 H), 3.65-3.74 (m, 1H), 3.74-3.87 (m, 2 H), 3.89-4.05 (m, 2 H), 4.15-4.25 (m, 1 H), 4.31-4.73 (m, 4 H), 4.96 (s, 2 H), 5.43 (s, 2 H), 5.92-6.06 (t, 1 H), 6.71-6.83 (m, 1 H), 6.83-6.94 (m, 1 H), 6.97-7.04 (m, 1 H), 7.16-7.35 (m, 2 H), 7.38-7.67 (m, 3 H), 7.75-7.88 (d, 1 H), 8.00-8.17 (m, 2 H), 10.01 (brs, 1 H), 10.55 (brs, 1 H)

LC-MS m/z: 1361.6 [M$^+$]$^+$, 1384.5 [M+Na]$^+$

PREPARATION EXAMPLE 3-24

Preparation of Compound (IV-28)

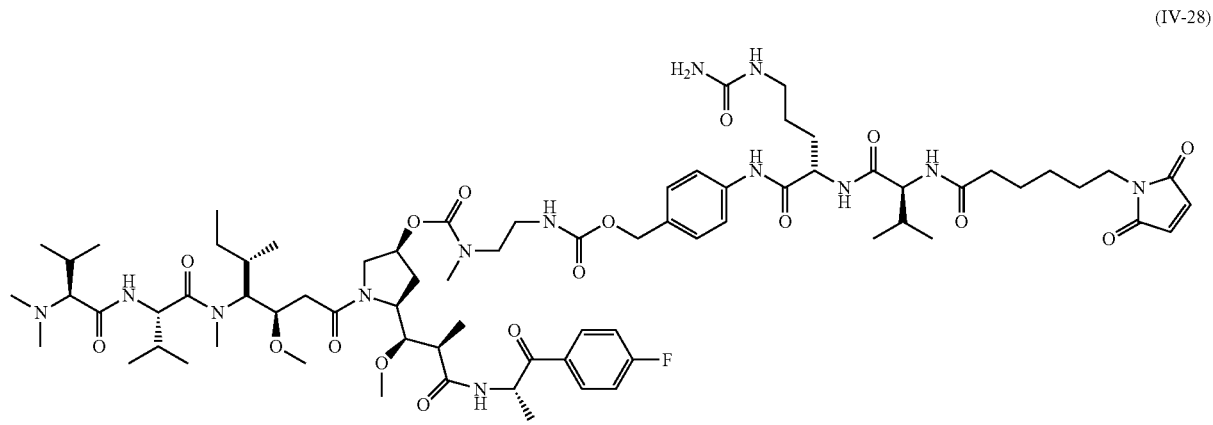 [SMILES: CC[C@H](C)[C@@H]([C@@H](CC(=O)N1C[C@@H](OC(=O)N(C)CCNC(=O)OCc2ccc(NC(=O)[C@H](CCCNC(N)=O)NC(=O)[C@@H](NC(=O)CCCCCN3C(=O)C=CC3=O)C(C)C)cc2)C[C@H]1[C@H](OC)[C@@H](C)C(=O)N[C@@H](C)C(=O)c1ccc(F)cc1)OC)N(C)C(=O)[C@@H](NC(=O)[C@H](C(C)C)N(C)C)C(C)C]

(IV-28)

Under an argon stream, the TFA salt of compound (II-3) (0.88 mg, 0.11 mmol), obtained in Preparation Example 1-2, was dissolved in 5 mL of anhydrous dimethyl formamide and added with diisopropylethylamine (0.18 mL, 1.03 mmol). To this solution, a solution of compound (III-28) (75 mg, 0.08 mmol), prepared in Preparation Example 2-24, in 5 mL of anhydrous dimethylformamide was dropwise added in an argon atmosphere, followed by stirring at 20-25° C. for 17 hrs. After completion of the reaction, vacuum concentration was carried out, and the residue was purified by silica gel column chromatography to afford the title compound (135 mg, 100%).

LC-MS m/z: 1462.9 [M+H]$^+$, 1485.9 [M+Na]$^+$

PREPARATION EXAMPLE 3-25

Preparation of Compound (IV-29)

(IV-29)

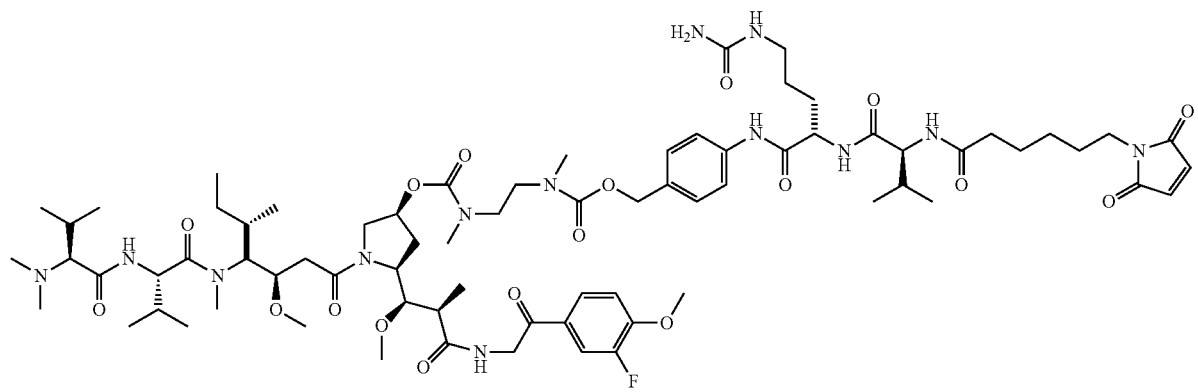

With the exception that the TFA salt of compound (II-4) (0.17 g, 0.212 mmol), obtained in Preparation Example 1-3, was used instead of the TFA salt of compound (II-3), obtained in Preparation Example 1-2, the same procedure as in Preparation Example 3-24 was repeated to afford the title compound (0.14 g, 44%).

$^1$H NMR (400 MHz, DMSO-d$_6$) δ 0.69-0.78 (m, 6H), 0.81-0.90 (m, 14H), 1.11-1.64 (m, 3H), 1.18-1.26 (m, 10H), 1.38-1.51 (m, 6H), 1.58-1.62 (m, 1H), 1.63-1.83 (m, 3H), 1.91-1.99 (m, 3H), 2.11-2.26 (m, 7H), 2.35-2.42 (m, 2H), 2.87 (s, 6H), 2.92-3.05 (m, 3H), 3.13-3.18 (m, 4H), 3.32-3.38 (m, 17H), 3.62 (brs, 1H), 3.92-3.99 (m, 4H), 4.07-4.09 (m, 1H), 4.15-4.84 (m, 9H), 4.98 (s, 2H), 5.4 (s, 2H), 5.96-5.99 (t, 1H), 6.99 (s, 1H), 7.22-7.3 (m, 2H), 7.53-7.65 (m, 2H), 7.77-7.80 (m, 2H), 7.84-7.89 (t, 1H), 8.05-8.07 (d, 1H), 8.37-8.43 (m, 1H), 9.97 (s, 1H)

LC-MS m/z: 1492.8 [M+H]$^+$, 1514.7 [M+Na]$^+$

PREPARATION EXAMPLE 3-26

Preparation of Compound (IV-30)

(IV-30)

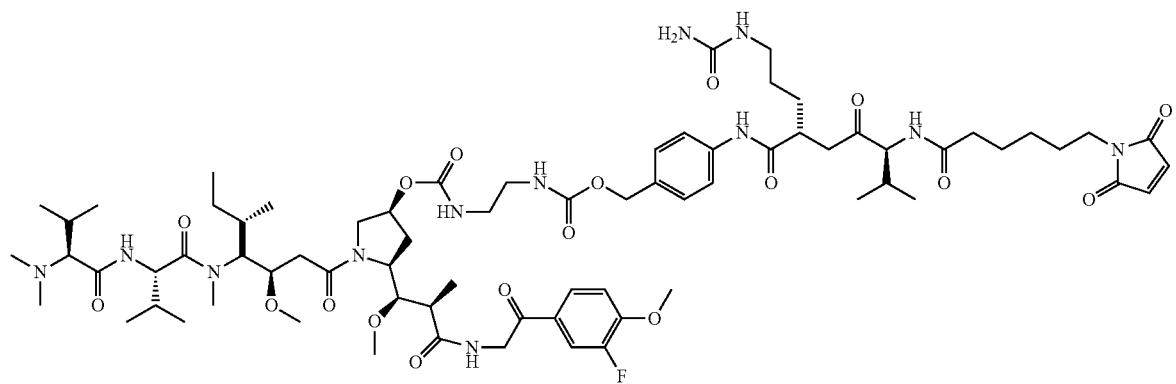

With the exception that the TFA salt of compound (II-5) (0.16 g, 0.212 mmol), obtained in Preparation Example 1-4, and compound (III-29) (0.2 g, 0.212 mmol), obtained in Preparation Example 2-25, were used respectively instead of the TFA salt of compound (II-3), obtained in Preparation Example 1-2, and the compound (III-28), obtained in Preparation Example 2-24, the same procedure as in Preparation Example 3-24 was repeated to afford the title compound (0.13 g, 40%).

$^1$H NMR (400 MHz, DMSO-$d_6$) δ 0.69-0.76 (m, 6H), 0.81-0.92 (m, 14H), 1.10-1.20 (m, 4H), 1.25-1.26 (m, 8H), 1.44-1.51 (m, 5H), 1.55-1.65 (m, 1H), 1.66-1.85 (3H), 1.86-2.05 (m, 3H), 2.06-2.27 (m, 6H), 2.28-2.46 m, 2H), 2.84 (s, 1H), 2.87-2.96 (m, 1H), 2.99-3.04 (m, 5H), 3.14-3.18 (m, 4H), 3.32-3.47 (m, 11H), 3.62 (brs, 1H), 3.92-3.93 (d, 3H), 4.00-4.91 (m, 8H), 4.94 (s, 2H), 5.41 (s, 2H), 5.97-6.00 (t, 1H), 7.00 (s, 1H), 7.24-7.32 (m, 3H), 7.58-7.60 (d, 2H), 7.77-7.80 (m, 2H), 7.85-7.89 (t, 1H), 8.05-8.07 (d, 1H), 8.19 (t, 1H), 8.44 (brs, 1H), 9.97 (s, 1H)

LC-MS m/z: 1464.8 [M+H]$^+$, 1487.9 [M+Na]$^+$

PREPARATION EXAMPLE 3-27

Preparation of Compound (IV-31)

(IV-31)

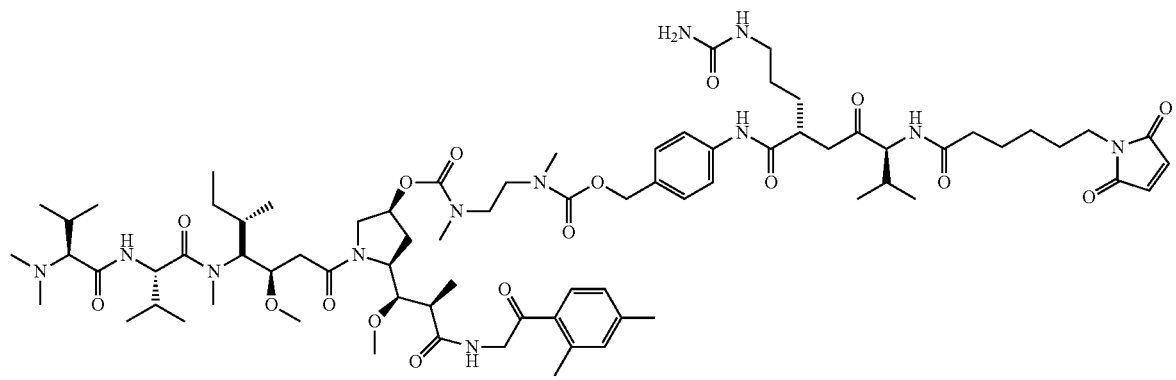

With the exception that the TFA salt of compound (II-4) (0.26 g, 0.324 mmol), obtained in Preparation Example 1-3, and compound (III-30) (0.2 g, 0.216 mmol), obtained in Preparation Example 2-26, were used respectively instead of the TFA salt of compound (II-3), obtained in Preparation Example 1-2, and the compound (III-28), obtained in Preparation Example 2-24, the same procedure as in Preparation Example 3-24 was repeated to afford the title compound (0.2 g, 64%).

$^1$H NMR (400 MHz, DMSO-$d_6$) δ 0.71-0.75 (m, 6H), 0.80-0.91 (m, 15H), 1.18-1.19 (m, 3H), 1.22-1.27 (m, 9H), 1.43-1.49 (m, 6H), 1.90-1.98 (m, 3H), 2.09-2.23 (m, 3H), 2.25-2.40 (m, 7H), 2.83-2.86 (m, 4H), 2.96-3.01 (m, 4H), 3.15-3.19 (m, 3H), 3.26 (s, 3H), 3.35-3.38 (m, 16H), 3.85-3.96 (m, 3H), 4.11-4.88 (m, 8H), 4.97 (s, 2H), 5.42 (s, 2H), 5.97-5.99 (t, 1H), 6.99-7.01 (m, 1H), 7.06-7.16 (m, 2H), 7.28 (brs, 2H), 7.60-7.69 (m, 2H), 7.81-7.83 (d, 1H), 8.09-8.12 (d, 1H), 8.29 (brs, 1H), 10.09 (s, 1H)

LC-MS m/z: 1472.9 [M+H]$^+$, 1494.9 [M+Na]$^+$

PREPARATION EXAMPLE 3-28

Preparation of Compound (IV-32)

(IV-32)

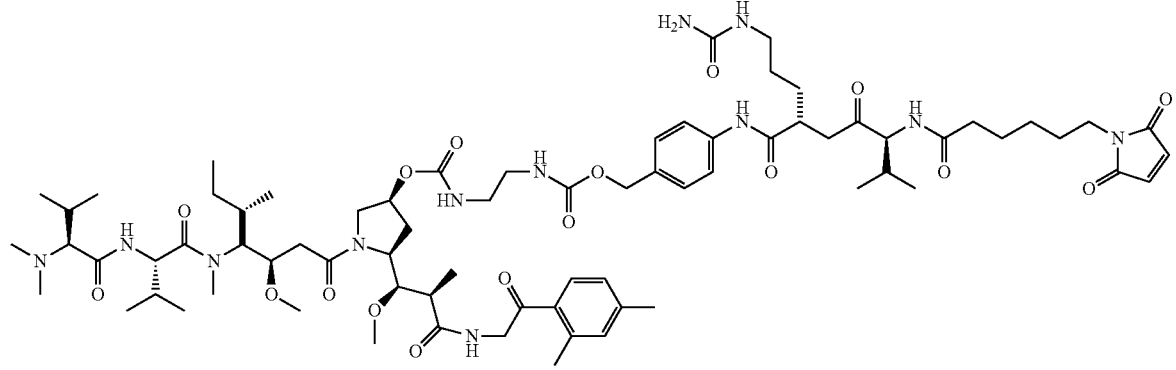

With the exception that the TFA salt of compound (I-5) (0.24 g, 0.324 mmol), obtained in Preparation Example 1-4, and compound (III-30) (0.2 g, 0.216 mmol), obtained in Preparation Example 2-24, were used respectively instead of the TFA salt of compound (II-3), obtained in Preparation Example 1-2, and the compound (III-28), obtained in Preparation Example 2-24, the same procedure as in Preparation Example 3-24 was repeated to afford the title compound (0.2 g, 67%).

$^1$H NMR (400 MHz, DMSO-d$_6$) δ 0.71-0.75 (m, 7H), 0.81-0.92 (m, 16H), 1.03-1.04 (m, 2H), 1.11-1.12 (m, 1H), 1.18-1.27 (m, 7H), 1.46-1.49 (m, 5H), 1.90-1.98 (m, 3H), 2.09-2.23 (m, 6H), 2.28-2.38 (m, 7H), 2.96-3.03 (m, 9H), 3.15-3.17 (m, 4H), 3.28 (s, 3H), 3.35-3.38 (m, 14H), 3.62-3.65 (m, 2H), 3.85-4.00 (m, 3H), 4.17-4.88 (m, 8H), 4.94 (s, 2H), 5.43 (s, 2H), 5.88-6.00 (t, 1H), 7.00 (s, 1H), 7.06-7.16 (m, 2H), 7.27-7.29 (m, 3H), 7.58-7.69 (m, 2H), 7.82-7.84 (d, 1H), 8.09-8.12 (d, 1H), 8.29 (brs, 1H), 10.00 (s, 1H)

LC-MS m/z: 1444.9 [M+H]$^+$, 1466.9 [M+Na]$^+$

PREPARATION EXAMPLE 3-29

Preparation of Compound (IV-33)

(IV-33)

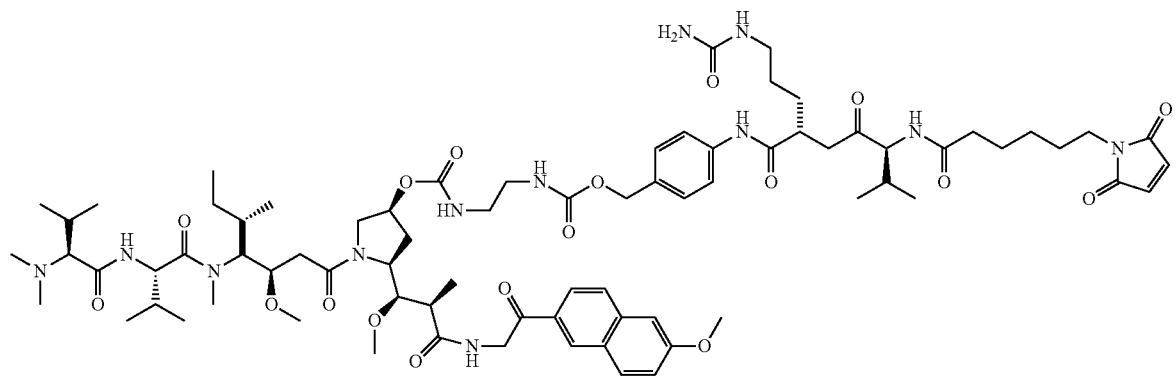

With the exception that the TFA salt of compound (II-5) (0.23 g, 0.307 mmol), obtained in Preparation Example 1-4, and compound (III-31) (0.2 g, 0.205 mmol), obtained in Preparation Example 2-27, were used respectively instead of the TFA salt of compound (II-3), obtained in Preparation Example 1-2, and the compound (III-28), obtained in Preparation Example 2-24, the same procedure as in Preparation Example 3-24 was repeated to afford the title compound (0.16 g, 51%).

$^1$H NMR (400 MHz, DMSO-d$_6$) δ 0.71-0.75 (m, 7H), 0.81-0.92 (m, 16H), 1.03-1.04 (m, 2H), 1.11-1.12 (m, 1H), 1.18-1.27 (m, 7H), 1.46-1.49 (m, 5H), 1.90-1.98 (m, 3H), 2.09-2.23 (m, 6H), 2.28-2.38 (m, 7H), 2.96-3.03 (m, 9H), 3.15-3.17 (m, 4H), 3.28 (s, 3H), 3.35-3.38 (m, 14H), 3.62-3.65 (m, 2H), 3.85-4.00 (m, 3H), 4.17-4.88 (m, 8H), 4.94 (s, 2H), 5.43 (s, 2H), 5.88-6.00 (t, 1H), 7.00 (s, 1H), 7.06-7.16 (m, 2H), 7.27-7.29 (m, 3H), 7.58-7.69 (m, 2H), 7.82-7.84 (d, 1H), 8.09-8.12 (d, 1H), 8.29 (brs, 1H), 10.00 (s, 1H)

LC-MS m/z: 1497.6 [M+H]$^+$, 1519.6 [M+Na]$^+$

PREPARATION EXAMPLE 3-30

Preparation of Compound (IV-34)

(IV-34)

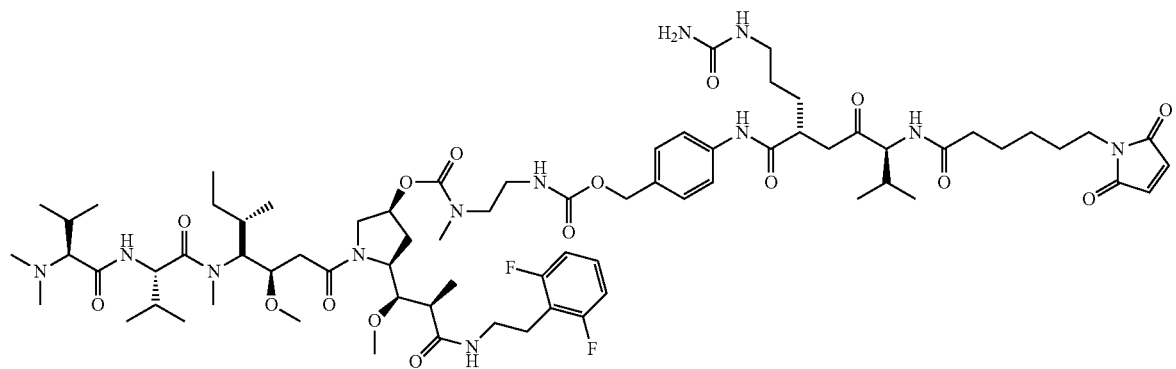

With the exception that compound (III-32) (1.2 g, 1.294 mmol), obtained in Preparation Example 2-28, instead of the compound (III-28), obtained in Preparation Example 2-24, was used together with the TFA salt of compound (II-3) (1 g, 1.294 mmol), obtained in Preparation Example 1-2, the same procedure as in Preparation Example 3-24 was repeated to afford the title compound (1.3 g, 72%).

$^1$H NMR (400 MHz, DMSO-$d_6$) δ 0.48-0.49 (m, 1H), 0.58-0.59 (m, 2H), 0.64-0.65 (m, 2H), 0.70-0.76 (m, 5H), 0.81-0.92 (m, 16H), 1.11-1.13 (m, 2H), 1.16-1.20 (m, 3H), 1.22-1.28 (m, 9H), 1.44-1.49 (m, 5H), 1.90-1.98 (m, 3H), 2.09-2.23 (m, 7H), 2.96-3.04 (m, 9H), 3.13-3.18 (m, 4H), 3.33-3.38 (m, 14H), 3.60-3.64 (m, 1H), 3.90-3.94 (m, 4H), 3.99-4.88 (m, 8H), 4.94 (s, 2H), 5.42 (s, 2H), 5.86-5.99 (t, 1H), 7.22-7.29 (m, 4H), 7.38-7.42 (m, 1H), 7.58-7.60 (d, 2H), 7.80-7.82 (d, 1H), 7.89-7.96 (m, 2H), 8.00-8.10 (m, 2H), 8.29 (brs, 1H), 8.70 (s, 1H), 10.00 (s, 1H)

LC-MS m/z: 1452.8 [M+H]$^+$, 1474.7 [M+Na]$^+$

PREPARATION EXAMPLE 3-31

Preparation of Compound (IV-35)

(IV-35)

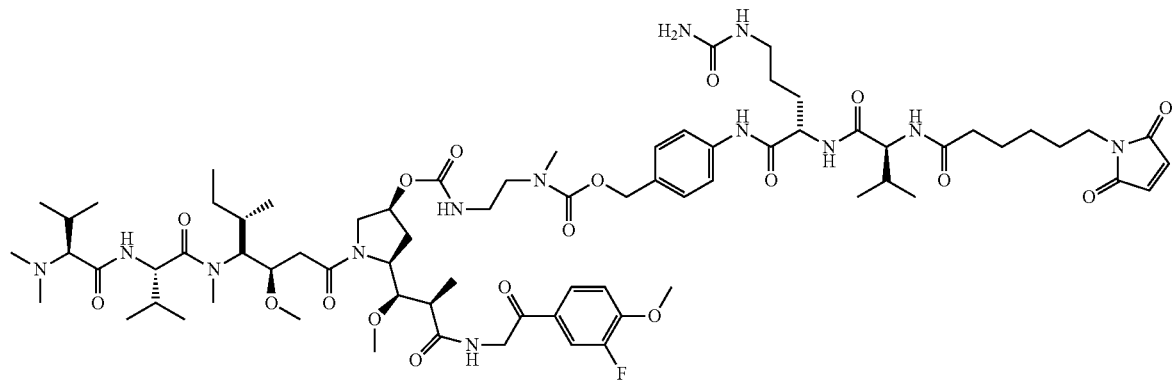

With the exception that the TFA salt of compound (II-6) (0.18 g, 0.233 mmol), obtained in Preparation Example 1-5, instead of the TFA salt of compound (II-3), obtained in Preparation Example 1-2, was used together with the compound (III-29) (0.2 g, 0.212 mmol), obtained in Preparation Example 2-25, the same procedure as in Preparation Example 3-24 was repeated to afford the title compound (0.16 g, 51%).

$^1$H NMR (400 MHz, DMSO-$d_6$) δ 0.68-0.76 (m, 6H), 0.81-0.90 (m, 14H), 1.08-1.20 (m, 4H), 1.23-1.27 (m, 9H), 1.44-1.49 (m, 6H), 1.58-1.62 (m, 1H), 1.63-1.83 (m, 3H), 1.91-1.99 (m, 3H), 2.13-2.20 (m, 6H), 2.35-2.42 (m, 2H), 2.85-2.87 (m, 4H), 2.99-3.01 (m, 4H), 3.14-3.17 (m, 4H), 3.28-3.38 (m, 19H), 3.62 (brs, 1H), 3.92-3.94 (m, 3H), 4.07-4.09 (m, 1H), 4.15-4.84 (m, 8H), 4.98 (s, 2H), 5.43 (s, 2H), 5.98-6.00 (t, 1H), 7.01 (s, 1H), 7.22-7.36 (m, 3H), 7.54-7.64 (m, 2H), 7.77-7.97 (m, 2H), 8.08-8.11 (d, 1H), 8.22-8.45 (m, 2H), 10.01 (s, 1H)

LC-MS m/z: 1478.5 [M+H]$^+$, 1500.5 [M+Na]$^+$

PREPARATION EXAMPLE 4

Preparation of Compounds of Chemical Formula VI-1, VI-2, VI-3, and VI-4

PREPARATION EXAMPLE 4-1

Preparation of Compound (VI-5)

(VI-5)

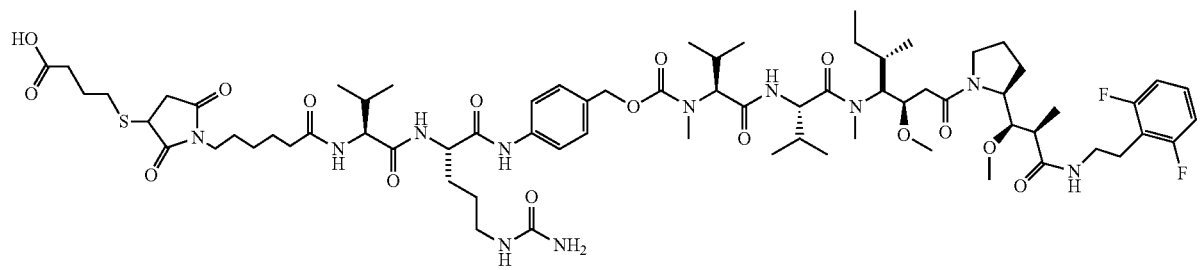

To a solution of compound (IV-5) (274 mg, 0.21 mmol), prepared in Preparation Example 3-1, in 5.0 mL of acetonitrile were added 4-mercaptobutyric acid (V–1) (126 mg, 1.05 mmol) and 0.5 mL of DMSO, followed by stirring at room temperature for 4 hrs. The reaction mixture was concentrated in a vacuum to afford the title compound (290 mg, 98%).

MALDI-TOF MS m/z: 1465.3 [M+Na]$^+$

PREPARATION EXAMPLE 4-2

Preparation of Compound (VI-6)

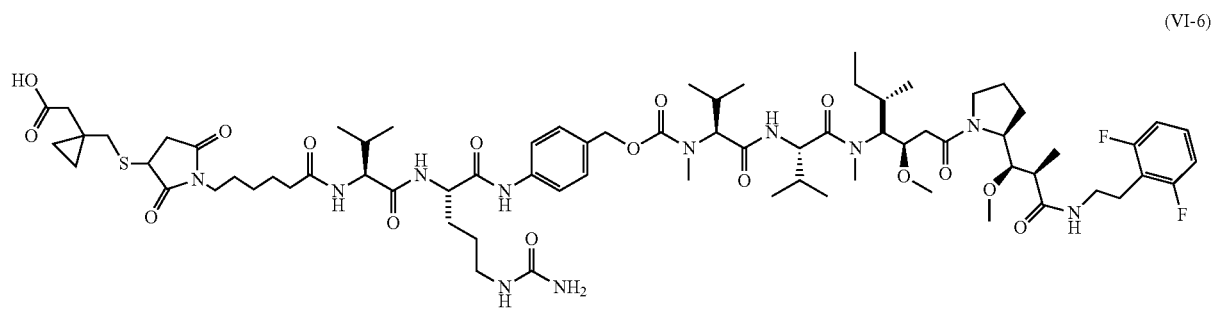 [SMILES: CC[C@H](C)[C@@H]([C@@H](CC(=O)N1CCC[C@H]1[C@H](OC)[C@@H](C)C(=O)NCCc1c(F)cccc1F)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)CC(SCC3(CC(=O)O)CC3)C2=O)C(C)C)cc1)C(C)C]
(VI-6)

To a solution of compound (IV-5) (70 mg, 0.053 mmol), obtained in Preparation Example 3-1, in 2.5 mL of acetonitrile were added 2-(1-(mercaptomethyl)cyclopropane)acetic acid (V-2) (44 mg, 0.3 mmol) and 0.7 mL of DMF, followed by stirring at room temperature for 4 hrs. The reaction mixture was concentrated in a vacuum, and the concentrate was purified by silica gel column chromatography to afford the title compound as a solid (60 mg, 77%).

MALDI-TOF MS m/z: 1492.0 [M+Na]$^+$

PREPARATION EXAMPLE 4-3

Preparation of Compound (VI-7)

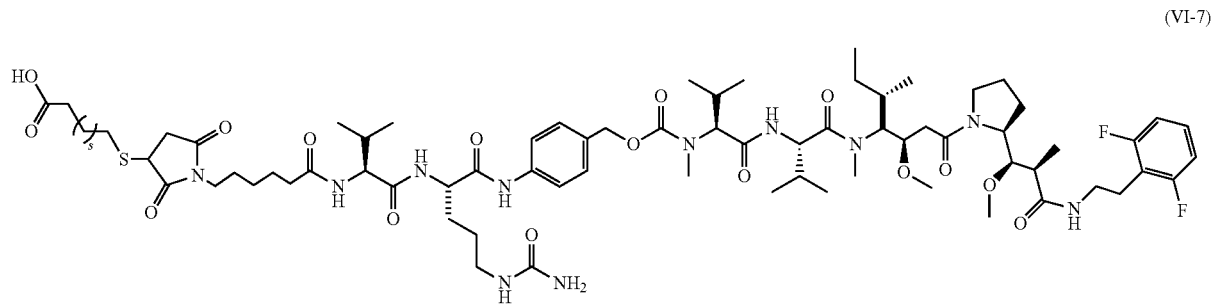
(VI-7)

With the exception that 6-mercaptohexanoic acid (V-3) was used instead of 2-(1-(mercaptomethyl)cyclopropane) acetic acid (V-2), the same procedure as in Preparation Example 4-2 was repeated to afford the title compound (54 mg, 69%).

MALDI-TOF MS m/z: 1493.2 [M+Na]$^+$

PREPARATION EXAMPLE 4-4

Preparation of Compound (VI-8)

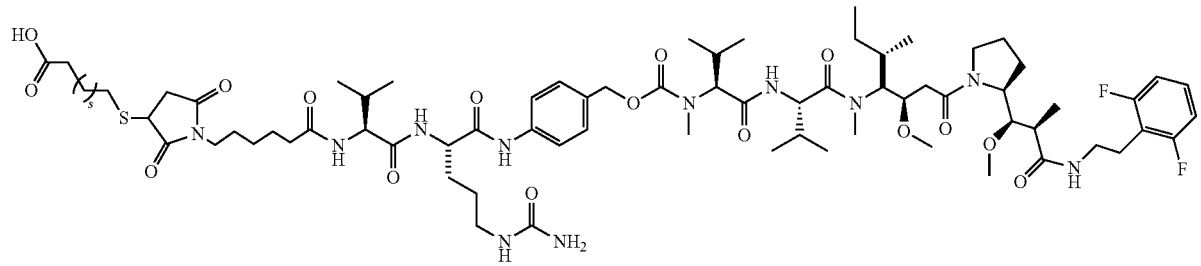

(VI-8)

With the exception that 8-mercaptooctanoic acid (V-4) was used instead of 2-(1-(mercaptomethyl)cyclopropane) acetic acid (V-2), the same procedure as in Preparation Example 4-2 was repeated to afford the title compound (66 mg, 84%).

MALDI-TOF MS m/z: 1522.0 [M+Na]$^+$

PREPARATION EXAMPLE 4-5

Preparation of Compound (VI-9)

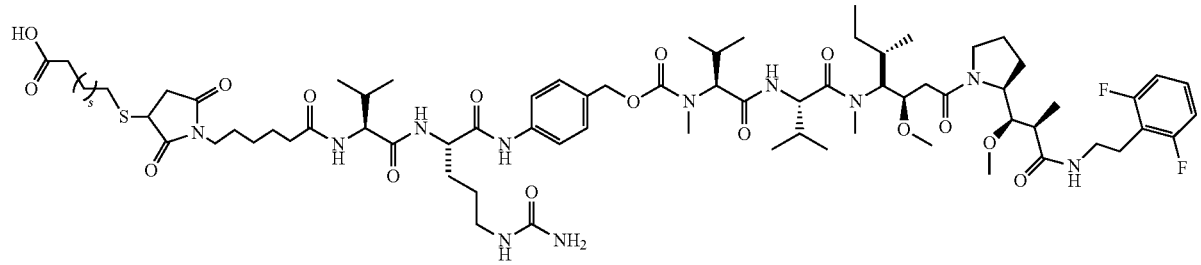

(VI-9)

With the exception that 11-mercaptoundecanoic acid (V-5) was used instead of 2-(1-(mercaptomethyl)cyclopropane)acetic acid (V-2), the same procedure as in Preparation Example 4-2 was repeated to afford the title compound (71 mg, 86%).

MALDI-TOF MS m/z: 1563.3 [M+Na]$^+$

PREPARATION EXAMPLE 4-6

Preparation of Compound (VI-10)

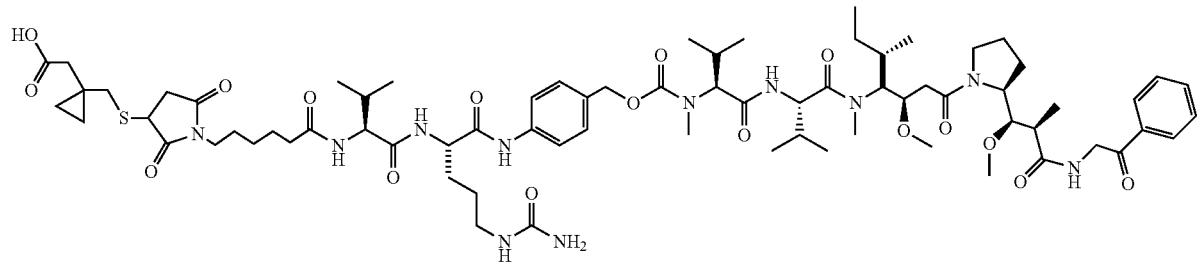

(VI-10)

With the exception that compound (IV-6) (70 mg, 0.054 mmol), obtained in Preparation Example 3-2 was used instead of compound (IV-5), obtained in Preparation Example 3-1, the same procedure as in Preparation Example 4-2 was repeated to afford the title compound (53 mg, 68%).

MALDI-TOF MS m/z: 1469.5 [M+Na]$^+$

PREPARATION EXAMPLE 4-7

Preparation of Compound (VI-11)

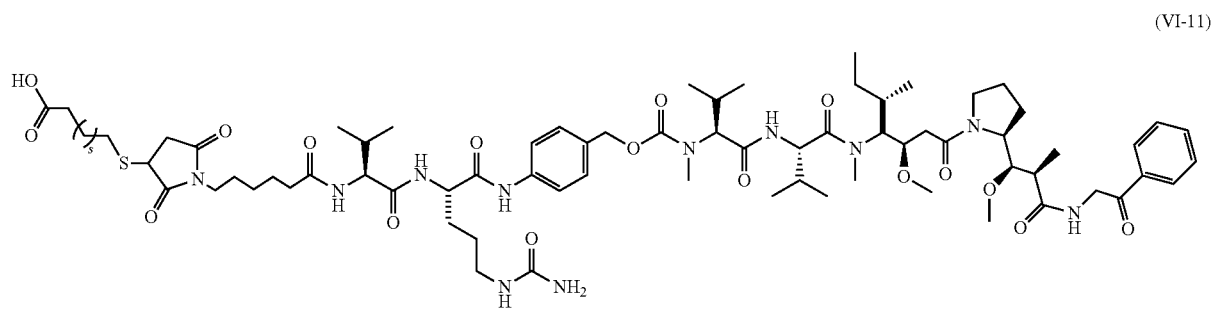

(VI-11)

With the exception that compound (IV-6) (70 mg, 0.054 mmol), obtained in Preparation Example 3-2, and 6-mercaptohexanoic acid (V-3) were used respectively instead of compound (IV-5), obtained in Preparation Example 3-1, and 2-(1-(mercaptomethyl)cyclopropane)acetic acid (V-2), the same procedure as in Preparation Example 4-2 was repeated to afford the title compound (46 mg, 59%).

MALDI-TOF MS m/z: 1471.6 [M+Na]$^+$

PREPARATION EXAMPLE 4-8

Preparation of Compound (VI-12)

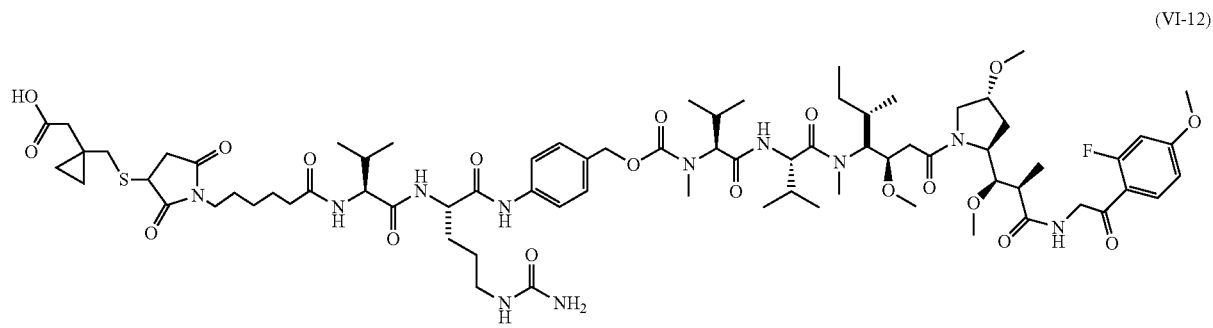 [SMILES: CC[C@H](C)[C@@H]([C@@H](CC(=O)N1C[C@H](OC)C[C@H]1[C@H](OC)[C@@H](C)C(=O)NCC(=O)c1ccc(OC)cc1F)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)CC(SCC3(CC(=O)O)CC3)C2=O)C(C)C)cc1)C(C)C]

(VI-12)

With the exception that compound (IV-7) (88 mg, 0.064 mmol), obtained in Preparation Example 3-1, was used instead of compound (IV-5), obtained in Preparation Example 3-1, the same procedure as in Preparation Example 4-2 was repeated to afford the title compound (48 mg, 49%).

MALDI-TOF MS m/z: 1548.1 [M+Na]$^+$

PREPARATION EXAMPLE 4-9

Preparation of Compound (VI-13)

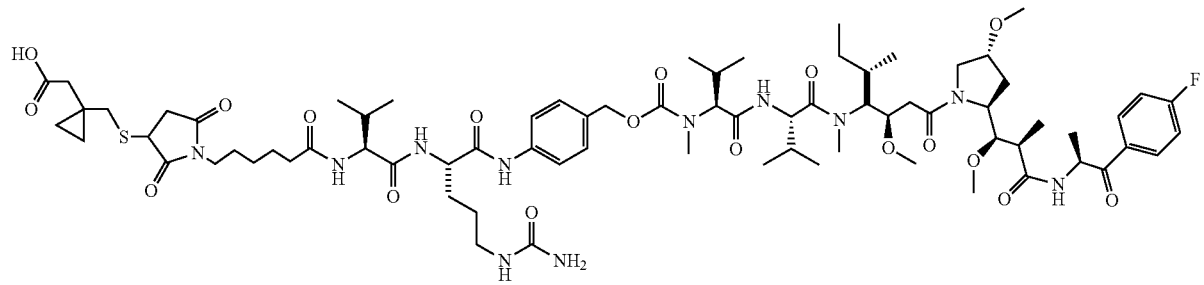

(VI-13)

With the exception that compound (IV-8) (71 mg, 0.052 mmol), obtained in Preparation Example 3-4, was used instead of compound (IV-5), obtained in Preparation Example 3-1, the same procedure as in Preparation Example 4-2 was repeated to afford the title compound (46 mg, 59%).
MALDI-TOF MS m/z: 1529.4 [M+Na]$^+$

PREPARATION EXAMPLE 4-10

Preparation of Compound (VI-14)

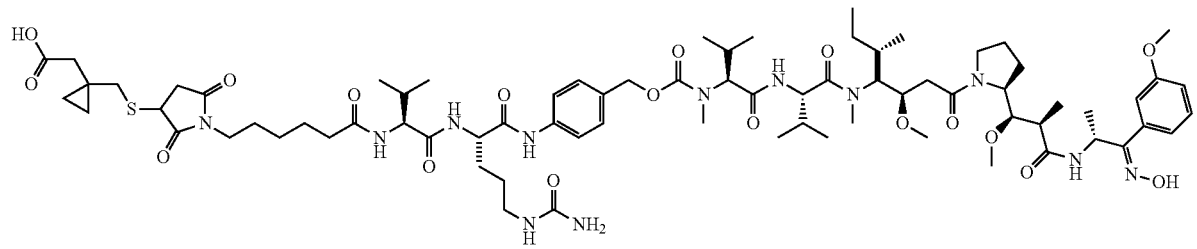

(VI-14)

With the exception that compound (IV-9) (35 mg, 0.026 mmol), obtained in Preparation Example 3-5, was used instead of compound (IV-5), obtained in Preparation Example 3-1, the same procedure as in Preparation Example 4-2 was repeated to afford the title compound (29 mg, 74%).
MALDI-TOF MS m/z: 1528.2 [M+Na]$^+$

PREPARATION EXAMPLE 4-11

Preparation of Compound (VI-15)

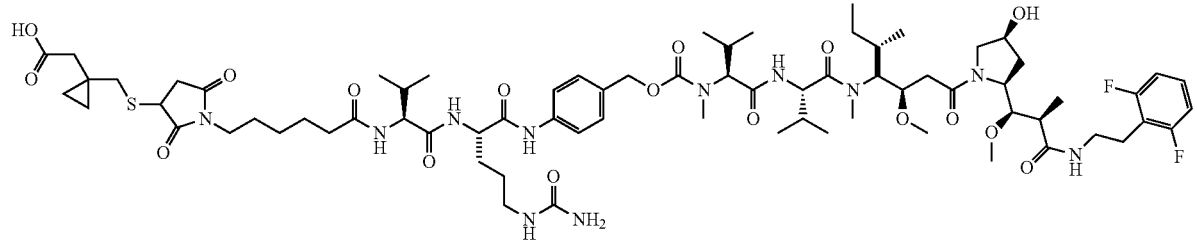

(VI-15)

With the exception that compound (IV-10) (78 mg, 0.058 mmol), obtained in Preparation Example 3-6, was used instead of compound (IV-5), obtained in Preparation Example 3-1, the same procedure as in Preparation Example 4-2 was repeated to afford the title compound (77 mg, 90%).

MALDI-TOF MS m/z: 1508.1 [M+Na]$^+$, 1524.8 [M+K]$^+$

PREPARATION EXAMPLE 4-12

Preparation of Compound (VI-16)

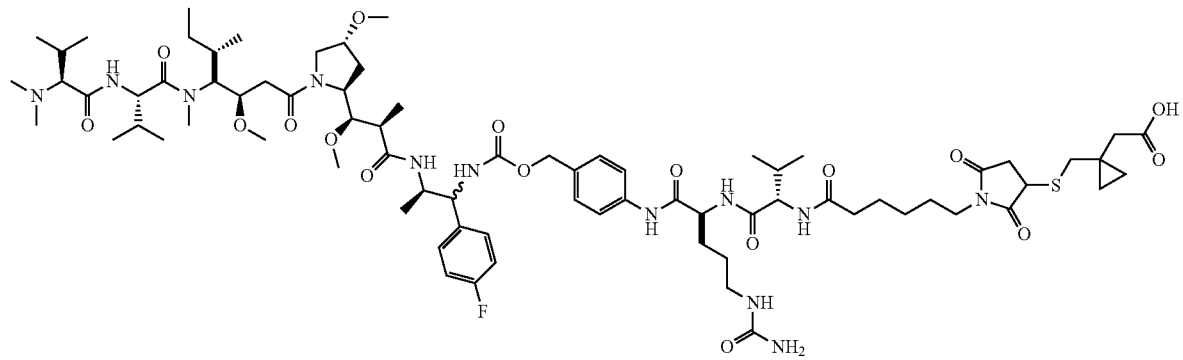

(VI-16)

To a solution of compound (IV-11)(58 mg, 0.042 mmol), obtained in Preparation Example 3-7, in 5 mL of methyl alcohol and 1.5 mL of anhydrous dimethylformamide was added 2-(1-(mercaptomethyl)cyclopropane)acetic acid (19 mg, 0.126 mmol), followed by stirring at room temperature for 4 hrs. The reaction mixture was concentrated in a vacuum, and the concentrate was purified by silica gel column chromatography to afford the title compound as a solid (60 mg, 93%).

LC-MS m/z: 1523.8 [M$^+$]$^+$, 1545.8 [M+Na]$^+$

PREPARATION EXAMPLE 4-13

Preparation of Compound (VI-17)

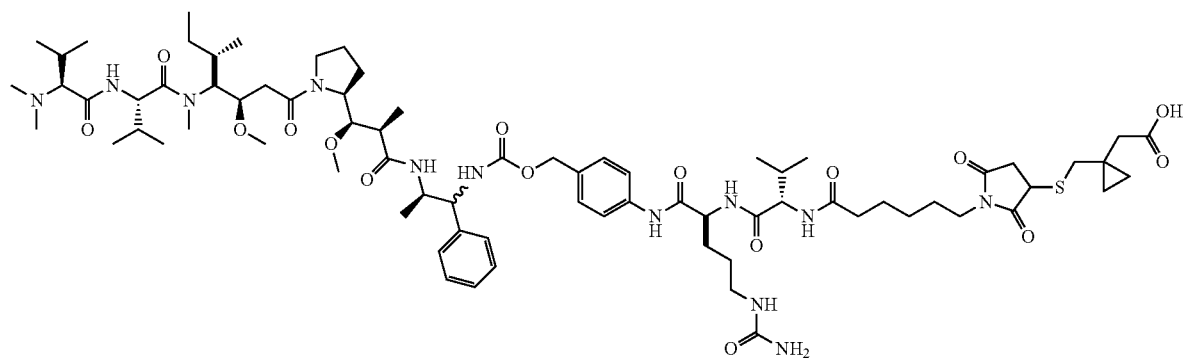

(VI-17)

With the exception that compound IV-12)(41 mg, 0.031 mmol), obtained in Preparation Example 3-8, was used instead of compound (IV-11), obtained in Preparation Example 3-7, the same procedure as in Preparation Example 4-12 was repeated to afford the title compound (39 mg, 85%).

MALDI-TOF MS m/z: 1496.8 [M+Na]$^+$

PREPARATION EXAMPLE 4-14

Preparation of Compound (VI-18)

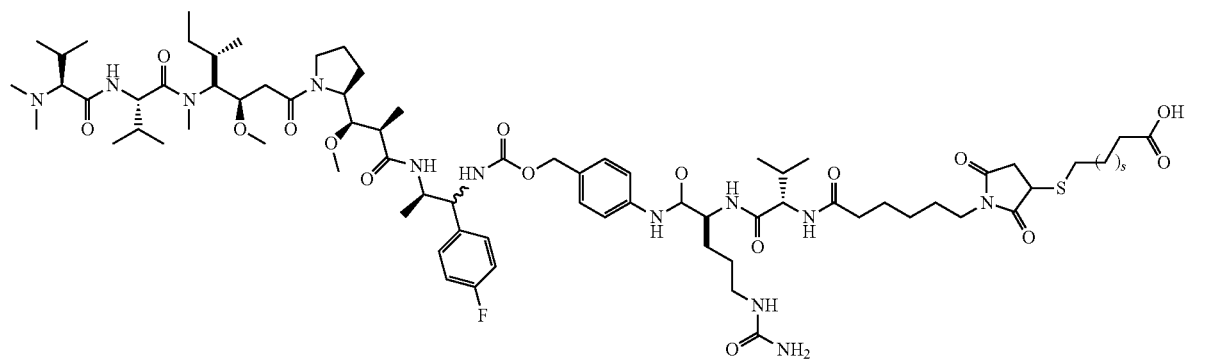

(VI-18)

With the exception that compound (IV-13) (347 mg, 0.257 mmol), obtained in Preparation Example 3-9, and 11-mercaptoundecanoic acid (112 mg, 0.514 mmol) were used respectively instead of compound (IVI-11), obtained in Preparation Example 3-7, and 2-(1-(mercaptomethyl)cyclopropane)acetic acid, the same procedure as in Preparation Example 4-12 was repeated to afford the title compound (266 mg, 66%).

LC-MS m/z: 1567 [M+1]$^+$ $^1$H NMR (400 MHz, CD$_3$OD) δ 0.76-0.90 (m, 10H), 0.90-1.14 (m, 20H), 1.17 (m, 3H), 1.26 (m, 4H), 1.29 (brs, 20H), 1.37 (m, 4H), 1.50-1.64 (m, 14H), 1.68-1.78 (m, 3H), 1.88 (m, 2H), 1.94 (s, 3H), 2.21-2.26 (m, 6H), 2.99-2.48 (m, 10H, N—CH$_3$*2), 2.70 (m, 1H), 2.84 (m, 1H), 3.07-3.19 (m, 6H), 3.26-3.45 (m, 6H), 3.45 (m, 4H), 3.82 (m, 1H), 4.15 (m, 1H), 4.47 (m, 2H), 4.64 (m, 1H), 4.81 (m, 1H), 4.98 (m, 3H), 6.96 (t, 1H), 7.08 (t, 1H), 7.25 (d, 2H), 7.28-7.40 (m, 2H), 7.53 (d, 2H)

PREPARATION EXAMPLE 4-15

Preparation of Compound (VI-19)

With the exception that compound (IV-14)(453 mg, 0.332 mmol), obtained in Preparation Example 3-10 was used instead of compound (IV-11), obtained in Preparation Example 3-7, the same procedure as in Preparation Example 4-12 was repeated to afford the title compound (60 mg, 93%).

LC-MS m/z: 1510 [M+1]$^+$, $^1$H NMR (400 MHz, CD$_3$OD) δ 0.46-0.68 (m, 5H), 0.82-1.10 (m, 27H), 1.17 (d, 2H), 1.22 (d, 1H), 1.30 (m, 2H), 1.40 (m, 1H), 1.50-1.63 (m, 6H), 1.68-1.80 (m, 2H), 1.82-1.90 (m, 2H), 1.94 (s, 3H), 2.00-2.15 (m, 4H), 2.20-2.35 (m, 5H), 2.42 (s, 6H), 2.38-2.50 (m, 2H), 2.81-2.89 (m, 1H), 2.91-2.98 (m, 2H), 3.08-3.40 (m, 6H), 3.26-3.33 (m, 10H, OCH$_3$), 3.43 (d, 2H), 3.45-3.48 (m, 5H, OCH$_3$), 3.52-3.64 (m, 1H), 3.74-3.86 (m, 1H), 3.906-4.10 (m, 3H), 4.15 (d, 1H), 4.24 (m, 1H), 4.44-4.54 (m, 2H), 4.66 (d, 1H), 4.74-5.10 (m, 5H), 7.09-7.12 (m, 2H), 7.23-7.27 (m, 2H), 7.33-7.37 (m, 2H), 7.52-7.59 (m, 2H)

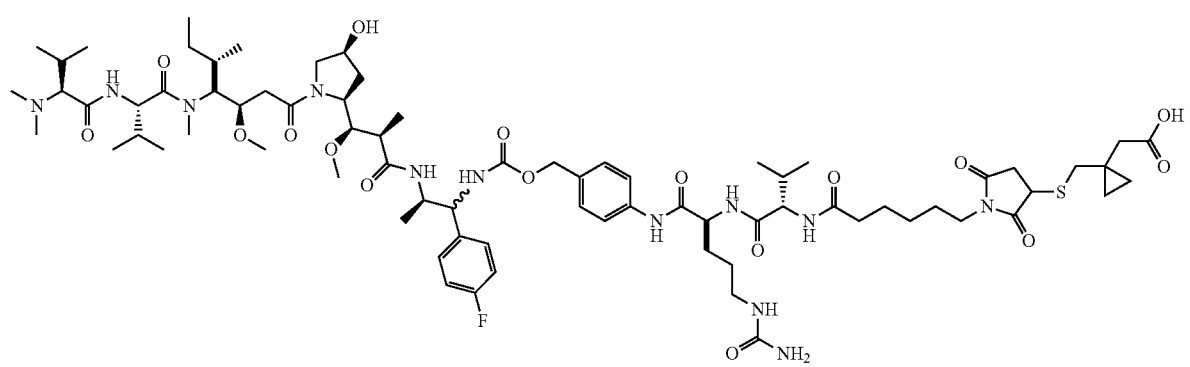

(VI-19)

PREPARATION EXAMPLE 4-16

Preparation of Compound (VI-20)

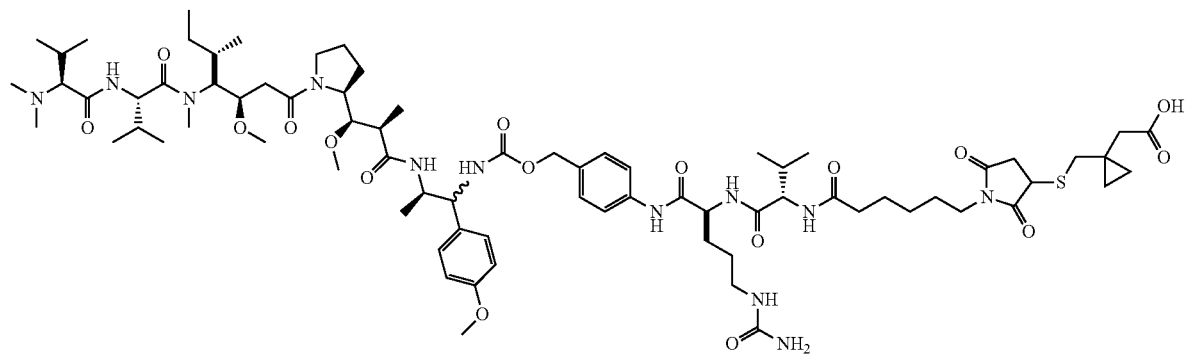

(VI-20)

With the exception that compound (IV-15)(82 mg, 0.063 mmol), obtained in Preparation Example 3-7, was used instead of compound (IV-11), obtained in Preparation Example 3-7, the same procedure as in Preparation Example 4-12 was repeated to afford the title compound (38 mg, 42%).

LC-MS m/z: 1506 [M+1]

$^1$H NMR (400 MHz, CD$_3$OD) δ 0.42-0.67 (m, 4H), 0.81-1.08 (m, 27H), 1.13-1.20 (m, 4H), 1.29 (m, 2H), 1.40 (m, 1H), 1.50-1.68 (m, 6H), 1.75 (m, 2H), 1.82-1.90 (m, 2H), 1.94 (s, 3H), 2.01-2.18 (m, 4H), 2.23-2.32 (m, 3H), 2.42 (s, 6H), 2.35-2.50 (m, 1H), 2.61 (m, 1H), 2.79-3.00 (m, 3H), 3.10-3.20 (m, 5H), 3.28-3.40 (m, 19H, 2*OCH$_3$), 3.43-3.48 (m, 3H), 3.60 (m, 1H), 3.74 (d, 3H), 3.85-4.00 (m, 3H), 4.14 (d, 1H), 4.21-4.30 (m, 1H), 4.48 (m, 2H), 4.64-5.10 (m, 5H), 6.86-7.60 (m, 8H)

PREPARATION EXAMPLE 4-17

Preparation of Compound (VI-21)

With the exception that compound (IV-16)(268 mg, 0.195 mmol), obtained in Preparation Example 3-12, was used instead of compound (IV-11), obtained in Preparation Example 3-7, the same procedure as in Preparation Example 4-12 was repeated to afford the title compound as a solid (132 mg, 46%).

LC-MS m/z: 1521 [M]$^+$ $^1$H NMR (400 MHz, DMSO-d$_6$) δ 0.48-0.50 (m, 6H), 0.71-1.08 (m, 27H), 1.16-1.22 (m, 4H), 1.42-1.54 (m, 9H), 1.60 (m, 1H), 1.70 (m, 1H), 1.94 (s, 3H), 2.10-2.32 (m, 8H), 2.32-2.46 (m, 6H), 2.50 (s, 6H), 2.78-3.10 (m, 8H), 3.16 (m, 2H), 3.21 (m, 1H), 3.28-3.40 (m, 6H), 3.62 (s, 1H), 3.70 (s, 2H), 3.86-4.00 (m, 5H), 4.19 (t, 2H), 4.38 (m, 2H), 4.52 (t, 1H), 4.60 (m, 1H), 4.76 (m, 1H), 4.88 (m, 1H), 5.00 (m, 2H), 5.08 (m, 1H), 5.42 (brs, 2H), 5.98 (m, 1H), 6.81 (d, 1H), 7.17 (d, 1H), 7.28 (dd, 1H), 7.50-7.70 (m, 3H), 7.82 (d, 1H), 8.10 (d, 1H), 10.0 (d, 1H)

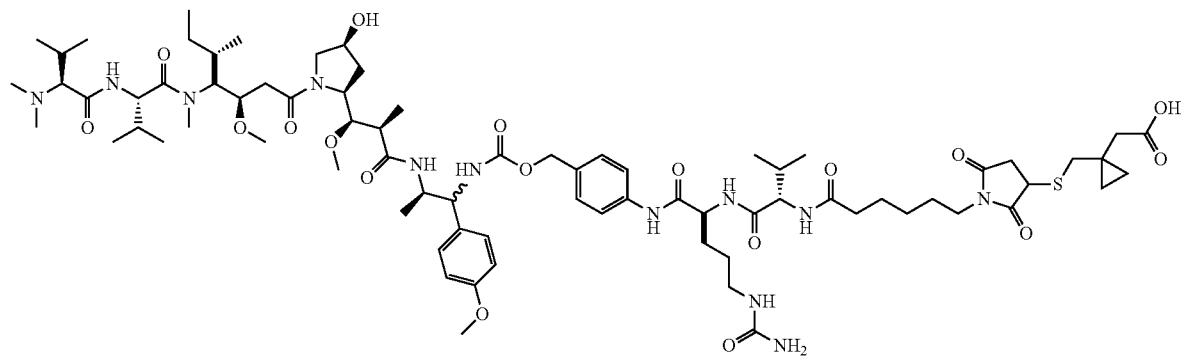

(VI-21)

PREPARATION EXAMPLE 4-18

Preparation of Compound (VI-22)

(VI-22)

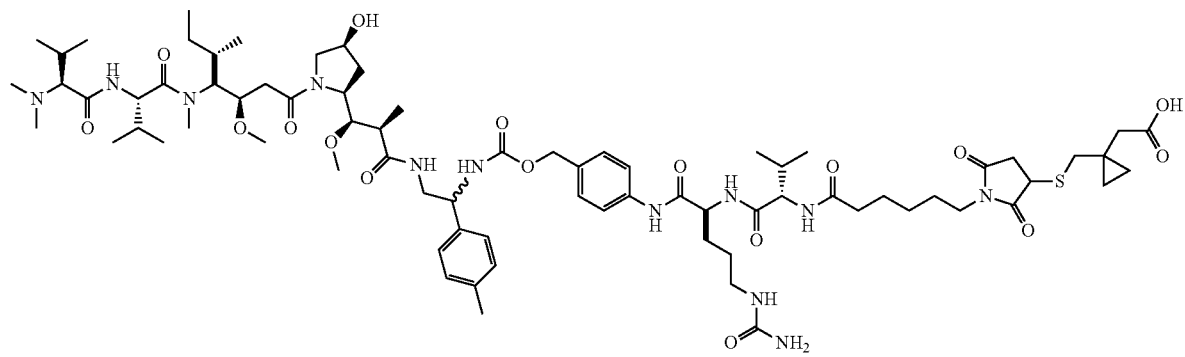

With the exception that compound (IV-17)(440 mg, 0.33 mmol), obtained in Preparation Example 3-13, was used instead of compound (IV-11), obtained in Preparation Example 3-7, the same procedure as in Preparation Example 4-12 was repeated to afford the title compound (296 mg, 60%).

LC-MS m/z: 1492 [M+1]$^+$ $^1$H NMR (400 MHz, CD$_3$OD) δ 0.47-0.62 (m, 5H), 0.81-1.02 (m, 26H), 1.13-1.20 (m, 3H), 1.25-1.32 (m, 2H), 1.40 (m, 1H), 1.50-1.68 (m, 6H), 1.72-1.78 (m, 2H), 1.82-1.98 (m, 3H), 1.96 (s, 3H), 2.00-2.09 (m, 4H), 2.25-2.35 (m, 5H), 2.38-2.48 (m, 6H), 2.850-2.90 (m, 3H), 3.05-3.20 (m, 6H), 3.26-3.35 (m, 9H, OCH$_3$), 3.40-3.48 (m, 6H, OCH$_3$), 3.50-3.60 (m, 2H), 3.65-3.80 (m, 3H), 3.90-4.18 (m, 5H), 4.48 (m, 1H), 4.64 (m, 1H), 4.70-5.10 (m, 8H), 7.09-7.58 (m, 8H)

PREPARATION EXAMPLE 4-19

Preparation of Compound (VI-23)

(VI-23)

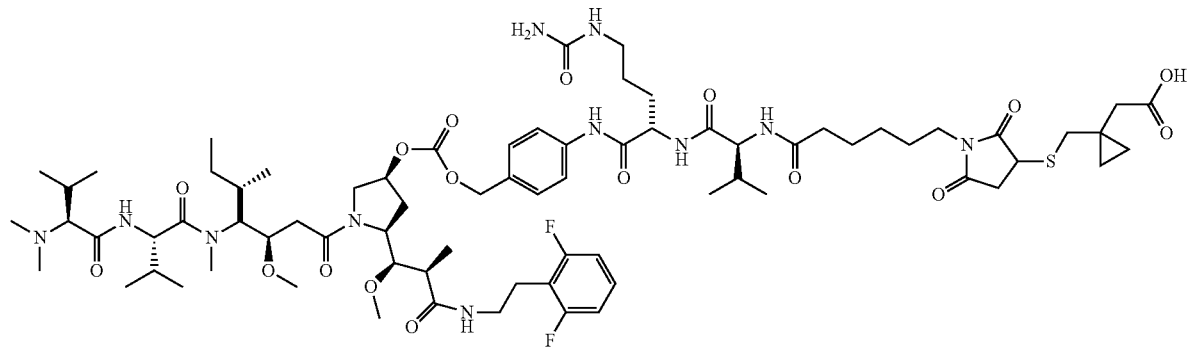

To a solution of compound (IV-18) (37 mg, 0.027 mmol), obtained in Preparation Example 3-14, in 5 mL of methyl alcohol and 1.5 mL of anhydrous dimethylformamide was added 2-(1-(mercaptomethyl)cyclopropane)acetic acid (12 mg, 0.083 mmol), followed by stirring at room temperature for 4 hrs. The reaction mixture was concentrated in a vacuum, and the concentrate was purified by silica gel column chromatography to afford the title compound as a solid (33 mg, 81%).

LC-MS m/z: 1499 [M$^+$]$^+$, 1451 [M+Na]$^+$

PREPARATION EXAMPLE 4-20

Preparation of Compound (VI-24)

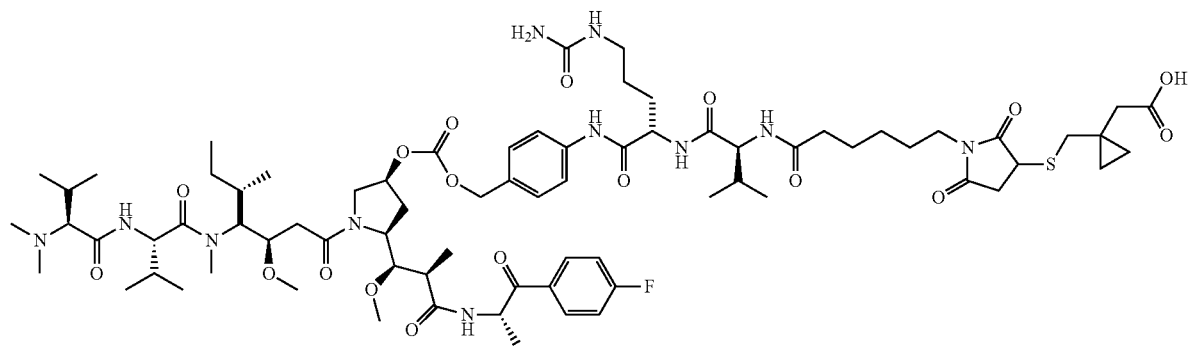

(VI-24)

With the exception that compound (IV-19) (69 mg, 0.051 mmol), obtained in Preparation Example 3-15, was used instead of compound (IV-18), obtained in Preparation Example 3-14, the same procedure as in Preparation Example 4-19 was repeated to afford the title compound as a solid (55 mg, 72%).

LC-MS m/z: 1508.9 [M$^+$]$^+$

PREPARATION EXAMPLE 4-21

Preparation of Compound (VI-25)

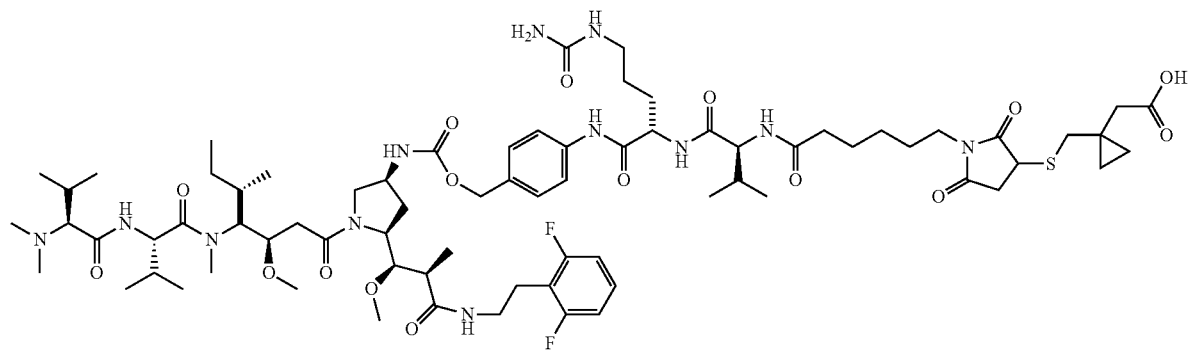

(VI-25)

With the exception that compound (IV-20) (94 mg, 0.07 mmol), obtained in Preparation Example 3-16, was used instead of compound (IV-18), obtained in Preparation Example 3-14, the same procedure as in Preparation Example 4-19 was repeated to afford the title compound (99 mg, 94%).

LC-MS m/z: 1498 [M$^+$]$^+$

PREPARATION EXAMPLE 4-22

Preparation of Compound (VI-26)

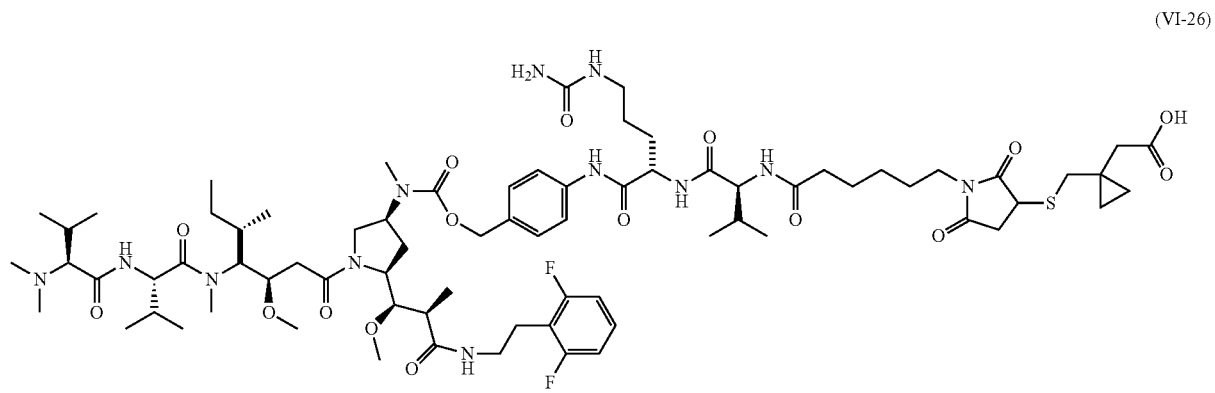 [SMILES: CC[C@H](C)[C@@H]([C@@H](CC(=O)N1C[C@@H](N(C)C(=O)OCc2ccc(NC(=O)[C@H](CCCNC(N)=O)NC(=O)[C@@H](NC(=O)CCCCCN3C(=O)CC(SCC4(CC(=O)O)CC4)C3=O)C(C)C)cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(VI-26)

With the exception that compound (IV-21) (144 mg, 0.105 mmol), obtained in Preparation Example 3-17, was used instead of compound (IV-18), obtained in Preparation Example 3-14, the same procedure as in Preparation Example 4-19 was repeated to afford the title compound as a solid (116 mg, 73%).

LC-MS m/z: 1512 [M$^+$]$^+$

PREPARATION EXAMPLE 4-23

Preparation of Compound (VI-27)

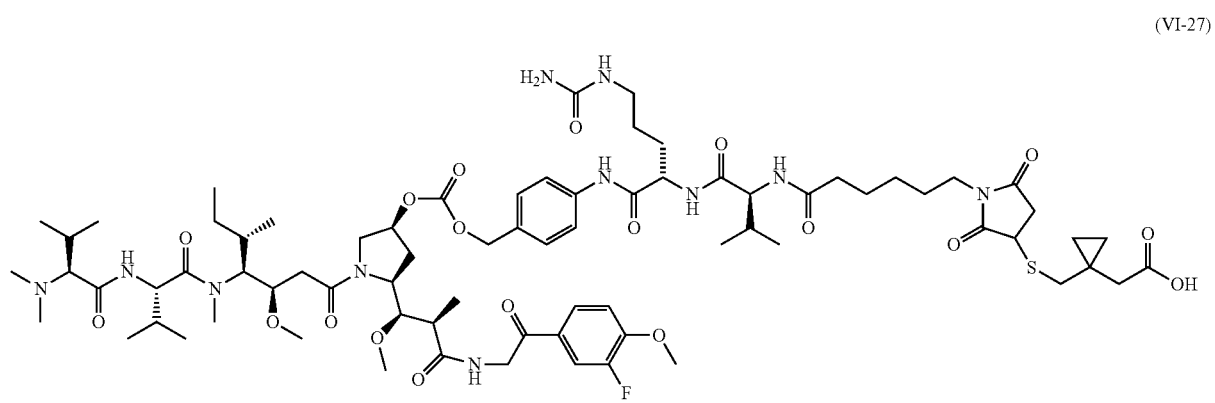 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)CC(SCC4(CC(=O)O)CC4)C3=O)C(C)C)cc2)C[C@H]1[C@H](OC)[C@@H](C)C(=O)NCC(=O)c1ccc(OC)c(F)c1)OC)N(C)C(=O)[C@@H](NC(=O)[C@H](C(C)C)N(C)C)C(C)C]

(VI-27)

With the exception that compound (IV-22) (0.14 g, 0.099 mmol), obtained in Preparation Example 3-18, was used instead of compound (IV-18), obtained in Preparation Example 3-14, the same procedure as in Preparation Example 4-19 was repeated to afford the title compound as a solid (0.11 g, 75%).

$^1$H NMR (400 MHz, DMSO-d$_6$) δ 0.50-0.52 (m, 4H), 0.65-0.76 (m, 6H), 0.82-0.92 (m, 13H), 1.08-1.24 (18H), 1.43-1.49 (m, 6H), 1.54-1.82 (m, 3H), 1.84-1.98 (m, 3H), 2.10-2.19 (m, 6H), 2.79-3.04 (m, 12H), 3.15-3.24 (m, 3H), 3.30-3.44 (m, 15H), 3.87-3.89 (m, 3H), 3.97-4.00 (m, 1H), 4.08-4.86 (m, 8H), 4.86-5.04 (m, 1H), 5.10 (s, 2H), 5.46 (s, 2H), 6.03 (t, 1H), 7.22-7.36 (m, 2H), 7.62-7.65 (d, 1H), 7.77-7.80 (d, 1H), 7.87-7.89 (m, 2H), 8.17-8.23 (m, 1H), 8.48 (brs, 1H), 10.11 (s, 1H)

LC-MS m/z: 1524.4 [M$^+$]$^+$

PREPARATION EXAMPLE 4-24

Preparation of Compound (VI-28)

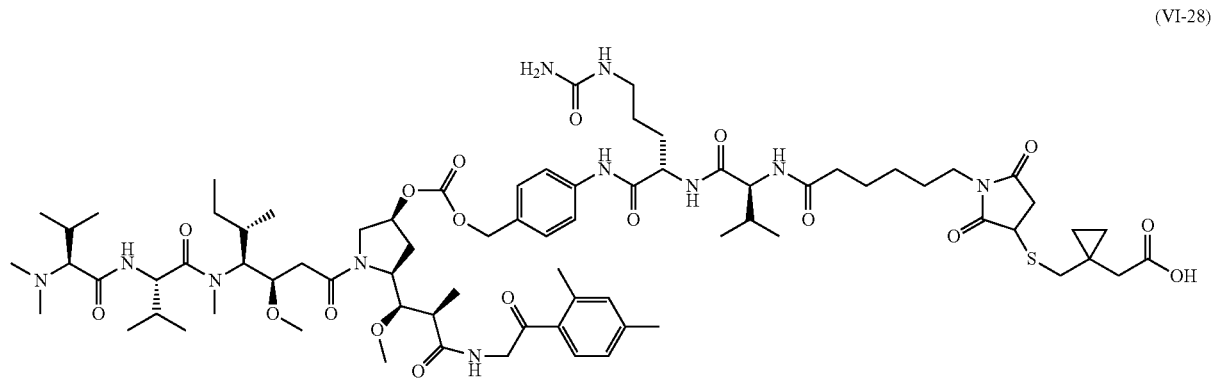 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)CC(SCC4(CC(=O)O)CC4)C3=O)C(C)C)cc2)C[C@H]1[C@H](OC)[C@@H](C)C(=O)NCC(=O)c1ccc(C)cc1C)OC)N(C)C(=O)[C@@H](NC(=O)[C@H](C(C)C)N(C)C)C(C)C]

(VI-28)

With the exception that compound (IV-23) (0.2 g, 0.15 mmol), obtained in Preparation Example 3-19, was used instead of compound (IV-18), obtained in Preparation Example 3-14, the same procedure as in Preparation Example 4-19 was repeated to afford the title compound as a solid (0.06 g, 27%).

$^1$H NMR (400 MHz, DMSO-$d_6$) δ 0.43-0.52 (m, 6H), 0.69-0.76 (m, 7H), 0.82-0.92 (m, 15H), 1.02-1.06 (m, 7H), 1.11-1.13 (m, 2H), 1.18-1.23 (m, 4H), 1.43-1.47 (m, 6H), 1.54-1.65 (m, 1H), 1.66-1.84 (m, 2H), 1.89-1.98 (m, 3H), 2.09-2.20 (m, 6H), 2.91-3.03 (m, 10H), 3.15-3.22 (m, 5H), 3.33-3.46 (m, 15H), 3.87-4.02 (m, 3H), 4.15-4.95 (m, 8H), 5.08 (s, 2H), 5.44 (s, 2H), 6.03 (t, 1H), 7.07-7.16 (m, 2H), 7.33-7.35 (m, 2H), 7.62-7.70 (d, 2H), 7.85-7.91 (m, 1H), 7.98-8.07 (m, 1H), 8.20 (brs, 1H), 8.28-8.49 (m, 1H), 10.10 (s, 1H)

LC-MS m/z: 1504.4 [M$^+$]$^+$

PREPARATION EXAMPLE 4-25

Preparation of Compound (VI-29)

With the exception that compound (IV-24) (0.1 g, 0.1 mmol), obtained in Preparation Example 3-20, was used instead of compound (IV-18), obtained in Preparation Example 3-14, the same procedure as in Preparation Example 4-19 was repeated to afford the title compound as a solid (0.08 g, 53%).

$^1$H NMR (400 MHz, DMSO-$d_6$) δ 0.43-0.47 (m, 5H), 0.48-0.50 (d, 1H), 0.58-0.59 (d, 1H) 0.69-0.76 (m, 3H), 0.82-0.92 (m, 16H), 1.05-1.09 (m, 6H), 1.11-1.13 (m, 2H), 1.16-1.23 (m, 4H), 1.43-1.47 (m, 6H), 1.54-1.65 (m, 1H), 1.66-1.84 (m, 2H), 1.89-1.98 (m, 3H), 2.10-2.20 (m, 8H), 2.31-2.43 (m, 2H), 2.58-2.68 (m, 1H), 2.70-2.82 (m, 3H), 2.87-2.88 (m, 2H), 2.95-3.00 (m, 4H), 3.13-3.22 (m, 4H), 3.31-3.46 (m, 16H), 3.90-3.92 (m, 3H), 3.97-4.00 (m, 1H), 4.06-5.00 (m, 8H), 5.10 (s, 2H), 5.47 (s, 2H), 6.10 (t, 1H), 7.22-7.28 (m, 1H), 7.33-7.43 (m, 2H), 7.55-7.58 (d, 1H), 7.88-7.99 (m, 2H), 8.01-8.03 (d, 1H), 8.22-8.54 (m, 2H), 8.64 (s, 1H), 10.15 (s, 1H)

LC-MS m/z: 1556.4 [M$^+$]$^+$

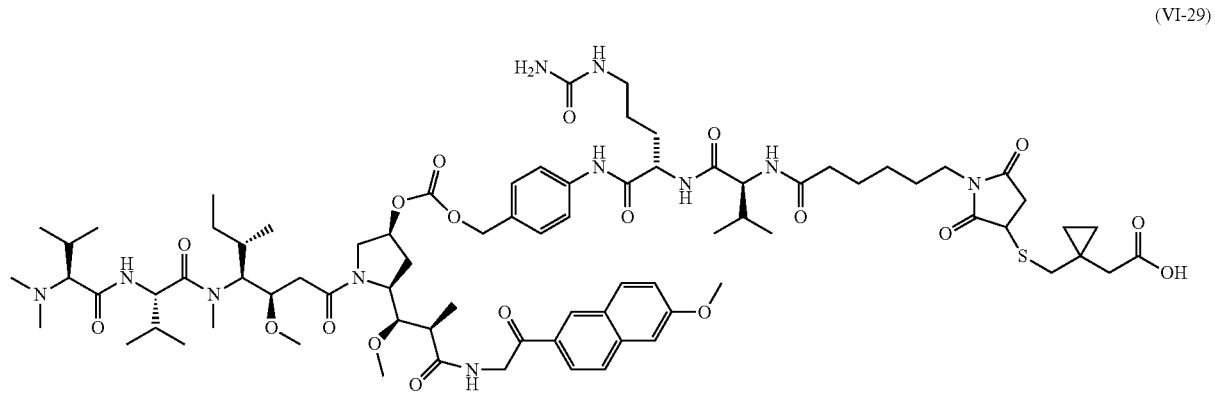 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)CC(SCC4(CC(=O)O)CC4)C3=O)C(C)C)cc2)C[C@H]1[C@H](OC)[C@@H](C)C(=O)NCC(=O)c1ccc2cc(OC)ccc2c1)OC)N(C)C(=O)[C@@H](NC(=O)[C@H](C(C)C)N(C)C)C(C)C]

(VI-29)

PREPARATION EXAMPLE 4-26

Preparation of Compound (VI-30)

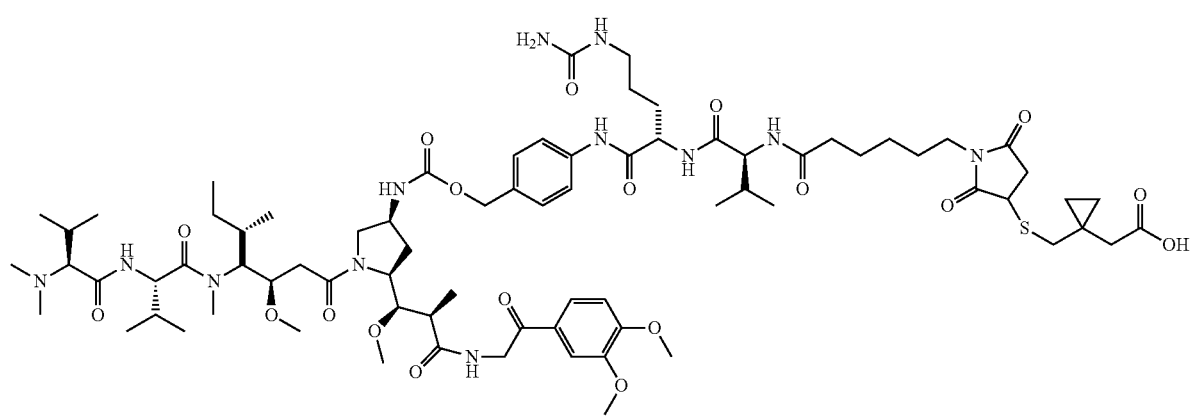

(VI-30)

With the exception that compound (IV-25) (0.46 g, 0.33 mmol), obtained in Preparation Example 3-21, was used instead of compound (IV-18), obtained in Preparation Example 3-14, the same procedure as in Preparation Example 4-19 was repeated to afford the title compound as a solid (0.49 g, 96%).

$^1$H NMR (400 MHz, DMSO-$d_6$) δ 0.30-0.58 (m, 6 H), 0.59-0.78 (m, 8 H), 0.78-1.00 (m, 16 H), 1.05-1.32 (m, 6 H), 1.32-1.54 (m, 6 H), 1.54-1.64 (m, 1 H), 1.64-1.84 (m, 3 H), 1.84-2.05 (m, 3 H), 2.06-2.27 (m, 10 H), 2.27-2.43 (m, 4 H), 2.55-2.71 (m, 1 H), 2.71-2.85 (m, 2 H), 2.85-3.07 (m, 7 H), 3.09-3.18 (m, 3 H), 3.18-3.30 (m, 3 H), 3.74-3.88 (m, 6 H), 3.88-4.05 (m, 4 H), 4.06-4.22 (m, 2 H), 4.22-4.43 (m, 2 H), 4.43-4.53 (m, 1 H), 4.59-4.75 (m, 2 H), 4.96 (s, 2 H), 5.43 (s, 2 H), 5.78 (s, 1 H), 5.96-6.10 (d, 1 H), 7.01-7.13 (d, 1 H), 7.21-7.37 (m, 2 H), 7.41-7.48 (s, 1 H), 7.49-7.57 (m, 1 H), 7.57-7.75 (m, 3 H), 8.00-8.11 (m, 1 H), 10.00-10.20 (brs, 1 H)

LC-MS m/z: 1535.5 [M$^+$]$^+$

PREPARATION EXAMPLE 4-27

Preparation of Compound (VI-31)

With the exception that compound (IV-26) (0.24 g, 0.17 mmol), obtained in Preparation Example 3-22, was used instead of compound (IV-18), obtained in Preparation Example 3-14, the same procedure as in Preparation Example 4-19 was repeated to afford the title compound as a solid (0.19 g, 73%).

$^1$H NMR (400 MHz, DMSO-$d_6$) δ 0.37-0.58 (m, 9 H), 0.60-0.78 (m, 6 H), 0.78-0.97 (m, 16 H), 1.06-1.37 (m, 7 H), 1.37-1.53 (m, 6 H), 1.54-1.85 (m, 5 H), 1.86-2.03 (m, 3 H), 2.05-2.26 (m, 10 H), 2.26-2.43 (m, 3 H), 2.58-2.67 (m, 1 H), 2.68-2.84 (m, 2 H), 2.85-3.09 (m, 8 H), 3.10-3.24 (m, 6 H), 3.24-3.33 (m, 3 H), 3.62-3.78 (m, 1 H), 3.78-4.05 (m, 3 H), 4.05-4.24 (m, 2 H), 4.27-4.40 (m, 1 H), 4.46-4.61 (m, 1 H), 4.61-4.72 (m, 1 H), 4.72-4.89 (m, 1 H), 5.01 (s, 2 H), 5.44 (s, 2 H), 5.96-6.14 (t, 1 H), 7.21-7.37 (m, 2 H), 7.45-7.56 (m, 1 H), 7.56-7.74 (m, 4 H), 7.93-8.08 (m, 3H), 8.08-8.19 (m, 1 H), 8.28-8.39 (m, 1 H), 8.49-8.61 (m, 1 H), 8.73 (s, 1 H), 10.14 (brs, 1 H)

LC-MS m/z: 1535.5 [M$^+$]$^+$

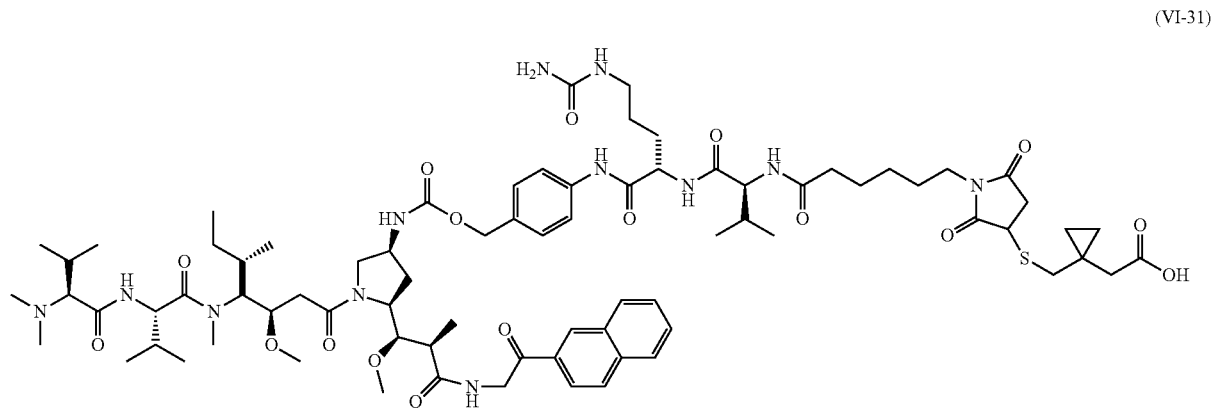 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)CC(SCC4(CC(=O)O)CC4)C3=O)C(C)C)cc2)C[C@H]1[C@H](OC)[C@@H](C)C(=O)NCC(=O)c1ccc2ccccc2c1)OC)N(C)C(=O)[C@@H](NC(=O)[C@H](C(C)C)N(C)C)C(C)C]

(VI-31)

PREPARATION EXAMPLE 4-28

Preparation of Compound (VI-32)

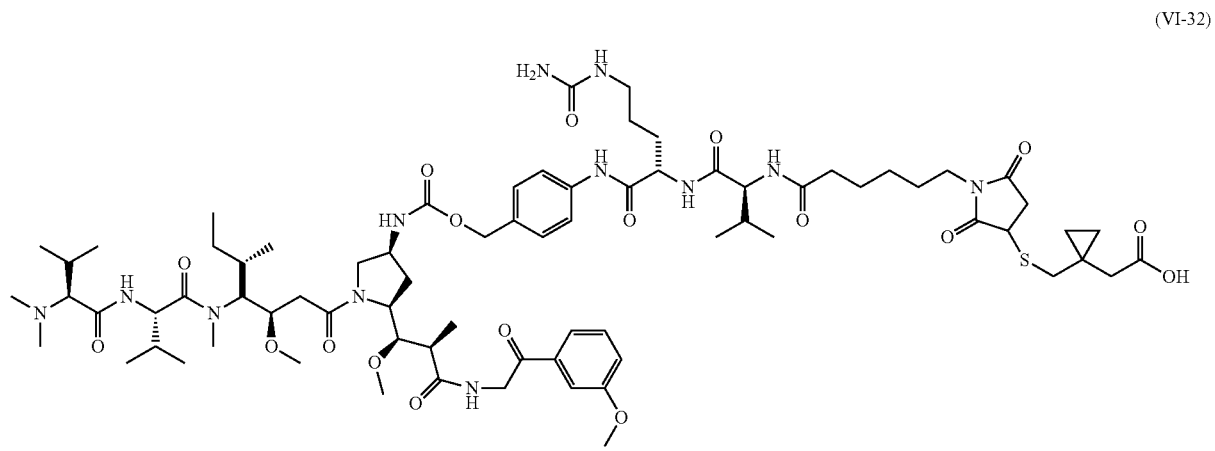 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)CC(SCC4(CC(=O)O)CC4)C3=O)C(C)C)cc2)C[C@H]1[C@H](OC)[C@@H](C)C(=O)NCC(=O)c1cccc(OC)c1)OC)N(C)C(=O)[C@@H](NC(=O)[C@H](C(C)C)N(C)C)C(C)C]

(VI-32)

With the exception that compound (IV-27) (0.21 g, 0.15 mmol), obtained in Preparation Example 3-23, was used instead of compound (IV-18), obtained in Preparation Example 3-14, the same procedure as in Preparation Example 4-19 was repeated to afford the title compound as a solid (0.21 g, 91%).

$^1$H NMR (400 MHz, DMSO-$d_6$) δ 0.34-0.56 (m, 5 H), 0.64-0.78 (m, 6 H), 0.78-0.96 (m, 15 H), 0.96-1.07 (m, 2 H), 1.07-1.27 (m, 5 H), 1.29-1.39 (m, 1 H), 1.39-1.54 (m, 5 H), 1.54-1.65 (m, 1 H), 1.65-1.84 (m, 3 H), 1.84-2.03 (m, 3 H), 2.05-2.31 (m, 10 H), 2.31-2.44 (m, 2 H), 2.44-2.48 (m, 1 H), 2.58-2.61 (m, 2 H), 2.75-2.85 (m, 1 H), 2.86-3.08 (m, 7 H), 3.09-3.15 (m, 1 H), 3.24-3.55 (m, 14 H), 3.64-3.76 (m, 2H), 3.77-3.86 (m, 2 H), 3.87-4.04 (m, 3 H), 4.04-4.14 (m, 2H), 4.14-4.25 (m, 2H), 4.33-4.40 (m, 1 H), 4.40-4.61 (m, 2 H), 4.61-4.76 (m, 1 H), 4.97 (s, 2 H), 5.44 (s, 2 H), 5.98-6.11 (t, 1H), 6.82-6.94 (m, 1 H), 7.16-7.25 (m, 1 H), 7.25-7.37 (m, 2 H), 7.40-7.49 (m, 1 H), 7.49-7.68 (m, 3 H), 7.81-7.99 (m, 1 H), 7.99-8.12 (m, 1 H), 8.24-8.45 (m, 1 H), 10.12 (brs, 1 H)

LC-MS m/z: 1535.5 [M$^+$]$^+$

PREPARATION EXAMPLE 4-29

Preparation of Compound (VI-33)

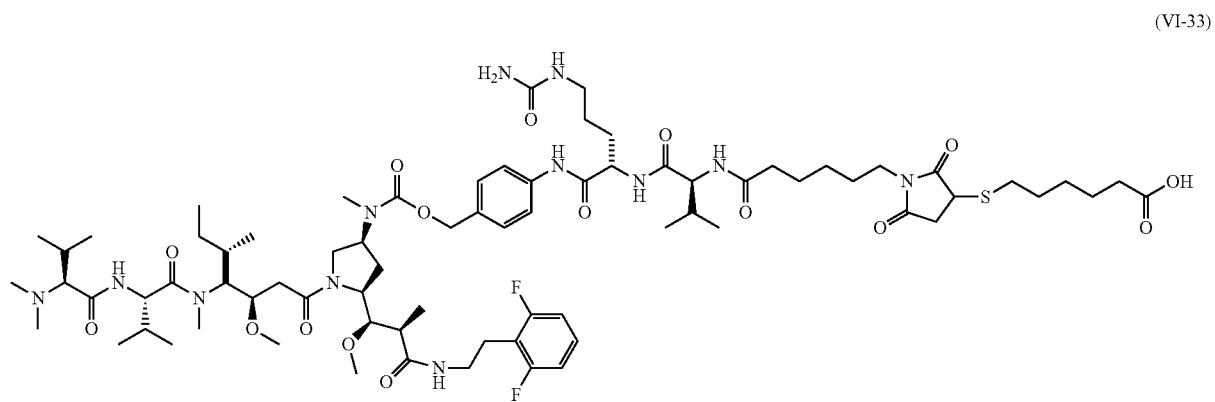 [SMILES: CC[C@H](C)[C@@H]([C@@H](CC(=O)N1C[C@@H](N(C)C(=O)OCc2ccc(NC(=O)[C@H](CCCNC(N)=O)NC(=O)[C@@H](NC(=O)CCCCCN3C(=O)CC(SCCCCCC(=O)O)C3=O)C(C)C)cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(VI-33)

With the exception that compound (IV-21) (0.28 g, 0.21 mmol), obtained in Preparation Example 3-17, and 6-mercaptohexanoic acid (0.07 g, 0.41 mmol) were used respectively instead of compound (IV-18), obtained in Preparation Example 3-14, and 2-(1-(mercaptomethyl)cyclopropane) acetic acid, the same procedure as in Preparation Example 4-19 was repeated to afford the title compound as a solid (0.26 g, 81%).

$^1$H NMR (400 MHz, DMSO-$d_6$) δ 0.64-0.79 (m, 5H), 0.79-0.98 (m, 17H), 0.98-1.14 (m, 4H), 1.14-1.28 (m, 5H), 1.28-1.41 (m, 6H), 1.41-1.65 (m, 14H), 1.65-1.79 (m, 2H), 1.83-2.05 (m, 7H), 2.05-2.32 (m, 13 H), 2.32-2.56 (m, 1 H), 2.57-2.88 (m, 10 H), 2.89-3.06 (m, 6 H), 3.06-3.24 (m, 3 H), 3.69-3.86 (m, 3 H), 3.86-4.09 (m, 3 H), 4.09-4.28 (m, 1 H), 4.29-4.48 (m, 2 H), 4.48-4.78 (m, 2 H), 5.04 (s, 2 H), 5.42 (s, 2 H), 6.03 (brs, 1 H), 7.01 (brs, 2 H), 7.14-7.45 (m, 2 H), 7.45-7.70 (m, 1 H), 7.83-8.06 (m, 2 H), 10.08 (brs, 1 H)

LC-MS m/z: 1514.4 [M$^+$H]$^+$, 1536.4 [M+Na]$^+$

PREPARATION EXAMPLE 4-30

Preparation of Compound (VI-34)

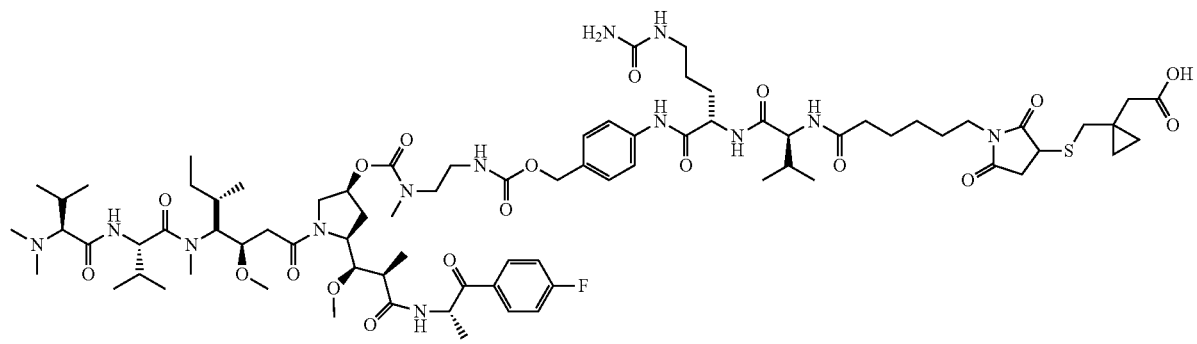

(VI-34)

To a solution of compound (IV-28)(137 mg, 0.093 mmol), obtained in Preparation Example 3-24, in 5 mL of methyl alcohol and 3 mL of anhydrous dimethylformamide was added 2-(1-(mercaptomethyl)cyclopropane)acetic acid (41 mg, 0.28 mmol), followed by stirring at room temperature for 15 hrs. The reaction mixture was concentrated in a vacuum, and the concentrate was purified by silica gel column chromatography to afford the title compound as a solid (25 mg, 17%).

LC-MS m/z: 1609.3 [M+H]$^+$

PREPARATION EXAMPLE 4-31

Preparation of Compound (VI-35)

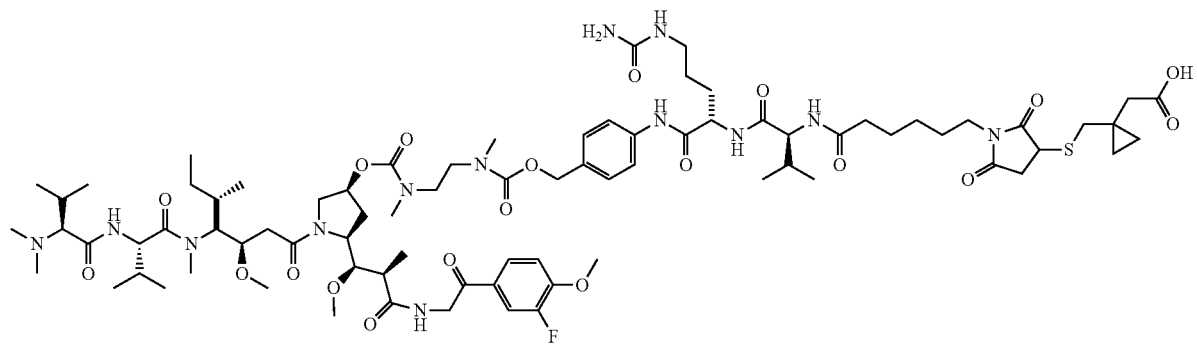

(VI-35)

With the exception that compound (IV-29) (0.19 g, 0.128 mmol), obtained in Preparation Example 3-25, was used instead of compound (IV-28), obtained in Preparation Example 3-24, the same procedure as in Preparation Example 4-30 was repeated to afford the title compound (0.085 g, 41%).

$^1$H NMR (400 MHz, DMSO-$d_6$) δ 0.42-0.55 (m, 6H), 0.66-0.75 (m, 8H), 0.81-0.87 (m, 14H), 1.10-1.23 (m, 6H), 1.37-1.49 (m, 6H), 1.54-1.79 (m, 3H), 1.91-1.98 (m, 7H), 2.27 (s, 1H), 2.30-2.37 (m, 1H), 2.38-2.42 (m, 1H), 2.44-2.45 (m, 1H), 2.56-2.64 (m, 2H), 2.75-2.86 (m, 6H), 2.93-2.99 (m, 4H), 3.12-3.24 (m, 4H), 3.31-3.35 (m, 17H), 3.91-4.06 (m, 6H), 4.14-4.86 (m, 8H), 4.98 (s, 2H), 5.43 (s, 2H), 5.97-5.98 (t, 1H), 7.29-7.30 (m, 2H), 7.58-7.60 (d, 2H), 7.77-7.90 (m, 2H), 7.93-8.10 (m, 2H), 8.11-8.13 (d, 2H), 8.46 (brs, 1H), 10.01 (s, 1H), 12.12 (brs, 1H)

LC-MS m/z: 1639.0 [M+H]$^+$, 1661.0 [M+Na]$^+$

PREPARATION EXAMPLE 4-32

Preparation of Compound (VI-36)

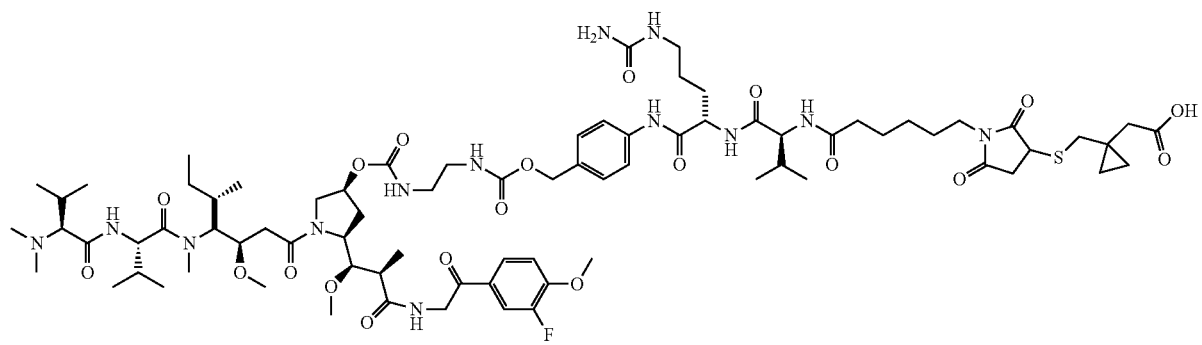

(VI-36)

With the exception that compound (IV-30) (0.18 g, 0.119 mmol), obtained in Preparation Example 3-26, was used instead of compound (IV-28), obtained in Preparation Example 3-24, the same procedure as in Preparation Example 4-30 was repeated to afford the title compound (0.12 g, 61%).

$^1$H NMR (400 MHz, DMSO-$d_6$) δ 0.44-0.52 (m, 5H), 0.66-0.75 (m, 7H), 0.82-0.92 (m, 12H), 1.09-1.23 (m, 6H), 1.43-1.47 (m, 5H), 1.54-1.83 (m, 3H), 1.94-1.97 (m, 4H), 2.10-2.22 (m, 7H), 2.25-2.26 (d, 1H), 2.38-2.46 (m, 4H), 2.56-2.67 (m, 2H), 2.78-2.81 (m, 2H), 2.86-2.91 (m, 2H), 2.96-3.04 (m, 5H), 3.10-3.24 (m, 4H), 3.32-3.35 (m, 17H), 3.91-3.93 (m, 3H), 3.97-4.00 (m, 2H), 4.13-4.65 (m, 8H), 4.80-4.86 (m, 2H), 4.94 (s, 2H), 5.44 (s, 2H), 6.00 (t, 1H), 7.22-7.32 (m, 4H), 7.54-7.56 (d, 2H), 7.78-7.81 (d, 1H), 7.85-8.00 (m, 2H), 8.09-8.23 (m, 2H), 8.47 (brs, 1H), 10.04 (s, 1H), 12.12 (brs, 1H)

LC-MS m/z: 1610.8 [M+H]$^+$, 1632.8 [M+Na]$^+$

PREPARATION EXAMPLE 4-33

Preparation of Compound (VI-37)

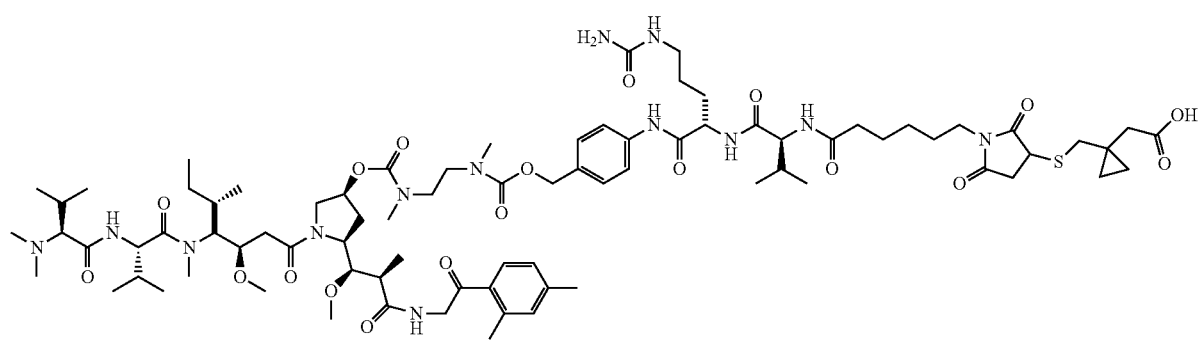

(VI-37)

With the exception that compound (IV-31) (0.2 g, 0.138 mmol), obtained in Preparation Example 3-27, was used instead of compound (IV-28), obtained in Preparation Example 3-24, the same procedure as in Preparation Example 4-30 was repeated to afford the title compound (0.17 g, 77%).

$^1$H NMR (400 MHz, DMSO-$d_6$) δ 0.00-0.57 (m, 6H), 0.69-0.76 (m, 8H), 0.82-0.87 (m, 14H), 0.95-1.08 (m, 2H), 1.09-1.18 (m, 2H), 1.20-1.24 (m, 2H), 1.43-1.49 (m, 6H), 1.54-1.64 (m, 1H), 1.81-2.05 (m, 4H), 2.20-2.23 (m, 6H), 2.27-2.38 (m, 9H), 2.56-2.69 (m, 1H), 2.70-2.81 (m, 2H), 2.82-2.86 (m, 7H), 2.96-3.00 (m, 5H), 3.15-3.20 (m, 5H), 3.27 (s, 3H), 3.32-3.34 (m, 15H), 3.89-4.00 (m, 3H), 4.14-4.25 (m, 2H), 4.26-4.82 (m, 8H), 4.98 (s, 2H), 5.43 (s, 2H), 6.00-6.03 (t, 1H), 7.06-7.16 (m, 2H), 7.28-7.30 (m, 2H), 7.59-7.69 (m, 3H), 7.84-7.86 (d, 1H), 7.97-8.05 (m, 1H), 8.14-8.15 (m, 1H), 8.23-8.28 (m, 1H), 8.49 (brs, 1H), 10.02 (s, 1H)

LC-MS m/z: 1619.6 [M+H]$^+$, 1641.6 [M+Na]$^+$

PREPARATION EXAMPLE 4-34

Preparation of Compound (VI-38)

(VI-38)

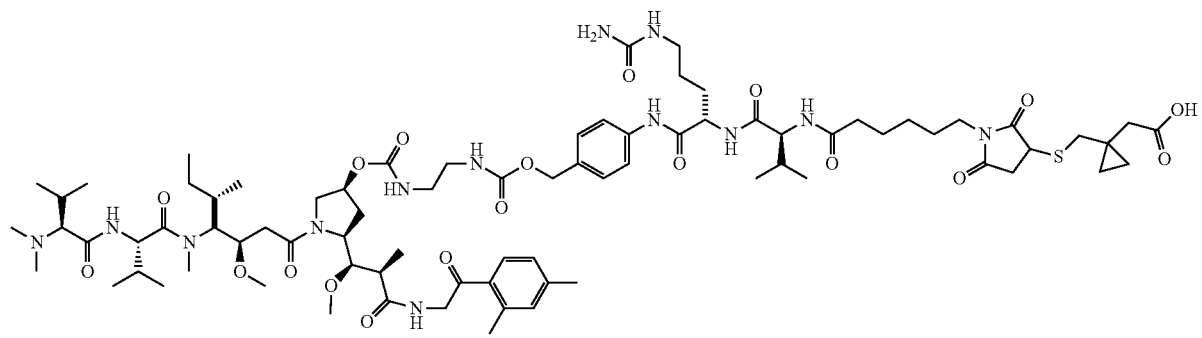

With the exception that compound (IV-32) (0.2 g, 0.137 mmol), obtained in Preparation Example 3-28, was used instead of compound (IV-28), obtained in Preparation Example 3-24, the same procedure as in Preparation Example 4-30 was repeated to afford the title compound (0.17 g, 76%).

$^1$H NMR (400 MHz, DMSO-$d_6$) δ 0.50-0.52 (m, 4H), 0.69-0.76 (m, 8H), 0.82-0.92 (m, 14H), 1.03-1.05 (m, 2H), 1.11-1.12 (m, 1H), 1.18-1.24 (m, 3H), 1.42-1.49 (m, 6H), 1.52-1.64 (m, 1H), 1.66-1.83 (m, 3H), 1.86-2.02 (m, 4H), 2.10-2.20 (m, 6H), 2.28-2.38 (m, 8H), 2.45-2.49 (m, 1H), 2.56-2.68 (m, 1H), 2.78-2.86 (m, 3H), 2.95-3.10 (m, 8H), 3.15-3.17 (m, 4H), 3.28 (s, 3H), 3.34-3.35 (m, 10H), 3.95-4.00 (m, 3H), 4.02-4.88 (m, 8H), 4.94 (s, 2H), 5.43 (s, 2H), 6.03 (t, 1H), 7.06-7.15 (m, 2H), 7.22-7.29 (m, 4H), 7.54-7.69 (m, 3H), 7.89 (brs, 1H), 7.87-7.99 (d, 1H), 8.03-8.05 (d, 1H), 8.19 (brs, 1H), 8.30 (m, 1H), 8.50 (m, 1H), 10.04 (s, 1H)

LC-MS m/z: 1591.7 [M+H]$^+$, 1613.7 [M+Na]$^+$

PREPARATION EXAMPLE 4-35

Preparation of Compound (VI-39)

(VI-39)

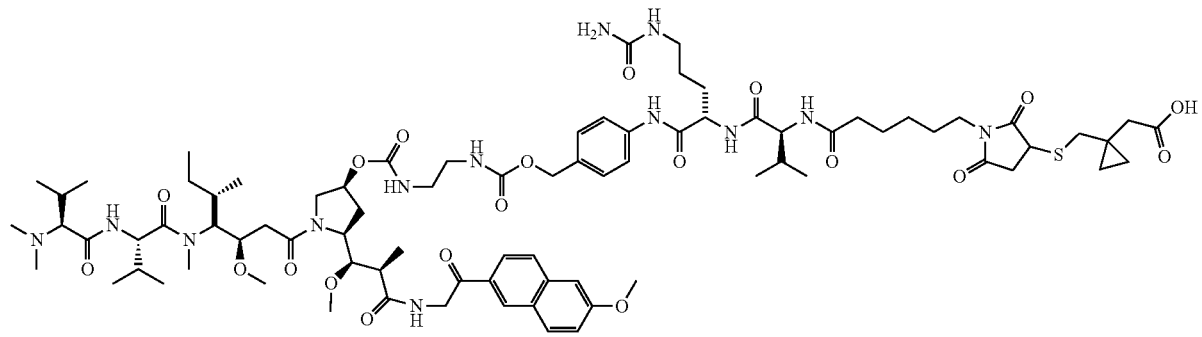

With the exception that compound (IV-33) (0.15 g, 0.099 mmol), obtained in Preparation Example 3-29, was used instead of compound (IV-28), obtained in Preparation Example 3-24, the same procedure as in Preparation Example 4-30 was repeated to afford the title compound (0.11 g, 70%).

$^1$H NMR (400 MHz, DMSO-d$_6$) δ 0.41-0.54 (m, 6H), 0.58-0.65 (m, 2H), 0.68-0.76 (m, 3H), 0.82-0.95 (m, 14H), 1.09-1.23 (m, 8H), 1.32-1.49 (m, 5H), 1.59-1.61 (m, 1H), 1.68-1.71 (m, 3H), 1.87-2.04 (m, 3H), 2.09-2.23 (m, 10H), 2.32-2.39 (m, 3H), 2.62-2.68 (m, 'H), 2.74-3.25 (m, 15H), 3.33-3.50 (m, 14H), 3.90-3.97 (m, 3H), 3.99-4.14 (m, 2H), 4.16-4.89 (m, 8H), 4.90 (s, 2H), 5.45 (s, 2H), 6.10 (t, 1H), 7.22-7.28 (m, 3H), 7.38-7.41 (d, 2H), 7.55-7.85 (d, 2H), 7.86-8.01 (m, 2H), 8.03-8.05 (m, 1H), 8.19-8.20 (brs, 1H), 8.29 (brs, 1H), 8.59 (brs, 1H), 8.84 (s, 1H), 10.08 (s, 1H)

LC-MS m/z: 1642.8 [M+H]$^+$, 1664.8 [M+Na]$^+$

PREPARATION EXAMPLE 4-36

Preparation of Compound (VI-40)

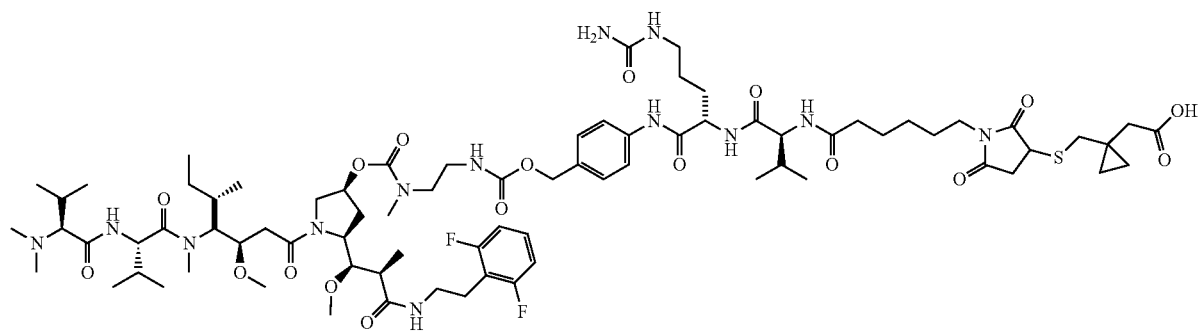

(VI-40)

With the exception that compound (IV-34) (1.3 g, 0.895 mmol), obtained in Preparation Example 3-30, was used instead of compound (IV-28), obtained in Preparation Example 3-24, the same procedure as in Preparation Example 4-30 was repeated to afford the title compound (1.1 g, 74%).

$^1$H NMR (400 MHz, DMSO-d$_6$) δ 0.40-0.50 (m, 7H), 0.70-0.77 (m, 8H), 0.82-0.89 (m, 18H), 1.02-0.07 (m, 3H), 1.18-1.29 (m, 3H), 1.44-1.47 (m, 6H), 1.54-1.76 (m, 4H), 1.89-1.94 (m, 5H), 2.10-2.23 (m, 12H), 2.32-2.44 (m, 3H), 2.61-2.64 (m, 2H), 2.74-3.00 (m, 10H), 3.13-3.17 (m, 3H), 3.20-3.33 (m, 10H), 3.90-4.00 (m, 4H), 4.16-4.84 (m, 8H), 4.95 (s, 2H), 5.41 (s, 2H), 6.01-6.02 (t, 1H), 7.01-7.05 (m, 2H), 7.28-7.29 (m, 4H), 7.59-7.60 (d, 2H), 7.84-7.99 (m, 2H), 8.13-8.16 (m, 1H), 8.23 (brs, 1H), 10.04 (s, 1H)

LC-MS m/z: 1598.9 [M+H]$^+$, 1621.9 [M+Na]$^+$

PREPARATION EXAMPLE 4-37

Preparation of Compound (VI-41)

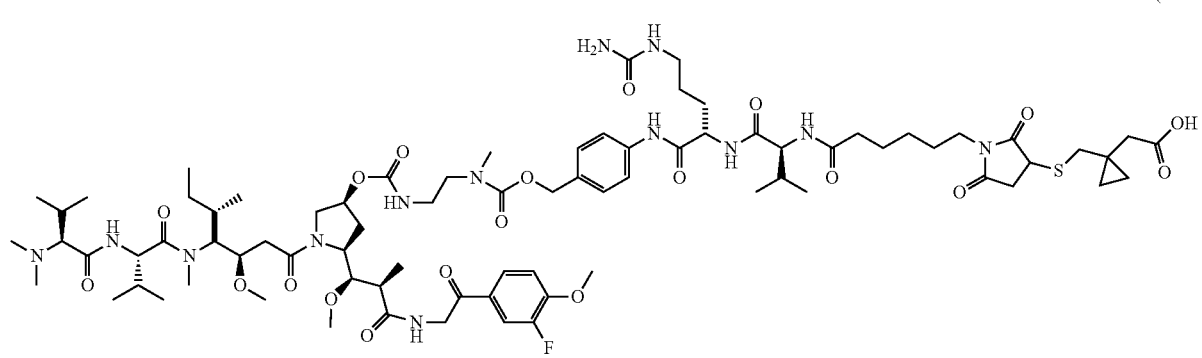

(VI-41)

With the exception that compound (IV-35) (0.14 g, 0.095 mmol), obtained in Preparation Example 3-31, was used instead of compound (IV-28), obtained in Preparation Example 3-24, the same procedure as in Preparation Example 4-30 was repeated to afford the title compound (0.072 g, 47%).

¹H NMR (400 MHz, DMSO-d6) δ 0.43-0.50 (m, 6H), 0.66-0.76 (m, 8H), 0.82-0.92 (m, 16H), 1.09-1.23 (m, 6H), 1.44-1.48 (m, 6H), 1.65-1.81 (m, 3H), 1.84-1.97 (m, 4H), 2.01-2.30 (m, 10H), 2.34-2.38 (m, 3H), 2.56-2.64 (m, 2H), 2.80-2.88 (m, 5H), 2.91-3.04 (m, 5H), 3.14-3.17 (m, 6H), 3.27-3.39 (m, 17H), 3.92-3.98 (m, 3H), 4.15-4.86 (m, 8H), 4.98 (s, 2H), 5.42 (s, 2H), 6.02-6.03 (t, 1H), 7.21-7.36 (m, 4H), 7.55-7.63 (d, 2H), 7.77-8.01 (m, 4H), 8.03-8.05 (d, 1H), 8.13 (brs, 1H), 8.45 (brs, 1H), 10.01 (s, 1H)

LC-MS m/z: 1624.9 [M+H]⁺, 1646.9 [M+Na]⁺

PREPARATION EXAMPLE 5

Preparation of Compounds of Chemical Formulas VII-1, VII-2, VII-3 and VII-4

PREPARATION EXAMPLE 5-1

Preparation of Compound (VII-5)

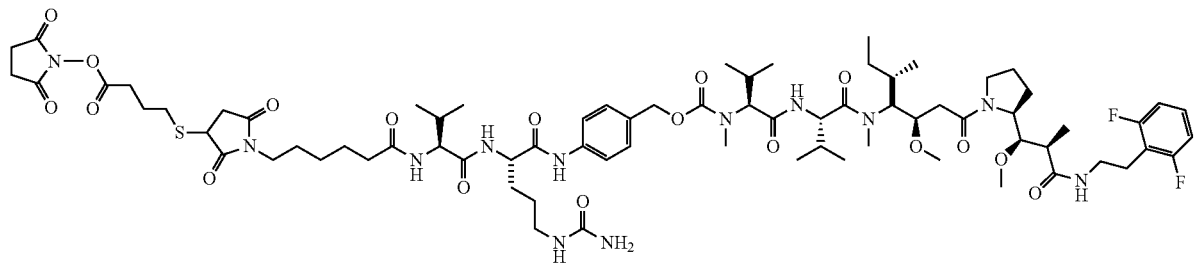

(VII-5)

Under an argon stream, compound (VI-5) (290 mg, 0.20 mmol), obtained in Preparation Example 4-1, was dissolved in 10 mL of anhydrous dimethyl formamide, and added with N-hydroxysuccinimide (35 mg, 0.30 mmol). The reaction mixture was cooled to 0° C., and added with EDC.HCl (58 mg, 0.30 mmol) before being stirred at room temperature for 15 hrs. After completion of the reaction, vacuum concentration was carried out. The residue was dissolved in 50 mL of ethylacetate, acidified with 5 mL of 1 M HCl, and washed with 30 mL of distilled water and 30 mL of saturated brine, sequentially. The organic layer was dried over anhydrous sodium sulfate, and concentrated in a vacuum. The concentrate was purified by silica gel column chromatography to afford the title compound (226 mg, 73%).

MALDI-TOF MS m/z: 1562.9 [M+Na]⁺

PREPARATION EXAMPLE 5-2

Preparation of Compound (VII-6)

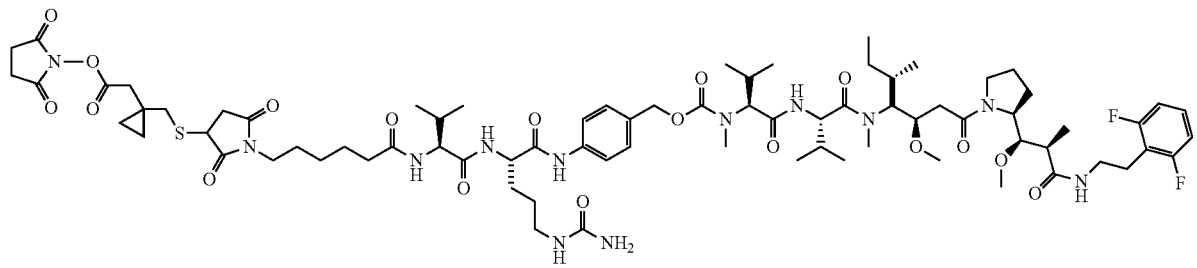

(VII-6)

With the exception that compound (VI-6) (60 mg, 0.041 mmol), obtained in Preparation Example 4-2, was used instead of compound (VI-5), obtained in Preparation Example 4-1, the same procedure as in Preparation Example 5-1 was repeated to afford the title compound as an ivory solid (53 mg, 83%).

MALDI-TOF MS m/z: 1586.7 [M+Na]$^+$

PREPARATION EXAMPLE 5-3

Preparation of Compound (VII-7)

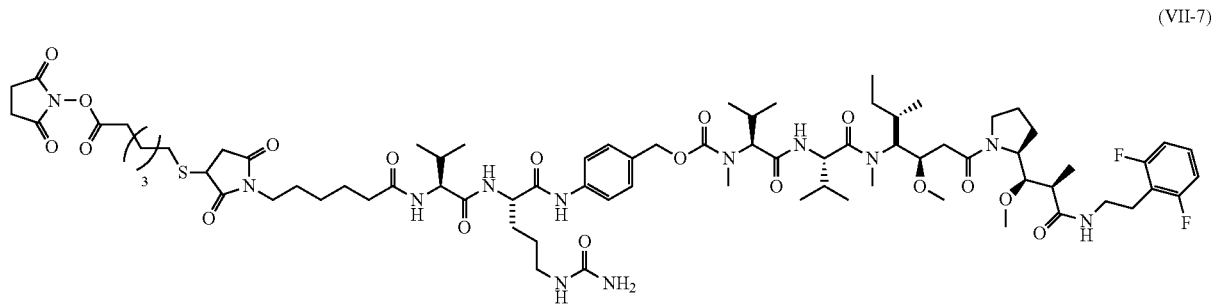

(VII-7)

With the exception that compound (VI-7) (54 mg, 0.037 mmol), obtained in Preparation Example 4-3, was used instead of compound (VI-5), obtained in Preparation Example 4-1, the same procedure as in Preparation Example 5-1 was repeated to afford the title compound as an ivory solid (57 mg, 98%).

MALDI-TOF MS m/z: 1607.4 [M+K]$^+$

PREPARATION EXAMPLE 5-4

Preparation of Compound (VII-8)

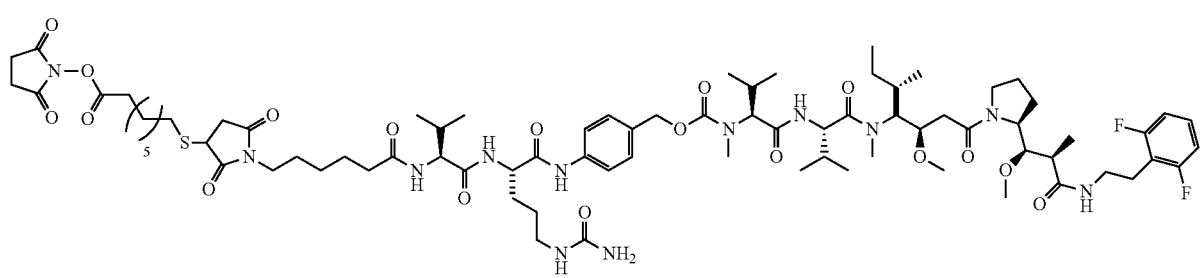

(VII-8)

With the exception that compound (VI-8) (66 mg, 0.044 mmol), obtained in Preparation Example 4-4, was used instead of compound (VI-5), obtained in Preparation Example 4-1, the same procedure as in Preparation Example 5-1 was repeated to afford the title compound as an ivory solid (53 mg, 84%).

MALDI-TOF MS m/z: 1617.0 [M+Na]$^+$

PREPARATION EXAMPLE 5-5

Preparation of Compound (VII-9)

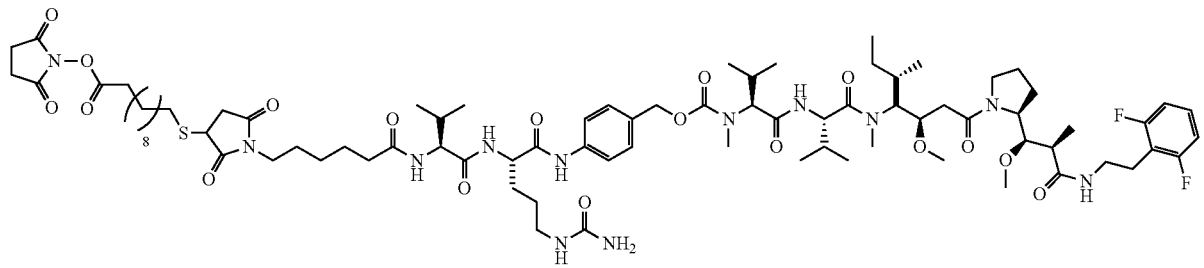

(VII-9)

With the exception that compound (VI-9) (71 mg, 0.046 mmol), obtained in Preparation Example 4-5, was used instead of compound (VI-5), obtained in Preparation Example 4-1, the same procedure as in Preparation Example 5-1 was repeated to afford the title compound as an ivory solid (66 mg, 88%).

MALDI-TOF MS m/z: 1660.9 [M+Na]$^+$, 1677.1 [M+K]$^+$

PREPARATION EXAMPLE 5-6

Preparation of Compound (VII-10)

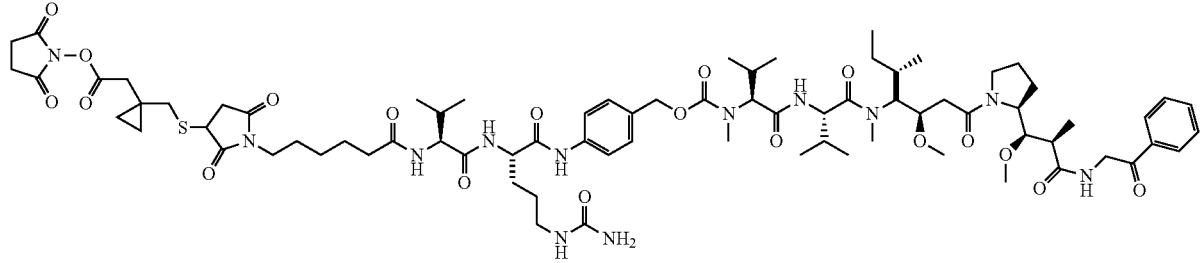

(VII-10)

With the exception that compound (VI-10) (53 mg, 0.037 mmol), obtained in Preparation Example 4-6, was used instead of compound (VI-5), obtained in Preparation Example 4-1, the same procedure as in Preparation Example 5-1 was repeated to afford the title compound as an ivory solid (38 mg, 67%).

MALDI-TOF MS m/z: 1565.5 [M+Na]$^+$

PREPARATION EXAMPLE 5-7

Preparation of Compound (VII-11)

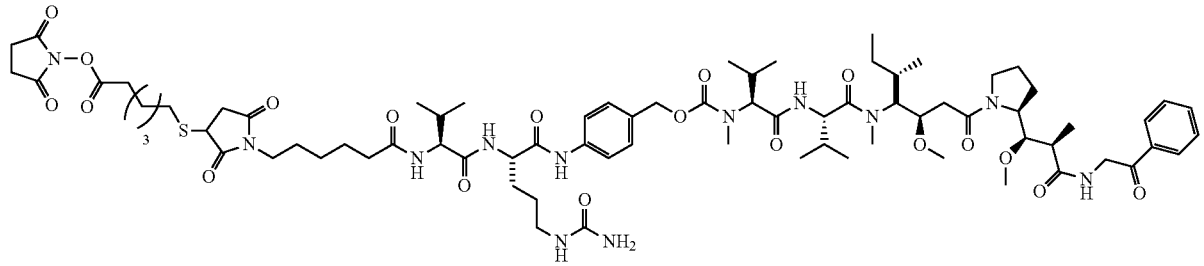

(VII-11)

With the exception that compound (VI-11) (46 mg, 0.032 mmol), obtained in Preparation Example 4-7, was used instead of compound (VI-5), obtained in Preparation Example 4-1, the same procedure as in Preparation Example 5-1 was repeated to afford the title compound as an ivory solid (30 mg, 61%).

MALDI-TOF MS m/z: 1568.9 [M+Na]⁺, 1585.0 [M+K]⁺

PREPARATION EXAMPLE 5-8

Preparation of Compound (VII-12)

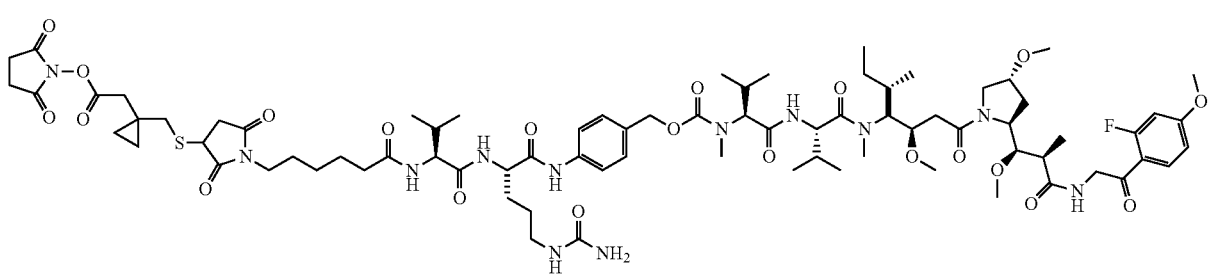

(VII-12)

With the exception that compound (VI-12) (38 mg, 0.025 mmol), obtained in Preparation Example 4-8, was used instead of compound (VI-5), obtained in Preparation Example 4-1, the same procedure as in Preparation Example 5-1 was repeated to afford the title compound as an ivory solid (31 mg, 78%).

MALDI-TOF MS m/z: 1643.7 [M+Na]⁺, 1660.2 [M+K]⁺

PREPARATION EXAMPLE 5-9

Preparation of Compound (VII-13)

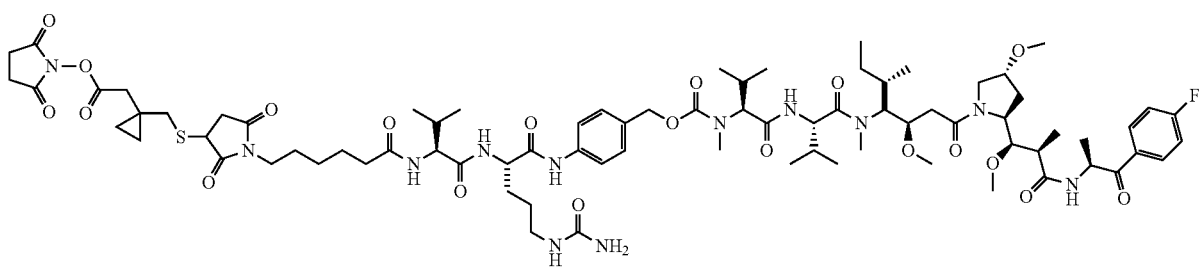

(VII-13)

With the exception that compound (VI-13) (34 mg, 0.023 mmol), obtained in Preparation Example 4-9, was used instead of compound (VI-5), obtained in Preparation Example 4-1, the same procedure as in Preparation Example 5-1 was repeated to afford the title compound as an ivory solid (27 mg, 75%).

MALDI-TOF MS m/z: 1627.7 [M+Na]⁺, 1644.8 [M+K]⁺

PREPARATION EXAMPLE 5-10

Preparation of Compound (VII-14)

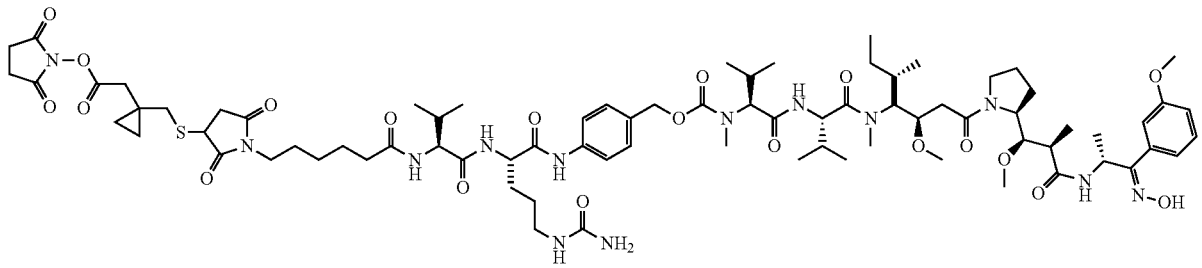

(VII-14)

With the exception that compound (VI-14) (29 mg, 0.019 mmol), obtained in Preparation Example 4-10, was used instead of compound (VI-5), obtained in Preparation Example 4-1, the same procedure as in Preparation Example 5-1 was repeated to afford the title compound as an ivory solid (8 mg, 27%).
MALDI-TOF MS m/z: 1625.4 [M+Na]$^+$, 1642.0 [M+K]$^+$

PREPARATION EXAMPLE 5-11

Preparation of Compound (VII-15)

Under an argon stream, compound (VI-16)(60 mg, 0.039 mmol), obtained in Preparation Example 4-12, was dissolved in 3 mL of anhydrous dimethyl formamide, and added with N-hydroxysuccinimide (18.1 mg, 0.157 mmol). The reaction mixture was cooled to 0° C., and added with EDC.HCl (30.2 mg, 0.157 mmol) before being stirred at room temperature for 15 hrs. After completion of the reaction, vacuum concentration was carried out. The residue was dissolved in 50 mL of ethylacetate, acidified with 5 mL of 1 M HCl, and washed with 30 mL of distilled water and 30 mL of saturated brine, sequentially. The organic layer was dried over anhydrous sodium sulfate, and concentrated in a vacuum. The concentrate was purified by silica gel column chromatography to afford the title compound (37 mg, 57%).
LC-MS m/z: 1620.8 [M+]$^+$, 1643.7 [M+Na]$^+$ (VII-15)

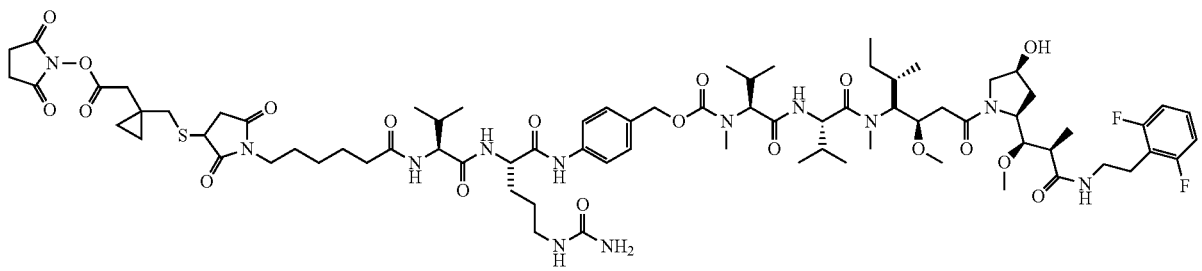

With the exception that compound (VI-15) (77 mg, 0.052 mmol), obtained in Preparation Example 4-11, was used instead of compound (VI-5), obtained in Preparation Example 4-1, the same procedure as in Preparation Example 5-1 was repeated to afford the title compound as an ivory solid (34 mg, 41%).
MALDI-TOF MS m/z: 1603.8 [M+Na]$^+$, 1621.2 [M+K]$^+$

PREPARATION EXAMPLE 5-12

Preparation of Compound (VII-16)

$^1$H NMR (400 MHz, CDCl3) δ 0.48 (m, 2H), 0.64 (m, 2H), 0.71 (m, 6H), 0.78-0.88 (m, 17H), 0.92-0.97 (m, 4H), 1.02-1.03 (d, 2H), 1.16 (m, 3H), 1.40-1.45 (m, 5H), 1.50-1.78 (m, 4H), 1.82-2.01 (m, 5H), 2.16 (S, 6H), 2.06-2.28 (m, 3H), 2.39 (m, 1H), 2.47 (S, 3H), 2.44-2.50 (m, 1H), 2.60 (m, 1H), 2.70 (m, 1H), 2.77 (S, 3H), 2.82-2.94 (m, 4H), 2.96-3.00 (m, 3H), 3.10-3.17 (m, 7H), 3.18-3.52 (m, 13H), 3.54-3.70 (m, 2H), 3.76 (m, 1H), 3.84-3.99 (m, 3H), 4.00-4.16 (m, 2H), 4.33 (m, 1H), 4.49 (t, 1H), 4.54-4.68 (m, 2H), 4.92 (m, 2H), 5.38 (s, 2H), 5.95 (m, 1H), 7.00-7.06 (m, 2H), 7.22-7.27 (m, 3H), 7.50-7.55 (m, 2H), 7.70-7.78 (m, 1H), 7.98-8.06 (m, 1H), 9.95 (S, 1H)

(VII-16)

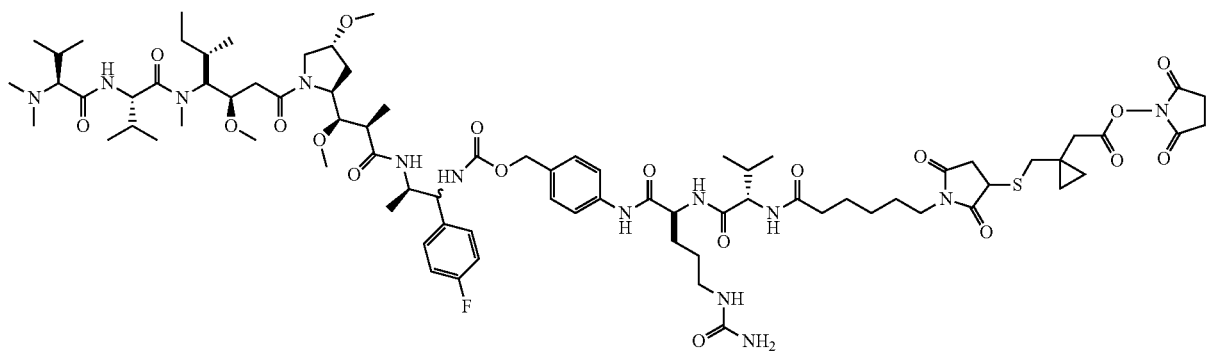

PREPARATION EXAMPLE 5-13

Preparation of Compound (VII-17)

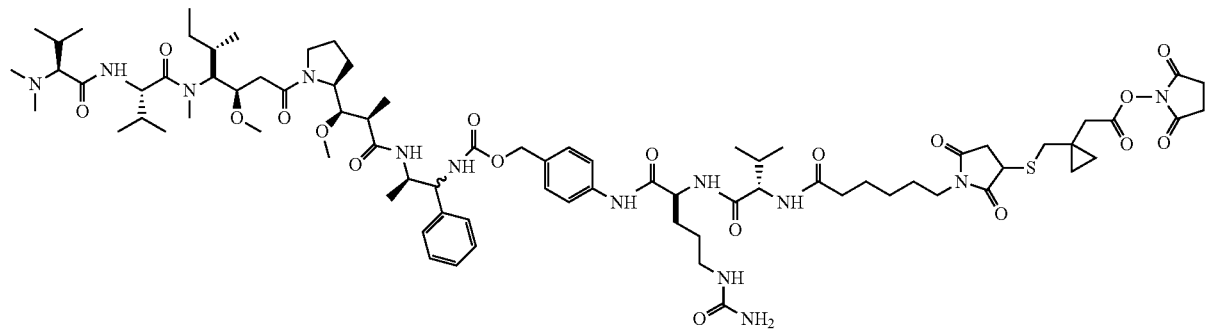

(VII-17)

With the exception that compound (VI-17) (39 mg, 0.026 mmol), obtained in Preparation Example 4-13, was used instead of compound (VI-16), obtained in Preparation Example 4-12, the same procedure as in Preparation Example 5-12 was repeated to afford the title compound (32 mg, 78%).

MALDI-TOF MS m/z: 1595.8 [M+Na]$^+$

PREPARATION EXAMPLE 5-14

Preparation of Compound (VII-18)

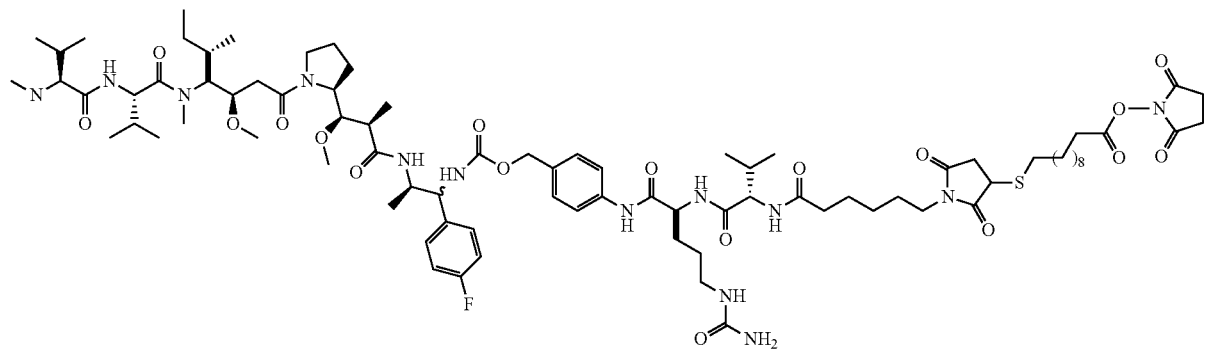

(VII-18)

With the exception that compound (VI-18) (266 mg, 0.170 mmol), obtained in Preparation Example 4-14, was used instead of compound (VI-16), obtained in Preparation Example 4-12, the same procedure as in Preparation Example 5-12 was repeated to afford the title compound (37 mg, 57%).

LC-MS m/z: 1590 [M+]$^+$

PREPARATION EXAMPLE 5-15

Preparation of Compound (VII-19)

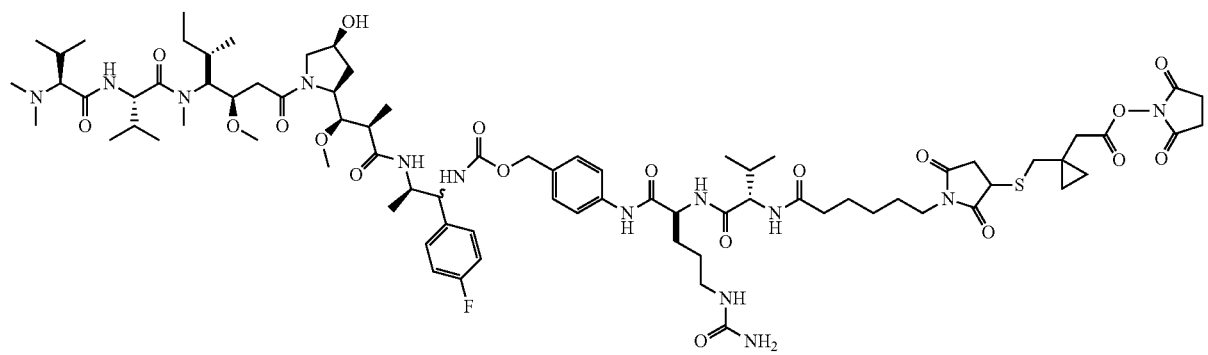

(VII-19)

With the exception that compound (VI-19) (247 mg, 0.16 mmol), obtained in Preparation Example 4-15, was used instead of compound (VI-16), obtained in Preparation Example 4-12, the same procedure as in Preparation Example 5-12 was repeated to afford the title compound (197 mg, 77%).

LC-MS m/z: 1607 [M]$^+$ $^1$H NMR (400 MHz, DMSO-d6) δ 0.54 (m, 1H), 0.65 (m, 3H), 0.70-0.78 (m, 5H), 0.80-1.00 (m, 18H), 1.00-1.08 (m, 6H), 1.20 (m, 3H), 1.47 (m, 5H), 1.60 (m, 2H), 1.94 (m, 5H), 2.08-2.20 (m, 3H), 2.25 (d, 6H), 2.40 (m, 1H), 2.60 (s, 6H), 2.73-3.02 (m, 13H), 2.84-3.42 (m, 17H, 2*OCH3), 3.60 (m, 1H), 3.70 (m, 1H), 3.80-4.06 (m, 3H), 4.20 (t, 2H), 4.38 (m, 2H), 4.53 (t, 1H), 4.66 (m, 2H), 4.78 (m, 1H), 4.88-5.10 (m, 3H), 5.42 (s, 2H), 6.00 (m, 1H), 7.07 (m, 1H), 7.27-7.37 (m, 3H), 7.50-7.58 (m, 2H), 7.65-7.85 (m, 1H), 8.10 (m, 1H), 9.95 (s, 1H)

PREPARATION EXAMPLE 5-16

Preparation of Compound (VII-20)

With the exception that compound (VI-20) (38 mg, 0.025 mmol), obtained in Preparation Example 4-16, was used instead of compound (VI-16), obtained in Preparation Example 4-12, the same procedure as in Preparation Example 5-12 was repeated to afford the title compound (25 mg, 62%).

LC-MS m/z: 1603 [M]$^+$ $^1$H NMR (400 MHz, DMSO-d6) δ 0.48 (m, 1H), 0.62 (m, 2H), 0.65-0.78 (m, 6H), 0.71-1.02 (m, 25H), 1.16 (m, 2H), 1.30-1.52 (m, 5H), 1.53-1.82 (m, 5H), 1.83-2.12 (m, 5H), 2.14 (d, 6H), 2.54 (s, 3H), 2.58-3.02 (m, 14H), 3.10-3.16 (m, 6H), 3.18-3.20 (m, 7H), 3.28-3.70 (m, 11H), 3.72-3.86 (m, 1H), 3.90-4.04 (m, 1H), 4.03-4.29 (m, 2H), 4.32 (m, 1H), 4.42-4.78 (m, 3H), 4.82-4.98 (m, 2H), 5.06 (m, 1H), 5.39 (s, 2H), 5.96 (m, 1H), 6.78 (m, 1H), 7.03-7.26 (m, 4H), 7.58 (m, 2H), 7.79 (d, 1H), 8.00 (d, 1H), 8.07 (d, 1H), 9.95 (S, 1H)

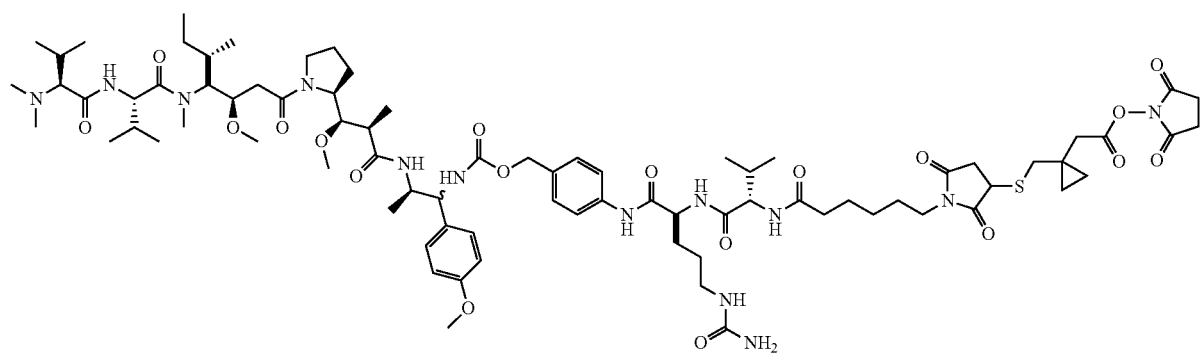

(VII-20)

PREPARATION EXAMPLE 5-17

Preparation of Compound (VII-21)

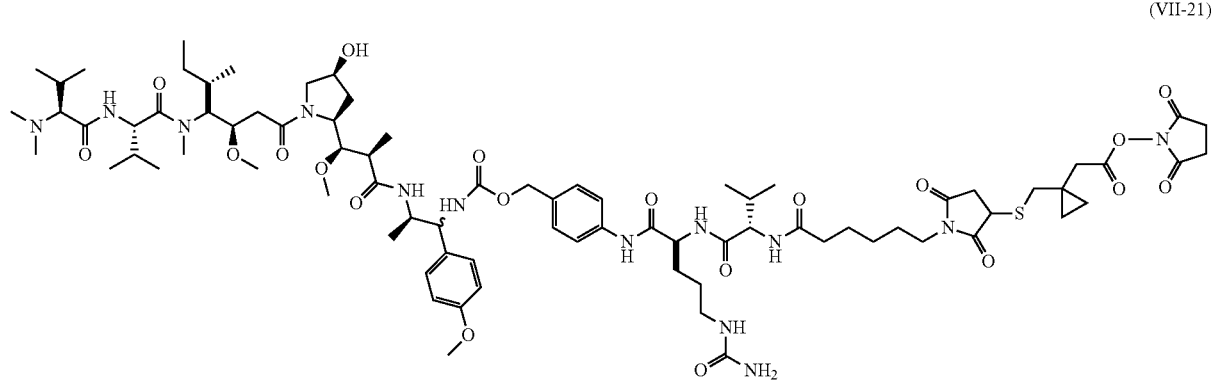 [SMILES: CC[C@H](C)[C@@H]([C@@H](CC(=O)N1C[C@@H](O)C[C@H]1[C@H](OC)[C@@H](C)C(=O)N[C@H](C)C(NC(=O)OCc1ccc(NC(=O)[C@H](CCCNC(N)=O)NC(=O)[C@@H](NC(=O)CCCCCN2C(=O)CC(SCC3(CC(=O)ON4C(=O)CCC4=O)CC3)C2=O)C(C)C)cc1)c1ccc(F)cc1)OC)N(C)C(=O)[C@@H](NC(=O)[C@H](C(C)C)N(C)C)C(C)C]

(VII-21)

With the exception that compound (VI-21) (132 mg, 0.09 mmol), obtained in Preparation Example 4-17, was used instead of compound (VI-16), obtained in Preparation Example 4-12, the same procedure as in Preparation Example 5-12 was repeated to afford the title compound (136 mg, 93%).

LC-MS m/z: 1619 [M]$^+$ $^1$H NMR (400 MHz, DMSO-d6) δ 0.54 (m, 1H), 0.63-0.68 (m, 3H), 0.70-0.80 (m, 5H), 0.81-0.90 (m, 17H), 1.00-1.1.08 (m, 8H), 1.22 (m, 3H), 1.40-1.54 (m, 6H), 1.56-1.74 (m, 3H), 1.80-2.00 (m, 3H), 2.26-2.30 (m, 7H), 2.51 (m, 6H), 2.56 (s, 1H), 2.64-3.04 (m, 14H), 3.13-3.30 (m, 6H), 3.36 (m, 6H), 3.62 (s, 1H), 3.69 (s, 2H), 3.87-4.04 (m, 4H), 4.19 (t, 2H0, 4.37 (m, 2H), 4.52 (t, 1H), 4.62 (m, 1H), 4.68 (m, 1H), 4.76 (m, 1H), 4.89 (m, 1H), 4.979 m, 2H), 5.08 (d, 1H), 5.42 (s, 2H), 5.98 (m, 1H), 6.81 (d, 1H), 7.17 (d, 1H), 7.30 (m, 1H), 7.60 (m, 3H), 7.82 (d, 1 h), 8.10 (m, 1H), 10.00 (d, 1H),

PREPARATION EXAMPLE 5-18

Preparation of Compound (VII-22)

With the exception that compound (VI-22) (296 mg, 0.198 mmol), obtained in Preparation Example 4-18, was used instead of compound (VI-16), obtained in Preparation Example 4-12, the same procedure as in Preparation Example 5-12 was repeated to afford the title compound (132 mg, 83%).

LC-MS m/z: 1589 [M]$^+$ $^1$H NMR (400 MHz, DMSO-d6) δ 0.48 (m, 1H), 0.60 (m, 2H), 0.71 (m, 5H), 0.71-0.88 (m, 17H), 0.98 (d, 3H), 0.93-1.08 (m, 3H), 1.16 (m, 3H), 1.37-1.45 (m, 5H), 1.50-1.86 (m, 4H), 1.91 (m, 3H), 2.0-2.42 (m, 11H), 2.68 (m, 1H), 2.77 (S, 3H), 2.82-3.02 (m, 5H), 3.10-3.19 (m, 6H), 3.21-3.30 (m, 7H), 3.36-3.50 (m, 16H), 3.54-3.72 (m, 3H), 3.80-4.00 (m, 4H), 4.15 (t, 1H), 4.33 (m, 1H), 4.49-4.71 (m, 3H), 4.86 (m, 2H), 5.04 (m, 1H), 5.39 (s, 2H), 5.96 (m, 1H), 7.03-7.21 (m, 5H), 7.55 (m, 2H), 7.79 (d, 1H), 8.06 (d, 1H) 9.95 (S, 1H)

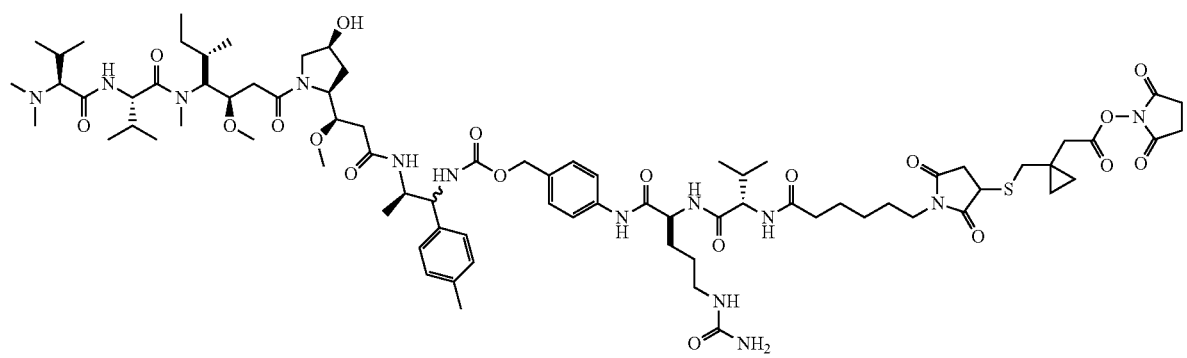

(VII-22)

PREPARATION EXAMPLE 5-19

Preparation of Compound (VII-23)

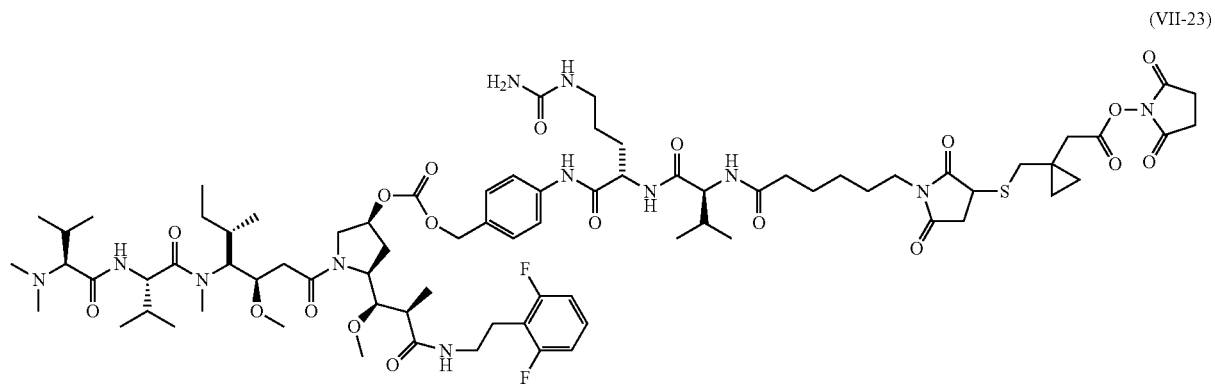 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(VII-23)

Under an argon stream, compound (VI-23) (33.4 mg, 0.022 mmol), obtained in Preparation Example 4-19, was dissolved in 3 mL of anhydrous dimethyl formamide, and added with N-hydroxysuccinimide (7.7 mg, 0.066 mmol). The reaction mixture was cooled to 0° C., and added with EDC.HCl (12.8 mg, 0.066 mmol) before being stirred at room temperature for 15 hrs. After completion of the reaction, vacuum concentration was carried out. The residue was dissolved in 50 mL of ethylacetate, acidified with 5 mL of 1 M HCl, and washed with 30 mL of distilled water and 30 mL of saturated brine, sequentially. The organic layer was dried over anhydrous sodium sulfate, and concentrated in a vacuum. The concentrate was purified by silica gel column chromatography to afford the title compound (32 mg, 91%).

LC-MS m/z: 1596 [M$^+$]$^+$, 1619 [M+Na]$^+$

PREPARATION EXAMPLE 5-20

Preparation of Compound (VII-24)

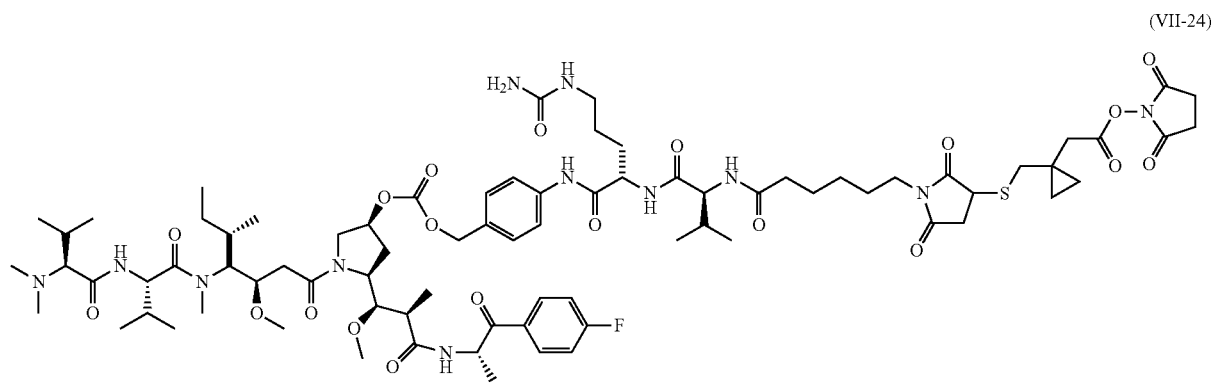 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)N[C@@H](C)C(=O)c1ccc(F)cc1)OC)N(C)C(=O)[C@@H](NC(=O)[C@H](C(C)C)N(C)C)C(C)C]

(VII-24)

With the exception that compound (VI-24) (55 mg, 0.037 mmol), obtained in Preparation Example 4-20, was used instead of compound (VI-23), obtained in Preparation Example 4-19, the same procedure as in Preparation Example 5-19 was repeated to afford the title compound as an ivory solid (49 mg, 84%).

LC-MS m/z: 1606 [M$^+$]$^+$

PREPARATION EXAMPLE 5-21

Preparation of Compound (VII-25)

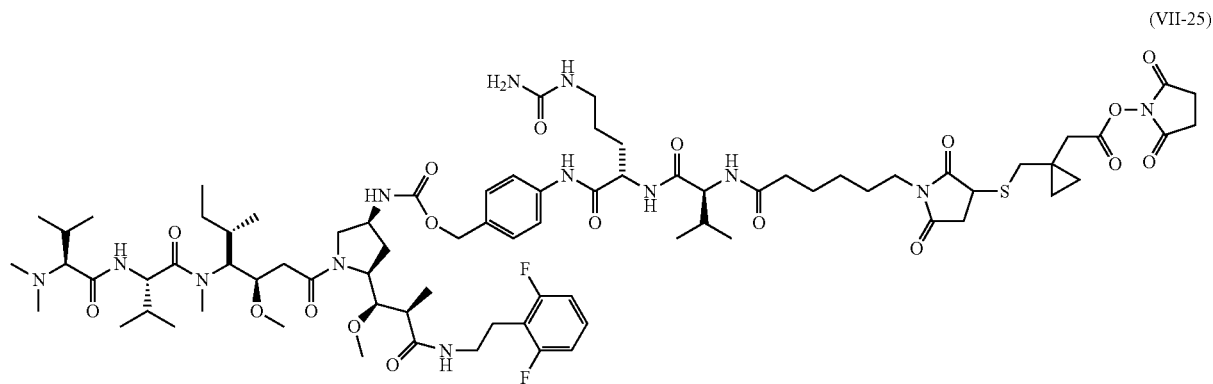 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(VII-25)

With the exception that compound (VI-25) (65 mg, 0.043 mmol), obtained in Preparation Example 4-21, was used instead of compound (VI-23), obtained in Preparation Example 4-19, the same procedure as in Preparation Example 5-19 was repeated to afford the title compound as an ivory solid (56 mg, 82%).

LC-MS m/z: 1592 [M$^+$]$^+$

PREPARATION EXAMPLE 5-22

Preparation of Compound (VII-26)

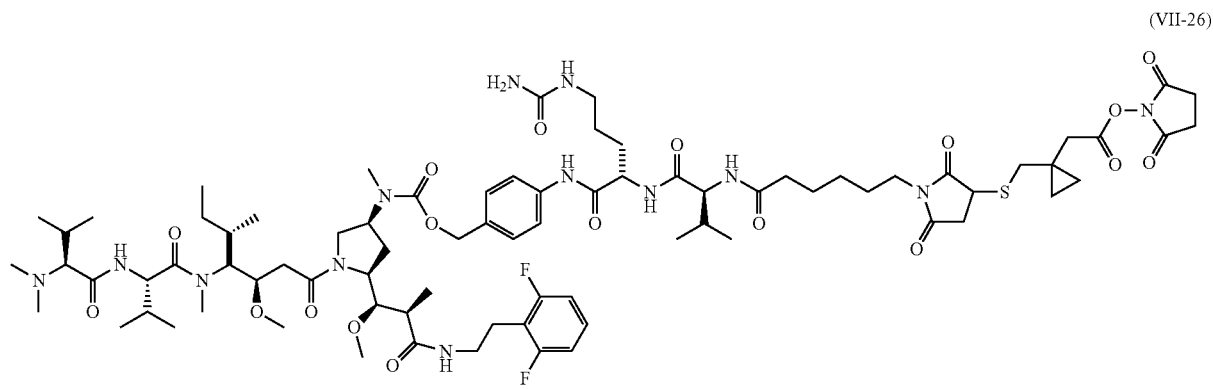 [SMILES: CC[C@H](C)[C@@H]([C@@H](CC(=O)N1C[C@@H](N(C)C(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

(VII-26)

With the exception that compound (VI-26) (114 mg, 0.075 mmol), obtained in Preparation Example 4-22, was used instead of compound (VI-23), obtained in Preparation Example 4-19, the same procedure as in Preparation Example 5-19 was repeated to afford the title compound as an ivory solid (94 mg, 78%).

LC-MS m/z: 1609 [M$^+$]$^+$

PREPARATION EXAMPLE 5-23

Preparation of Compound (VII-27)

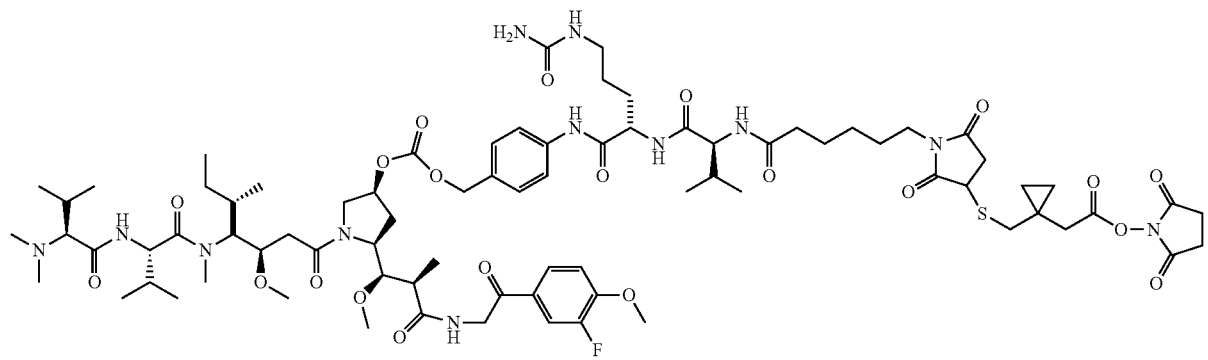

(VII-27)

With the exception that compound (VI-27) (91 mg, 0.0597 mmol), obtained in Preparation Example 4-23, was used instead of compound (VI-23), obtained in Preparation Example 4-19, the same procedure as in Preparation Example 5-19 was repeated to afford the title compound as an ivory solid (25 mg, 25%).

$^1$H NMR (400 MHz, DMSO-d6) δ 0.51-0.53 (m, 1H), 0.62-0.71 (m, 7H), 0.78-0.87 (m, 12H), 1.05-1.17 (m, 4H), 1.38-1.43 (m, 4H), 1.84-1.98 (m, 3H), 2.10-2.14 (m, 5H), 2.79-3.04 (m, 10H), 3.09-3.13 (m, 3H), 3.25-3.36 (m, 10H), 3.38-3.49 (m, 19H), 3.87-3.89 (m, 4H), 3.98-4.00 (m, 2H), 4.12-4.99 (m, 8H), 5.05 (s, 2H), 5.39 (s, 2H), 6.00-6.03 (t, 1H), 7.23-7.31 (m, 3H), 7.56-7.58 (d, 2H), 7.72-7.80 (m, 3H), 8.06-8.08 (d, 2H), 8.16-8.41 (m, 1H), 10.01 (s, 1H)

LC-MS m/z: 1621.5 [M$^+$]$^+$

PREPARATION EXAMPLE 5-24

Preparation of Compound (VII-28)

With the exception that compound (VI-28) (60 mg, 0.0399 mmol), obtained in Preparation Example 4-24, was used instead of compound (VI-23), obtained in Preparation Example 4-19, the same procedure as in Preparation Example 5-19 was repeated to afford the title compound as an ivory solid (14 mg, 23%).

$^1$H NMR (400 MHz, DMSO-d6) δ 0.51-0.53 (m, 1H), 0.62-0.71 (m, 7H), 0.78-0.87 (m, 12H), 1.05-1.17 (m, 4H), 1.38-1.43 (m, 4H), 1.84-1.98 (m, 3H), 2.14-2.15 (m, 7H), 2.24-2.33 (m, 6H), 2.79-3.04 (m, 10H), 3.09-3.13 (m, 3H), 3.25-3.36 (m, 10H), 3.38-3.49 (m, 19H), 3.87-3.89 (m, 4H), 3.98-4.00 (m, 2H), 4.12-4.99 (m, 8H), 5.05 (s, 2H), 5.39 (s, 2H), 5.97 (t, 1H), 7.02-7.11 (m, 2H), 7.28-7.29 (m, 1H), 7.57-7.65 (d, 2H), 7.88-7.98 (m, 1H), 8.07-8.08 (m, 1H), 8.22-8.44 (m, 1H), 10.00 (s, 1H)

LC-MS m/z: 1601.7 [M$^+$]$^+$

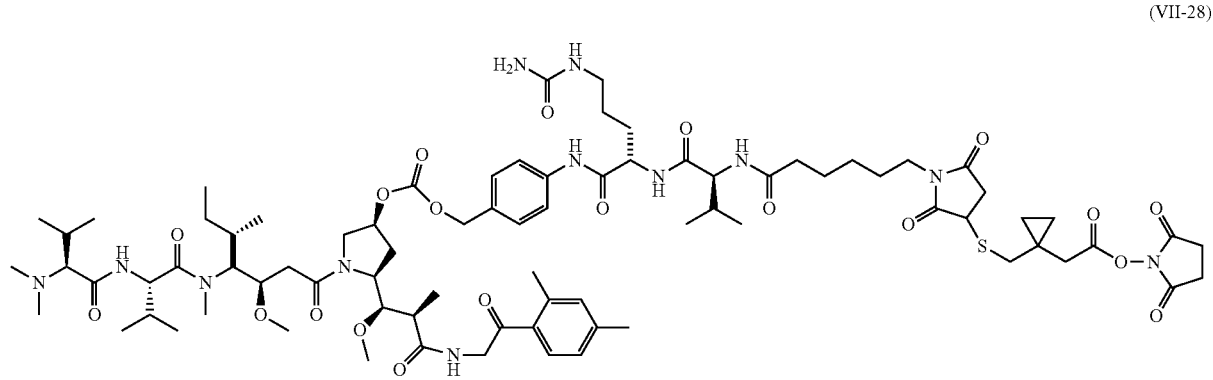 [SMILES: CC[C@H](C)[C@@H]([C@@H](CC(=O)N1C[C@@H](OC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCC(=O)c1ccc(C)cc1C)OC)N(C)C(=O)[C@@H](NC(=O)[C@H](C(C)C)N(C)C)C(C)C]

(VII-28)

PREPARATION EXAMPLE 5-25

Preparation of Compound (VII-29)

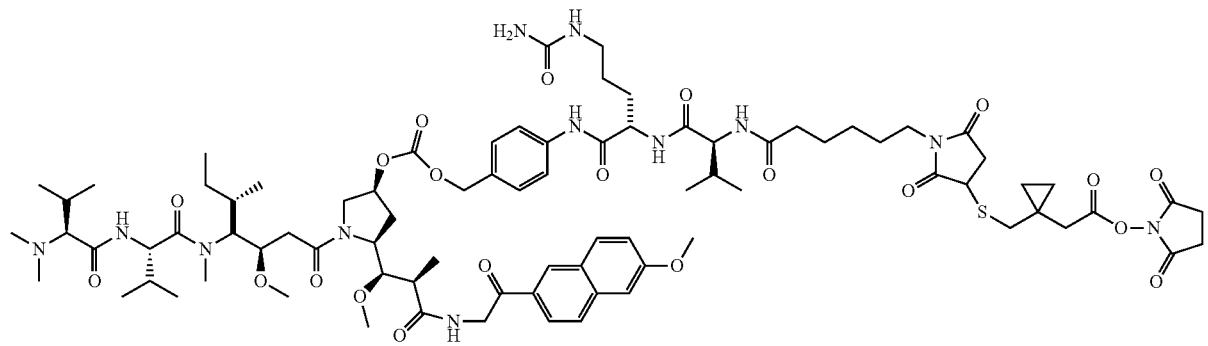

(VII-29)

With the exception that compound (VI-29) (83 mg, 0.053 mmol), obtained in Preparation Example 4-25, was used instead of compound (VI-23), obtained in Preparation Example 4-19, the same procedure as in Preparation Example 5-19 was repeated to afford the title compound as an ivory solid (23 mg, 25%).

$^1$H NMR (400 MHz, DMSO-$d_6$) δ 0.51-0.53 (m, 2H), 0.62-0.71 (m, 5H), 0.78-0.87 (m, 9H), 1.05-1.17 (m, 4H), 1.38-1.43 (m, 4H), 1.84-1.98 (m, 3H), 2.14-2.15 (m, 4H), 2.79-3.04 (m, 10H), 3.09-3.13 (m, 3H), 3.25-3.36 (m, 10H), 3.38-3.49 (m, 19H), 3.87-3.89 (m, 4H), 3.98-4.00 (m, 2H), 4.12-4.99 (m, 8H), 5.05 (s, 2H), 5.39 (s, 2H), 5.97 (t, 1H), 7.18-7.24 (m, 1H), 7.29-7.37 (m, 2H), 7.57-7.58 (m, 1H), 7.78-8.07 (m, 5H), 8.22-8.46 (m, 1H), 8.58 (s, 1H), 10.02 (s, 1H)

LC-MS m/z: 1653.4 [M$^+$]$^+$

PREPARATION EXAMPLE 5-26

Preparation of Compound (VII-30)

With the exception that compound (VI-30) (0.48 g, 0.31 mmol), obtained in Preparation Example 4-26, was used instead of compound (VI-23), obtained in Preparation Example 4-19, the same procedure as in Preparation Example 5-19 was repeated to afford the title compound as an ivory solid (0.44 g, 86%).

$^1$H NMR (400 MHz, DMSO-$d_6$) δ 0.44-0.54 (m, 1 H), 0.55-0.75 (m, 10 H), 0.75-0.96 (m, 17 H), 0.96-1.04 (m, 1 H), 1.04-1.25 (m, 6 H), 1.27-1.51 (m, 6 H), 1.51-1.82 (m, 3 H), 1.82-2.02 (m, 3 H), 2.02-2.21 (m, 6 H), 2.21-2.36 (m, 3 H), 2.52-2.64 (m, 1 H), 2.65-2.75 (m, 4 H), 2.75-2.80 (m, 5 H), 2.80-2.84 (m, 2 H), 2.84-2.93 (m, 4 H), 2.93-3.06 (m, 4 H), 3.06-3.22 (m, 4 H), 3.25-3.28 (m, 3 H), 3.38-3.46 (m, 2 H), 3.48-3.64 (m, 1 H), 3.71-3.86 (m, 7 H), 3.86-4.04 (m, 4 H), 4.04-4.21 (m, 2 H), 4.21-4.31 (m, 1 H), 4.31-4.44 (m, 2 H), 4.44-4.56 (m, 1 H), 4.56-4.71 (m, 2 H), 4.71-4.87 (m, 1 H), 4.93 (s, 2 H), 5.38 (s, 2 H), 5.87-6.01 (t, 1 H), 6.95-7.09 (d, 1 H), 7.18-7.33 (m, 2 H), 7.37-7.54 (m, 1 H), 7.54-7.68 (m, 3 H), 7.71-7.85 (d, 1 H), 8.02-8.12 (d, 1 H), 9.96 (brs, 1 H)

LC-MS m/z: 1633 [M$^+$]$^+$

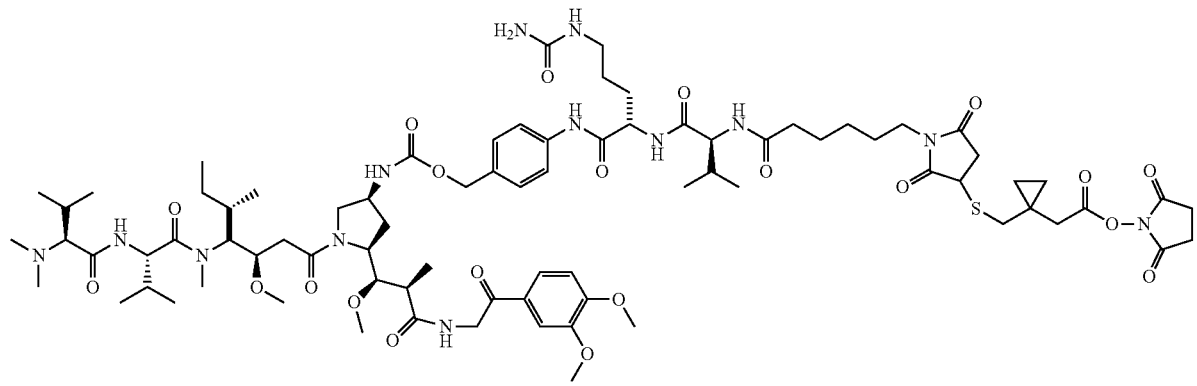

(VII-30)

PREPARATION EXAMPLE 5-27

Preparation of Compound (VII-31)

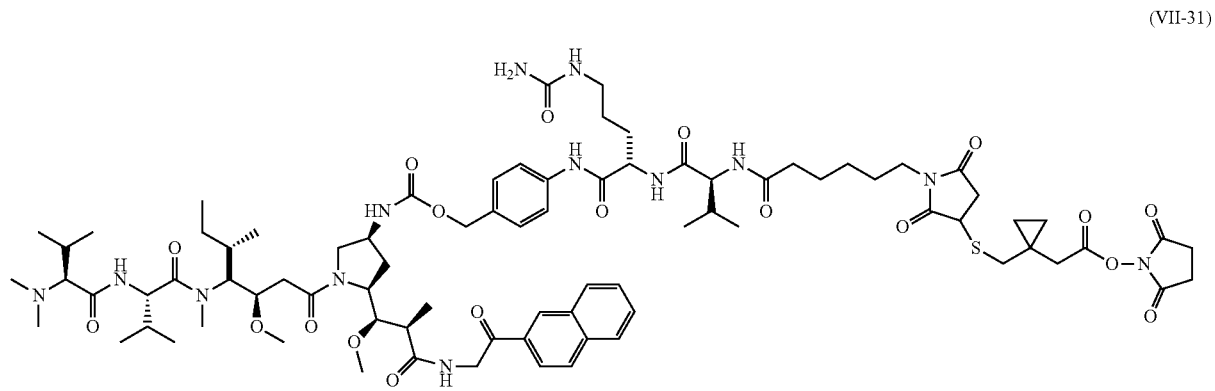 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCC(=O)c1ccc2ccccc2c1)OC)N(C)C(=O)[C@@H](NC(=O)[C@H](C(C)C)N(C)C)C(C)C]

(VII-31)

With the exception that compound (VI-31) (0.18 g, 0.12 mmol), obtained in Preparation Example 4-27, was used instead of compound (VI-23), obtained in Preparation Example 4-19, the same procedure as in Preparation Example 5-19 was repeated to afford the title compound as an ivory solid (0.13 g, 68%).

$^1$H NMR (400 MHz, DMSO-d$_6$) δ 0.38-0.59 (m, 8 H), 0.60-0.79 (m, 8 H), 0.79-0.98 (m, 16 H), 1.05-1.36 (m, 7 H), 1.36-1.52 (m, 6 H), 1.54-1.86 (m, 5 H), 1.86-2.02 (m, 3 H), 2.04-2.28 (m, 10 H), 2.28-2.44 (m, 3 H), 2.59-2.68 (m, 1 H), 2.69-2.86 (m, 6 H), 2.86-3.09 (m, 8 H), 3.10-3.25 (m, 6 H), 3.25-3.43 (m, 3 H), 3.71-3.86 (m, 1 H), 3.88-4.07 (m, 2 H), 4.07-4.26 (m, 2 H), 4.31-4.43 (m, 1 H), 4.48-4.74 (m, 2 H), 4.74-4.90 (m, 1 H), 4.97 (s, 2 H), 5.41 (m, 2 H), 5.86-6.13 (t, 1H), 7.16-7.43 (m, 2 H), 7.43-7.55 (m, 1 H), 7.56-7.75 (m, 2 H), 7.75-7.92 (m, 1 H), 7.92-8.21 (m, 4 H), 8.21-8.44 (m, 1 H), 8.44-8.66 (m, 1 H), 8.72 (s, 1 H), 9.38-9.82 (brs, 1 H), 10.01 (brs, 1 H)

LC-MS m/z: 1622 [M$^+$]$^+$

PREPARATION EXAMPLE 5-28

Preparation of Compound (VII-32)

With the exception that compound (VI-32) (0.21 g, 0.14 mmol), obtained in Preparation Example 4-28, was used instead of compound (VI-23), obtained in Preparation Example 4-19, the same procedure as in Preparation Example 5-19 was repeated to afford the title compound as an ivory solid (0.19 g, 88%).

$^1$H NMR (400 MHz, DMSO-d$_6$) δ 0.43-0.59 (m, 2 H), 0.59-0.78 (m, 8 H), 0.79-1.00 (m, 16 H), 1.00-1.08 (m, 3 H), 1.08-1.29 (m, 5 H), 1.29-1.64 (m, 9 H), 1.64-1.73 (m, 3 H), 1.74-2.04 (m, 4 H), 2.04-2.44 (m, 10 H), 2.56-2.64 (m, 2 H), 2.65-2.92 (m, 12 H), 2.92-3.08 (m, 6 H), 3.08-3.23 (m, 5 H), 3.23-3.32 (m, 3 H), 3.42-3.54 (m, 1 H), 3.55-3.64 (m, 1 H), 3.68-3.88 (m, 3 H), 3.88-4.06 (m, 2 H), 4.06-4.26 (m, 2 H), 4.26-4.46 (m, 2 H), 4.46-4.71 (m, 2 H), 4.74-4.88 (m, 1 H), 4.96 (s, 2 H), 5.41 (s, 2 H), 5.90-6.08 (t, 1 H), 6.74-7.04 (m, 1 H), 7.10-7.38 (m, 3 H), 7.38-7.68 (m, 4 H), 7.72-7.88 (d, 1 H), 8.01-8.18 (d, 1 H), 8.18-8.35 (m, 1 H), 10.00 (brs, 1 H)

LC-MS m/z: 1602 [M$^+$]$^+$

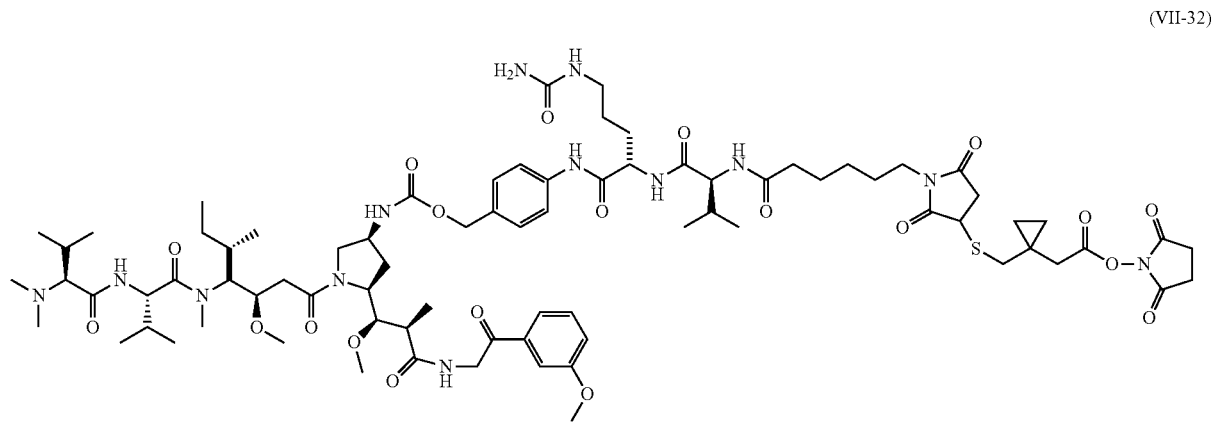 [SMILES: CC[C@H](C)[C@@H]([C@@H](CC(=O)N1C[C@@H](NC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCC(=O)c1cccc(OC)c1)OC)N(C)C(=O)[C@@H](NC(=O)[C@H](C(C)C)N(C)C)C(C)C]

(VII-32)

PREPARATION EXAMPLE 5-29

Preparation of Compound (VII-33)

(VII-33)

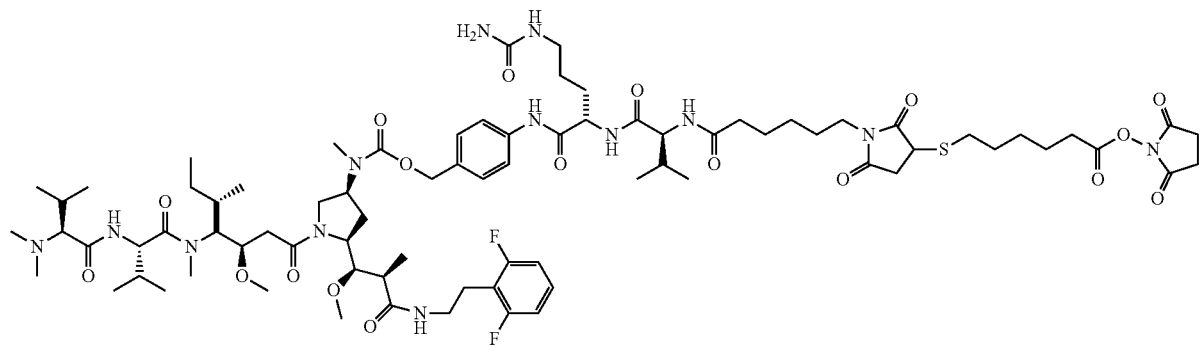

With the exception that compound (VI-33) (0.26 g, 0.17 mmol), obtained in Preparation Example 4-29, was used instead of compound (VI-23), obtained in Preparation Example 4-19, the same procedure as in Preparation Example 5-19 was repeated to afford the title compound as an ivory solid (0.14 g, 52%).

$^1$H NMR (400 MHz, DMSO-$d_6$) δ 0.53-0.94 (m, 28 H), 0.95-1.28 (m, 9 H), 1.28-1.74 (m, 18 H), 1.76-2.25 (m, 13 H), 2.27-2.43 (m, 1 H), 2.54-2.84 (m, 16 H), 2.84-3.03 (m, 5 H), 3.03-3.21 (m, 7 H), 3.60-3.82 (m, 2 H), 3.82-4.00 (m, 3 H), 4.05-4.24 (m, 1 H), 4.29-4.45 (m, 1 H), 4.45-4.78 (m, 2 H), 5.01 (s, 2 H), 5.39 (s, 2 H), 5.90-6.09 (t, 1 H), 6.97 (brs, 2 H), 7.09-7.43 (m, 2 H), 7.43-7.70 (m, 2 H), 7.70-7.87 (m, 1 H), 8.00-7.33 (m, 2 H), 10.01 (brs, 1 H)

LC-MS m/z: 1610 [M$^+$]$^+$

PREPARATION EXAMPLE 5-30

Preparation of Compound (VII-34)

(VII-34)

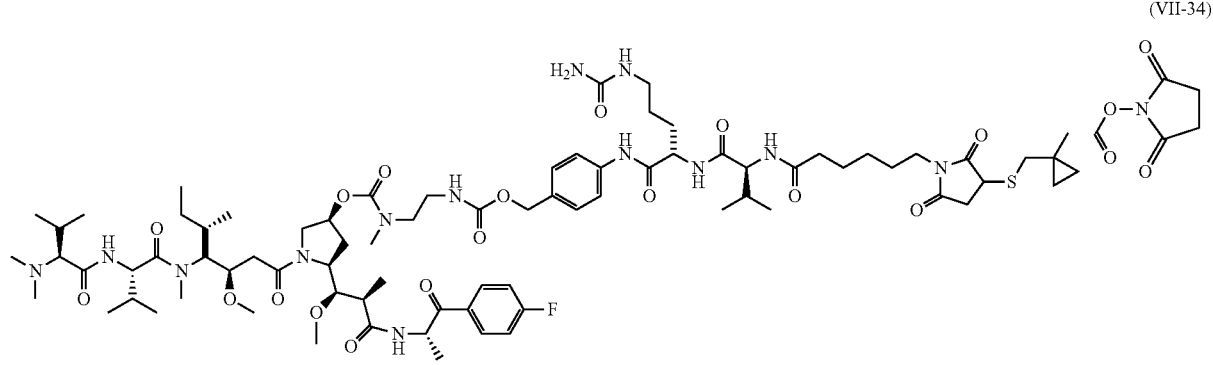

Under an argon stream, compound (VI-34) (25 mg, 0.016 mmol), obtained in Preparation Example 4-30, was dissolved in 3 mL of anhydrous dimethyl formamide, and added with N-hydroxysuccinimide (7.2 mg, 0.062 mmol). The reaction mixture was cooled to 0° C., and added with EDC.HCl (11.9 mg, 0.062 mmol) before being stirred at room temperature for 15 hrs. After completion of the reaction, vacuum concentration was carried out. The residue was purified by silica gel column chromatography to afford the title compound (20 mg, 76%).

LC-MS m/z: 1706.9 [M+H]$^+$, 1728.9 [M+Na]$^+$

PREPARATION EXAMPLE 5-31

Preparation of Compound (VII-35)

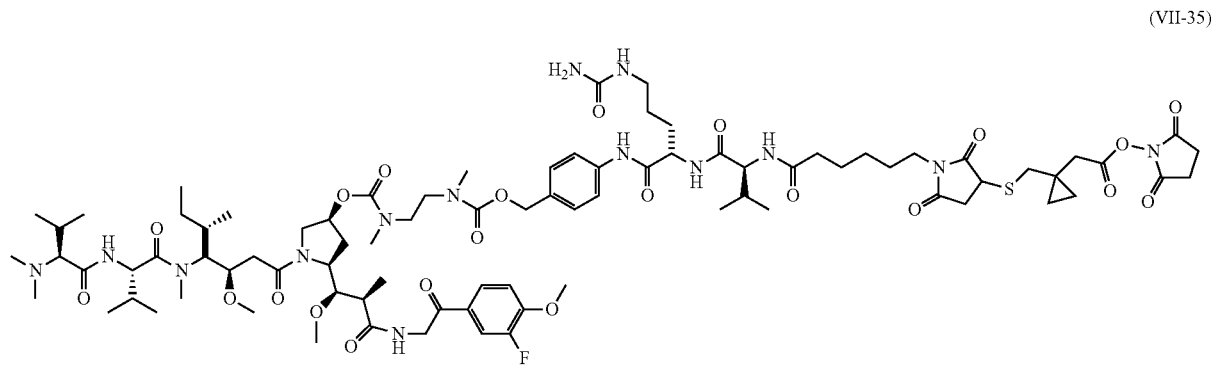 [SMILES: CC[C@H](C)[C@@H]([C@@H](CC(=O)N1C[C@@H](OC(=O)N(C)CCN(C)C(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCC(=O)c1ccc(OC)c(F)c1)OC)N(C)C(=O)[C@@H](NC(=O)[C@H](C(C)C)N(C)C)C(C)C]

(VII-35)

With the exception that compound (VI-35) (0.074 g, 0.0452 mmol), obtained in Preparation Example 4-31, was used instead of compound (VI-34), obtained in Preparation Example 4-30, the same procedure as in Preparation Example 5-30 was repeated to afford the title compound (0.049 g, 62.4%).

$^1$H NMR (400 MHz, DMSO-$d_6$) δ 0.51-0.53 (m, 1H), 0.63-0.76 (m, 12H), 0.81-0.86 (m, 18H), 1.02-1.04 (d, 4H), 1.11-1.14 (m, 4H), 1.18-1.22 (m, 2H), 1.42-1.49 (m, 6H), 1.94-1.97 (m, 3H), 2.18-2.19 (m, 6H), 2.73-2.89 (m, 13H), 2.93-2.99 (m, 5H), 3.14-3.21 (m, 5H), 3.31-3.39 (m, 17H), 3.91-4.03 (m, 5H), 4.14-4.85 (m, 8H), 4.98 (s, 2H), 5.42 (s, 2H), 5.96-5.98 (t, 1H), 7.27-7.30 (m, 3H), 7.58-7.59 (d, 2H), 7.77-7.87 (m, 2H), 7.94-8.03 (m, 2H), 8.08-8.11 (d, 1H), 8.46 (brs, 1H), 10.01 (s, 1H)

LC-MS m/z: 1735.4 [M+H]$^+$, 1758.4 [M+Na]$^+$

PREPARATION EXAMPLE 5-32

Preparation of Compound (VII-36)

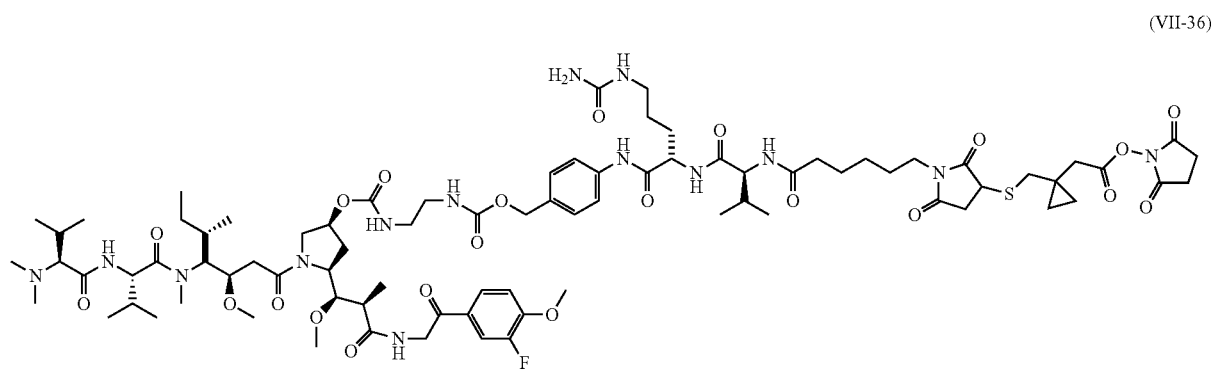 [SMILES: CC[C@H](C)[C@@H]([C@@H](CC(=O)N1C[C@@H](OC(=O)NCCNC(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCC(=O)c1ccc(OC)c(F)c1)OC)N(C)C(=O)[C@@H](NC(=O)[C@H](C(C)C)N(C)C)C(C)C]

(VII-36)

With the exception that compound (VI-36) (0.11 g, 0.0664 mmol), obtained in Preparation Example 4-32, was used instead of compound (VI-34), obtained in Preparation Example 4-30, the same procedure as in Preparation Example 5-30 was repeated to afford the title compound (0.079 g, 69.6%).

$^1$H NMR (400 MHz, DMSO-$d_6$) δ 0.51-0.53 (m, 1H), 0.63-0.76 (m, 7H), 0.82-0.92 (m, 12H), 1.02-1.04 (d, 1H), 1.09-1.24 (m, 7H), 1.42-1.49 (m, 8H), 1.91-1.99 (m, 4H), 2.11-2.19 (m, 8H), 2.81-2.83 (m, 10H), 2.99-3.14 (m, 6H), 3.17-0.21 (m, 5H), 3.32-3.35 (m, 20H), 3.92-3.93 (m, 4H), 3.97-4.04 (m, 2H), 4.13-4.85 (m, 8H), 4.94 (s, 2H), 5.43 (s, 2H), 6.00-6.03 (t, 1H), 7.27-7.32 (m, 5H), 7.58-7.61 (d, 2H), 7.77-7.96 (m, 3H), 8.10-8.12 (m, 1H), 8.47 (brs, 1H), 10.02 (s, 1H)

LC-MS m/z: 1708.4 [M+H]$^+$, 1730.4 [M+Na]$^+$

PREPARATION EXAMPLE 5-33

Preparation of Compound (VII-37)

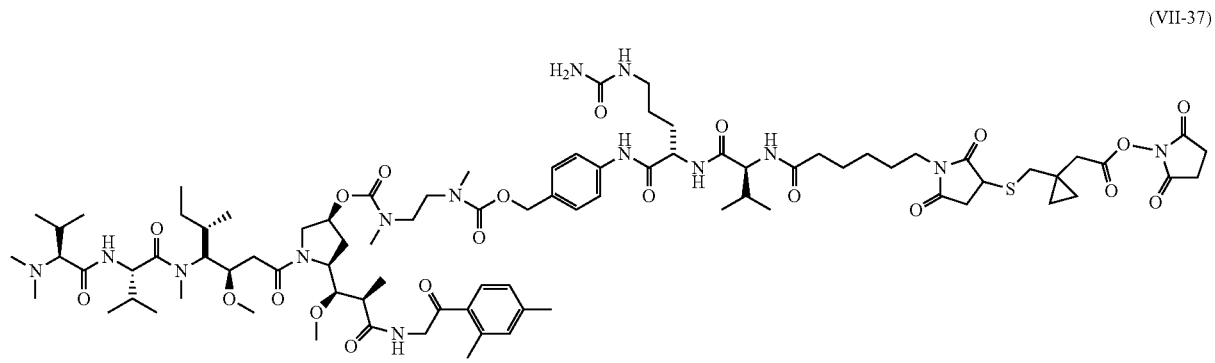 [SMILES: CC[C@H](C)[C@@H]([C@@H](CC(=O)N1C[C@@H](OC(=O)N(C)CCN(C)C(=O)OCc2ccc(NC(=O)[C@H](CCCNC(N)=O)NC(=O)[C@@H](NC(=O)CCCCCN3C(=O)CC(SCC4(CC(=O)ON5C(=O)CCC5=O)CC4)C3=O)C(C)C)cc2)C[C@H]1[C@H](OC)[C@@H](C)C(=O)NCC(=O)c1ccc(C)cc1C)OC)N(C)C(=O)[C@@H](NC(=O)[C@H](C(C)C)N(C)C)C(C)C]

(VII-37)

With the exception that compound (VI-37) (0.16 g, 0.096 mmol), obtained in Preparation Example 4-33, was used instead of compound (VI-34), obtained in Preparation Example 4-30, the same procedure as in Preparation Example 5-30 was repeated to afford the title compound (0.12 g, 71%).

$^1$H NMR (400 MHz, DMSO-$d_6$) δ 0.51-0.53 (m, 1H), 0.70-0.75 (m, 8H), 0.82-0.87 (m, 14H), 1.03-1.05 (m, 4H), 1.08-1.14 (m, 1H), 1.18-1.23 (m, 4H), 1.44-1.49 (m, 7H), 2.08-2.20 (m, 10H), 2.28-2.37 (m, 8H), 2.77-2.89 (m, 13H), 2.93-3.00 (m, 6H), 3.14-3.20 (m, 5H), 3.28 (s, 3H), 3.32-3.34 (m, 18H), 3.88-4.04 (m, 4H), 4.08-4.87 (m, 8H), 4.97 (s, 2H), 5.42 (s, 2H), 5.99-6.00 (t, 1H), 7.05-7.15 (m, 2H), 7.28-7.30 (m, 2H), 7.59-7.69 (m, 2H), 7.80-7.83 (d, 1H), 7.97-8.05 (m, 1H), 8.10-8.11 (m, 1H), 8.23-8.28 (m, 1H), 8.49 (brs, 1H), 10.02 (s, 1H)

LC-MS m/z: 1716.5 [M+H]$^+$, 1740.5 [M+Na]$^+$

PREPARATION EXAMPLE 5-34

Preparation of Compound (VII-38)

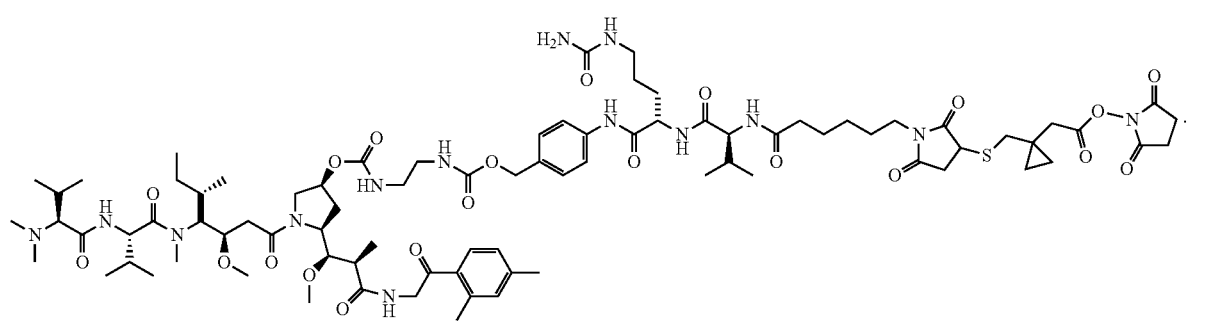

(VII-38)

With the exception that compound (VI-38) (0.15 g, 0.093 mmol), obtained in Preparation Example 4-34, was used instead of compound (VI-34), obtained in Preparation Example 4-30, the same procedure as in Preparation Example 5-30 was repeated to afford the title compound (0.1 g, 67%).

$^1$H NMR (400 MHz, DMSO-$d_6$) δ 0.51-0.53 (m, 1H), 0.63-0.66 (m, 3H), 0.69-0.76 (m, 8H), 0.82-0.92 (m, 14H), 1.03-1.05 (m, 2H), 1.11-1.12 (m, 1H), 1.18-1.24 (m, 3H), 1.44-1.49 (m, 7H), 2.13-2.20 (m, 9H), 2.28-2.37 (m, 7H), 2.73-2.89 (m, 7H), 2.93-3.03 (m, 9H), 3.15-3.19 (m, 5H), 3.28 (s, 3H), 3.31-3.35 (m, 15H), 3.85-3.87 (m, 1H), 3.95-4.04 (m, 3H), 4.16-4.88 (m, 8H), 4.94 (s, 2H), 5.42 (s, 2H), 5.99-6.02 (t, 1H), 7.06-7.15 (m, 2H), 7.27-7.29 (m, 4H), 7.58-7.63 (m, 3H), 7.81-7.83 (d, 1H), 7.87-8.04 (m, 1H), 8.10-8.11 (d, 1H), 8.30-8.50 (m, 1H), 10.02 (s, 1H)

LC-MS m/z: 1687.6 [M+H]$^+$, 1709.5 [M+Na]$^+$

PREPARATION EXAMPLE 5-35

Preparation of Compound (VII-39)

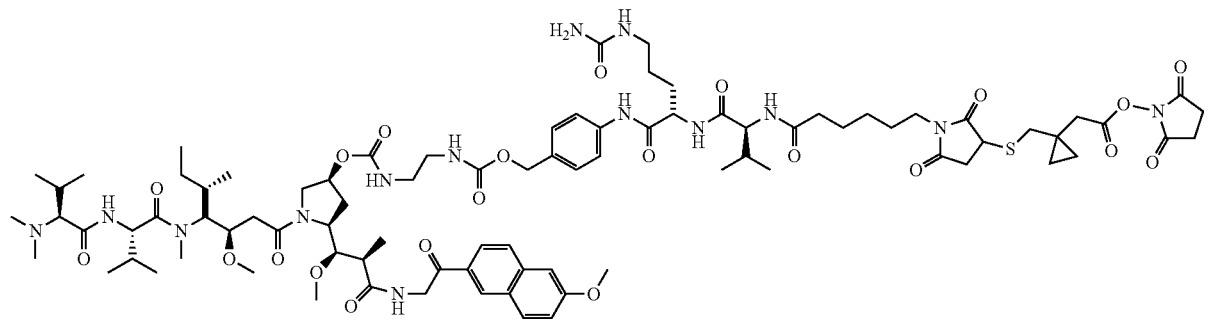

(VII-39)

With the exception that compound (VI-39) (0.12 g, 0.073 mmol), obtained in Preparation Example 4-35, was used instead of compound (VI-34), obtained in Preparation Example 4-30, the same procedure as in Preparation Example 5-30 was repeated to afford the title compound (0.058 g, 46%).

$^1$H NMR (400 MHz, DMSO-$d_6$) δ 0.48-0.53 (m, 1H), 0.58-0.59 (m, 1H), 0.64-0.76 (m, 8H), 0.82-0.92 (m, 15H), 1.03-1.04 (d, 2H), 1.11-1.22 (m, 6H), 1.42-1.49 (m, 6H), 1.86-1.97 (m, 3H), 2.11-2.20 (m, 9H), 2.73-2.95 (m, 10H), 2.98-3.13 (m, 6H), 3.14-3.21 (m, 5H), 3.33-3.37 (m, 2H), 3.90-3.92 (m, 4H), 3.98-4.04 (m, 2H), 4.14-4.80 (m, 8H), 4.94 (s, 2H), 5.42 (s, 2H), 6.00-6.01 (t, 1H), 7.22-7.29 (m, 4H), 7.38-7.42 (d, 1H), 7.59-7.61 (d, 2H), 7.81-7.83 (d, 1H), 7.89-7.96 (m, 2H), 8.00-8.03 (d, 1H), 8.09-8.12 (d, 1H), 8.28-8.51 (m, 1H), 8.64 (s, 1H), 10.02 (s, 1H),

LC-MS m/z: 1740.4 [M+H]$^+$, 1762.3 [M+Na]$^+$

PREPARATION EXAMPLE 5-36

Preparation of Compound (VII-40)

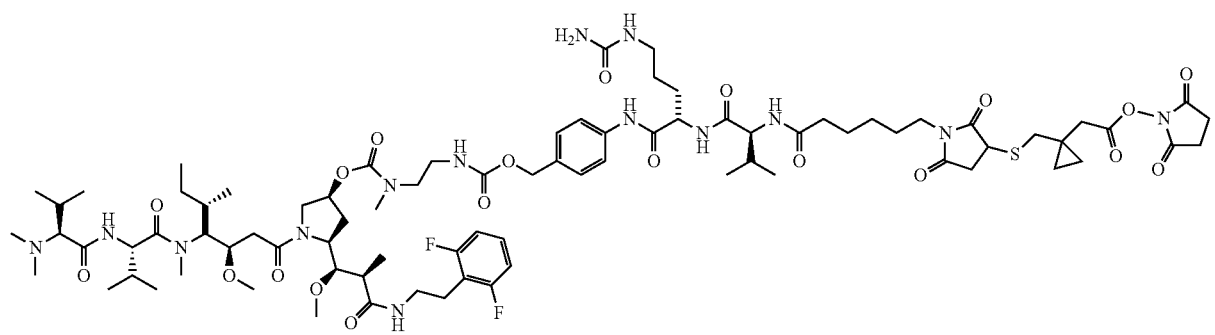

(VII-40)

With the exception that compound (VI-40) (0.1 g, 0.063 mmol), obtained in Preparation Example 4-36, was used instead of compound (VI-34), obtained in Preparation Example 4-30, the same procedure as in Preparation Example 5-30 was repeated to afford the title compound (0.072 g, 68%).

$^1$H NMR (400 MHz, DMSO-$d_6$) δ 0.51-0.53 (m, 1H), 0.62-0.69 (m, 2H), 0.70-0.77 (m, 7H), 0.82-0.89 (m, 18H), 1.02-0.07 (m, 3H), 1.18-1.29 (m, 3H), 1.44-1.47 (m, 6H), 2.19-2.21 (m, 10H), 2.61-2.64 (m, 2H), 2.74-3.00 (m, 10H), 3.17-3.18 (m, 7H), 3.25-3.33 (m, 25H), 3.90-4.01 (m, 5H), 4.16-4.84 (m, 8H), 4.95 (s, 2H), 5.40 (s, 2H), 6.01-6.02 (t, 1H), 7.01-7.05 (m, 2H), 7.26-7.29 (m, 4H), 7.58-7.60 (d, 2H), 7.79-7.82 (m, 1H), 7.94-7.99 (m, 2H), 8.08-8.10 (m, 1H), 10.00 (s, 1H)

LC-MS m/z: 1697.2 [M+H]$^+$, 1719.1 [M+Na]$^+$

PREPARATION EXAMPLE 5-37

Preparation of Compound (VII-41)

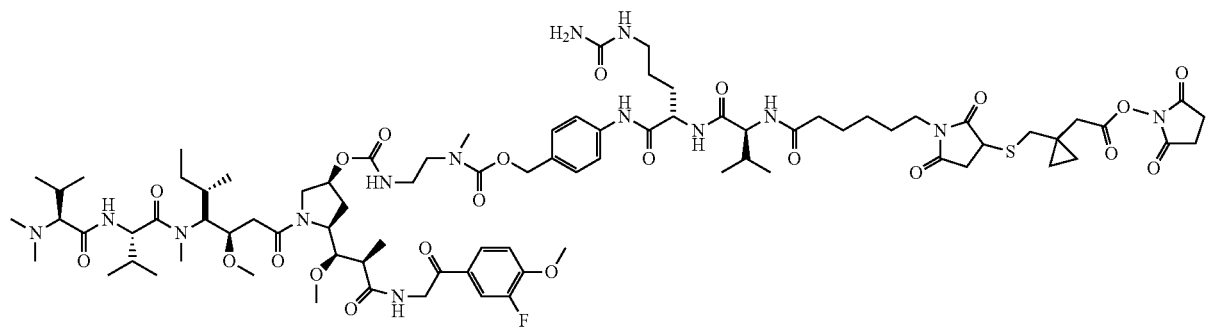

(VII-41)

With the exception that compound (VI-41) (0.062 g, 0.038 mmol), obtained in Preparation Example 4-37, was used instead of compound (VI-34), obtained in Preparation Example 4-30, the same procedure as in Preparation Example 5-30 was repeated to afford the title compound (0.037 g, 56%).

$^1$H NMR (400 MHz, DMSO-$d_6$) δ 0.51-0.53 (m, 1H), 0.63-0.77 (m, 13H), 0.81-0.91 (m, 17H), 1.03-1.04 (d, 2H), 1.09-1.22 (m, 6H), 1.42-1.49 (m, 6H), 1.95-1.97 (m, 3H), 2.11-2.19 (m, 7H), 2.77-2.89 (m, 13H), 3.13-3.17 (m, 7H), 3.32-3.36 (m, 18H), 3.92-3.93 (m, 4H), 4.00-4.04 (m, 2H), 4.14-4.85 (m, 8H), 4.99 (s, 2H), 5.42 (s, 2H), 5.88-6.00 (t, 1H), 7.28-7.41 (m, 4H), 7.58-7.65 (d, 2H), 7.77-8.06 (m, 4H), 8.10-8.11 (d, 1H), 8.21-8.45 (m, 1H), 10.00 (s, 1H)

LC-MS m/z: 1722.5 [M+H]$^+$, 1744.3 [M+Na]$^+$

EXAMPLES

Preparation of Antibody-Linker-Drug conjugate of Chemical Formulas I-1, I-2, I-3 and I-4

Example 1

Preparation of Conjugate (I-5)

After being subjected to exchange treatment with PBS, pH 7.5 (10 mM phosphate, 137 mM NaCl, 2.7 mM KCl included), 5 mL of a trastuzumab (Herceptin) solution (4.0 g/mL, 27 μM) was further treated with 2.5 ml of PBS, pH 7.5, and 7.5 mL of 0.05 M sodium borate, pH 8.5. Then, the trastuzumab solution was mixed with a solution of compound (VII-5) (2 mg, 0.001 mmol, 10 equivalents), obtained in Preparation Example 5-1, in 3.75 mL of 20% DMSO at 25° C. for 4 hrs while stirring.

When the reaction was completed, the reaction mixture was filtered through a 0.45 μm filter. The filtrate was loaded into a centrifugal filter (Amicon Ultra-15 30K), and concentrated two or three times by use of PBS, pH 7.5, until the organic solvent and the materials that did not react were removed.

The resulting concentrate was loaded into a Sephadex G-25 resin-packed column (30×300 mm) equilibrated with PBS, pH 7.5, and purified by MPLC (280 nm, UV range 0.08, flow rate 10 mL/min) to afford 13.5 mg of the title compound. (1.28 mg/mL, a total of 10.5 mL, 68%). The concentration of the compound thus obtained was determined by measuring absorbance at three wavelengths (280 nm, 320 nm, 350 nm) with the aid of a UV spectrometer.

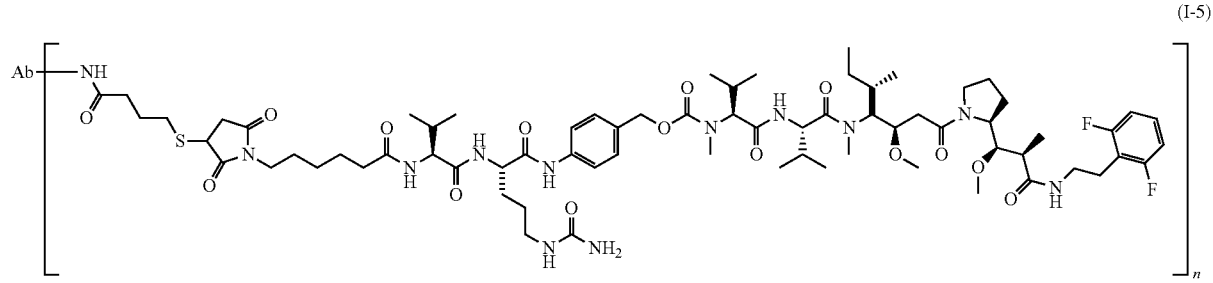

(I-5)

Example 2

Preparation of Conjugate (I-6)

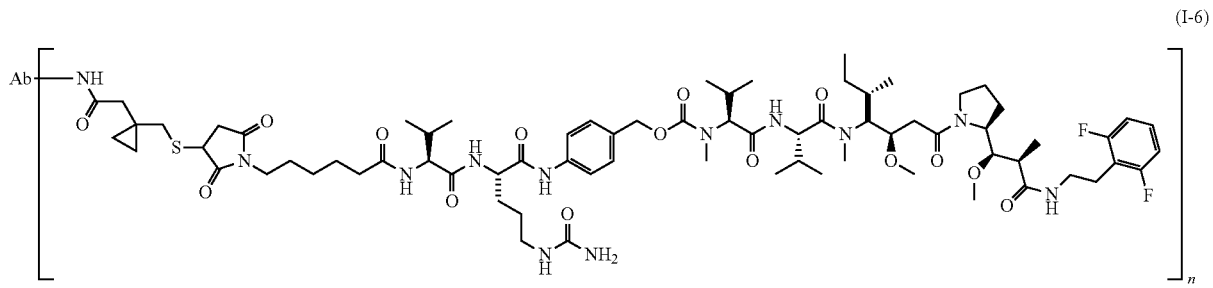

(I-6)

With the exception that compound (VII-6) (4.2 mg, 0.003 mmol, 15 eqs.), obtained in Preparation Example 5-2, was used instead of compound (VII-5), obtained in Preparation Example 5-1, the same procedure as in Example 1 was repeated to afford the title compound 12.1 mg (1.1 mg/mL, a total of 11 mL, 45%).

Example 3

Preparation of Conjugate (I-7)

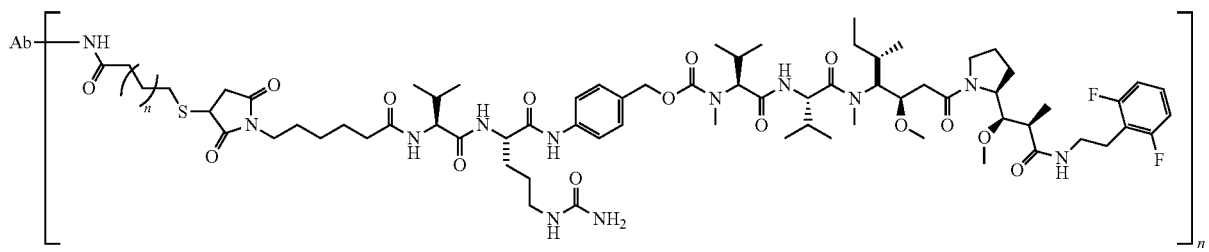

n = 3; (I-7)
n = 5; (I-8)
n = 8; (I-9)

With the exception that compound (VII-7) (3.12 mg, 0.002 mmol, 15 eqs.), obtained in Preparation Example 5-3, was used instead of compound (VII-5), obtained in Preparation Example 5-1, the same procedure as in Example 1 was repeated to afford the title compound. 13.7 mg (1.71 mg/mL, a total of 8 mL, 68%).

Example 4

Preparation of Conjugate (I-8)

With the exception that compound (VII-8) (3.20 mg, 0.002 mmol, 15 eqs.), obtained in Preparation Example 5-4, was used instead of compound (VII-5), obtained in Preparation Example 5-1, the same procedure as in Example 1 was repeated to afford the title compound. 13.9 mg (1.54 mg/mL, a total of 9 mL, 68%).

Example 5

Preparation of Conjugate (I-9)

With the exception that compound (VII-9) (3.27 mg, 0.002 mmol, 15 eqs.), obtained in Preparation Example 5-4, was used instead of compound (VII-5), obtained in Preparation Example 5-1, the same procedure as in Example 1 was repeated to afford the title compound. 15.3 mg (1.53 mg/mL, a total of 10 mL, 77%).

Example 6

Preparation of Conjugate (I-10)

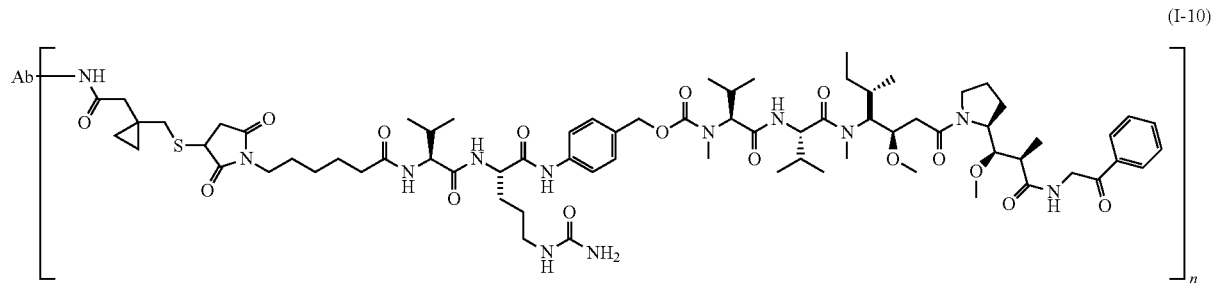

(I-10)

With the exception that compound (VII-10) (4.17 mg, 0.003 mmol, 15 eqs.), obtained in Preparation Example 5-6, was used instead of compound (VII-5), obtained in Preparation Example 5-1, the same procedure as in Example 1 was repeated to afford the title compound. 14.2 mg (1.29 mg/mL, a total of 11 mL, 53%)

Example 7

Preparation of Conjugate (I-11)

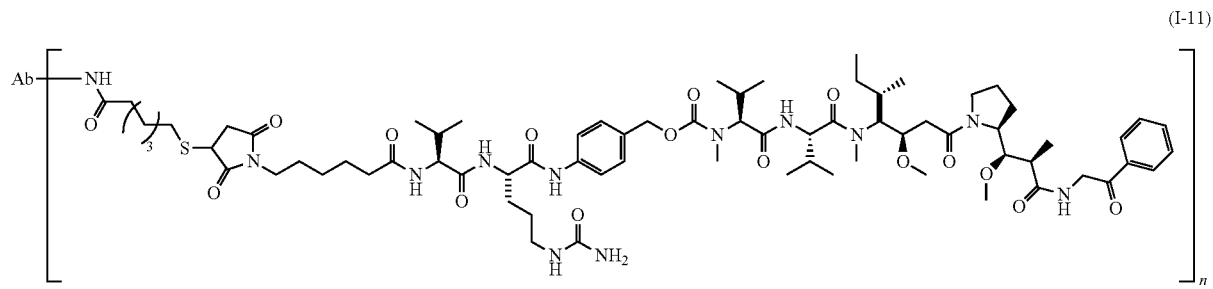

(I-11)

With the exception that compound (VII-11) (3.08 mg, 0.002 mmol, 15 eqs.), obtained in Preparation Example 5-7, was used instead of compound (VII-5), obtained in Preparation Example 5-1, the same procedure as in Example 1 was repeated to afford the title compound. 9.5 mg (1.19 mg/mL, a total of 8 mL, 48%).

Example 8

Preparation of Conjugate (I-12)

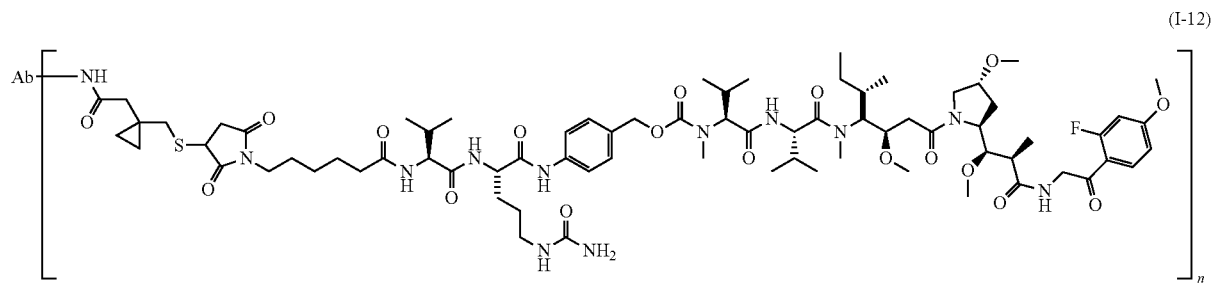

(I-12)

With the exception that compound (VII-12) (5.4 mg, 0.003 mmol, 10 eqs.), obtained in Preparation Example 5-8, was used instead of compound (VII-5), obtained in Preparation Example 5-1, the same procedure as in Example 1 was repeated to afford the title compound. 50 mg (2.5 mg/mL, a total of 20 mL, 100%)

Example 9

Preparation of Conjugate (I-13)

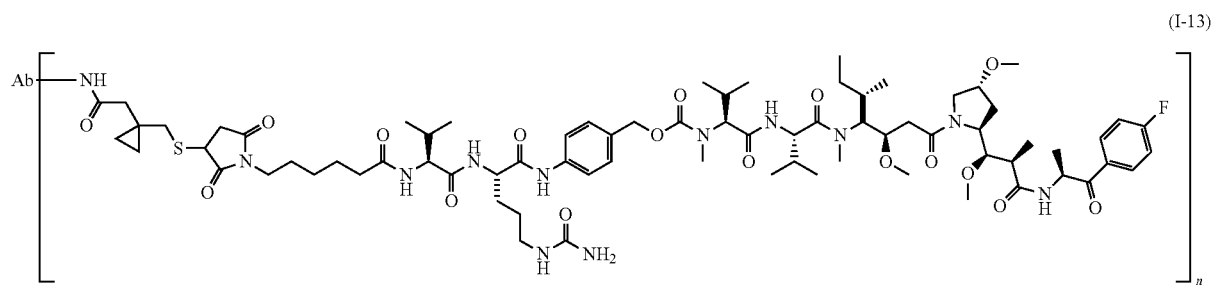

(I-13)

With the exception that compound (VII-13) (5.7 mg, 0.004 mmol, 20 eqs.), obtained in Preparation Example 5-9, was used instead of compound (VII-5), obtained in Preparation Example 5-1, the same procedure as in Example 1 was repeated to afford the title compound. 15.2 mg (1.01 mg/mL, a total of 15 mL, 56%).

Example 10

Preparation of Conjugate (I-14)

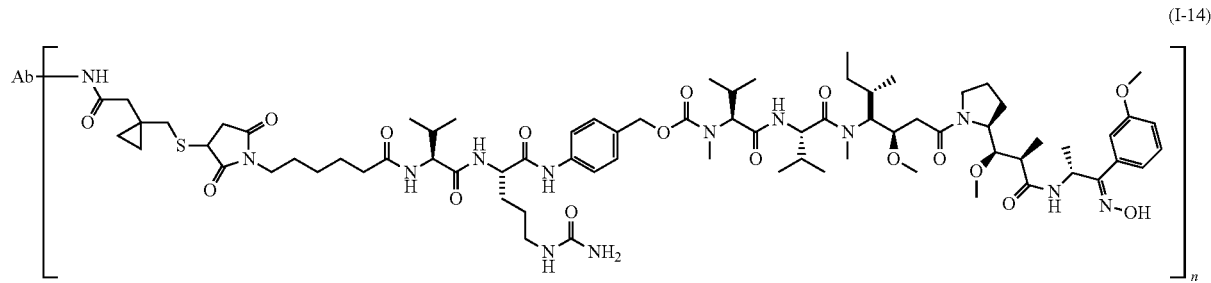

(I-14)

With the exception that compound (VII-14) (4.3 mg, 0.003 mmol, 15 eqs.), obtained in Preparation Example 5-10, was used instead of compound (VII-5), obtained in Preparation Example 5-1, the same procedure as in Example 1 was repeated to afford the title compound. 19.4 mg (1.55 mg/mL, a total of 12.5 mL, 72%).

Example 11

Preparation of Conjugate (I-15)

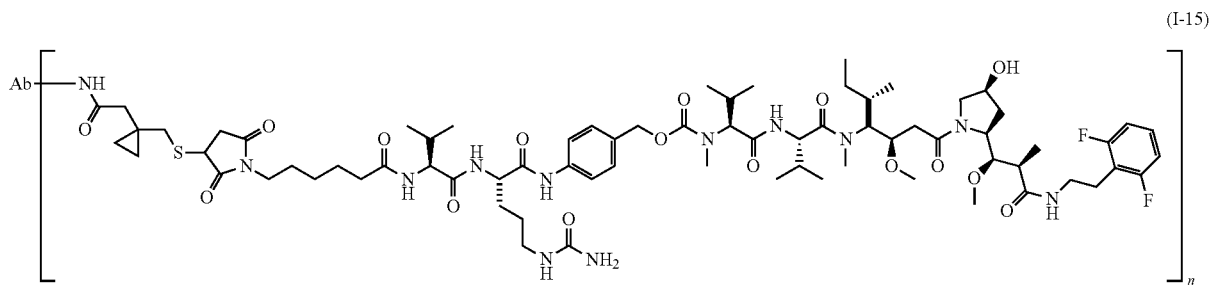

With the exception that compound (VII-15) (2.3 mg, 0.0015 mmol, 10 eqs.), obtained in Preparation Example 5-11, was used instead of compound (VII-5), obtained in Preparation Example 5-1, the same procedure as in Example 1 was repeated to afford the title compound. 20.1 mg (1.6 mg/mL, a total of 12.5 mL, 92%).

Example 12

Preparation of Conjugate (I-16)

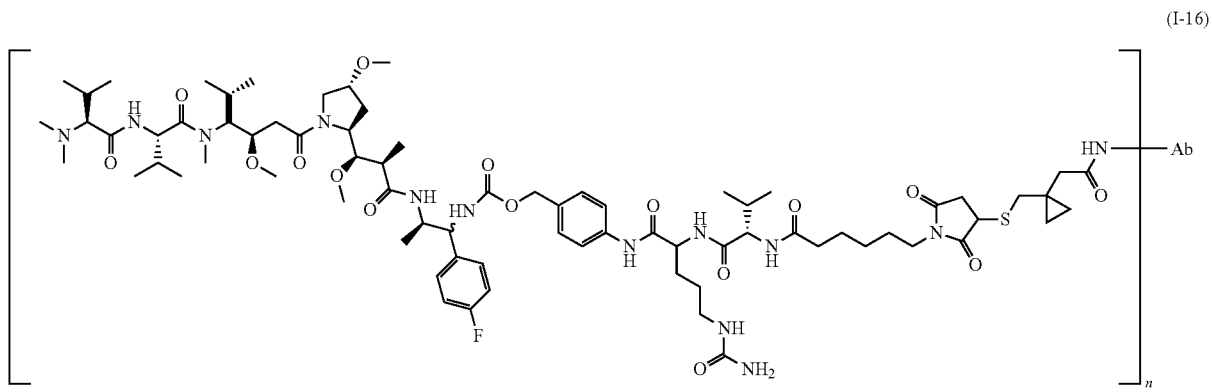

After being subjected to exchange treatment with PBS, pH 7.5 (10 mM phosphate, 137 mM NaCl, 2.7 mM KCl included), 5 mL of a trastuzumab (Herceptin) solution (5.4 g/mL, 36 μM) was further treated with 2.5 ml of PBS, pH 7.5, and 7.5 mL of 0.05 M sodium borate, pH 8.5. Then, the trastuzumab solution was mixed with a solution of compound (VII-16) (4.4 mg, 0.003 mmol, 15 eqs.), obtained in Preparation Example 5-12, in 3.75 mL of 20% DMSO at 25° C. for 4 hrs while stirring. When the reaction was completed, the reaction mixture was filtered through a 0.45 μm filter. The filtrate was loaded into a centrifugal filter (Amicon Ultra-15 30K), and concentrated two or three times by use of PBS, pH 7.5, until the organic solvent and the materials that did not react were removed. The resulting concentrate was loaded to a Sephadex G-25 resin-packed column (30× 300 mm) equilibrated with PBS, pH 7.5, and purified by MPLC (280 nm, UV range 0.08, flow rate 10 mL/min) to afford the title compound. 22.5 mg (1.73 mg/mL, a total of 13 mL, 83%). The concentration of the compound thus obtained was determined by measuring absorbance at three wavelengths (280 nm, 320 nm, 350 nm) with the aid of a UV spectrometer.

Example 13

Preparation of Conjugate (I-17)

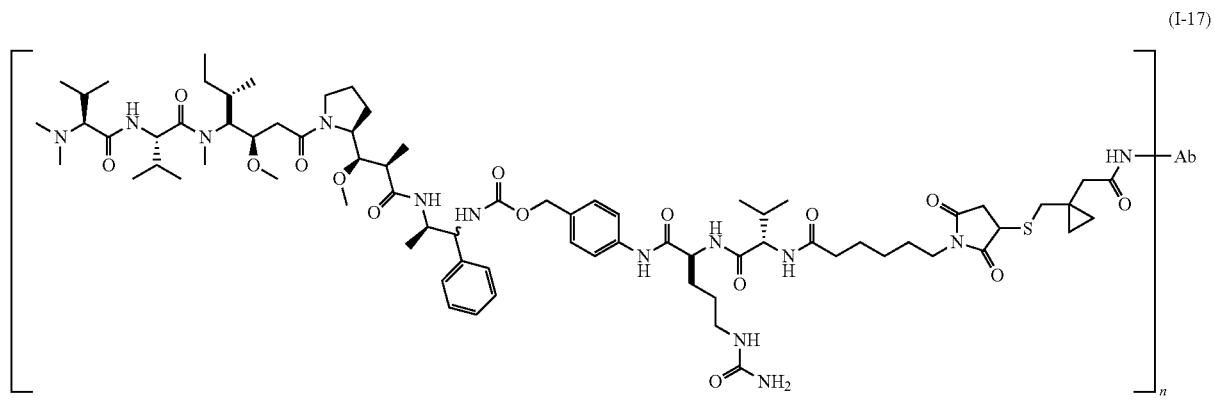

(I-17)

With the exception that compound (VII-17) (5.6 mg, 0.004 mmol, 20 eqs.), obtained in Preparation Example 5-13, was used instead of compound (VII-16), obtained in Preparation Example 5-13, the same procedure as in Example 12 was repeated to afford the title compound. 25.6 mg (2.05 mg/mL, a total of 12.5 mL, 95%).

Example 14

Preparation of Conjugate (I-18)

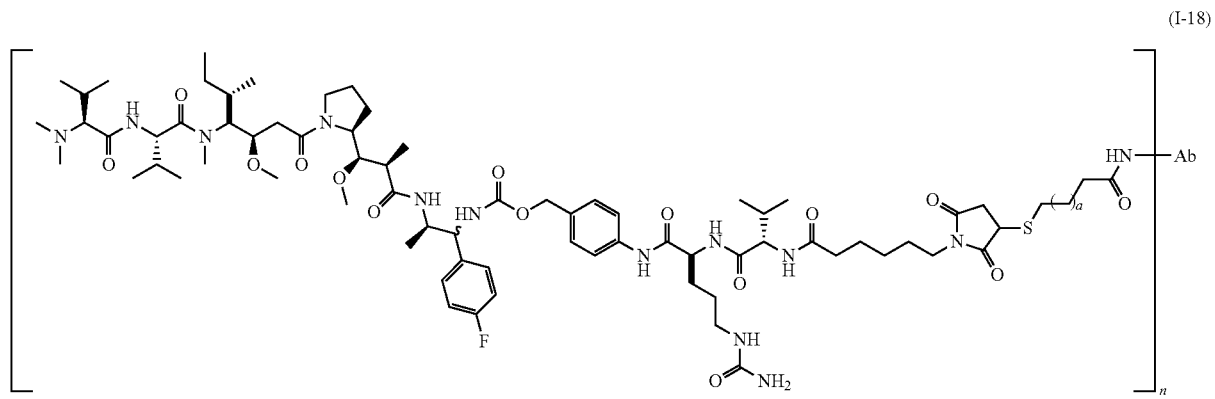

(I-18)

With the exception that compound (VII-18) (4.0 mg, 0.0024 mmol, 15 eqs.), obtained in Preparation Example 5-14, was used instead of compound (VII-16), obtained in Preparation Example 5-12, the same procedure as in Example 12 was repeated to afford the title compound. 23.8 mg (1.98 mg/mL, a total of 12 mL, 99%).

Example 15

Preparation of Conjugate (I-19)

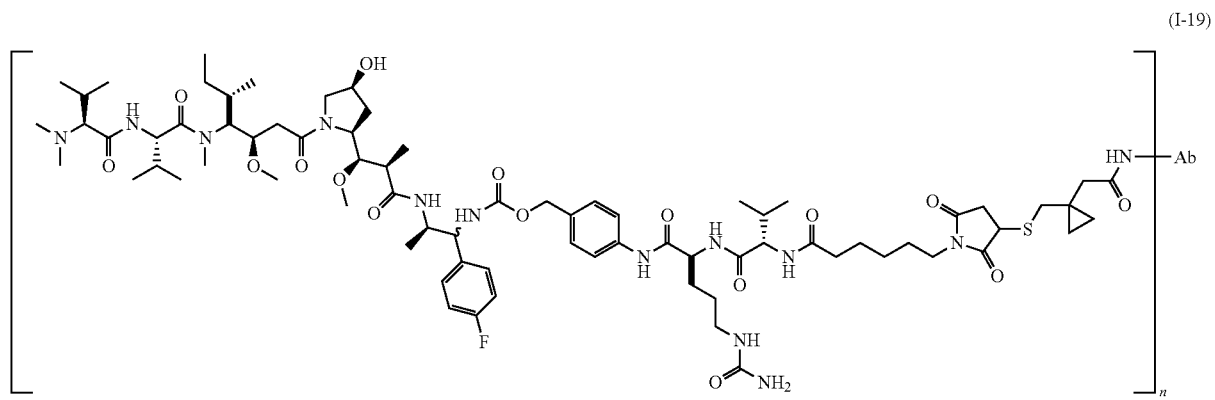

With the exception that compound (VII-19) (4.0 mg, 0.0025 mmol, 15 eqs.), obtained in Preparation Example 5-14, was used instead of compound (VII-16), obtained in Preparation Example 5-12, the same procedure as in Example 12 was repeated to afford the title compound. 20.4 mg (1.86 mg/mL, a total of 11 mL, 82%).

Example 16

Preparation of Conjugate (I-20)

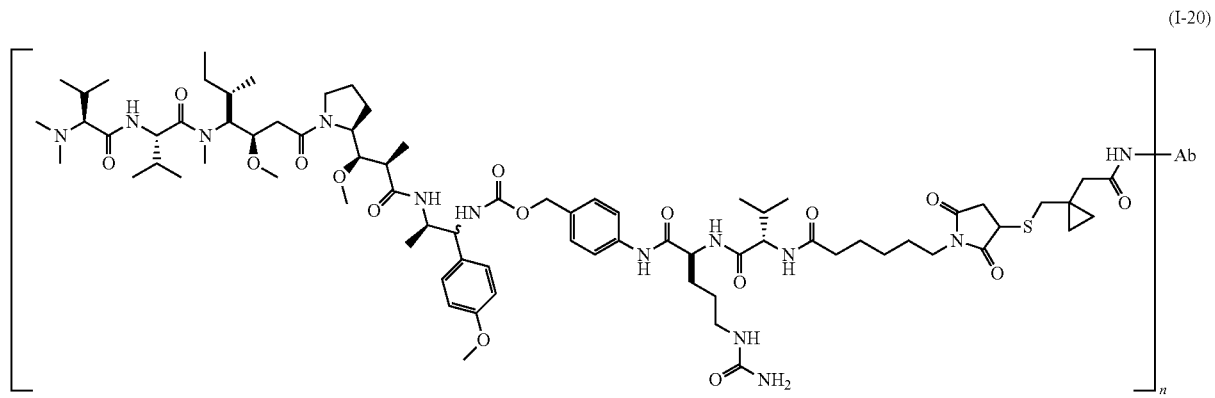

With the exception that compound (VII-20) (3.8 mg, 0.0024 mmol, 15 eqs.), obtained in Preparation Example 5-16, was used instead of compound (VII-16), obtained in Preparation Example 5-12, the same procedure as in Example 12 was repeated to afford the title compound. 18.9 mg (1.72 mg/mL, a total of 11 mL, 79%).

Example 17

Preparation of Conjugate (I-21)

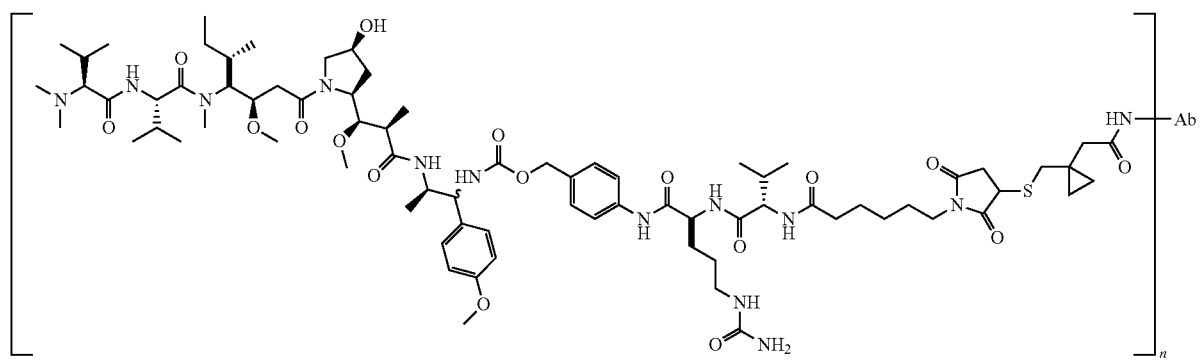

(I-21)

With the exception that compound (VII-21) (4.0 mg, 0.0025 mmol, 15 eqs.), obtained in Preparation Example 5-17, was used instead of compound (VII-16), obtained in Preparation Example 5-12, the same procedure as in Example 12 was repeated to afford the title compound. 19.8 mg (1.8 mg/mL, a total of 11 mL, 80%).

Example 18

Preparation of Conjugate (I-22)

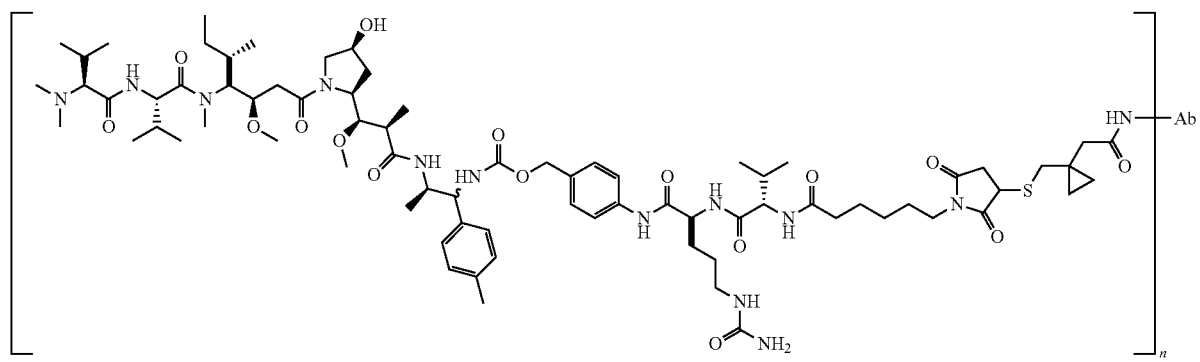

(I-22)

With the exception that compound (VII-22) (3.8 mg, 0.0024 mmol, 15 eqs.), obtained in Preparation Example 5-18, was used instead of compound (VII-16), obtained in Preparation Example 5-12, the same procedure as in Example 12 was repeated to afford the title compound. 13.0 mg (1.18 mg/mL, a total of 11 mL, 54%).

Example 19

Preparation of Conjugate (I-23)

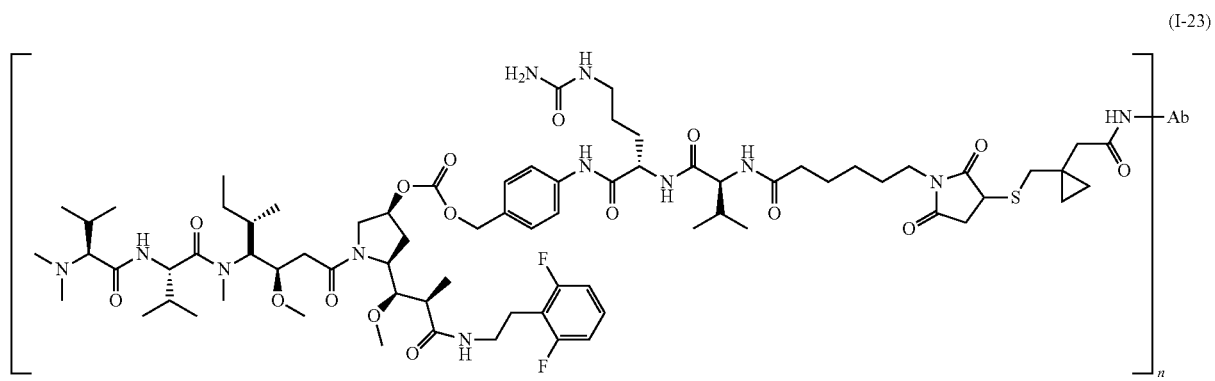

After being subjected to exchange treatment with PBS, pH 7.5 (10 mM phosphate, 137 mM NaCl, 2.7 mM KCl included), 5 mL of a trastuzumab (Herceptin) solution (5.4 g/mL, 36 μM) was further treated with 2.5 ml of PBS, pH 7.5, and 7.5 mL of 0.05 M sodium borate, pH 8.5. Then, the trastuzumab solution was mixed with a solution of compound (VII-23) (5.7 mg, 0.0036 mmol, 20 eqs.), obtained in Preparation Example 5-19, in 3.75 mL of 20% DMSO at 25° C. for 4 hrs while stifling. When the reaction was completed, the reaction mixture was filtered through a 0.45 μm filter. The filtrate was loaded into a centrifugal filter (Amicon Ultra-15 30K), and concentrated two or three times by use of PBS, pH 7.5, until the organic solvent and the materials that did not react were removed. The resulting concentrate was loaded to a Sephadex G-25 resin-packed column (30× 300 mm) equilibrated with PBS, pH 7.5, and purified by MPLC (280 nm, UV range 0.08, flow rate 10 mL/min) to afford the title compound. 16.9 mg (1.21 mg/mL, a total of 15 mL, 67%). The concentration of the compound thus obtained was determined by measuring absorbance at three wavelengths (280 nm, 320 nm, 350 nm) with the aid of a UV spectrometer.

Example 20

Preparation of Conjugate (I-24)

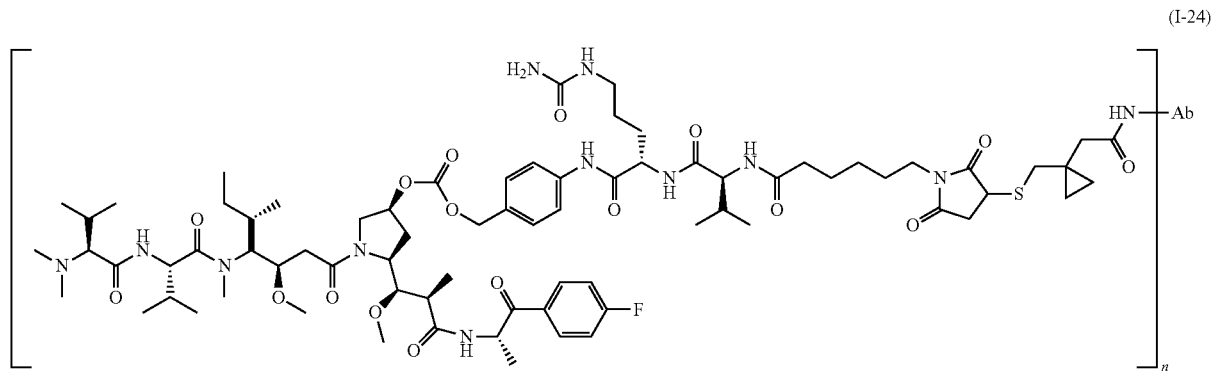

With the exception that compound (VII-24) (4.3 mg, 0.0027 mmol, 15 eqs.), obtained in Preparation Example 5-20, was used instead of compound (VII-23), obtained in Preparation Example 5-19, the same procedure as in Example 19 was repeated to afford the title compound. 19.2 mg (1.54 mg/mL, a total of 11.5 mL, 71%).

Example 21

Preparation of Conjugate (I-25)

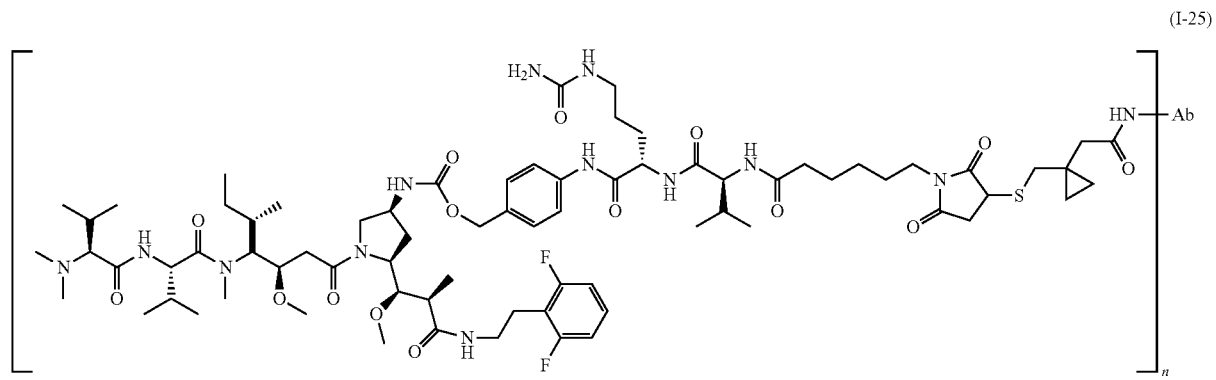

With the exception that compound (VII-25) (5.74 mg, 0.0036 mmol, 20 eqs.), obtained in Preparation Example 5-20, was used instead of compound (VII-23), obtained in Preparation Example 5-19, the same procedure as in Example 19 was repeated to afford the title compound. 14.7 mg (1.23 mg/mL, a total of 12 mL, 54%).

Example 22

Preparation of Conjugate (I-26)

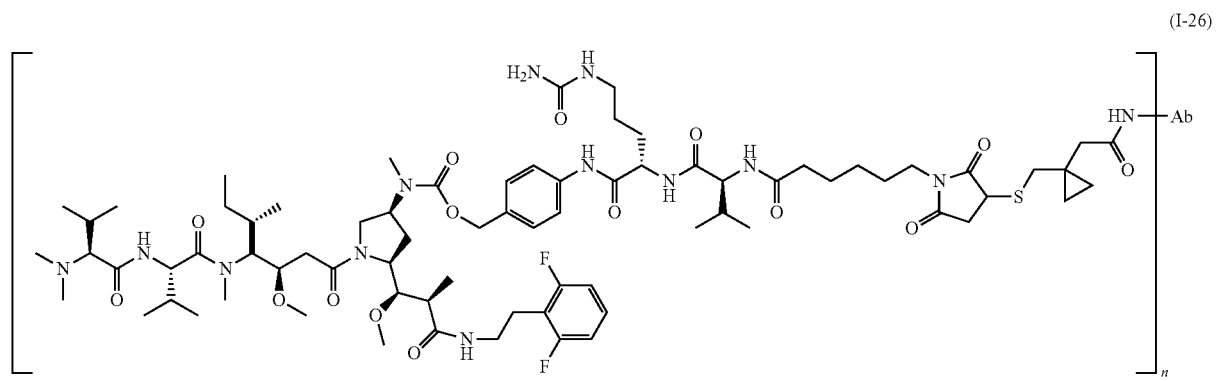

With the exception that compound (VII-26) (4.38 mg, 0.0027 mmol, 15 eqs.), obtained in Preparation Example 5-20, was used instead of compound (VII-23), obtained in Preparation Example 5-19, the same procedure as in Example 19 was repeated to afford the title compound. 23.7 mg (1.58 mg/mL, a total of 14 mL, 88%).

Example 23

Preparation of Conjugate (I-27)

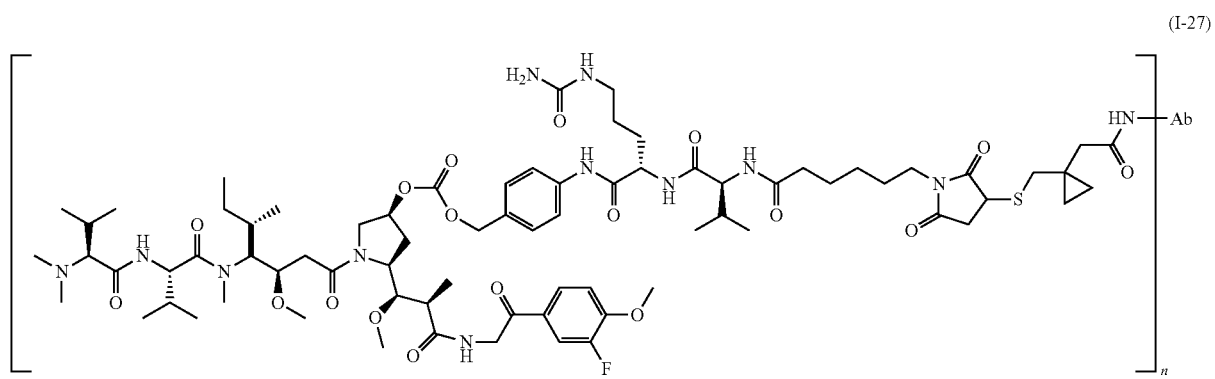

With the exception that compound (VII-27) (4.0 mg, 0.0025 mmol, 15 eqs.), obtained in Preparation Example 5-23, was used instead of compound (VII-23), obtained in Preparation Example 5-19, the same procedure as in Example 19 was repeated to afford the title compound. 21.1 mg (1.15 mg/mL, a total of 14 mL, 85%).

Example 24

Preparation of Conjugate (I-28)

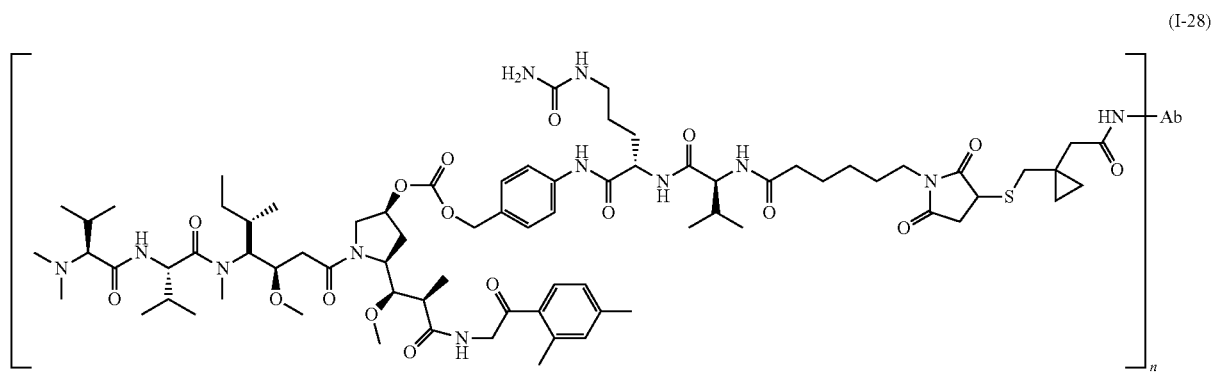

With the exception that compound (VII-28) (3.9 mg, 0.0025 mmol, 15 eqs.), obtained in Preparation Example 5-24, was used instead of compound (VII-23), obtained in Preparation Example 5-19, the same procedure as in Example 19 was repeated to afford the title compound. 17.3 mg (1.58 mg/mL, a total of 13 mL, 70%)

Example 25

Preparation of Conjugate (I-29)

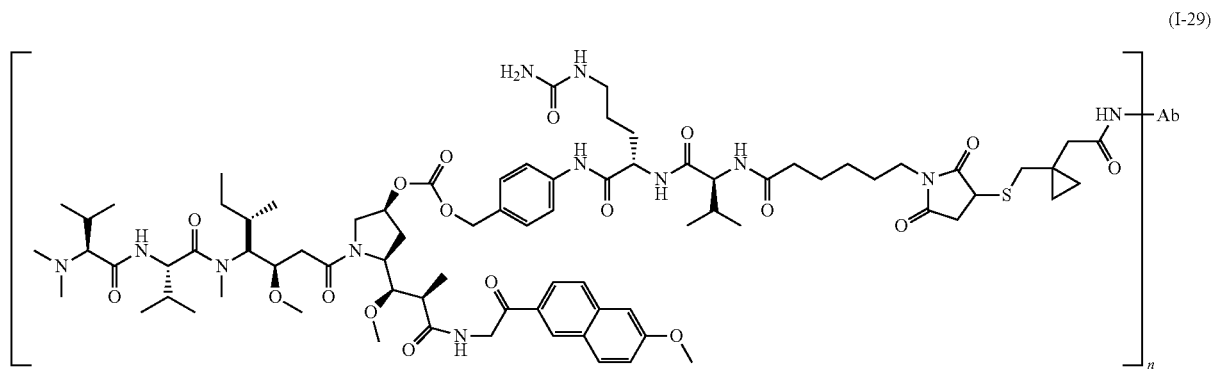

(I-29)

With the exception that compound (VII-29) (4.1 mg, 0.0025 mmol, 15 eqs.), obtained in Preparation Example 5-25, was used instead of compound (VII-23), obtained in Preparation Example 5-19, the same procedure as in Example 19 was repeated to afford the title compound. 9.2 mg (0.92 mg/mL, a total of 10 mL, 24.8%)

Example 26

Preparation of Conjugate (I-30)

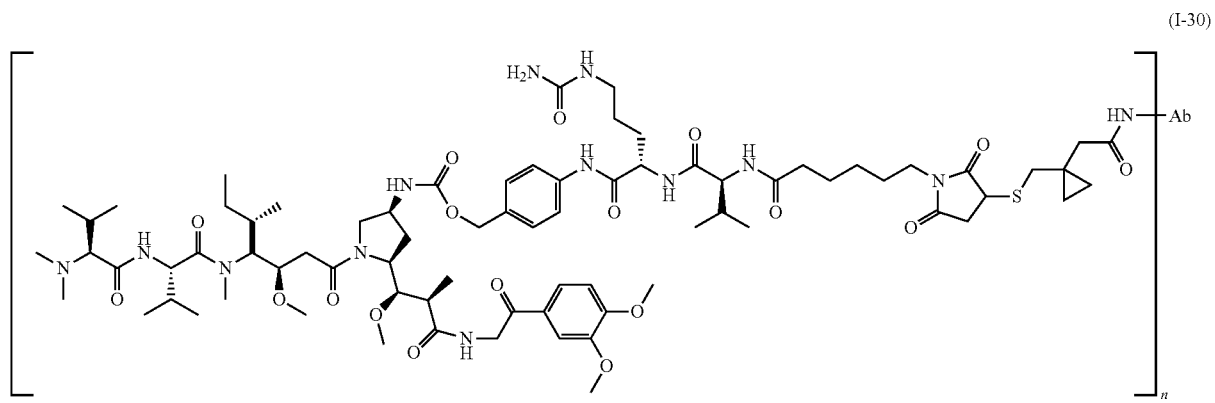

(I-30)

With the exception that compound (VII-30) (4.0 mg, 0.0025 mmol, 15 eqs.), obtained in Preparation Example 5-26, was used instead of compound (VII-23), obtained in Preparation Example 5-19, the same procedure as in Example 19 was repeated to afford the title compound. 16.7 mg (1.19 mg/mL, a total of 14 mL, 67%).

Example 27

Preparation of Conjugate (I-31)

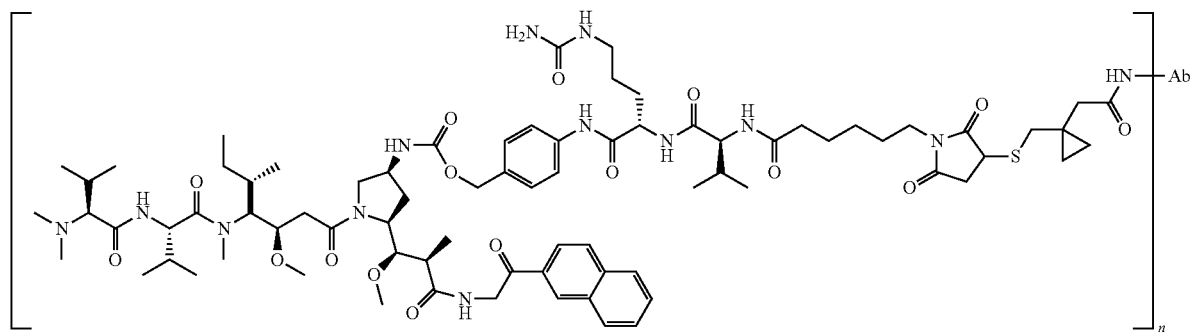

With the exception that compound (VII-31) (4.0 mg, 0.0025 mmol, 15 eqs.), obtained in Preparation Example 5-27, was used instead of compound (VII-23), obtained in Preparation Example 5-19, the same procedure as in Example 19 was repeated to afford the title compound. 21 mg (1.61 mg/mL, a total of 13 mL, 85%).

Example 28

Preparation of Conjugate (I-32)

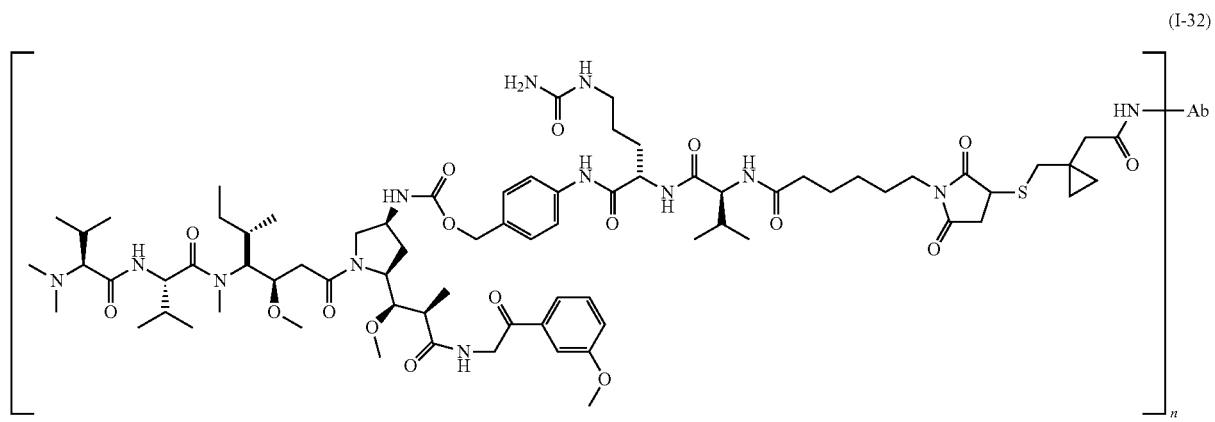

With the exception that compound (VII-32) (4.0 mg, 0.0025 mmol, 15 eqs.), obtained in Preparation Example 5-27, was used instead of compound (VII-23), obtained in Preparation Example 5-19, the same procedure as in Example 19 was repeated to afford the title compound. 12.3 mg (0.88 mg/mL, a total of 14 mL, 50%).

Example 29

Preparation of Conjugate (I-33)

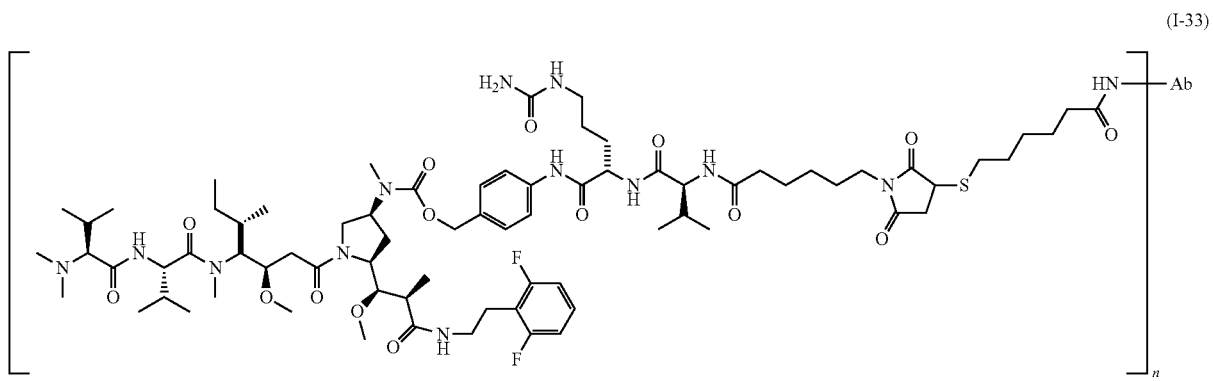

With the exception that compound (VII-33) (4.0 mg, 0.0025 mmol, 15 eqs.), obtained in Preparation Example 5-29, was used instead of compound (VII-23), obtained in Preparation Example 5-19, the same procedure as in Example 19 was repeated to afford the title compound. 15.3 mg (1.18 mg/mL, a total of 13 mL, 62%).

Example 30

Preparation of Conjugate (I-34)

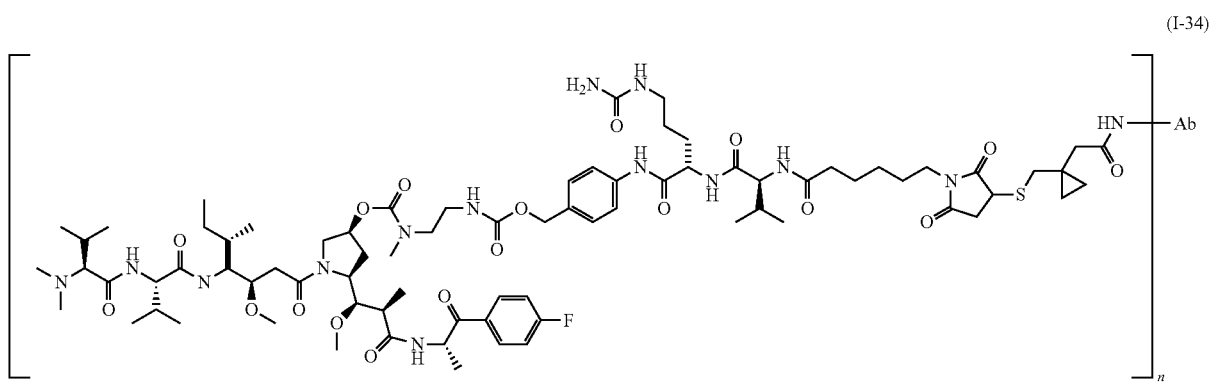

After being subjected to exchange treatment with PBS, pH 7.5 (10 mM phosphate, 137 mM NaCl, 2.7 mM KCl included), 5 mL of a trastuzumab (Herceptin) solution (5.4 g/mL, 36 μM) was further treated with 2.5 ml of PBS, pH 7.5, and 7.5 mL of 0.05 M sodium borate, pH 8.5. Then, the trastuzumab solution was mixed with a solution of compound (VII-34) (5.7 mg, 0.0036 mmol, 20 eqs.), obtained in Preparation Example 5-30, in 3.75 mL of 20% DMSO at 25° C. for 18 hrs while stirring. When the reaction was completed, the reaction mixture was filtered through a 0.45 μm filter. The filtrate was loaded into a centrifugal filter (Amicon Ultra-15 30K), and concentrated two or three times by use of PBS, pH 7.5, until the organic solvent and the materials that did not react were removed. The resulting concentrate was loaded into a Sephadex G-25 resin-packed column (30×300 mm) equilibrated with PBS, pH 7.5, and purified by MPLC (280 nm, UV range 0.08, flow rate 10 mL/min) to afford the title compound. 26.4 mg (2.20 mg/mL, a total of 12 mL, 98%). The concentration of the compound thus obtained was determined by measuring absorbance at three wavelengths (280 nm, 320 nm, 350 nm) with the aid of a LTV spectrometer.

Example 31

Preparation of Conjugate (I-35)

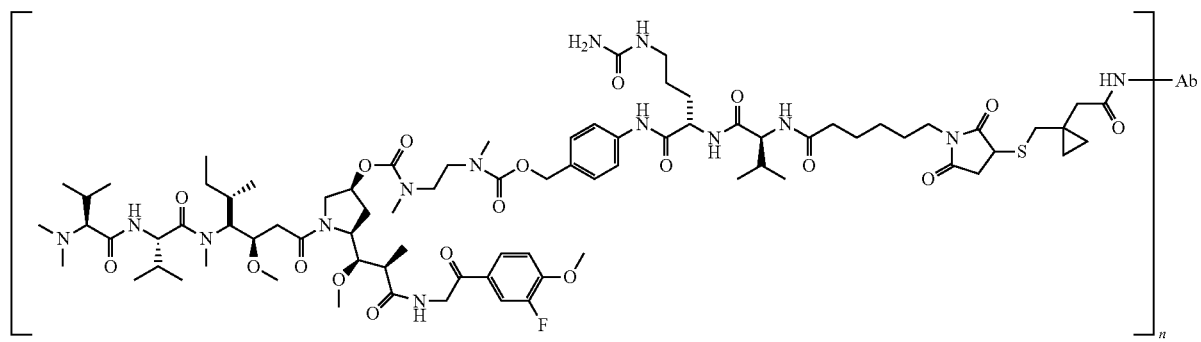

With the exception that compound (VII-35) (4.2 mg, 0.0024 mmol, 15 eqs.), obtained in Preparation Example 5-31, was used instead of compound (VII-34), obtained in Preparation Example 5-30, the same procedure as in Example 30 was repeated to afford the title compound. 14.5 mg (1.21 mg/mL, a total of 12 mL, 61%).

Example 32

Preparation of Conjugate (I-36)

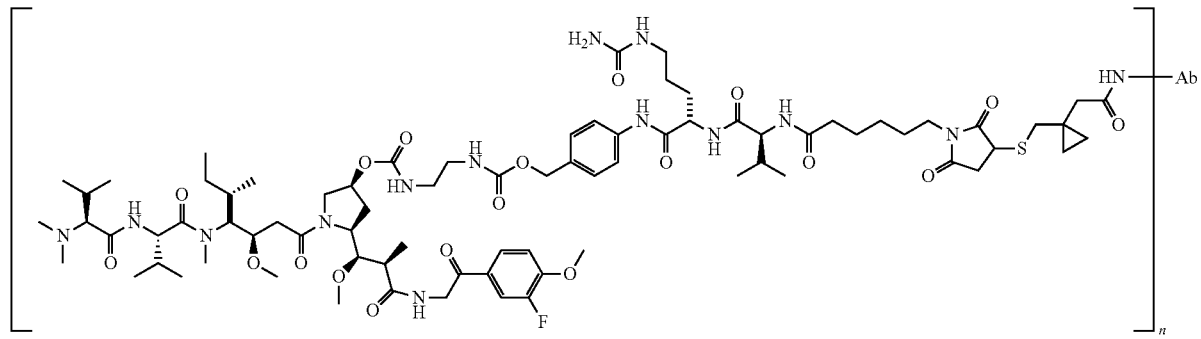

With the exception that compound (VII-36) (4.2 mg, 0.0024 mmol, 15 eqs.), obtained in Preparation Example 5-32, was used instead of compound (VII-34), obtained in Preparation Example 5-30, the same procedure as in Example 30 was repeated to afford the title compound. 17.9 mg (1.63 mg/mL, a total of 11 mL, 75%).

Example 33

Preparation of Conjugate (I-37)

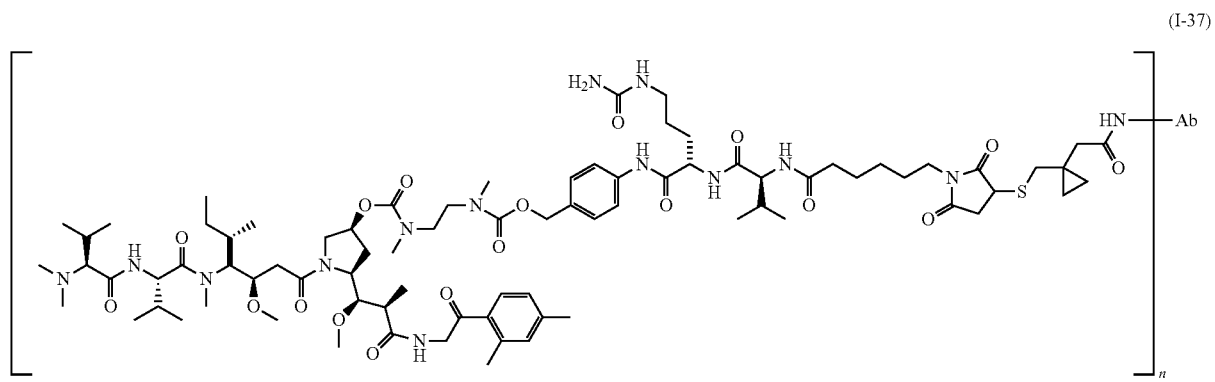

With the exception that compound (VII-37) (4.1 mg, 0.0024 mmol, 15 eqs.), obtained in Preparation Example 5-33, was used instead of compound (VII-34), obtained in Preparation Example 5-30, the same procedure as in Example 30 was repeated to afford the title compound. 11.8 mg (1.48 mg/mL, a total of 8 mL, 50%).

Example 34

Preparation of Conjugate (I-38)

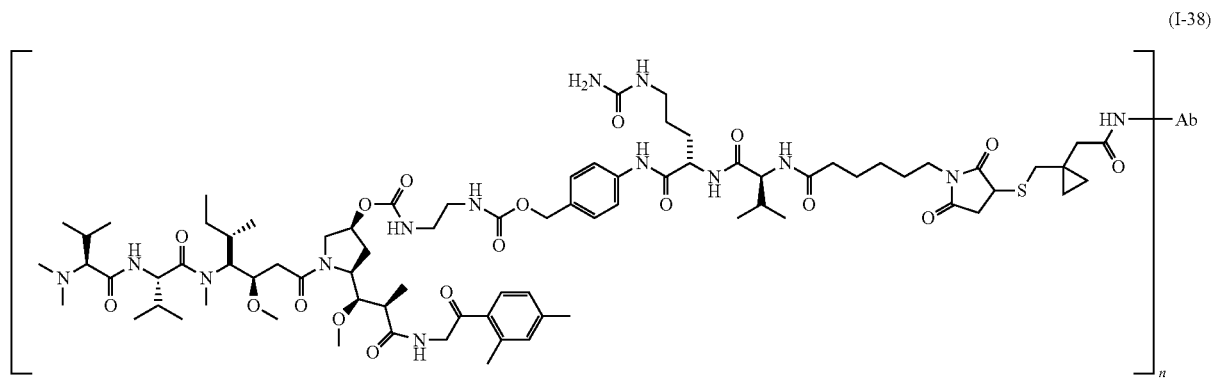

With the exception that compound (VII-38) (4.0 mg, 0.0024 mmol, 15 eqs.), obtained in Preparation Example 5-34, was used instead of compound (VII-34), obtained in Preparation Example 5-30, the same procedure as in Example 30 was repeated to afford the title compound. 15.8 mg (1.21 mg/mL, a total of 13 mL, 66%).

Example 35

Preparation of Conjugate (I-39)

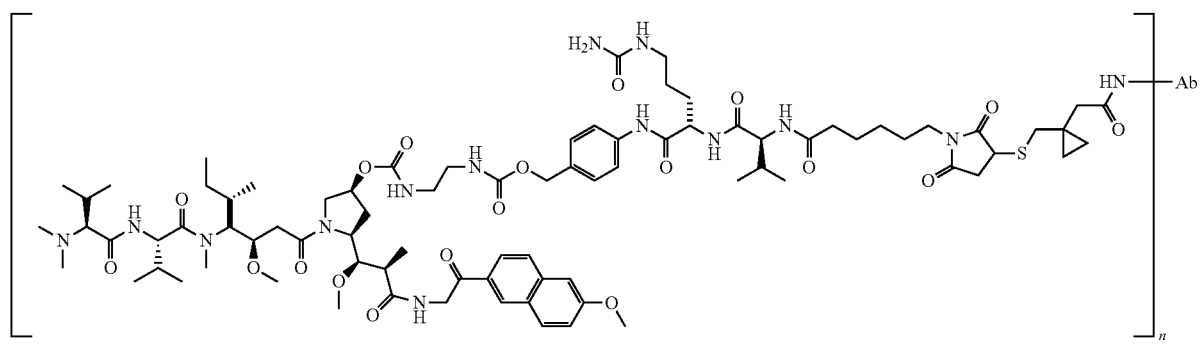

With the exception that compound (VII-39) (4.2 mg, 0.0024 mmol, 15 eqs.), obtained in Preparation Example 5-35, was used instead of compound (VII-34), obtained in Preparation Example 5-30, the same procedure as in Example 30 was repeated to afford the title compound. 18.3 mg (1.52 mg/mL, a total of 12 mL, 77%).

Example 36

Preparation of Conjugate (I-40)

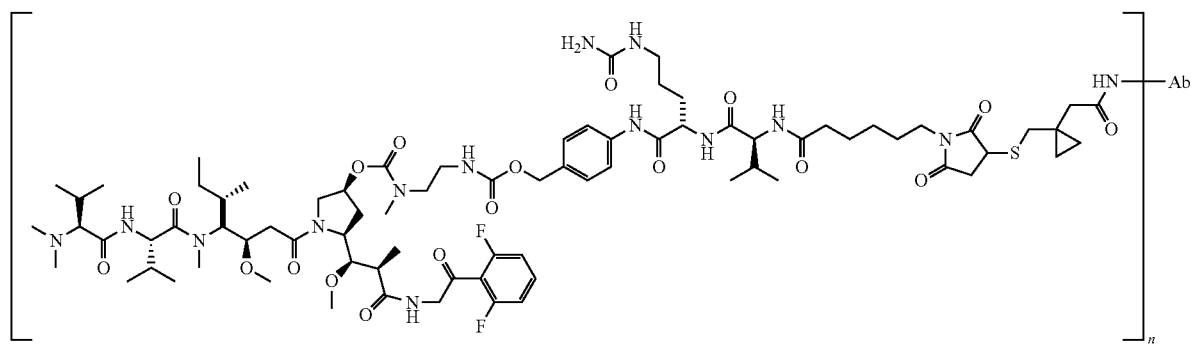

With the exception that compound (VII-40) (4.6 mg, 0.0027 mmol, 15 eqs.), obtained in Preparation Example 5-36, was used instead of compound (VII-34), obtained in Preparation Example 5-30, the same procedure as in Example 30 was repeated to afford the title compound. 12.7 mg (1.15 mg/mL, a total of 11 mL, 47%).

Example 37

Preparation of Conjugate (I-41)

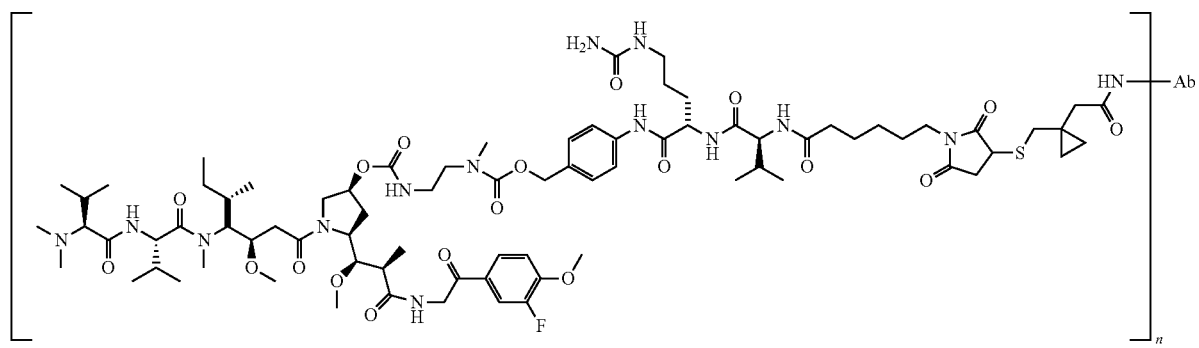

(I-41)

With the exception that compound (VII-41) (4.1 mg, 0.0024 mmol, 15 eqs.), obtained in Preparation Example 5-37, was used instead of compound (VII-34), obtained in Preparation Example 5-30, the same procedure as in Example 30 was repeated to afford the title compound. 16.1 mg (1.24 mg/mL, a total of 13 mL, 67%).

Test Example 1

DAR Determination by Protein Mass Spectrometry

From each of the antibody-linker-drug conjugates prepared in the Preparation Examples, N-linked glycan were removed by treatment with the endoglycosidic enzyme PNGase F at 37° C. for 15±3 hrs. The deglycosylated antibody-linker-drug conjugates were analyzed by an LC-ESI-MS system including Agilent 1200 HPLC and Agilent 6530 Q-TOF. The chromatographic separation of antibody-linker-drug conjugates was accomplished on an Agilent Zorbax column (300SB-C18, 2.1 mm×75 mm, 5 μm) using a gradient elution of 0.1% formic acid in water solution/0.1% formic acid in acetonitrile solution, and m/z (mass to charge) data were obtained at a scan rate of 1 spectrum per second within a range of 900 to 4000 m/z, and subjected to deconvolution, in which molecular weights and the % (percentage) abundance of each peak to integrated peaks (D0, D1, D2 . . . Dn) are used to calculate DAR.

Relative abundance of each peak was calculated according to the following equation. % Relative abundance of each peak was calculated by dividing the abundance of each peak by the total abundance of peaks.

$$\text{\% Relative Abundance of Each Peak} = \frac{\text{Abundance of each peak}}{\text{Total abundance of peaks } (D0 + D1 + \ldots + Dn)} \times 100$$

The DAR of antibody-linker-drug conjugates was calculated using the % relative abundance according to the following equation, and the results are given in Tables 1 to 4.

$$DAR = \frac{\text{Abundance of } D0 \times 0 + \text{Abundance of } D1 \times 1 + \ldots + \text{Abundance of } Dn \times n}{100}$$

TABLE 1

| | D0 | D1 | D2 | D3 | D4 | D5 | D6 | D7 | D8 | Sum |
|---|---|---|---|---|---|---|---|---|---|---|
| | | | | | Conjugate (I-6) | | | | | |
| Mass (Da) | 145179.9 | 146631.2 | 148080.8 | 149535.2 | 150983.3 | 152436.5 | 153888.3 | | | |
| Area | 3080 | 5170 | 6730 | 5764 | 4659 | 2430 | 1059 | | | 28892 |
| % Area | 10.7 | 17.9 | 23.3 | 20.0 | 16.1 | 8.4 | 3.7 | | | 100 |
| DAR | | | | | 2.53 | | | | | |
| | | | | | Conjugate (I-10) | | | | | |
| Mass (Da) | 145170.3 | 146616.1 | 148043.7 | 149473.9 | 150904.2 | 152340.0 | 153771.2 | 155201.9 | 156631.2 | |
| Area | 474 | 2570 | 5670 | 6155 | 6765 | 5567 | 3940 | 2430 | 655 | 34226 |
| % Area | 1.4 | 7.5 | 16.6 | 18 | 19.8 | 16.3 | 11.5 | 7.1 | 1.9 | 100 |
| DAR | | | | | 3.89 | | | | | |
| | | | | | Conjugate (I-11) | | | | | |
| Mass (Da) | 145173.9 | 146631.36 | 148048.1 | 149481.0 | 150912.6 | 152348.0 | 153781.7 | 155215.2 | 156641.7 | |
| Area | 330 | 1788 | 4947 | 6111 | 6769 | 7133 | 4975 | 3005 | 784 | 35842 |
| % Area | 0.9 | 5.0 | 13.8 | 17.0 | 18.9 | 19.9 | 13.9 | 8.4 | 2.2 | 100 |
| DAR | | | | | 4.18 | | | | | |

TABLE 2

|  | D0 | D1 | D2 | D3 | D4 | D5 | D6 | D7 | D8 | D9 | Sum |
|---|---|---|---|---|---|---|---|---|---|---|---|
| Conjugate (I-16) | | | | | | | | | | | |
| Mass (Da) | 145183.4 | 146693.5 | 148201.3 | 149712.0 | 151221.6 | 152733.2 | 154245.0 | 155747.8 | 157256.0 | 158782.5 | |
| Area | 102 | 1424 | 3455 | 4709 | 5143 | 4244 | 3996 | 2766 | 1683 | 762 | 28284 |
| % Area | 0.4 | 5.0 | 12.2 | 16.6 | 18.2 | 15.0 | 14.1 | 9.8 | 6.0 | 2.7 | 100 |
| DAR | | | | | | 4.52 | | | | | |
| Conjugate (I-19) | | | | | | | | | | | |
| Mass (Da) | 145180.0 | 146700.0 | 148195.7 | 149700.2 | 151191.8 | 152675.1 | 154214.2 | | | | |
| Area | 0 | 659 | 2225 | 3104 | 2632 | 1969 | 1031 | | | | 11620 |
| % Area | 0 | 5.7 | 19.1 | 26.7 | 22.7 | 16.9 | 8.9 | | | | 100 |
| DAR | | | | | | 3.53 | | | | | |
| Conjugate (I-20) | | | | | | | | | | | |
| Mass (Da) | 145180.0 | 146682.2 | 148171.4 | 149661.6 | 151149.2 | 152635.6 | 154120.6 | 155616.1 | | | |
| Area | 0 | 1192 | 4051 | 5884 | 5670 | 4260 | 2553 | 1374 | | | 24984 |
| % Area | 0 | 4.8 | 16.2 | 23.6 | 22.7 | 17.1 | 10.2 | 5.5 | | | 100 |
| DAR | | | | | | 3.84 | | | | | |
| Conjugate (I-21) | | | | | | | | | | | |
| Mass (Da) | 145180 | 146696.3 | 148185.3 | 149697.7 | 151205.5 | 152699.3 | 154228.8 | 155742.3 | | | |
| Area | 0 | 204 | 832 | 1650 | 1996 | 906 | 480 | 135 | | | 6203 |
| % Area | 0 | 3.3 | 13.4 | 26.6 | 32.2 | 14.6 | 7.7 | 2.2 | | | 100 |
| DAR | | | | | | 3.73 | | | | | |
| Conjugate (I-22) | | | | | | | | | | | |
| Mass (Da) | 145180 | 146696.3 | 148150.3 | 149640.7 | 151168 | 152613.7 | 15087.2 | 15554.7 | 157093.4 | 158600 | |
| Area | 0 | 204 | 1040 | 1925 | 2478 | 2635 | 1932 | 886 | 929 | 328 | 12333 |
| % Area | 0 | 1.7 | 8.2 | 15.6 | 20.1 | 21.4 | 15.7 | 7.2 | 7.5 | 2.7 | 100 |
| DAR | | | | | | 4.81 | | | | | |

TABLE 3

|  | D0 | D1 | D2 | D3 | D4 | D5 | D6 | D7 | D8 | D9 | Sum |
|---|---|---|---|---|---|---|---|---|---|---|---|
| Conjugate (I-23) | | | | | | | | | | | |
| Mass (Da) | 145188.9 | 146664.0 | 148148.6 | 149631.3 | 151108.4 | 152593.1 | 154080.0 | 155567.8 | | | |
| Area | 2036 | 5337 | 7002 | 5759 | 4434 | 2120 | 1133 | 207 | | | 28028 |
| % Area | 7.3 | 19.0 | 25.0 | 20.0 | 15.8 | 7.6 | 4.0 | 0.7 | | | 100 |
| DAR | | | | | | 2.56 | | | | | |
| Conjugate (I-24) | | | | | | | | | | | |
| Mass (Da) | 145188.9 | 146664.0 | 148148.6 | 149631.3 | 151108.4 | 152593.1 | 154080.0 | | | | |
| Area | 2036 | 5337 | 7002 | 5759 | 4434 | 2120 | 1133 | | | | 27821 |
| % Area | 7.3 | 19.2 | 25.2 | 20.7 | 15.9 | 7.6 | 4.1 | | | | 100 |
| DAR | | | | | | 2.58 | | | | | |
| Conjugate (I-25) | | | | | | | | | | | |
| Mass (Da) | 148184.2 | 146662.2 | 148139.3 | 149624.8 | 151109.1 | 152587.6 | 154068.8 | 155555.1 | 158517.7 | 158517.7 | |
| Area | 977 | 4474 | 8992 | 9929 | 9912 | 7176 | 4842 | 2313 | 977 | 240 | 49832 |
| % Area | 2.0 | 9.0 | 18.0 | 19.9 | 19.9 | 14.4 | 9.7 | 4.6 | 2.0 | 0.5 | 100 |
| DAR | | | | | | 3.67 | | | | | |
| Conjugate (I-26) | | | | | | | | | | | |
| Mass (Da) | 145188.0 | 146689.5 | 148201.7 | 149713.7 | 151226.1 | 152731.6 | 154241.5 | 155753.7 | 157258.4 | 158773.3 | |
| Area | 136 | 1285 | 3717 | 5699 | 5756 | 5280 | 4541 | 3287 | 2348 | 955 | 33004 |
| % Area | 0.4 | 3.9 | 11.3 | 17.3 | 17.4 | 16.0 | 13.8 | 10.0 | 7.1 | 2.9 | 100 |
| DAR | | | | | | 4.63 | | | | | |

TABLE 3-continued

| | D0 | D1 | D2 | D3 | D4 | D5 | D6 | D7 | D8 | D9 | Sum |
|---|---|---|---|---|---|---|---|---|---|---|---|
| Conjugate (I-27) | | | | | | | | | | | |
| Mass (Da) | 145182.4 | 146692.2 | 148195.4 | 149705.6 | 151213.7 | 152718.3 | 154222.6 | 155731.2 | | | |
| Area | 2008 | 3562 | 5553 | 4675 | 3576 | 1662 | 1105 | 456 | | | 22597 |
| % Area | 8.9 | 15.8 | 24.6 | 20.7 | 15.8 | 7.4 | 4.9 | 2.0 | | | 100 |
| DAR | | | | | | 2.71 | | | | | |
| Conjugate (I-28) | | | | | | | | | | | |
| Mass (Da) | 145185.4 | 146672.2 | 148158.1 | 149641.9 | 151128.8 | 152626.0 | 154108.0 | | | | |
| Area | 789 | 4780 | 5411 | 3780 | 3281 | 1342 | 428 | | | | 19811 |
| % Area | 4.0 | 24.1 | 27.3 | 19.1 | 16.6 | 6.8 | 2.2 | | | | 100 |
| DAR | | | | | | 2.49 | | | | | |
| Conjugate (I-30) | | | | | | | | | | | |
| Mass (Da) | 145180.0 | 146711.4 | 148226.3 | 149742.3 | 151267.9 | 152788.8 | 154311.3 | 155837.3 | | | |
| Area | 0 | 144 | 968 | 1227 | 2001 | 1550 | 519 | 153 | | | 6562 |
| % Area | 0 | 2.2 | 14.8 | 18.7 | 30.5 | 23.6 | 7.9 | 2.3 | | | 100 |
| DAR | | | | | | 3.92 | | | | | |
| Conjugate (I-31) | | | | | | | | | | | |
| Mass (Da) | 145181.5 | 146691.4 | 148203.8 | 149717.6 | 151228.5 | | | | | | |
| Area | 6412 | 9396 | 6548 | 3337 | 1388 | | | | | | |
| % Area | 23.7 | 34.7 | 24.2 | 12.3 | 5.1 | | | | | | |
| DAR | | | | | | 1.41 | | | | | |
| Conjugate (I-32) | | | | | | | | | | | |
| Mass (Da) | 145185.5 | 146679.8 | 148182.7 | 149670.4 | 151166.1 | 152687.2 | 154165.9 | 155657.3 | 157164.6 | | |
| Area | 240 | 696 | 1841 | 2965 | 3326 | 3067 | 2007 | 897 | 260 | | 15299 |
| % Area | 1.6 | 4.5 | 12.0 | 19.4 | 21.7 | 20.0 | 13.1 | 5.9 | 1.7 | | 100 |
| DAR | | | | | | 4.07 | | | | | |
| Conjugate (I-33) | | | | | | | | | | | |
| Mass (Da) | 145177.6 | 146681.5 | 148183.2 | 149668.3 | 151168.4 | 152663.0 | 154161.2 | 155656.4 | 157868.3 | | |
| Area | 149 | 432 | 1535 | 2946 | 4174 | 3528 | 2278 | 1803 | 375 | | 17220 |
| % Area | 0.9 | 2.5 | 8.9 | 17.1 | 24.2 | 20.5 | 13.2 | 10.5 | 2.2 | | 100 |
| DAR | | | | | | 4.41 | | | | | |

TABLE 4

| | D0 | D1 | D2 | D3 | D4 | D5 | D6 | D7 | D8 | D9 | Sum |
|---|---|---|---|---|---|---|---|---|---|---|---|
| Conjugate (I-34) | | | | | | | | | | | |
| Mass (Da) | 145177.7 | 146777.9 | 148378.3 | 149972.4 | 151563.0 | 153163.7 | | | | | |
| Area | 5864 | 10420 | 8579 | 5125 | 1867 | 849 | | | | | 32704 |
| % Area | 17.9 | 31.9 | 26.2 | 15.7 | 5.7 | 2.6 | | | | | 100 |
| DAR | | | | | | 1.67 | | | | | |
| Conjugate (I-35) | | | | | | | | | | | |
| Mass (Da) | 145180.0 | 146805.8 | 148427.5 | 150051.7 | 151669.0 | 153291.4 | 154912.5 | 156539.5 | 158132.1 | 159784.1 | |
| Area | 0 | 1791 | 7950 | 11577 | 11722 | 9767 | 7214 | 4651 | 1852 | 949 | 57473 |
| % Area | 0 | 3.1 | 13.8 | 20.1 | 20.4 | 17.0 | 12.6 | 8.1 | 3.2 | 1.7 | 100 |
| DAR | | | | | | 4.3 | | | | | |
| Conjugate (I-36) | | | | | | | | | | | |
| Mass (Da) | 145180.0 | 146784.9 | 148374.9 | 149964.2 | 151552.3 | 153144.0 | 154742.7 | 156334.3 | 157940.4 | 159524.4 | |
| Area | 0 | 232 | 2467 | 5116 | 6483 | 4829 | 3222 | 1457 | 716 | 356 | 24878 |
| % Area | 0 | 0.9 | 9.9 | 20.6 | 26.1 | 19.4 | 13.0 | 5.9 | 2.9 | 1.4 | 100 |
| DAR | | | | | | 4.38 | | | | | |
| Conjugate (I-37) | | | | | | | | | | | |
| Mass (Da) | 145180.0 | 146787.7 | 148387.9 | 149985.8 | 151588.4 | 153191.5 | 154798.6 | 156392.1 | 157995.3 | | |
| Area | 0 | 3495 | 7843 | 10015 | 8988 | 6940 | 4126 | 1274 | 389 | | 43070 |
| % Area | 0 | 8.1 | 18.2 | 23.3 | 20.9 | 16.1 | 9.6 | 3.0 | 0.9 | | 100 |
| DAR | | | | | | 3.64 | | | | | |

TABLE 4-continued

|  | D0 | D1 | D2 | D3 | D4 | D5 | D6 | D7 | D8 | D9 | Sum |
|---|---|---|---|---|---|---|---|---|---|---|---|
| Conjugate (I-38) | | | | | | | | | | | |
| Mass (Da) | 145180.0 | 146759.0 | 148331.1 | 149903.0 | 151476.4 | 153055.9 | 154631.0 | 156203.6 | | | |
| Area | 0 | 2221 | 7557 | 9075 | 7933 | 5512 | 3044 | 968 | | | |
| % Area | 0 | 3.1 | 20.8 | 25.0 | 21.8 | 15.2 | 8.4 | 2.7 | | | |
| DAR | | | | | | 3.55 | | | | | |
| Conjugate (I-39) | | | | | | | | | | | |
| Mass (Da) | 145187.1 | 146810.7 | 148434.4 | 150059.8 | 151687.1 | 153320.3 | 154948.4 | | | | |
| Area | 1463 | 5565 | 11616 | 11593 | 6224 | 2476 | 710 | | | | 39647 |
| % Area | 3.7 | 14.0 | 29.3 | 29.2 | 15.7 | 6.2 | 1.8 | | | | 100 |
| DAR | | | | | | 2.65 | | | | | |
| Conjugate (I-40) | | | | | | | | | | | |
| Mass (Da) | 145180.0 | 146770.5 | 148351.3 | 149928.2 | 151506.8 | 153095.0 | 154671.9 | 156259.1 | 157840.3 | 159429.5 | |
| Area | 0 | 1848 | 6545 | 10020 | 11504 | 9447 | 6600 | 4246 | 2260 | 661 | 53131 |
| % Area | 0 | 3.5 | 12.3 | 18.9 | 21.6 | 17.8 | 12.4 | 8.0 | 4.3 | 1.3 | 100 |
| DAR | | | | | | 4.36 | | | | | |
| Conjugate (I-41) | | | | | | | | | | | |
| Mass (Da) | 145180.0 | 146792.1 | 148401.0 | 150007.0 | 151601.6 | 153213.6 | 154823.1 | | | | |
| Area | 0 | 236 | 1671 | 3110 | 3322 | 2200 | 1234 | | | | 11773 |
| % Area | 0 | 2.0 | 14.2 | 26.4 | 28.2 | 18.7 | 105 | | | | 100 |
| DAR | | | | | | 3.79 | | | | | |

Test Example 2

SEC-HPLC Analysis

Using size exclusion chromatography (SEC-HPLC), examination was made to see whether the antibody was abnormally fragmented or aggregated during the coupling of the antibody with the drug. Having negative influences on antibody's intrinsic properties including antigen-specific affinity, in vivo pharmacokinetics, etc., such abnormal protein structures may be used as an index indirectly indicative of the quality of prepared antibody-linker-drug conjugates.

The antibody-linker-drug conjugates prepared in the Preparation Examples were analyzed for normal antibody structure ratios, using SEC-HPLC. The results are summarized in Tables 5 to 8, below.

TABLE 5

| Sample | Main peak [1] (%) | HMW [2] (%) | LMW [3] (%) |
|---|---|---|---|
| Pre-coupled antibody | 99.16 | 0.65 | 0.19 |
| Conjugate (I-6) | 98.55 | 1.07 | 0.38 |
| Conjugate (I-10) | 98.21 | 1.40 | 0.39 |
| Conjugate (I-11) | 98.42 | 1.16 | 0.42 |

[1] Main peak: ratio of materials corresponding to the size of normal antibody
[2] HMW (High molecular weight): ratio of materials larger than normal antibody due to aggregation
[3] LMW (Low molecular weight): ratio of materials smaller than normal antibody due to fragmentation The antibody-linker-drug conjugates prepared in Examples 2, 6 and 7 were observed to have a normal antibody structure ratio of 98.21 to 98.55%, which was comparable with that of the pre-coupled antibody (99.16%).

TABLE 6

| Sample | Main peak [1] (%) | HMW [2] (%) | LMW [3] (%) |
|---|---|---|---|
| Pre-coupled antibody | 99.48 | 0.27 | 0.25 |
| Conjugate (I-16) | 99.24 | 0.40 | 0.35 |
| Conjugate (I-17) | 99.25 | 0.38 | 0.32 |
| Conjugate (I-18) | 98.44 | 1.38 | 0.18 |
| Conjugate (I-19) | 93.56 | 6.25 | 0.18 |
| Conjugate (I-20) | 94.06 | 5.73 | 0.20 |
| Conjugate (I-21) | 97.27 | 2.52 | 0.20 |
| Conjugate (I-22) | 92.43 | 7.37 | 0.19 |

[1] Main peak: ratio of materials corresponding to the size of normal antibody
[2] HMW (High molecular weight): ratio of materials larger than normal antibody due to aggregation
[3] LMW (Low molecular weight): ratio of materials smaller than normal antibody due to fragmentation The antibody-linker-drug conjugates prepared in Examples 12 to 18 were observed to have a normal antibody structure ratio of 92.43 to 99.25%, which was comparable with that of the pre-coupled antibody (99.48%).

TABLE 7

| Sample | Main peak [1] (%) | HMW [2] (%) | LMW [3] (%) |
|---|---|---|---|
| Pre-coupled antibody | 99.48 | 0.27 | 0.25 |
| Conjugate (I-23) | 99.13 | 0.53 | 0.34 |
| Conjugate (I-24) | 97.77 | 1.71 | 0.52 |
| Conjugate (I-25) | 96.94 | 2.71 | 0.35 |
| Conjugate (I-26) | 98.39 | 1.30 | 0.31 |
| Conjugate (I-27) | 97.12 | 2.63 | 0.24 |
| Conjugate (I-28) | 97.44 | 2.32 | 0.24 |
| Conjugate (I-29) | 97.07 | 2.68 | 0.25 |
| Conjugate (I-30) | 90.68 | 9.08 | 0.24 |
| Conjugate (I-31) | 93.80 | 6.00 | 0.20 |
| Conjugate (I-32) | 94.27 | 5.51 | 0.22 |
| Conjugate (I-33) | 97.09 | 2.60 | 0.32 |

[1] Main peak: ratio of materials corresponding to the size of normal antibody
[2] HMW (High molecular weight): ratio of materials larger than normal antibody due to aggregation
[3] LMW (Low molecular weight): ratio of materials smaller than normal antibody due to fragmentation The antibody-linker-drug conjugates prepared in Examples 19 to 29 were observed to have a normal antibody structure ratio of 90.68 to 99.13%, which was comparable with that of the pre-coupled antibody (99.48%).

TABLE 8

| Sample | Main peak [1] (%) | HMW [2] (%) | LMW [3] (%) |
|---|---|---|---|
| Pre-coupled antibody | 99.48 | 0.27 | 0.25 |
| Conjugate (I-34) | 98.63 | 1.02 | 0.35 |
| Conjugate (I-35) | 98.93 | 0.77 | 0.29 |
| Conjugate (I-36) | 98.33 | 1.43 | 0.24 |
| Conjugate (I-37) | 98.85 | 0.87 | 0.28 |
| Conjugate (I-38) | 98.31 | 1.44 | 0.25 |
| Conjugate (I-39) | 97.00 | 2.75 | 0.24 |
| Conjugate (I-40) | 98.15 | 1.49 | 0.36 |
| Conjugate (I-41) | 97.61 | 2.15 | 0.24 |

[1] Main peak: ratio of materials corresponding to the size of normal antibody
[2] HMW (High molecular weight): ratio of materials larger than normal antibody due to aggregation
[3] LMW (Low molecular weight): ratio of materials smaller than normal antibody due to fragmentation The antibody-linker-drug conjugates prepared in Examples 30 to 37 were observed to have a normal antibody structure ratio of 97.00 to 98.93, which was comparable with that of the pre-coupled antibody (99.48%).

Test Example 3

IEF Analysis

Using isoelectric focusing (IEF) analysis, the antibody-linker-drug conjugates (I-6), (I-8), (I-10) and (I-11), prepared respectively in Preparation Examples 2, 4, 6 and 7, were analyzed for isoelectric point (pI) values, and the results are listed in Table 9, below.

TABLE 9

| | Lane | | | | | | | |
|---|---|---|---|---|---|---|---|---|
| Sample | 2 Pre-coupled antibody | 3 Conjugate (I-8) | 4 Conjugate (I-6) | 5 Conjugate (I-11) | 6 Conjugate (I-11) | 7 Conjugate (I-10) | 8 Conjugate (I-10) | 9 Pre-coupled antibody |
| Band 1 | 8.96 | 8.87 | 8.90 | 8.78 | 8.80 | 8.78 | 8.78 | 8.98 |
| Band 2 | 8.85 | 8.78 | 8.82 | 8.71 | 8.72 | 8.70 | 8.69 | 8.86 |
| Band 3 | 8.76 | 8.69 | 8.74 | 8.62 | 8.62 | 8.6 | 8.59 | 8.77 |
| Band 4 | 8.68 | 8.59 | 8.63 | 8.51 | 8.51 | 8.49 | 8.48 | 8.68 |
| Band 5 | — | 8.48 | 8.52 | 8.39 | 8.4 | 8.38 | 8.37 | — |
| Band 6 | — | — | 8.41 | 8.29 | 8.3 | 8.27 | 8.26 | — |
| Band 7 | — | — | — | 8.21 | 8.2 | 8.18 | 8.17 | — |

* Lane 1 and 10 are pI marker.

Coincident with the DAR results, as can be seen in Table 9, lower pI bands were detected from Conjugates (I-10) and (I-11) with more drugs coupled thereto. That is, the number of drugs coupled to the antibody increased.

Test Example 4

In Vitro Cytotoxicity Assay

The antibody-linker-drug conjugates were analyzed for anticancer potency by evaluating antiproliferative activity against the HER-2-overexpressing breast cancer cell line (BT-474) in vitro. For a control, trastuzumab, which was employed for the preparation of the antibody-linker-drug conjugates, was used alone. Trastuzumab is a monoclonal antibody against the HER-2 antigen specifically expressed in breast cancer cells.

BT-474 cells were seeded at a density of $1\times10^4$ cells/well into 96-well microplates, and incubated for 5 days with various concentrations of the control trastuzumab or the antibody-linker-drug conjugates prepared in the Preparation Examples. The number of viable cells after 5 days incubation was indirectly evaluated by measuring absorbance via colorimetric reagent (CCK-8). The correlation of concentration and potency was fitted as 4-parameter logistic curve and the relative potency was evaluated with the $EC_{50}$ (effective concentration of 50%) in the curve fit. The results are given in FIGS. 1 to 17 and Tables 10 to 13.

As seen in Table 10, the antibody-linker-drug conjugates prepared in Examples 2, 6 and 7 decreased in $EC_{50}$ by 13.2 to 17.8 times, compared to the control trastuzumab, indicating that the antibody-linker-drug conjugates of the present invention can exert the same efficacy as the control even at far smaller doses, with the consequent decrease of side effects.

Figure 2:
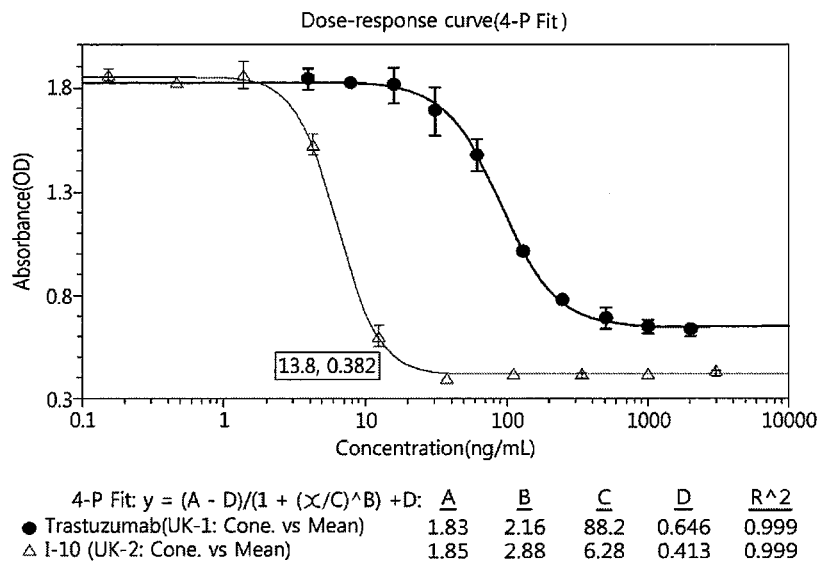
FIG. 2 is a dose-response curve showing in vitro antiproliferative activity of antibody-linker-drug conjugate (I-10) according to the present invention against BT-474 cells.
Figure 3:
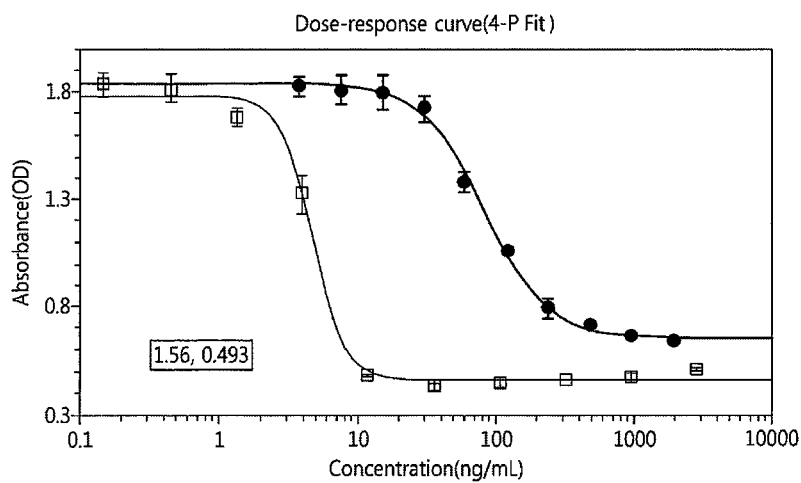
FIG. 3 is a dose-response curve showing in vitro antiproliferative activity of antibody-linker-drug conjugate (I-11) according to the present invention against BT-474 cells.
Figure 4:
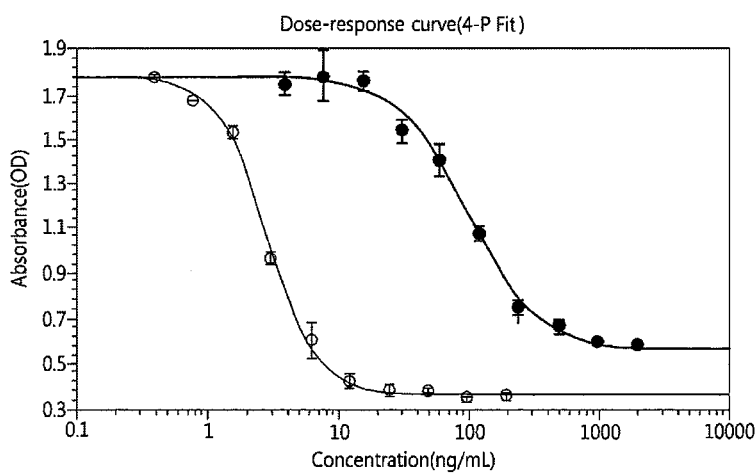
FIG. 4 is a dose-response curve showing in vitro antiproliferative activity of antibody-linker-drug conjugate (I-16) according to the present invention against BT-474 cells.
Figure 5:
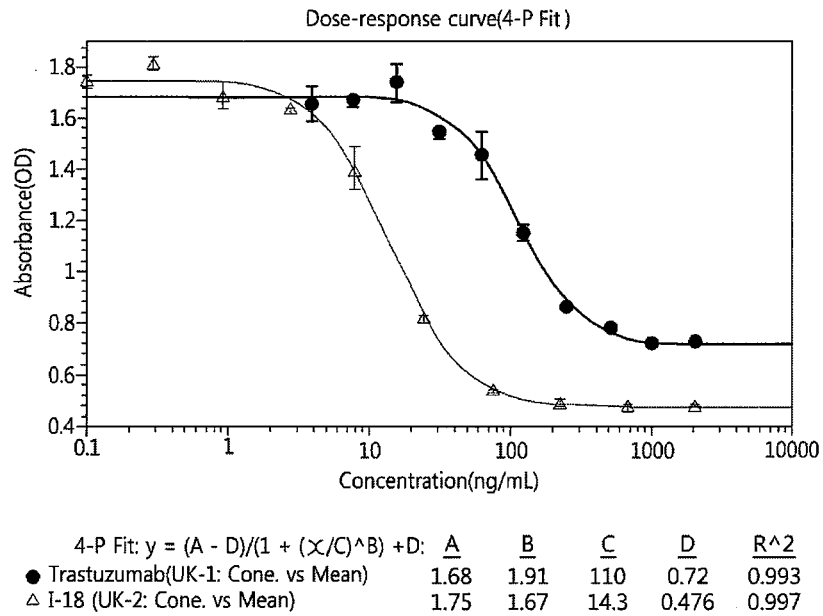
FIG. 5 is a dose-response curve showing in vitro antiproliferative activity of antibody-linker-drug conjugate (I-18) according to the present invention against BT-474 cells.
Figure 6:
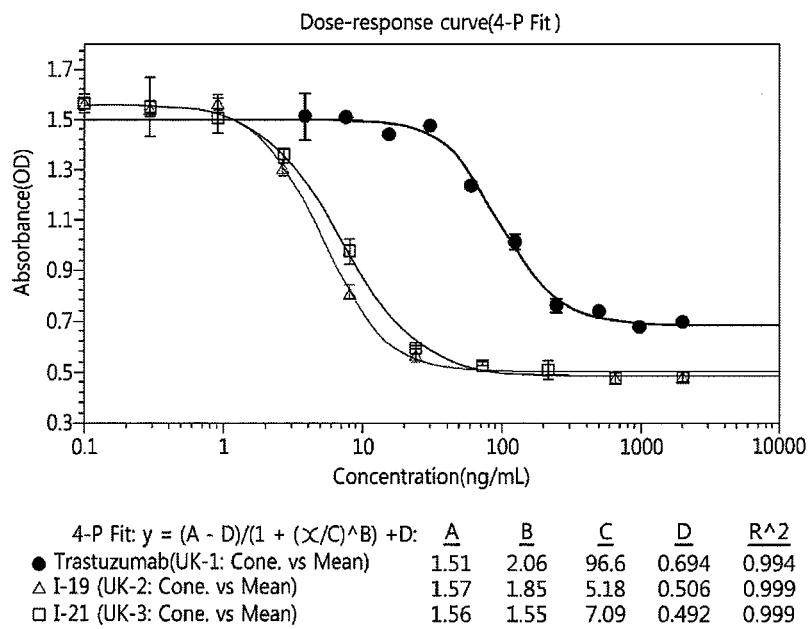
FIG. 6 is a dose-response curve showing in vitro antiproliferative activity of antibody-linker-drug conjugates (I-19) and (I-21) according to the present invention against BT-474 cells.
Figure 7:
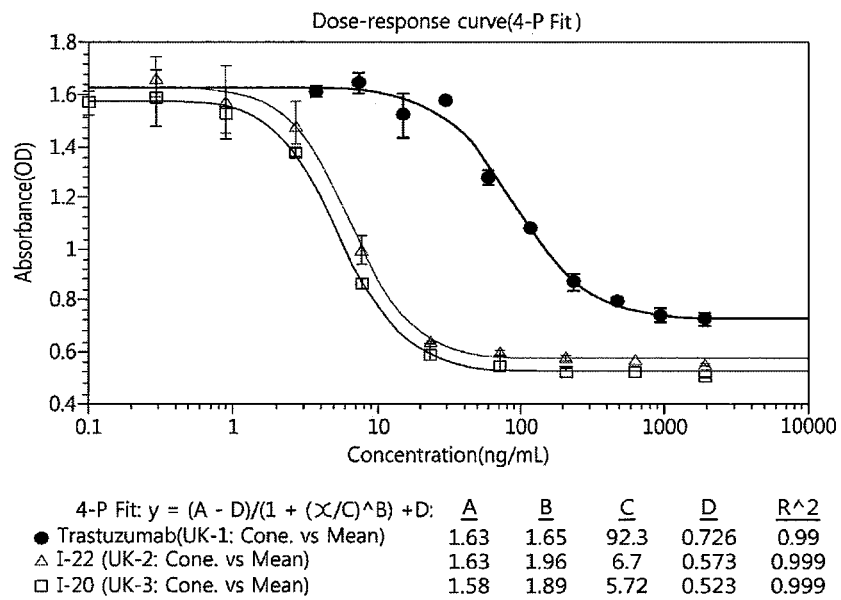
FIG. 7 is a dose-response curve showing in vitro antiproliferative activity of antibody-linker-drug conjugates (I-20) and (I-22) according to the present invention against BT-474 cells.
Figure 8:
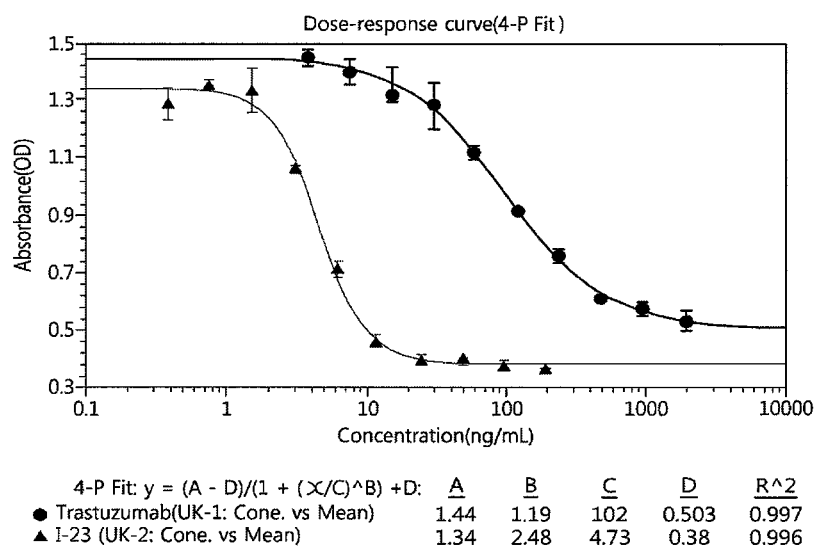
FIG. 8 is a dose-response curve showing in vitro antiproliferative activity of antibody-linker-drug conjugate (I-23) according to the present invention against BT-474 cells.
Figure 9:
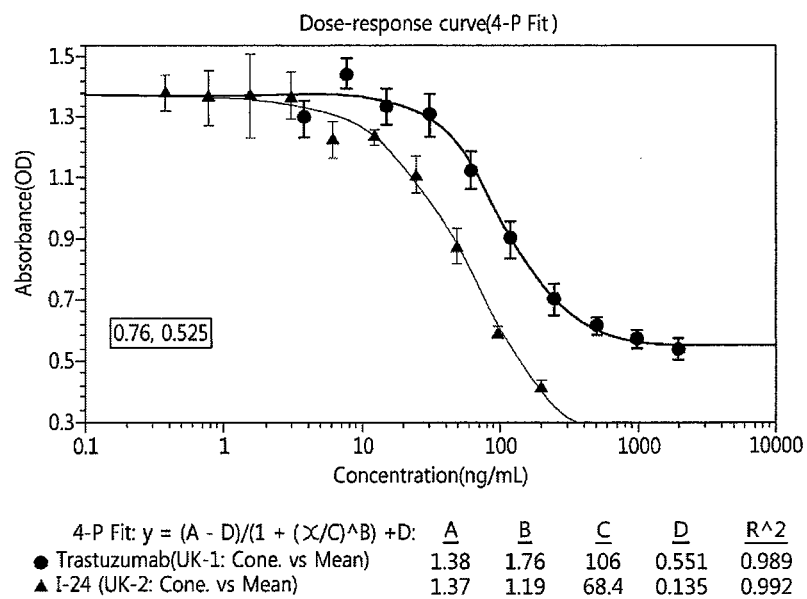
FIG. 9 is a dose-response curve showing in vitro antiproliferative activity of antibody-linker-drug conjugate (I-24) according to the present invention against BT-474 cells.
Figure 10:
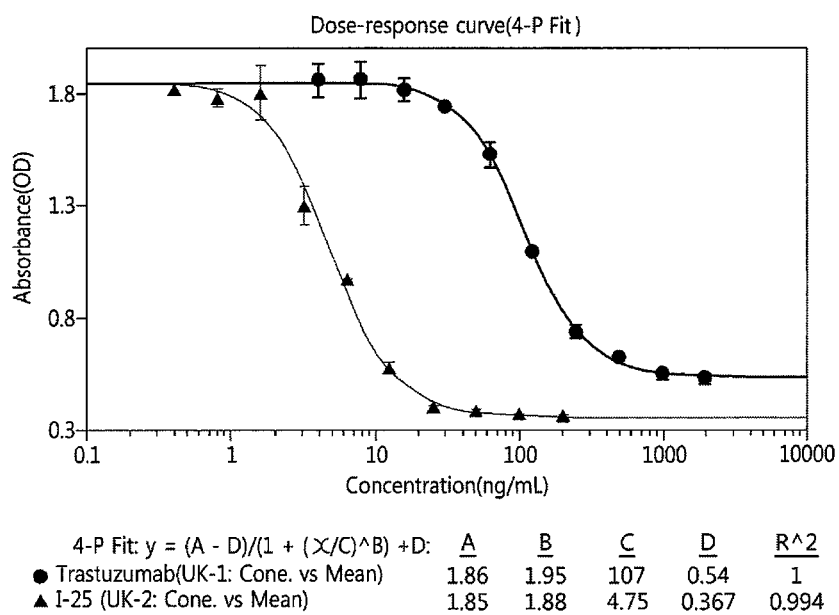
FIG. 10 is a dose-response curve showing in vitro antiproliferative activity of antibody-linker-drug conjugate (I-25) according to the present invention against BT-474 cells.
Figure 11:
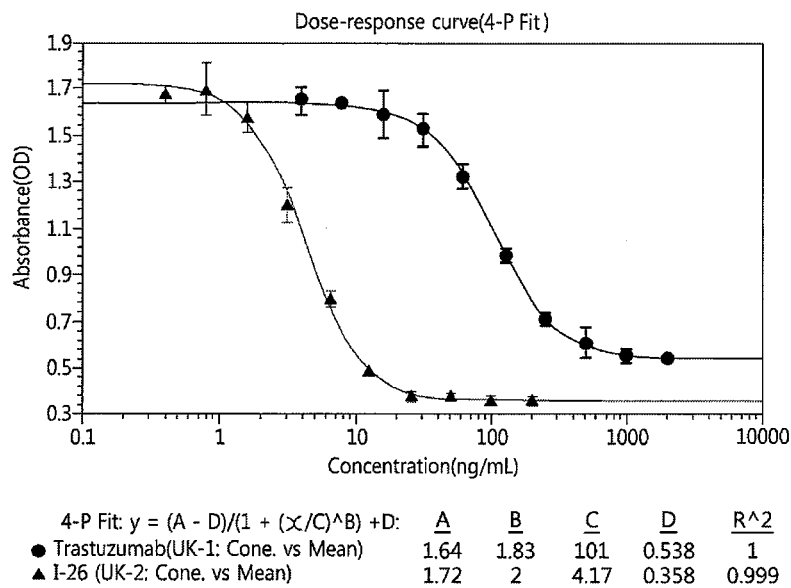
FIG. 11 is a dose-response curve showing in vitro antiproliferative activity of antibody-linker-drug conjugate (I-26) according to the present invention against BT-474 cells.
Figure 12:
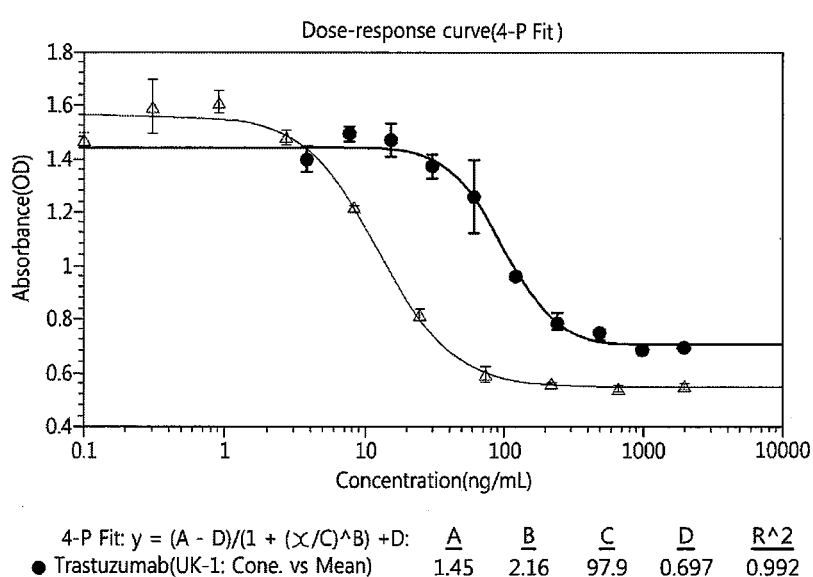
FIG. 12 is a dose-response curve showing in vitro antiproliferative activity of antibody-linker-drug conjugate (I-32) according to the present invention against BT-474 cells.
Figure 13:
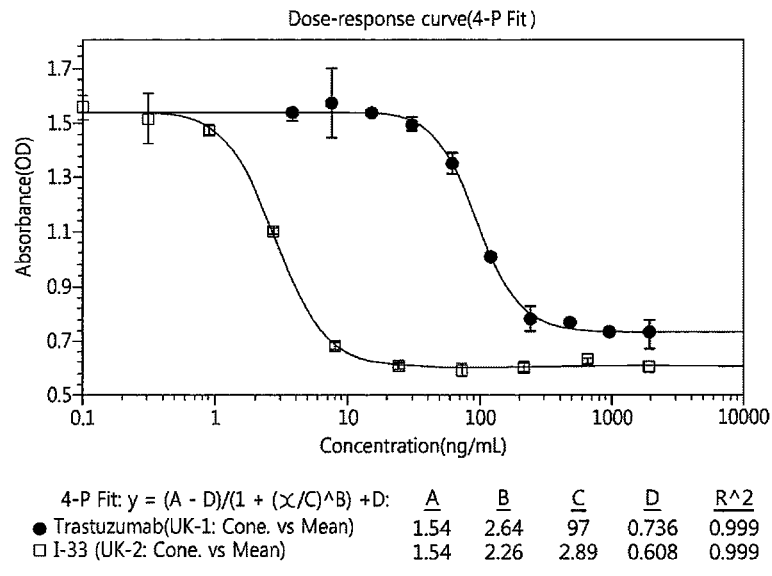
FIG. 13 is a dose-response curve showing in vitro antiproliferative activity of antibody-linker-drug conjugate (I-33) according to the present invention against BT-474 cells.
Figure 14:
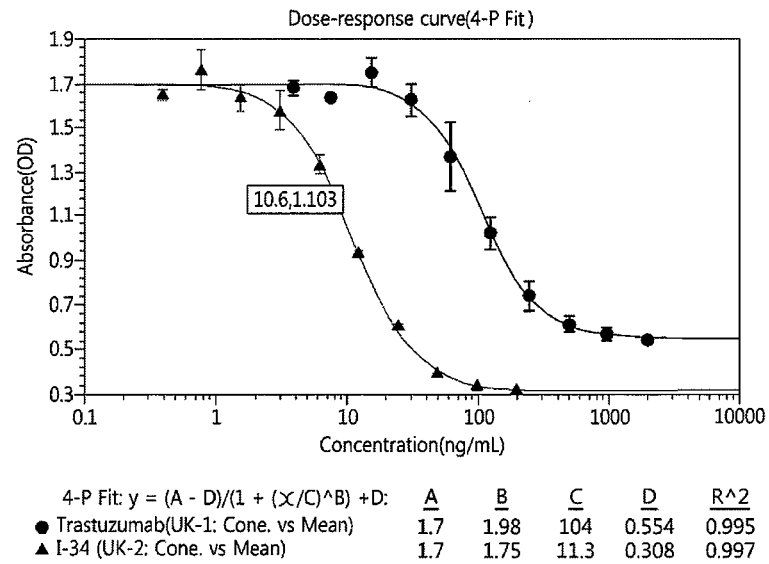
FIG. 14 is a dose-response curve showing in vitro antiproliferative activity of antibody-linker-drug conjugate (I-34) according to the present invention against BT-474 cells.
Figure 15:
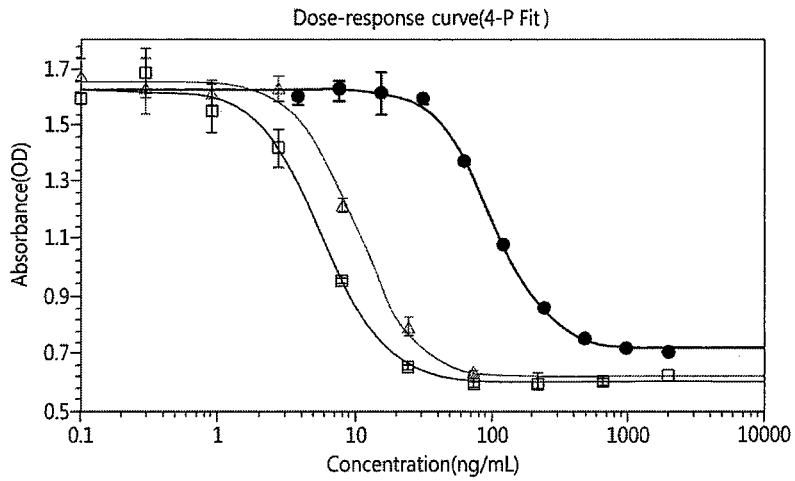
FIG. 15 is a dose-response curve showing in vitro antiproliferative activity of antibody-linker-drug conjugates (I-35) and (I-36) according to the present invention against BT-474 cells.
Figure 16:
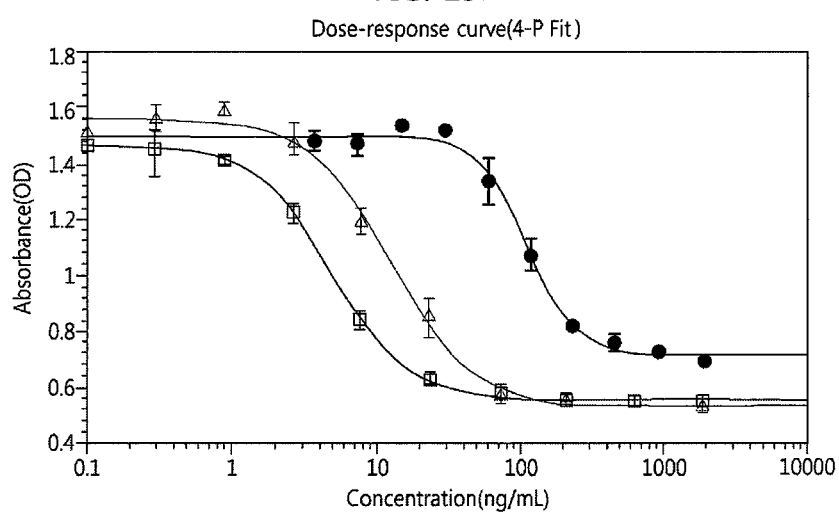
FIG. 16 is a dose-response curve showing in vitro antiproliferative activity of antibody-linker-drug conjugates (I-37) and (I-38) according to the present invention against BT-474 cells.
Figure 17:
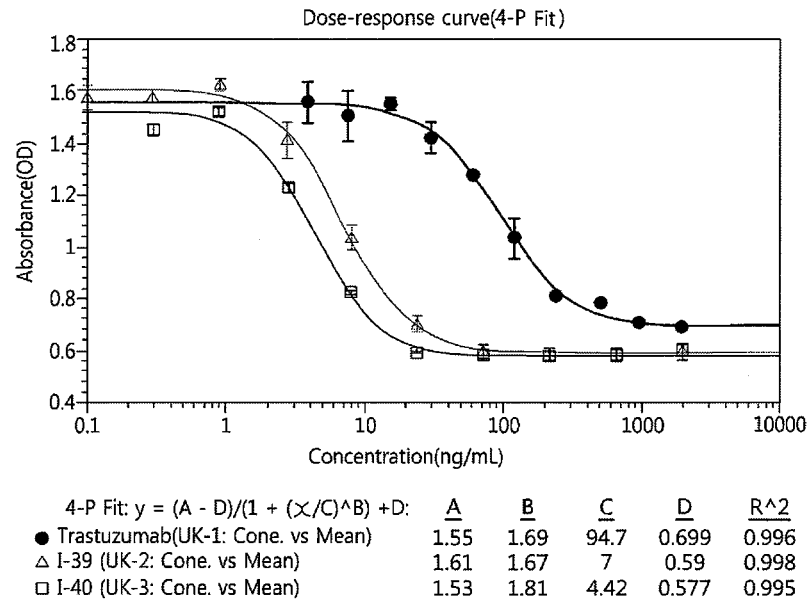
FIG. 17 is a dose-response curve showing in vitro antiproliferative activity of antibody-linker-drug conjugates (I-39) and (I-40) according to the present invention against BT-474 cells.

In addition, the antibody-linker-drug conjugates prepared in Preparation Examples 2, 4, 6 and 7, as depicted in quartic curves of FIGS. 1 to 3, reached lower absorbance, compared to the control trastuzumab, indicating that the conjugates of the present invention are superior in antiproliferative activity to the control trastuzumab. This is owing to the fact that tumor cells are suppressed by not only the antibody-dependent inhibitory activity but also cytotoxic effect of the drug conjugated to the antibody.

TABLE 10

| Sample | $EC_{50}$ ($1^{st}$) (ng/ml) | $EC_{50}$ ($2^{nd}$) (ng/ml) | $EC_{50}$ (Mean) (ng/ml) | Relative Potency (fold) |
|---|---|---|---|---|
| trastuzumab | 125 | — | 125 | 1 |
| Conjugate (I-6) | 9.47 | — | 9.47 | 13.2 |

TABLE 10-continued

| Sample | $EC_{50}$ ($1^{st}$) (ng/ml) | $EC_{50}$ ($2^{nd}$) (ng/ml) | $EC_{50}$ (Mean) (ng/ml) | Relative Potency (fold) |
|---|---|---|---|---|
| trastuzumab | 88.2 | — | 88.2 | 1 |
| Conjugate (I-10) | 6.28 | 6.28 | 6.28 | 14.0 |
| trastuzumab | 85.1 | — | 85.1 | 1 |
| Conjugate (I-11) | 4.66 | 4.88 | 4.77 | 17.8 |

As is understood from the data of Table 11, the antibody-linker-drug conjugates prepared in Examples 1 to 7 decreased in $EC_{50}$ by 7.7 to 34.2 times, compared to the control trastuzumab, indicating that the antibody-linker-drug conjugates of the present invention can exert the same efficacy as that of the control even at far smaller doses, with the consequent decrease of side effects.

In addition, the antibody-linker-drug conjugates prepared in Preparation Examples 1 to 7, as depicted in 4-parameter logistic curves of FIGS. 4 to 7, reached lower absorbance, compared to the control trastuzumab, indicating that the conjugates of the present invention are superior in antiproliferative activity to the control trastuzumab. This is owing to the fact that tumor cells are further suppressed by not only the antibody-dependent inhibitory activity but also cytotoxic effect of the drug conjugated to the antibody.

TABLE 11

| Sample | $EC_{50}$ (ng/ml) | Relative Potency (fold) |
| --- | --- | --- |
| trastuzumab | 98.6 | 1 |
| Conjugate(I-16) | 2.88 | 34.2 |
| trastuzumab | 110 | 1 |
| Conjugate(I-18) | 14.3 | 7.7 |
| trastuzumab | 96.6 | 1 |
| Conjugate(I-19) | 5.18 | 18.6 |
| trastuzumab | 92.3 | 1 |
| Conjugate(I-20) | 5.72 | 16.1 |
| trastuzumab | 96.6 | 1 |
| Conjugate(I-21) | 7.09 | 13.6 |
| trastuzumab | 92.3 | 1 |
| Conjugate(I-22) | 6.7 | 13.8 |

As seen in Table 12, the antibody-linker-drug conjugates prepared in Examples 19 to 29 decreased in $EC_{50}$ by 0.5 to 33.6 times, compared to the control trastuzumab. For the antibody-linker-drug conjugates (I-23), (I-25), (1-26), and (I-33), $EC_{50}$ values were detected at levels 20- or higher fold lower than that of the control, indicating that the antibody-linker-drug conjugates can exert the same efficacy as that of the control even at 20- or higher fold smaller doses, with the consequent decrease of side effects.

In addition, the antibody-linker-drug conjugates prepared in Preparation Examples 19 to 29, as depicted in 4-parameter logistic curves of FIGS. 8 to 13, reached lower absorbance, compared to the control trastuzumab, indicating that the conjugates of the present invention are superior in antiproliferative activity to the control trastuzumab. This is owing to the fact that tumor cells are further suppressed by not only the antibody-dependent inhibitory activity but also cytotoxic effect of the drug conjugated to the antibody.

TABLE 12

| Sample | $EC_{50}$ (ng/mL) | Relative Potency (fold) |
| --- | --- | --- |
| trastuzumab | 102 | 1 |
| Conjugate (I-23) | 4.73 | 21.6 |
| trastuzumab | 106 | 1 |
| Conjugate (I-24) | 68.4 | 1.5 |
| trastuzumab | 107 | 1 |
| Conjugate (I-25) | 4.75 | 22.2 |
| trastuzumab | 101 | 1 |
| Conjugate (I-26) | 4.17 | 24.2 |
| trastuzumab | 97.9 | 1 |
| Conjugate (I-32) | 12.7 | 7.7 |
| trastuzumab | 97 | 1 |
| Conjugate (I-33) | 2.89 | 33.6 |

As is apparent from the data of Table 10, the antibody-linker-drug conjugates prepared in Examples 30 to 36 decreased in $EC_{50}$ by 8.9 to 22.6 times, compared to the control trastuzumab, indicating that the antibody-linker-drug conjugates of the present invention can exert the same efficacy as that of the control even at far smaller doses, with the consequent decrease of side effects.

In addition, the antibody-linker-drug conjugates prepared in Preparation Examples 30 to 36, as depicted in quartic curves of FIGS. 14 to 17, reached lower absorbance, compared to the control trastuzumab, indicating that the conjugates of the present invention are superior in antiproliferative activity to the control trastuzumab. This is owing to the fact that tumor cells are further suppressed by not only the antibody-dependent inhibitory activity but also cytotoxic effect of the drug conjugated to the antibody.

TABLE 13

| Sample | $EC_{50}$ (ng/ml) | Relative Potency (fold) |
| --- | --- | --- |
| trastuzumab | 104 | 1 |
| Conjugate(I-34) | 11.3 | 9.2 |
| trastuzumab | 104 | 1 |
| Conjugate(I-35) | 10.3 | 10.1 |
| trastuzumab | 104 | 1 |
| Conjugate(I-36) | 5.74 | 18.1 |
| trastuzumab | 116 | 1 |
| Conjugate(I-37) | 13 | 8.9 |
| trastuzumab | 116 | 1 |
| Conjugate(I-38) | 5.13 | 22.6 |
| trastuzumab | 94.7 | 1 |
| Conjugate(I-39) | 7 | 13.5 |
| trastuzumab | 94.7 | 1 |
| Conjugate(I-40) | 4.42 | 21.4 |

Test Example 5

Pharmacokinetic (PK) Assay

The antibody-linker-drug conjugates (I-6) and (I-8), respectively prepared in Preparation Examples 2 and 4, and the control trastuzumab were each intravenously injected once at a dose of 20 mg/kg to Balb/c Slc-nu mice, and assayed for pharmacokinetics (PK) for one month.

The antibody-linker-drug conjugates (I-8) and (I-6) were observed to have the half-life of 8.3 and 7.9 days, respectively, with no significant differences from the control trastuzumab's half-life, 8.6 days, implying that the cytotoxic drug is not directly coupled to the neonatal Fc region (FcRn), a site affecting the PK of the antibody itself, during the conjugation.

TABLE 14

| Parameter | Conjugate (I-8) | Conjugate (I-6) | trastuzumab |
| --- | --- | --- | --- |
| $AUC_{all}$ (hr*µg/mL) | 507280 | 575495 | 607582 |
| $C_0$ (µg/mL) | 375.2 | 403.7 | 379.9 |
| $T_{1/2}$ (day) [1] | 8.3 | 7.9 | 8.6 |

[1] User specified lambda-z range (4 m~27 day, 9 points)

Test Example 6

Efficacy Study in Animal Model

For an animal model efficacy test, the antibody-linker-drug conjugates (I-6), (I-10), and (I-11), prepared respectively in Preparation Examples 2, 6 and 7, were intravenously injected once at three different doses (1.25, 5, and 20 mg/kg) into nude mice which were previously xenografted HER-2-overexpressing breast cancer cells (BT-474). For 56 days after injection, the volumes and final weights of the tumors were monitored. The phosphate buffered saline (PBS) was used as a negative control while trastuzumab (Herceptin®) was injected at a dose of 20 mg/kg into a positive control. The results are shown in FIGS. 18 and 19.

Figure 18:
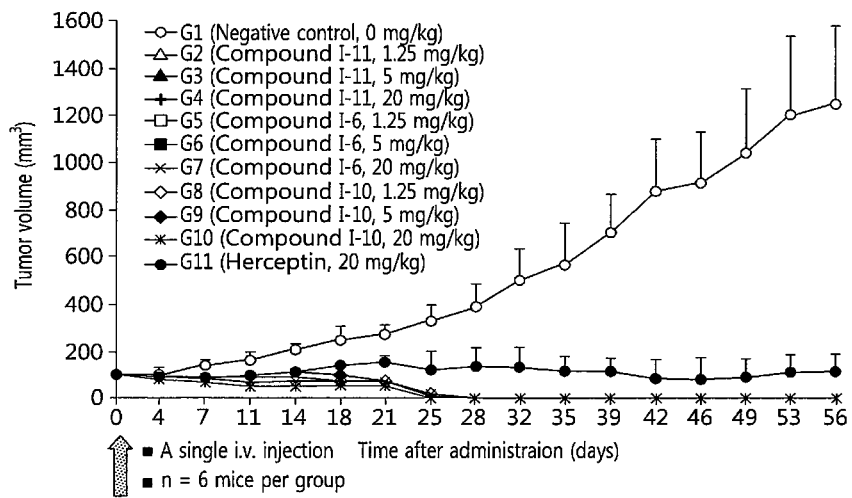
FIG. 18 is a graph in which respective tumor volumes are plotted against time after the injection of the antibody-linker-drug conjugates (I-6), (I-10), and (I-11) according to the present invention to cancer-induced animal models.
Figure 19:
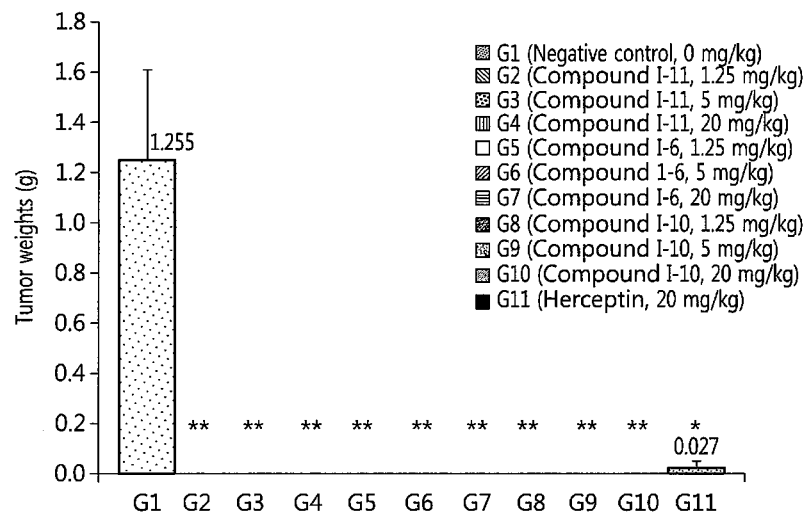
FIG. 19 is a graph showing respective tumor weights 56 days after the injection of the antibody-linker-drug conjugates (I-6), (I-10), and (I-11) according to the present invention to cancer-induced animal models.

As is understood from the data of FIGS. 18 and 19, the tumor sizes were reduced significantly by the positive control trastuzumab (Herceptin®), compared to the negative control, and more remarkably diminished by the antibody-linker-drug conjugates (I-6), (I-10), and (I-11) than the positive control. Particularly, the xenografted tumor had completely disappeared by 28 days after the injection of the conjugates, and did not recur afterwards.

Separately, the antibody-linker-drug conjugate (I-16), prepared in Preparation Examples 12, was intravenously injected once at three different doses (0.05, 0.5, and 5 mg/kg) into nude mice which were previously xenografted with HER-2-overexpressing breast cancer cells (BT-474). For 28 days after injection, volumes and final weights of the tumors were monitored. The phosphate buffered saline (PBS) was used as a negative control while trastuzumab (Herceptin®) was injected at a dose of 5 mg/kg into a positive control. The results are shown in FIGS. 20 and 21.

Figure 20:
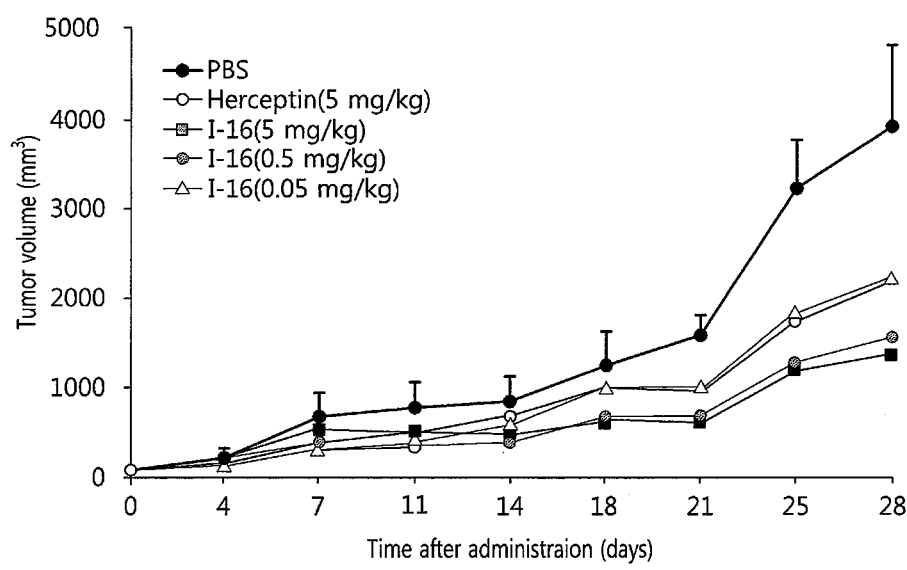
FIG. 20 is a graph in which tumor volumes are plotted against time after the injection of the antibody-linker-drug conjugate (I-16) according to the present invention to a cancer-induced animal model.
Figure 21:
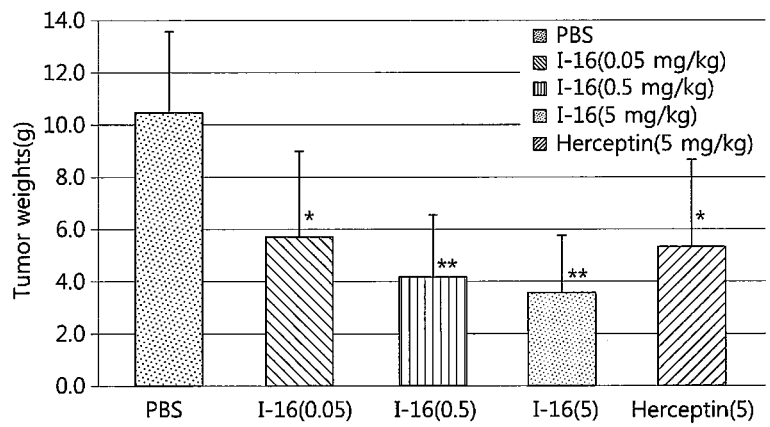
FIG. 21 is a graph showing tumor weights 28 days after the injection of the antibody-linker-drug conjugate (I-16) according to the present invention to a cancer-induced animal model.

As is understood from the data of FIGS. 20 and 21, the positive control trastuzumab (Herceptin®) significantly reduced tumor sizes, compared to the negative control, with the further reduction of tumor sizes made by the antibody-linker-drug conjugate (I-16) than the positive control.

Figure 22:
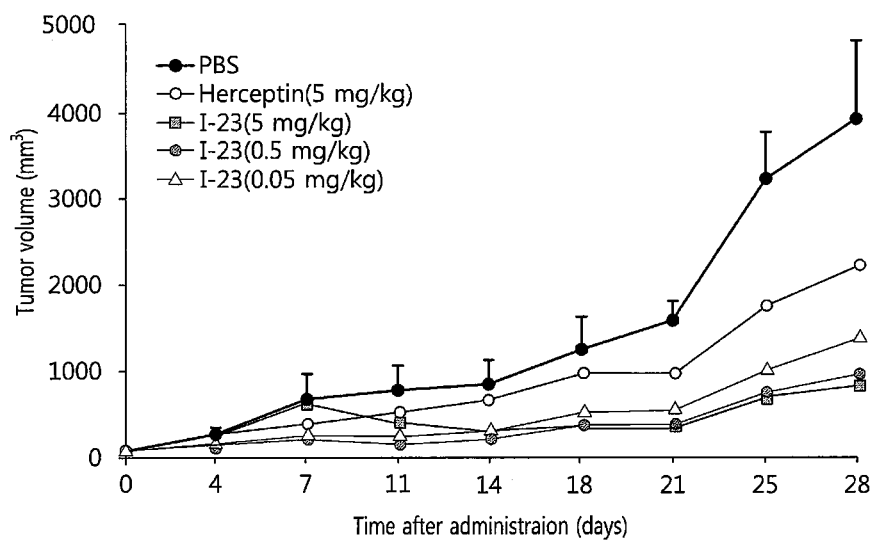
FIG. 22 is a graph in which tumor volumes are plotted against time after the injection of the antibody-linker-drug conjugate (I-23) according to the present invention to a cancer-induced animal model.
Figure 23:
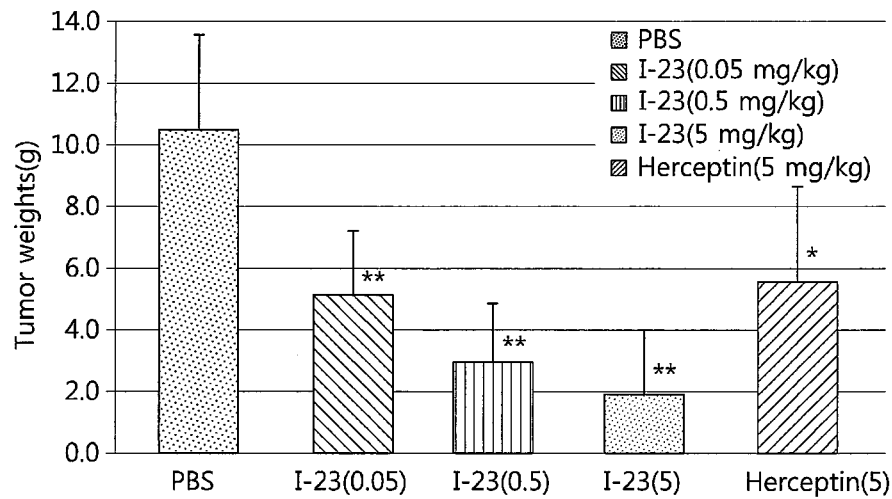
FIG. 23 is a graph showing tumor weights 28 days after the injection of the antibody-linker-drug conjugate (I-23) according to the present invention to a cancer-induced animal model.
Figure 24:
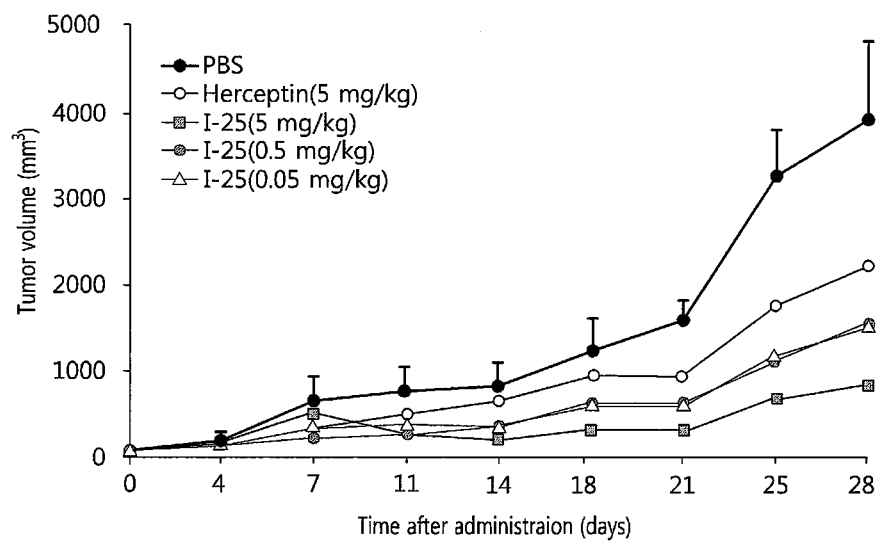
FIG. 24 is a graph in which tumor volumes are plotted against time after the injection of the antibody-linker-drug conjugate (I-25) according to the present invention to a cancer-induced animal model.
Figure 25:
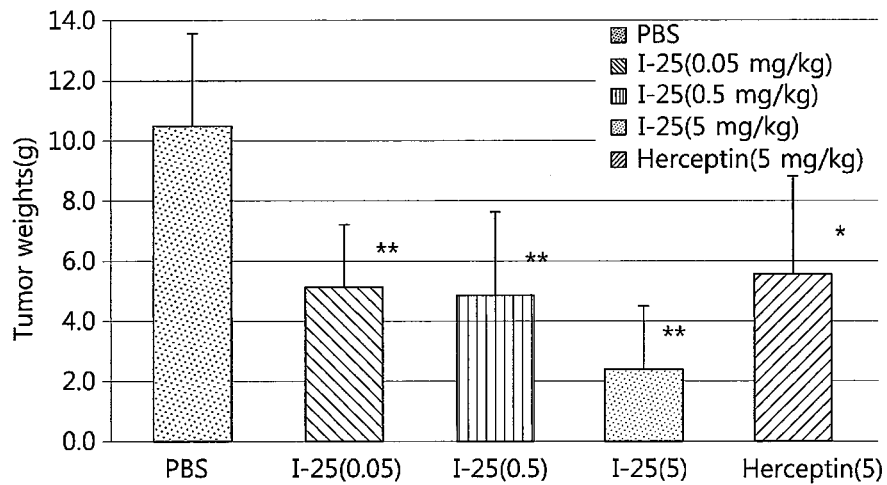
FIG. 25 is a graph showing tumor weights 28 days after the injection of the antibody-linker-drug conjugate (I-25) according to the present invention to a cancer-induced animal model.
Figure 26:
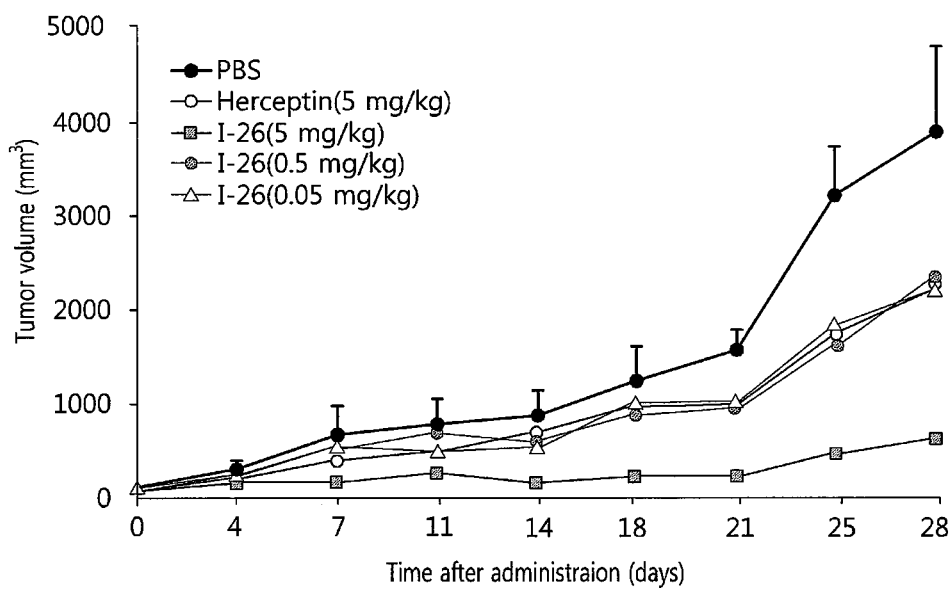
FIG. 26 is a graph in which tumor volumes are plotted against time after the injection of the antibody-linker-drug conjugate (I-26) according to the present invention to a cancer-induced animal model.
Figure 27:
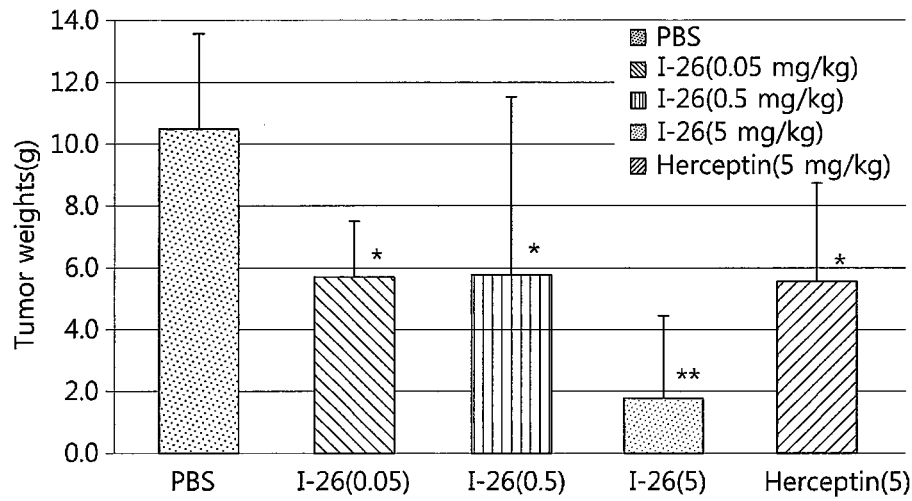
FIG. 27 is a graph showing tumor weights 28 days after the injection of the antibody-linker-drug conjugate (I-26) according to the present invention to a cancer-induced animal model.

In addition, the antibody-linker-drug conjugates (I-23), (1-25), and (I-26), prepared respectively in Preparation Examples 19, 21, and 22, were intravenously injected once at three different doses (0.05, 0.5, and 5 mg/kg) into nude mice which were previously xenografted with HER-2-over-expressing breast cancer cells (BT-474). For 28 days after injection, the volumes and final weights of the tumors were monitored. The phosphate buffered saline (PBS) was used as a negative control while trastuzumab (Herceptin®) was injected at a dose of 5 mg/kg into a positive control. The results are shown in FIGS. 22 and 27.

As is understood from the data of FIGS. 22 to 27, a significant reduction in tumor size was observed in the positive control trastuzumab (Herceptin®) group, compared to the negative control group, while the tumor size was more remarkably diminished by the antibody-linker-drug conjugates (I-23), (1-25), and (I-26) than by the positive control.

In another experiment, nude mice xenografted with HER-2-overexpressing breast cancer cell line (BT-474) were intravenously injected once with three difference doses (0.05, 0.5, and 5 mg/kg) of the antibody-linker-drug conjugate (I-34), prepared in Preparation Example 30. For 28 days after injection, the volumes and final weights of the tumors were monitored. The phosphate buffered saline (PBS) was used as a negative control while trastuzumab (Herceptin®) was injected at a dose of 5 mg/kg into a positive control. The results are shown in FIGS. 28 and 29.

Figure 28:
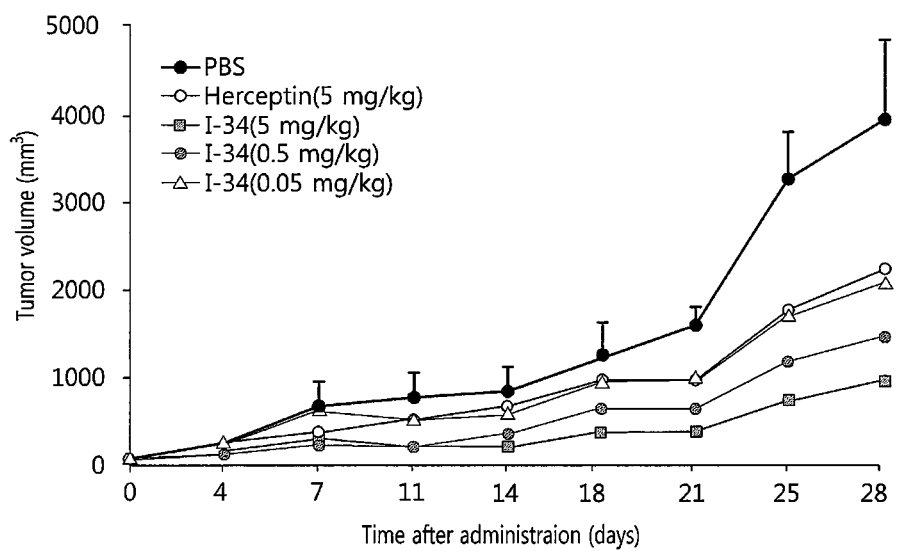
FIG. 28 is a graph in which tumor volumes are plotted against time after the injection of the antibody-linker-drug conjugate (I-34) according to the present invention to a cancer-induced animal model.
Figure 29:
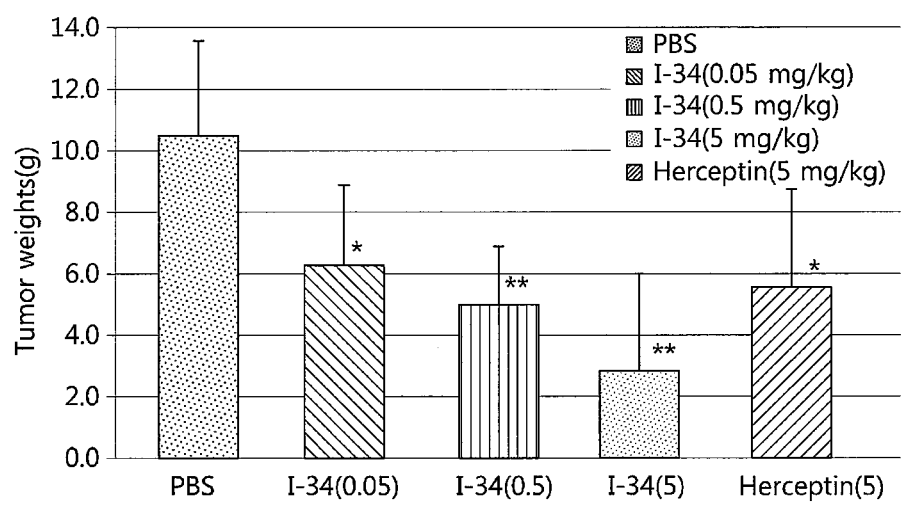
FIG. 29 is a graph showing tumor weights 28 days after the injection of the antibody-linker-drug conjugate (I-34) according to the present invention to a cancer-induced animal model.

As is understood from the data of FIGS. 28 and 29, the positive control trastuzumab (Herceptin®) significantly reduced tumor sizes, compared to the negative control, with the further reduction of tumor sizes made by the antibody-linker-drug conjugate (I-34) than the positive control.

The invention claimed is:

1. An antibody-linker-drug conjugate, wherein the linker-drug moiety is directly bonded to a lysine residue of the antibody, represented by Chemical Formula I-1, or a pharmaceutically acceptable salt thereof:

[Chemical Formula I-1]

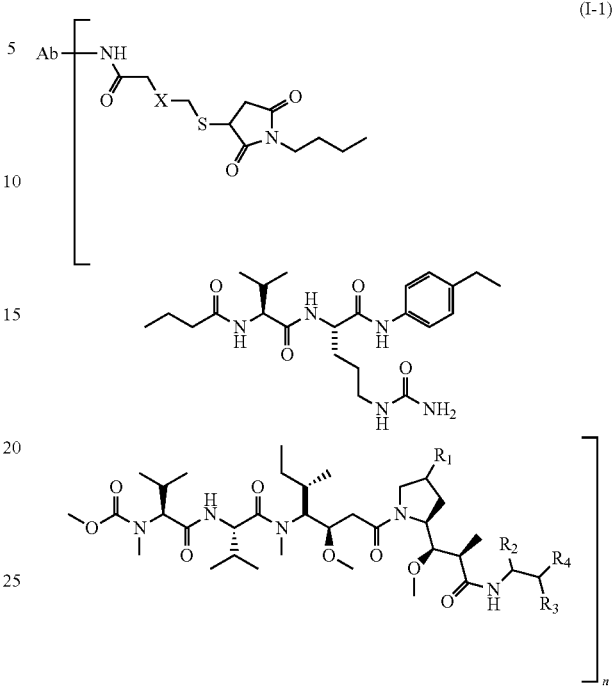

(I-1)

wherein,
Ab is an antibody,
X is $C_1$-$C_8$ alkyl or $C_3$-$C_6$ cycloalkyl,
$R_1$ is a hydroxy, $C_1$-$C_4$ alkoxy, or oxo (=O),
$R_2$ is a hydrogen atom or $C_1$-$C_4$ alkyl,
$R_3$ is a hydrogen atom, hydroxy, $C_1$-$C_4$ alkoxy, amino, oxo (=O), or hydroxyimino (=N—OH),
$R_4$ is aryl, and
n is an integer ranging from 1 to 5.

2. The antibody-linker-drug conjugate of claim 1, or a pharmaceutically acceptable salt thereof, wherein:
Ab is an antibody immunospecifically binding to a cancer cell antigen,
X is $C_1$-$C_8$ alkyl or $C_3$-$C_6$ cycloalkyl,
$R_1$ is a hydroxy, or $C_1$-$C_4$ alkoxy,
$R_2$ is a hydrogen atom or $C_1$-$C_4$ alkyl,
$R_3$ is a hydrogen atom, oxo (=O) or hydroxyimino (=N—OH),
$R_4$ is phenyl unsubstituted or substituted with at least one substituent selected from the group consisting of $C_1$-$C_4$ alkyl, $C_1$-$C_4$ alkoxy, and a halogen atom.

3. The antibody-linker-drug conjugate of claim 1, or a pharmaceutically acceptable salt thereof, wherein:
Ab is trastuzumab,
X is methyl, n-propyl, n-pentyl, n-octyl, or cyclopropyl,
$R_1$ is a, hydroxy, or methoxy,
$R_2$ is a hydrogen atom or methyl,
$R_3$ is a hydrogen atom, oxo (=O) or hydroxyimino (=N—OH), and
$R_4$ is phenyl unsubstituted or substituted with at least one substituent selected from the group consisting of methyl, methoxy, and a halogen atom.

4. The antibody-linker-drug conjugate of claim 1, being selected from the group consisting of the following compounds, or a pharmaceutically acceptable salt thereof:

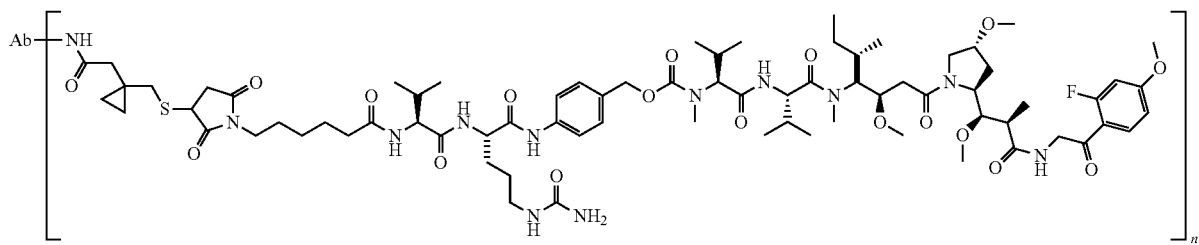

(I-12)

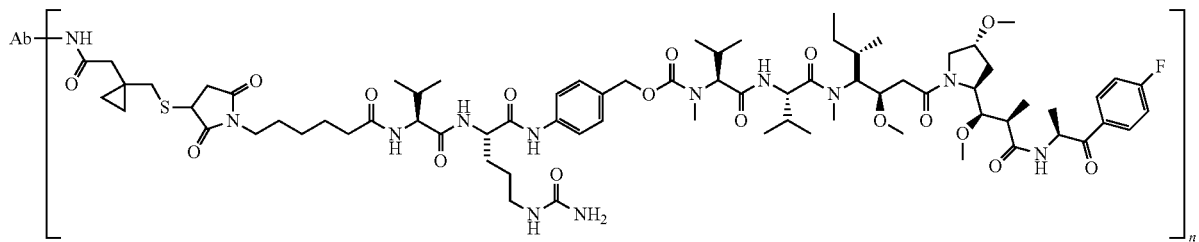

(I-13)

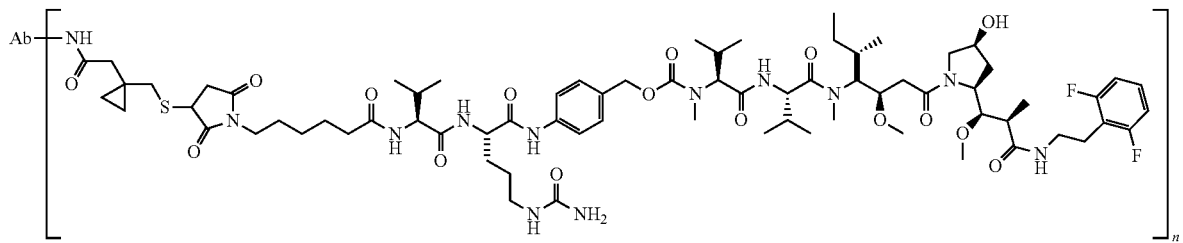

(I-15)

wherein, n is an integer ranging from 1 to 5.

5. The antibody-linker-drug conjugate of claim 1, or a pharmaceutically acceptable salt thereof, wherein the antibody-linker-drug conjugate has a normal antibody structure at a rate of 98% or higher.

6. An antibody-linker-drug conjugate, wherein the linker-drug moiety is directly bonded to a lysine residue of the antibody, represented by Chemical Formula I-3, or a pharmaceutically acceptable salt thereof:

wherein,
Ab is an antibody,
X is $C_1$-$C_8$ alkyl, or $C_3$-$C_6$ cycloalkyl,
$R_1$, $R_2$, $R_3$, and $R_4$ are each independently a hydrogen atom, or $C_1$-$C_4$ alkyl,
$R_5$ is a hydrogen atom, hydroxy, $C_1$-$C_4$ alkoxy, amino, oxo (=O), or hydroxyimino (=N—OH),
Ar is aryl,
Y is a nitrogen atom or an oxygen atom,

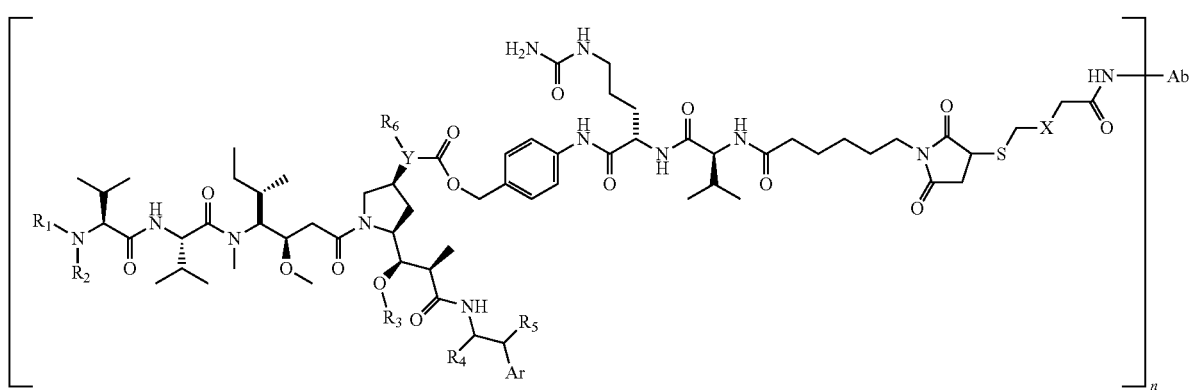

(I-3)

249

R$_6$ is a hydrogen atom or C$_1$-C$_4$ alkyl when Y is a nitrogen atom; or is absent when Y is an oxygen atom, and n is an integer ranging from 1 to 5.

7. The antibody-linker-drug conjugate of claim 6, or a pharmaceutically acceptable salt thereof,
wherein
Ab is an antibody immunospecifically binding to a cancer cell antigen,
X is C$_1$-C$_8$ alkyl or C$_3$-C$_6$ cycloalkyl,
R$_1$, R$_2$, and R$_4$ are each independently a hydrogen atom or C$_1$-C$_4$ alkyl,
R$_3$ is C$_1$-C$_4$ alkyl,
R$_5$ is a hydrogen atom, amino, oxo (=O), or hydroxyimino (=N—OH),
Ar is phenyl or naphthyl unsubstituted or substituted with at least one substituent selected from the group consisting of C$_1$-C$_4$ alkyl, C$_1$-C$_4$ alkoxy, and a halogen atom,
Y is a nitrogen atom or an oxygen atom, and

250

R$_6$ is a hydrogen atom or C$_1$-C$_4$ alkyl when Y is a nitrogen atom, or is absent when Y is an oxygen atom.

8. The antibody-linker-drug conjugate of claim 6, or a pharmaceutically acceptable salt thereof, wherein:
Ab is trastuzumab,
X is methyl, n-propyl, n-pentyl, n-octyl, or cyclopropyl,
R$_1$, R$_2$, and R$_3$ are each methyl,
R$_4$ is a hydrogen atom, or methyl,
R$_5$ is a hydrogen atom, oxo (=O), or hydroxyimino (=N—OH),
Ar is phenyl or naphthyl unsubstituted or substituted with at least one substituent selected from the group consisting of methyl, methoxy, and a halogen atom,
Y is a nitrogen atom or an oxygen atom, and
R$_6$ is a hydrogen atom, or methyl when Y is a nitrogen atom, or is absent when Y is an oxygen atom.

9. The antibody-linker-drug conjugate of claim 6, being selected from the group consisting of the following compounds, or a pharmaceutically acceptable salt thereof:

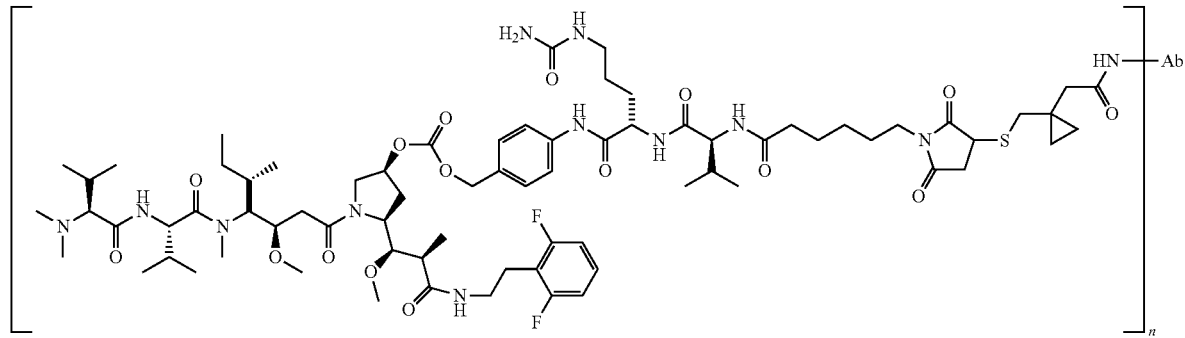
(I-23)

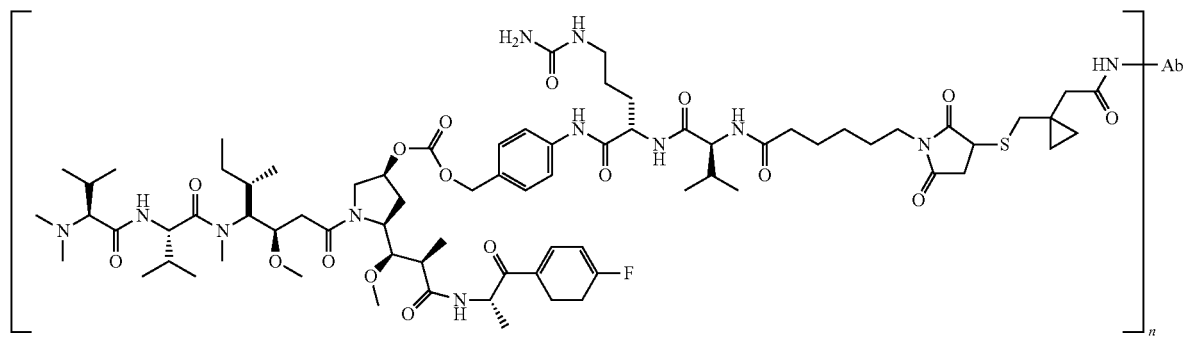
(I-24)

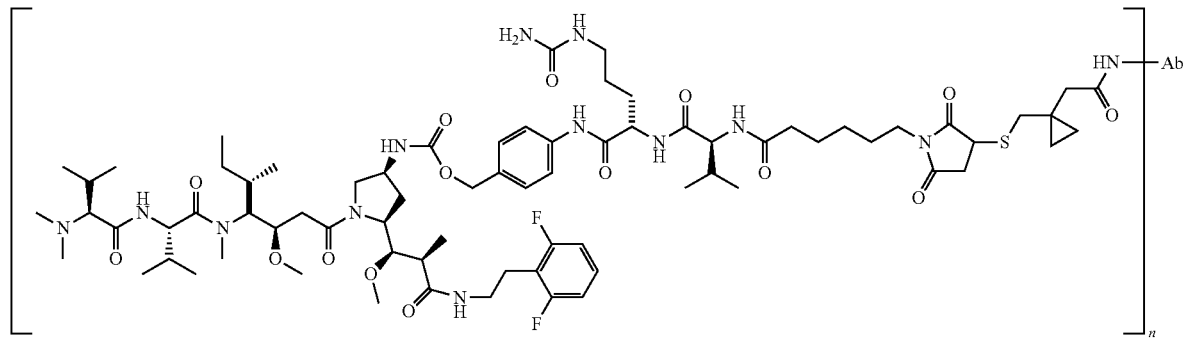
(I-25)

-continued
(I-26)
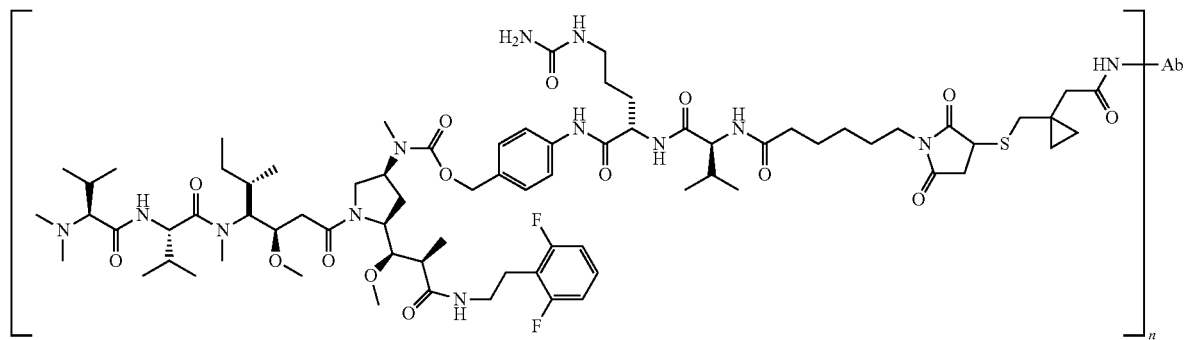
(I-27)
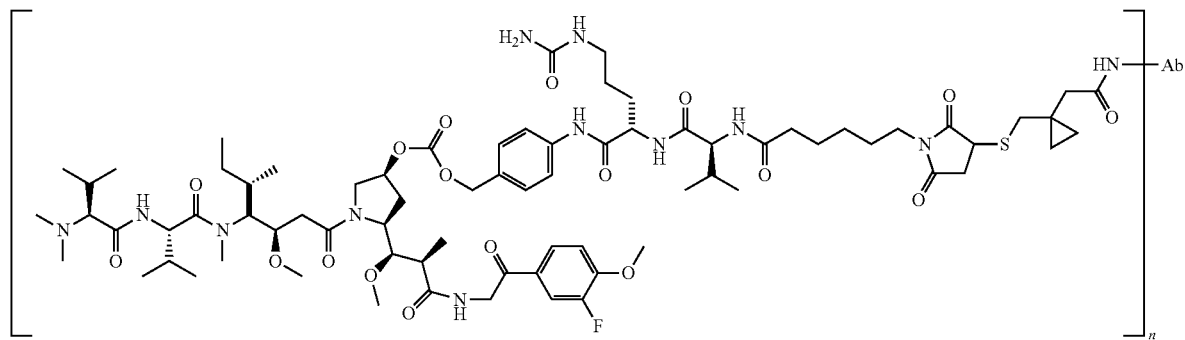
(I-28)
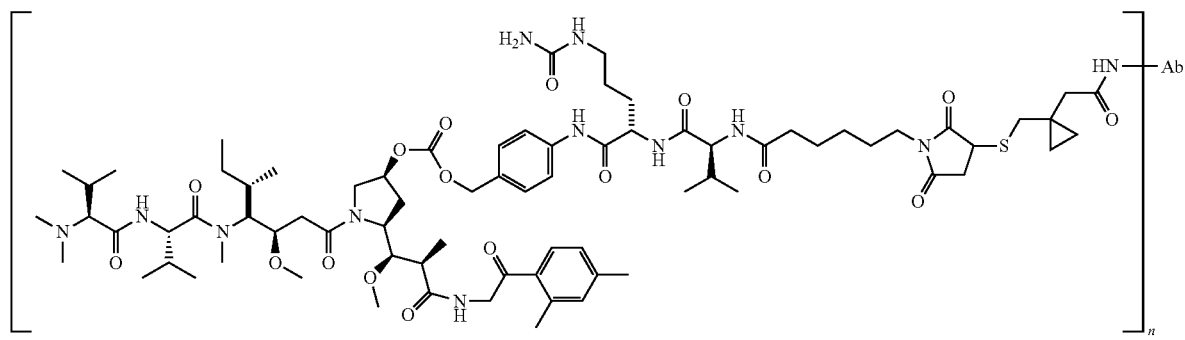
(I-29)
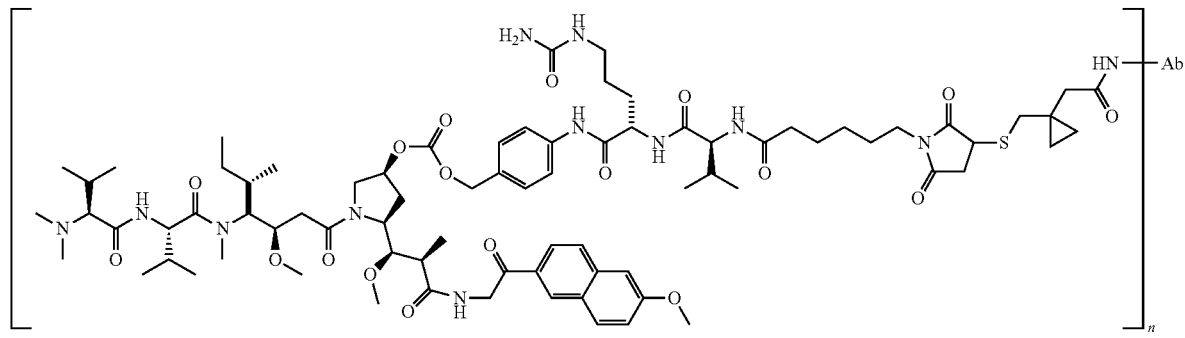

-continued

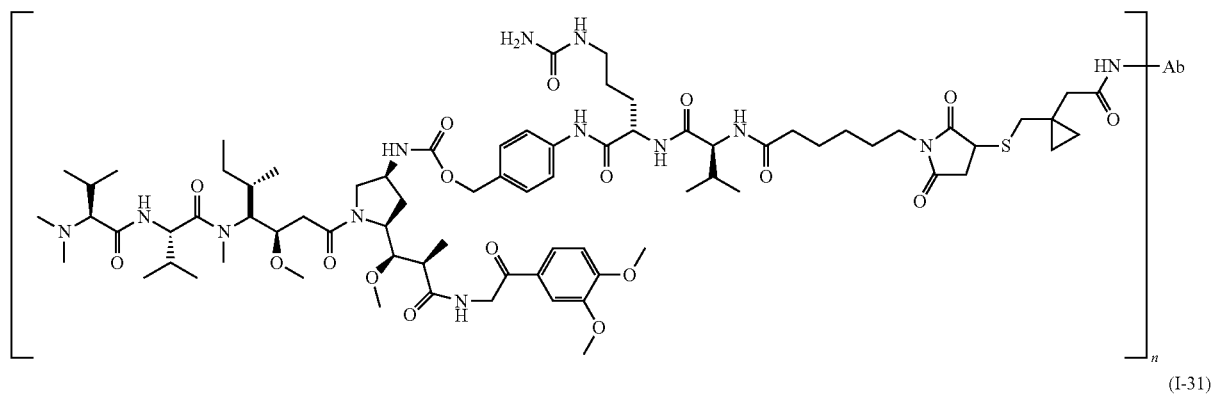
(I-30)

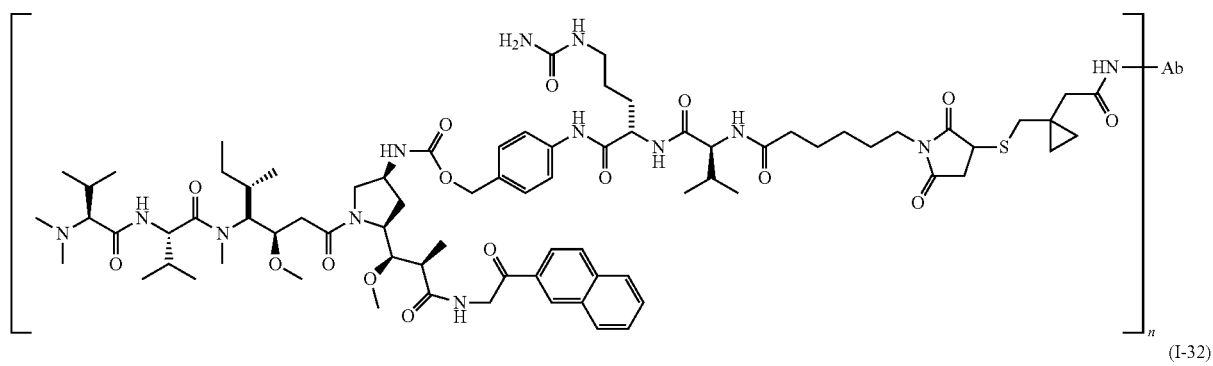
(I-31)

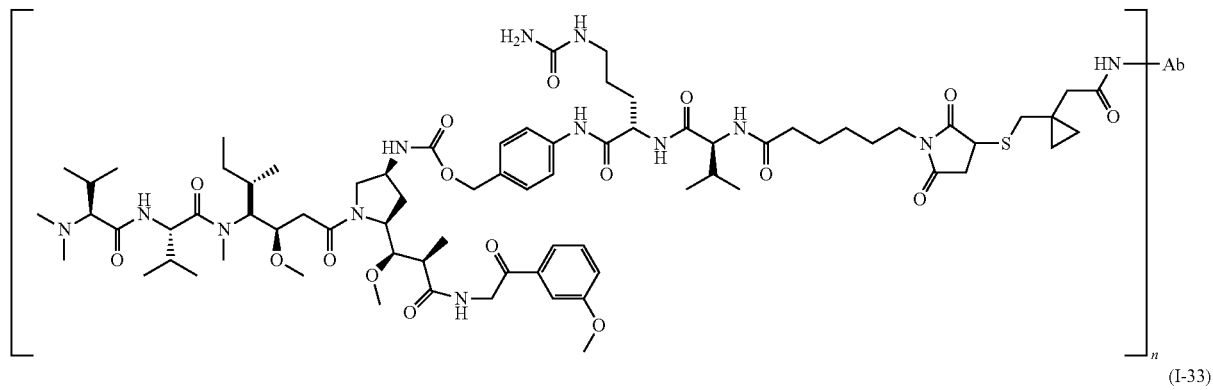
(I-32)

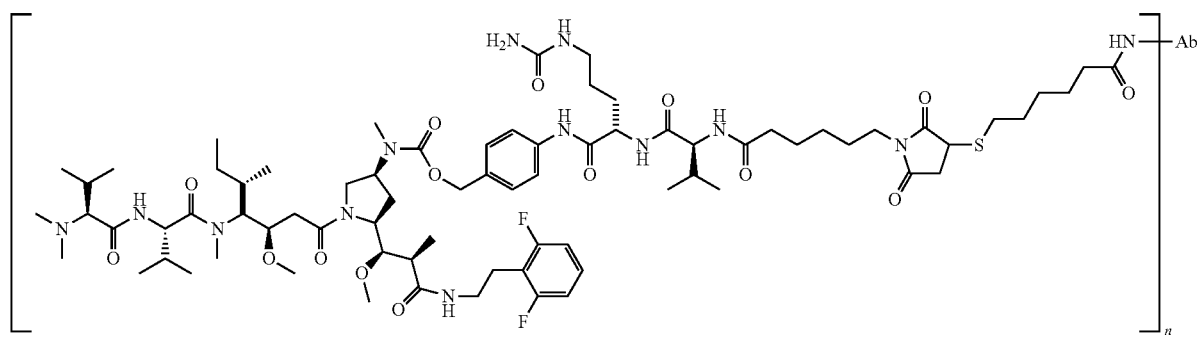
(I-33)

wherein, n is an integer ranging from 1 to 5.

10. The antibody-linker-drug conjugate of claim 6, or a pharmaceutically acceptable salt thereof, wherein the antibody-linker-drug conjugate has a normal antibody structure at a rate of 90% or higher.

11. A method for preparing an antibody-linker-drug conjugate represented by Chemical Formula I-1, comprising the steps of:

(i) condensating a compound of the following Chemical Formula II-1 with a dolastatin 10 derivative of the following Chemical Formula III-1 to give a compound of the following Chemical Formula IV-1;

(ii) subjecting the compound of the following Chemical Formula IV-1 to an addition reaction with a compound of the following Chemical Formula V to give a compound of the following Chemical Formula VI-1;

(iii) condensating the compound of the following Chemical Formula VI-1 with N-hydroxysuccinimide to give a compound of the following Chemical Formula VII-1; and (iv) reacting the compound of the following Chemical Formula VII-1 with an antibody:

[Chemical Formula II-1]

(II-1)

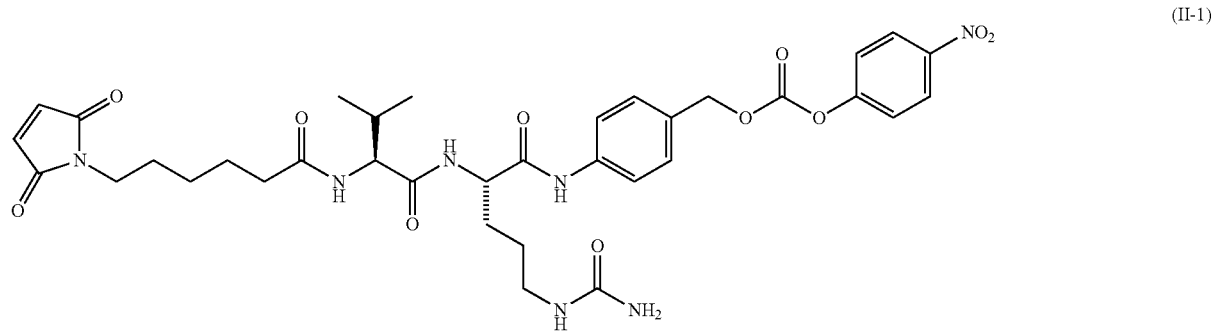

[Chemical Formula III-1]

(III-1)

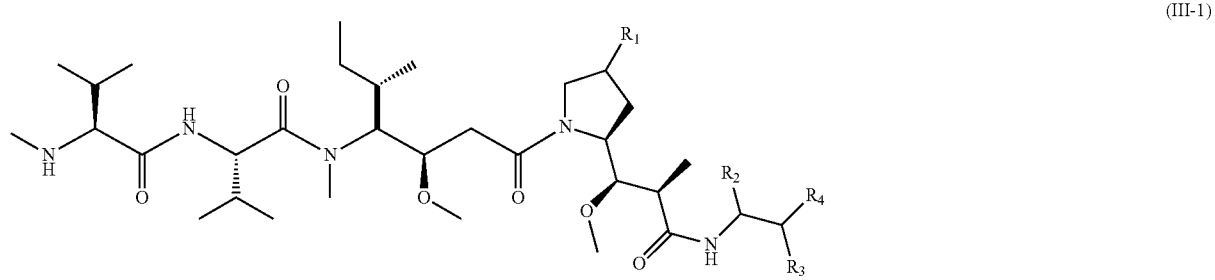

[Chemical Formula IV-1]

(IV-1)

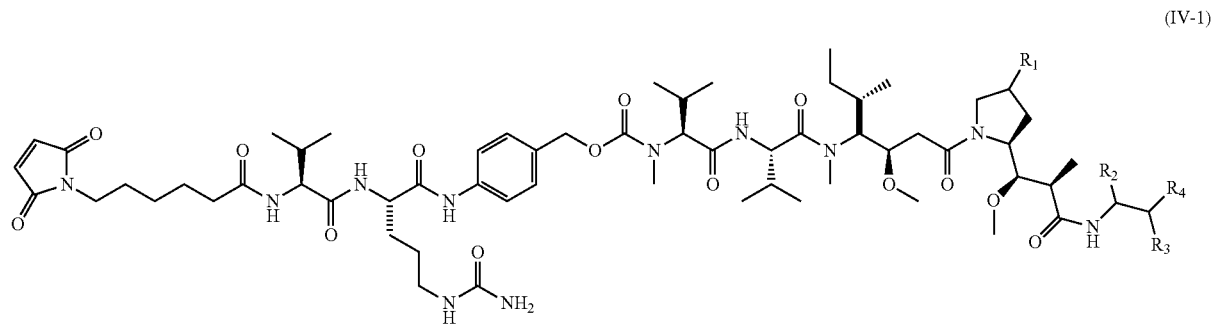

[Chemical Formula V]

(V)

[Chemical Formula VI-1]

(VI-1)

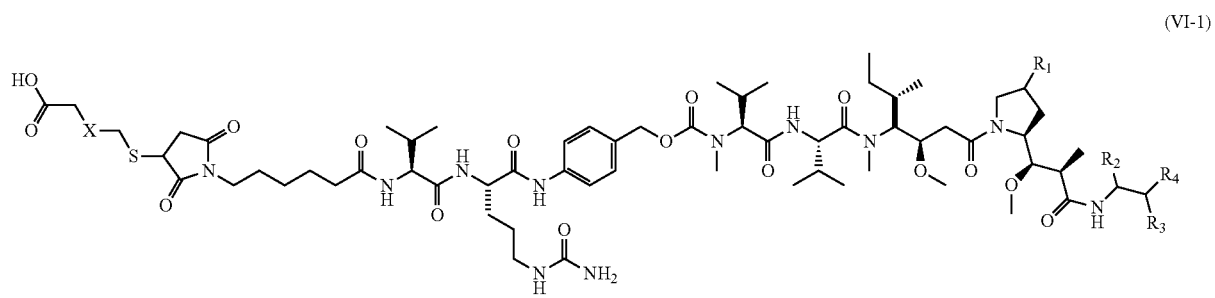

[Chemical Formula VII-1]

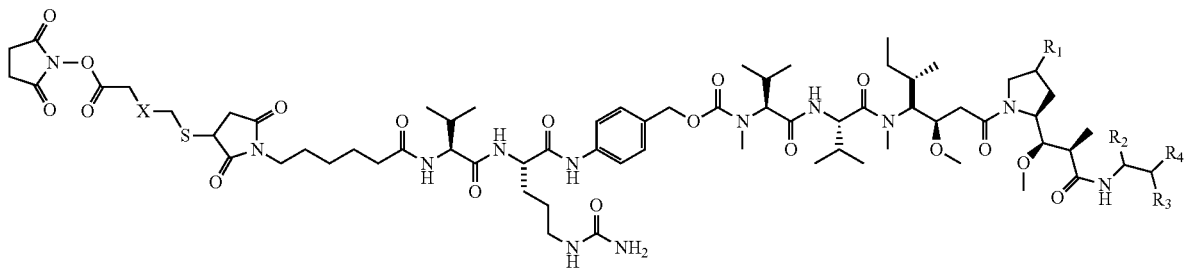

(VII-1)

[Chemical Formula I-1]

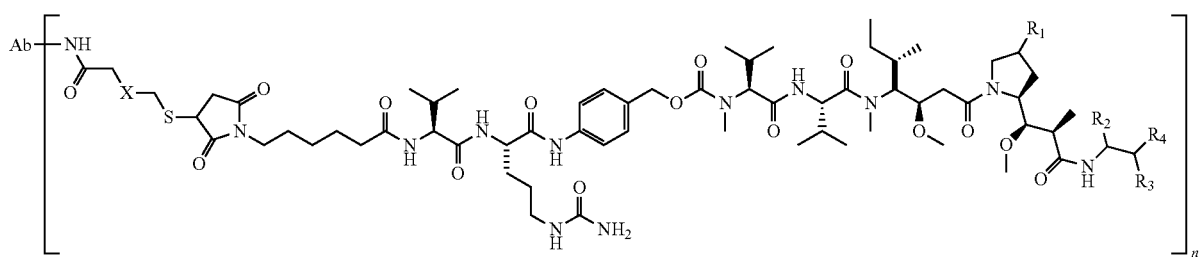

(I-1)

wherein,
Ab is an antibody,
X is $C_1$-$C_8$ alkyl or $C_3$-$C_6$ cycloalkyl,
$R_1$ is, hydroxy, $C_1$-$C_4$ alkoxy or oxo (=O),
$R_2$ is a hydrogen atom or $C_1$-$C_4$ alkyl,
$R_3$ is a hydrogen atom, hydroxy, $C_1$-$C_4$ alkoxy, amino, oxo (=O), or hydroxyimino (=N—OH),
$R_4$ is aryl, and
n is an integer ranging from 1 to 5.

12. The method of claim 11, wherein the condensation reaction of step (i) is carried out in presence of a condensing agent selected from the group consisting of hydroxybenzotriazole (HOBt), hydroxyazabenzotriazole (HOAt), and hydroxysuccinimide (HOSu), and an organic base selected from the group consisting of pyridine and diisopropylethylamine.

13. The method of claim 11, wherein the condensation reaction of step (iii) is carried out in presence of a condensing agent selected from the group consisting of dicyclohexylcarbodiimide (DCC), and (3-dimethylaminopropyl)carbodiimide (EDC).

14. The method of claim 11, wherein the reaction of step (iv) is carried out in a phosphate buffer having a pH of 6.0 to 8.0 as a reaction solvent.

15. The method of claim 11, wherein the reaction of step (iv) is carried out in a mixed reaction solvent of a phosphate buffer having a pH of 6.0 to 8.0 and an organic solvent.

16. The method of claim 15, wherein the organic solvent amounts to 50% or less of the mixed solvent.

17. The method of claim 11, wherein the compound of Chemical Formula VII-1is used in an amount of 3 to 25 equivalents, based on the antibody, in step (iv).

18. A method for preparing an antibody-linker-drug conjugate represented by Chemical Formula I -3, comprising the steps of:
(i) condensating a compound of the following Chemical Formula II-1 with a dolastatin 10 derivative of the following Chemical Formula III-3 to give a compound of the following Chemical Formula IV-3;
(ii) subjecting the compound of the following Chemical Formula IV-3 to an addition reaction with a compound of the following Chemical Formula V to give a compound of the following Chemical Formula VI-3;
(iii) condensating the compound of the following Chemical Formula VI-3 with N-hydroxysuccinimide to give a compound of the following Chemical Formula VII-3; and
(iv) reacting the compound of the following Chemical Formula VII-3 with an antibody:

[Chemical Formula II-1]
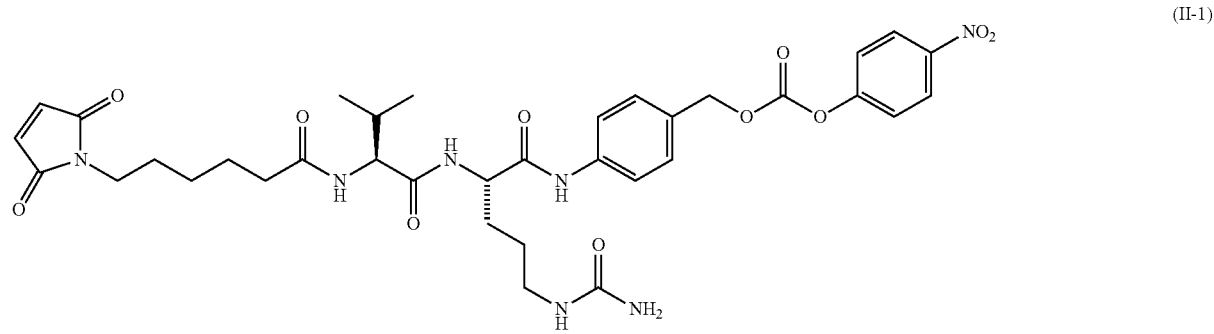
(II-1)
[Chemical Formula III-3]
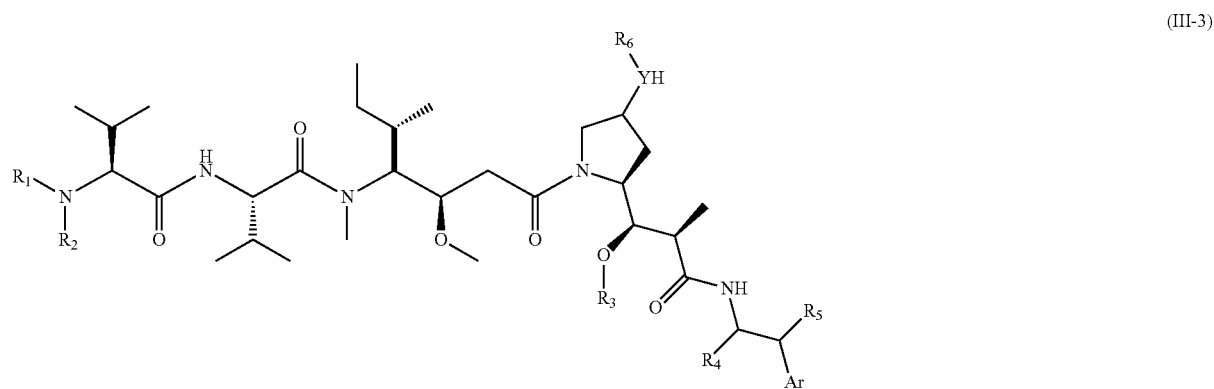
(III-3)
[Chemical Formula IV-3]
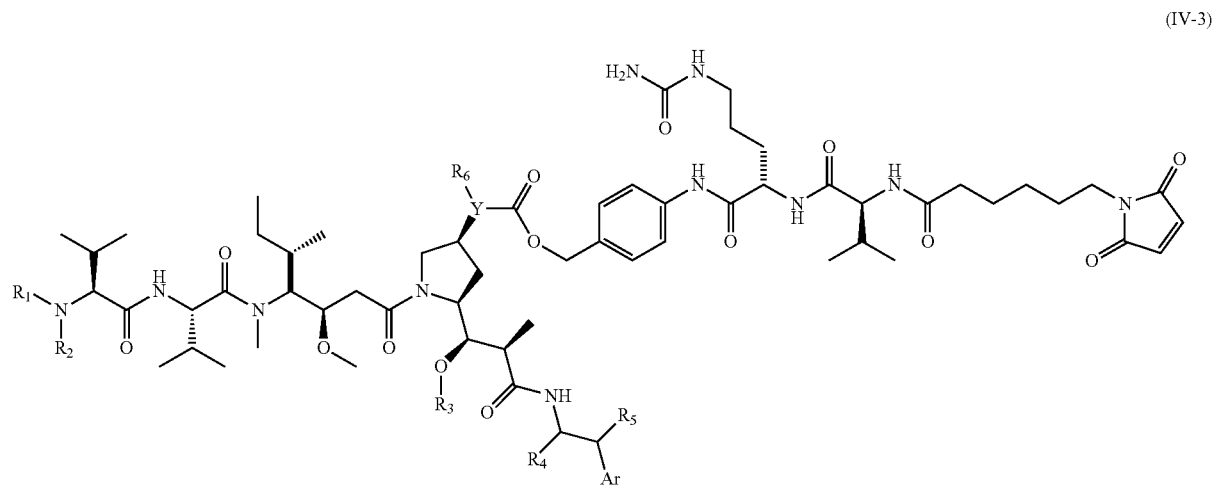
(IV-3)
[Chemical Formula V]
(V)

[Chemical Formula VI-3]

(VI-3)

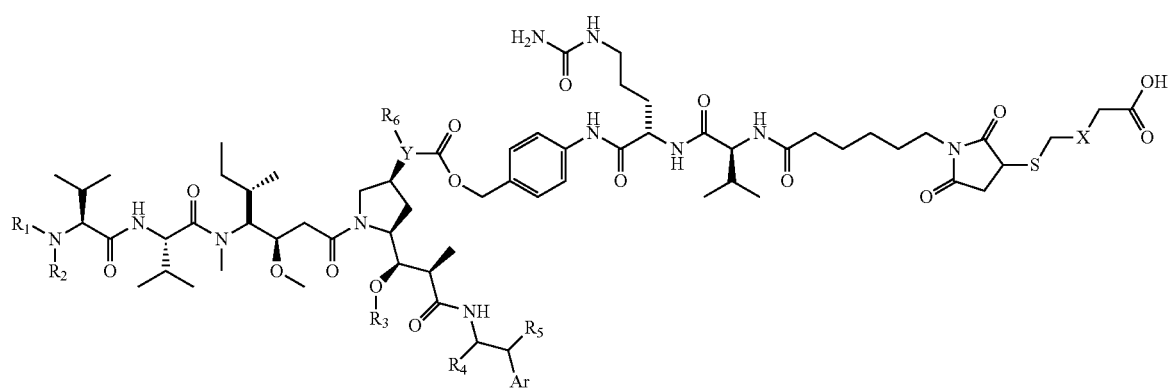

[Chemical Formula VII-3]

(VII-3)

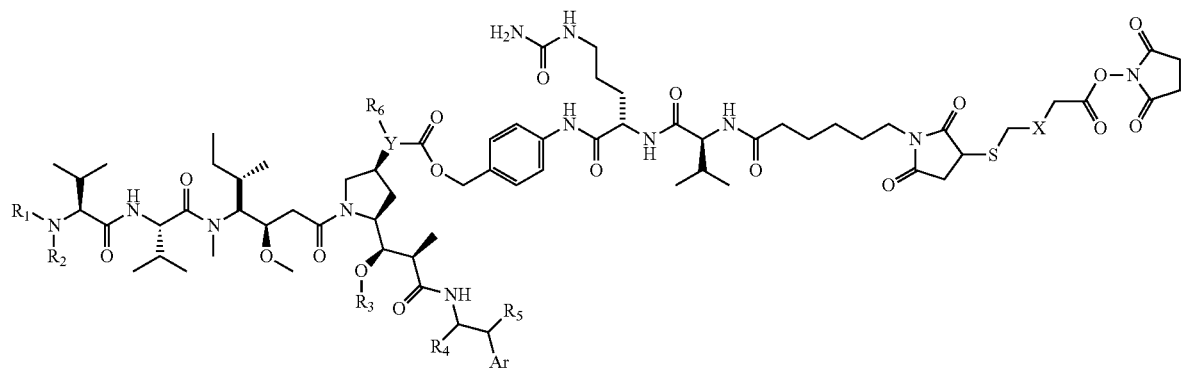

[Chemical Formula I-3]

(I-3)

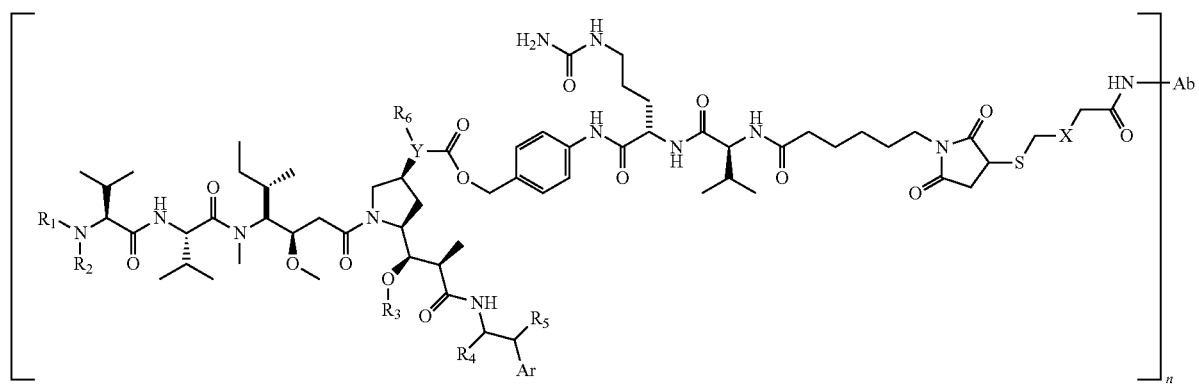

wherein,
Ab is an antibody,
X is $C_1$-$C_8$ alkyl, or $C_3$-$C_6$ cycloalkyl,
$R_1$, $R_2$, $R_3$, and $R_4$ are each independently a hydrogen atom, or $C_1$-$C_4$ alkyl,
$R_5$ is a hydrogen atom, hydroxy, $C_1$-$C_4$ alkoxy, amino, oxo (=O), or hydroxyimino (=N—OH),
Ar is aryl,
Y is a nitrogen atom or an oxygen atom,
$R_6$ is a hydrogen atom or $C_1$-$C_4$ alkyl when Y is a nitrogen atom; or is absent when Y is an oxygen atom, and
n is an integer ranging from 1 to 5.

19. The method of claim 18, wherein the condensation reaction of step (i) is carried out in presence of a condensing agent selected from the group consisting of hydroxybenzotriazole (HOBt), hydroxyazabenzotriazole (HOAt), and hydroxysuccinimide (HOSu), and an organic base selected from the group consisting of pyridine and diisopropylethylamine.

20. The method of claim 18, wherein the condensation reaction of step (iii) is carried out in presence of a condensing agent selected from the group consisting of dicyclohexylcarbodiimide (DCC), and (3-dimethylaminopropyl)carbodiimide (EDC).

21. The method of claim 18, wherein the reaction of step (iv) is carried out in a phosphate buffer having a pH of 6.0 to 8.0 as a reaction solvent.

22. The method of claim 18, wherein the reaction of step (iv) is carried out in a mixed reaction solvent of a phosphate buffer having a pH of 6.0 to 8.0 and an organic solvent.

23. The method of claim 22, wherein the organic solvent amounts to 50% or less of the mixed solvent.

24. The method of claim 18, wherein the compound of Chemical Formula VII-3 is used in an amount of 3 to 25 equivalents, based on the antibody, in step (iv).

* * * * *